United States Patent
Fuchs et al.

(10) Patent No.: US 9,079,905 B2
(45) Date of Patent: Jul. 14, 2015

(54) COMPOUNDS FOR THE TREATMENT OF CNS DISORDERS

(75) Inventors: Klaus Fuchs, Mittelbiberach (DE); Cornelia Dorner-Ciossek, Warthausen (DE); Christian Eickmeier, Mittelbiberach (DE); Dennis Fiegen, Biberach (DE); Thomas Fox, Biberach (DE); Riccardo Giovannini, Verona (IT); Niklas Heine, Biberach (DE); Martin Hendrix, Tarrytown, NY (US); Holger Rosenbrock, Mittelbiberach (DE); Gerhard Schaenzle, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 751 days.

(21) Appl. No.: 13/062,625

(22) PCT Filed: Sep. 4, 2009

(86) PCT No.: PCT/EP2009/061455
§ 371 (c)(1),
(2), (4) Date: May 5, 2011

(87) PCT Pub. No.: WO2010/026214
PCT Pub. Date: Mar. 11, 2010

(65) Prior Publication Data
US 2012/0115863 A1 May 10, 2012

(30) Foreign Application Priority Data

Sep. 8, 2008 (EP) .......................... 08163879
Aug. 12, 2009 (EP) .......................... 09167675

(51) Int. Cl.
*C07D 487/04* (2006.01)
*A61K 31/519* (2006.01)

(52) U.S. Cl.
CPC ..................... *C07D 487/04* (2013.01)

(58) Field of Classification Search
CPC ............................. A61K 31/519; C07D 487/04
USPC ........................................ 544/262; 514/262.1
See application file for complete search history.

(56) References Cited

U.S. PATENT DOCUMENTS

| | | | |
|---|---|---|---|
| 3,165,520 A | 1/1965 | Schmidt et al. | |
| 3,169,965 A | 2/1965 | Schmidt et al. | |
| 3,211,731 A | 10/1965 | Schmidt et al. | |
| 3,244,328 A | 4/1966 | Brown | |
| 3,732,225 A | 5/1973 | Breuer et al. | |
| 3,847,908 A | 11/1974 | Breuer et al. | |
| 3,884,906 A | 5/1975 | Van Der Meer et al. | |
| 4,602,023 A | 7/1986 | Kiely et al. | |
| 5,002,949 A | 3/1991 | Peseckis et al. | |
| 5,041,449 A | 8/1991 | Belleau et al. | |
| 5,047,407 A | 9/1991 | Belleau et al. | |
| 5,053,499 A | 10/1991 | Kojima et al. | |
| 5,113,855 A | 5/1992 | Newhouse | |
| 5,201,308 A | 4/1993 | Newhouse | |
| 5,239,992 A | 8/1993 | Bougamont et al. | |
| 5,256,668 A | 10/1993 | Hsu et al. | |
| 5,270,315 A | 12/1993 | Belleau et al. | |
| 5,294,612 A | 3/1994 | Bacon et al. | |
| 5,341,801 A | 8/1994 | Zechner | |
| 5,466,806 A | 11/1995 | Belleau et al. | |
| 5,503,144 A | 4/1996 | Bacon | |
| 5,541,187 A | 7/1996 | Bacon et al. | |
| 5,563,049 A | 10/1996 | Kojima et al. | |
| 5,568,884 A | 10/1996 | Bruna | |
| 5,634,900 A | 6/1997 | Makino et al. | |
| 5,656,629 A | 8/1997 | Bacon et al. | |
| 5,684,164 A | 11/1997 | Belleau et al. | |
| 5,750,673 A | 5/1998 | Martin | |
| 5,948,812 A | 9/1999 | Kraft | |

(Continued)

FOREIGN PATENT DOCUMENTS

CA 2090227 A1 3/1992
CA 1311201 C 12/1992

(Continued)

OTHER PUBLICATIONS

Schmidt et al., Helvitica Chimica Acta, 1962, 45, pp. 1620-1627.*
International Search Report for corresponding PCT Application No. PCT/EP2009/061455 mailed on Feb. 19, 2010.
Accessed on Dec. 18, 2008: wikipedia: "Amnesia", http://www.mentalhealth.org.uk/information/mental-health-a-z/dementia/, last accessed on Dec. 18, 2008.
Accessed on Jun. 30, 2008, Intelihealth: "Alzheimer's Disease," http://www.intelihealth.com/IH/ihtIH/WSIHW/8303/9117/195703.html?d=dmtHelathAZ.
Accessed on Sep. 22, 2009: Intelihealth: "Dementia," http://www.intelihealth.com/IH/ihtIH/WSIHW000/244798/00084.html.
Accessed on Sep. 22, 2009: Intelihealth: "Parkinson's Disease", http://www.intelihealth.com/IH/ihtIH?d=dmtHealthAZ&c=201957.
Andreeva, Svetlana G, et al; "Expression of cGMP-Specific Phosphodiesterase 9A . . . ", J. of Neuroscience, 2001, Vo. 21, No. 22, pp. 9068-9076.

(Continued)

*Primary Examiner* — Susanna Moore
(74) *Attorney, Agent, or Firm* — Michael P. Morris; Edward S. Lazer

(57) ABSTRACT

The invention relates to novel cycloalkyl- or cycloalkenyl-substituted pyrazolopyrimidinones of formula (I).

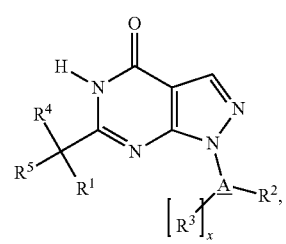

wherein A, $R^1$-$R^5$ and x are as defined herein, and their use as medicaments for improving perception, concentration, learning and/or memory in patients in need thereof.

4 Claims, No Drawings

(56) References Cited

U.S. PATENT DOCUMENTS

| | | |
|---|---|---|
| 5,969,116 A | 10/1999 | Martin |
| 5,969,499 A | 10/1999 | Shaffer |
| 5,977,118 A | 11/1999 | Bacon et al. |
| 5,977,332 A | 11/1999 | Martin |
| 6,100,037 A | 8/2000 | Phillips et al. |
| 6,174,884 B1 | 1/2001 | Haning et al. |
| 6,175,008 B1 | 1/2001 | Belleau et al. |
| 6,211,158 B1 | 4/2001 | Seela et al. |
| 6,225,315 B1 | 5/2001 | Ellis |
| 6,350,753 B1 | 2/2002 | Belleau et al. |
| 6,458,796 B1 | 10/2002 | Haning et al. |
| 6,479,463 B1 | 11/2002 | Wang et al. |
| 6,831,174 B2 | 12/2004 | Belleau et al. |
| 6,903,224 B2 | 6/2005 | Belleau et al. |
| 7,022,709 B2 | 4/2006 | Boss et al. |
| 7,067,507 B2 | 6/2006 | Pulley et al. |
| 7,122,693 B2 | 10/2006 | Belleau et al. |
| 7,375,213 B2 | 5/2008 | Deshpande et al. |
| 7,488,733 B2 | 2/2009 | Hendrix et al. |
| 7,488,766 B2 | 2/2009 | Peters et al. |
| 7,541,341 B2 | 6/2009 | Fushimi et al. |
| 7,579,449 B2 | 8/2009 | Eckhardt et al. |
| 7,615,558 B2 | 11/2009 | Hendrix et al. |
| 7,662,790 B2 | 2/2010 | Himmelsbach et al. |
| 7,683,160 B2 | 3/2010 | Eckhardt et al. |
| 7,687,469 B2 | 3/2010 | Eckhardt et al. |
| 7,708,011 B2 | 5/2010 | Hochrainer et al. |
| 7,713,938 B2 | 5/2010 | Himmelsbach et al. |
| 7,723,309 B2 | 5/2010 | Himmelsbach et al. |
| 7,737,156 B2 | 6/2010 | Böβ et al. |
| 7,745,414 B2 | 6/2010 | Eckhardt et al. |
| 7,772,191 B2 | 8/2010 | Eckhardt et al. |
| 7,772,378 B2 | 8/2010 | Himmelsbach et al. |
| 7,776,830 B2 | 8/2010 | Eckhardt et al. |
| 7,847,074 B2 | 12/2010 | Eckhardt et al. |
| 7,851,602 B2 | 12/2010 | Himmelsbach et al. |
| 7,858,587 B2 | 12/2010 | Eckhardt et al. |
| 7,870,856 B2 | 1/2011 | Boeck |
| 7,879,806 B2 | 2/2011 | Himmelsbach et al. |
| 7,879,807 B2 | 2/2011 | Himmelsbach et al. |
| 7,984,713 B2 | 7/2011 | Hochrainer et al. |
| 8,039,441 B2 | 10/2011 | Himmelsbach et al. |
| 8,039,477 B2 | 10/2011 | Hendrix et al. |
| 8,044,060 B2 | 10/2011 | Hendrix et al. |
| 8,088,769 B2 | 1/2012 | Hendrix et al. |
| 8,158,633 B2 * | 4/2012 | Hendrix et al. ............ 514/262.1 |
| 2001/0041797 A1 | 11/2001 | Belleau et al. |
| 2001/0044441 A1 | 11/2001 | Campbell et al. |
| 2002/0016348 A1 | 2/2002 | Simitchieva et al. |
| 2002/0074774 A1 | 6/2002 | Hsu et al. |
| 2002/0086160 A1 | 7/2002 | Qiu et al. |
| 2002/0100222 A1 | 8/2002 | Koenig et al. |
| 2002/0132754 A1 | 9/2002 | Boss et al. |
| 2002/0137903 A1 | 9/2002 | Ellsworth et al. |
| 2003/0064935 A1 | 4/2003 | Gougoutas |
| 2003/0087918 A1 | 5/2003 | Belleau et al. |
| 2003/0114390 A1 | 6/2003 | Washburn et al. |
| 2003/0195205 A1 | 10/2003 | DeNinno et al. |
| 2004/0185459 A1 | 9/2004 | Otsuka et al. |
| 2004/0187868 A1 | 9/2004 | Hochrainer et al. |
| 2004/0220186 A1 | 11/2004 | Bell et al. |
| 2004/0254201 A1 | 12/2004 | Belleau et al. |
| 2004/0266736 A1 | 12/2004 | Wunder et al. |
| 2005/0187168 A1 | 8/2005 | Eickelmann et al. |
| 2005/0209251 A1 | 9/2005 | Linker et al. |
| 2005/0233982 A1 | 10/2005 | Himmelsbach et al. |
| 2005/0263151 A1 | 12/2005 | Hochrainer et al. |
| 2006/0009400 A1 | 1/2006 | Eckhardt et al. |
| 2006/0025349 A1 | 2/2006 | Eckhardt et al. |
| 2006/0074031 A1 | 4/2006 | Eckhardt et al. |
| 2006/0100222 A1 | 5/2006 | Boss et al. |
| 2006/0106035 A1 | 5/2006 | Hendrix et al. |
| 2006/0111372 A1 | 5/2006 | Hendrix et al. |
| 2006/0111375 A1 * | 5/2006 | Shimizu et al. ............ 514/266.3 |
| 2007/0037977 A1 | 2/2007 | Belleau et al. |
| 2007/0105876 A1 | 5/2007 | Hendrix et al. |
| 2007/0105881 A1 | 5/2007 | Hendrix et al. |
| 2007/0161662 A1 | 7/2007 | Hendrix et al. |
| 2007/0240713 A1 | 10/2007 | Boeck |
| 2007/0281940 A1 | 12/2007 | Dugi et al. |
| 2008/0255118 A1 | 10/2008 | Hendrix et al. |
| 2009/0023913 A1 | 1/2009 | Eckhardt et al. |
| 2009/0111838 A1 | 4/2009 | Hendrix et al. |
| 2009/0121919 A1 | 5/2009 | Kihara |
| 2009/0194105 A1 | 8/2009 | Besseler et al. |
| 2009/0235929 A1 | 9/2009 | Egen et al. |
| 2009/0318547 A1 | 12/2009 | Eckhardt et al. |
| 2009/0326215 A1 | 12/2009 | Eckhardt et al. |
| 2010/0024815 A1 | 2/2010 | Kladders |
| 2010/0035900 A1 | 2/2010 | Hendrix et al. |
| 2010/0069310 A1 | 3/2010 | Himmelsbach et al. |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0210839 A1 | 8/2010 | Boss et al. |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0015193 A1 | 1/2011 | Eickmeier et al. |
| 2011/0046076 A1 | 2/2011 | Eickelmann et al. |
| 2011/0046087 A1 | 2/2011 | Eickelmann et al. |
| 2011/0065730 A1 | 3/2011 | Hendrix et al. |
| 2011/0065731 A1 | 3/2011 | Dugi et al. |
| 2011/0082137 A1 | 4/2011 | Giovannini et al. |
| 2011/0098240 A1 | 4/2011 | Dugi et al. |
| 2011/0178033 A1 | 7/2011 | Eckhardt et al. |
| 2011/0184000 A1 | 7/2011 | Giovannini et al. |
| 2011/0203586 A1 | 8/2011 | Egen et al. |
| 2011/0207735 A1 | 8/2011 | Hendrix et al. |
| 2011/0212960 A1 | 9/2011 | Heine et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2011/0294834 A1 | 12/2011 | Hendrix et al. |
| 2012/0010224 A1 | 1/2012 | Hendrix et al. |
| 2012/0115863 A1 | 5/2012 | Fuchs et al. |
| 2012/0165349 A1 | 6/2012 | Hendrix et al. |
| 2012/0202829 A1 | 8/2012 | Heine et al. |

FOREIGN PATENT DOCUMENTS

| | | |
|---|---|---|
| CA | 2283211 A1 | 9/1998 |
| CA | 2238211 A1 | 12/1998 |
| CA | 2357146 A1 | 7/2000 |
| CA | 2437240 A1 | 8/2002 |
| CA | 2438890 A1 | 9/2002 |
| CA | 2417631 A1 | 1/2003 |
| CA | 2466824 A1 | 5/2003 |
| CA | 2484997 A1 | 11/2003 |
| CA | 2496194 A1 | 3/2004 |
| CA | 2496292 A1 | 4/2004 |
| CA | 2496306 A1 | 4/2004 |
| CA | 2496308 A1 | 4/2004 |
| CA | 2524900 A1 | 11/2004 |
| CA | 2539032 A1 | 3/2005 |
| CH | 396923 A | 8/1965 |
| CH | 396924 A | 8/1965 |
| CH | 396925 A | 8/1965 |
| CH | 396926 A | 8/1965 |
| CH | 396927 A | 8/1965 |
| CH | 398626 A | 3/1966 |
| DE | 1147234 B | 4/1963 |
| DE | 1149013 B | 5/1963 |
| DE | 1153023 B | 8/1963 |
| DE | 1156415 B | 10/1963 |
| DE | 2408906 A1 | 9/1974 |
| DE | 4004558 A1 | 9/1990 |
| DE | 4027391 A1 | 3/1992 |
| DE | 10156249 A1 | 5/2003 |
| DE | 10238722 A1 | 3/2004 |

(56) References Cited

FOREIGN PATENT DOCUMENTS

| | | |
|---|---|---|
| EP | 0130735 A1 | 1/1985 |
| EP | 0286028 A2 | 10/1988 |
| EP | 0496617 A1 | 7/1992 |
| EP | 0516510 A1 | 12/1992 |
| EP | 0546996 A2 | 6/1993 |
| EP | 0626387 A1 | 11/1994 |
| EP | 0679657 A2 | 11/1995 |
| EP | 0995751 A2 | 4/2000 |
| EP | 1460077 A1 | 9/2004 |
| GB | 937723 A | 9/1963 |
| GB | 937724 A | 9/1963 |
| GB | 937726 A | 9/1963 |
| GB | 973361 A | 10/1964 |
| JP | 2001513638 A | 9/2001 |
| JP | 2001514638 A | 9/2001 |
| JP | 2002523507 A | 7/2002 |
| JP | 2004536933 A | 12/2004 |
| JP | 2005531549 A | 10/2005 |
| JP | 2006501272 A | 1/2006 |
| JP | 2006503051 A | 1/2006 |
| WO | 9414802 A1 | 7/1994 |
| WO | 9417803 A1 | 8/1994 |
| WO | 9510506 A1 | 4/1995 |
| WO | 9628429 A1 | 9/1996 |
| WO | 9716456 A1 | 5/1997 |
| WO | 9746569 A2 | 12/1997 |
| WO | 9800434 A1 | 1/1998 |
| WO | 9810765 A1 | 3/1998 |
| WO | 9816184 A2 | 4/1998 |
| WO | 9840384 A1 | 9/1998 |
| WO | 9941253 A1 | 8/1999 |
| WO | 0018758 A1 | 4/2000 |
| WO | 0043394 A1 | 7/2000 |
| WO | 0160315 A2 | 8/2001 |
| WO | 0177075 A2 | 10/2001 |
| WO | 0206288 A1 | 1/2002 |
| WO | 0209713 A2 | 2/2002 |
| WO | 0216348 A1 | 2/2002 |
| WO | 02055082 A1 | 7/2002 |
| WO | 02057425 A2 | 7/2002 |
| WO | 02068423 A1 | 9/2002 |
| WO | 02074774 A1 | 9/2002 |
| WO | 02086160 A1 | 10/2002 |
| WO | 02098864 A1 | 12/2002 |
| WO | 03011923 A1 | 2/2003 |
| WO | 03011925 A1 | 2/2003 |
| WO | 03022859 A2 | 3/2003 |
| WO | 03031458 A1 | 4/2003 |
| WO | 03037432 A1 | 5/2003 |
| WO | 03037899 A1 | 5/2003 |
| WO | 03041725 A2 | 5/2003 |
| WO | 03072757 A2 | 9/2003 |
| WO | 03093269 A2 | 11/2003 |
| WO | 03099840 A1 | 12/2003 |
| WO | 2004002999 A2 | 1/2004 |
| WO | 2004018474 A1 | 3/2004 |
| WO | 2004026286 A2 | 4/2004 |
| WO | 2004026876 A1 | 4/2004 |
| WO | 2004046331 A2 | 6/2004 |
| WO | 2004096811 A1 | 11/2004 |
| WO | 2004099210 A1 | 11/2004 |
| WO | 2004099211 A1 | 11/2004 |
| WO | 2004108139 A2 | 12/2004 |
| WO | 2004113306 A1 | 12/2004 |
| WO | 2005021566 A2 | 3/2005 |
| WO | 2005051944 A1 | 6/2005 |
| WO | 2005068436 A1 | 7/2005 |
| WO | 2006076455 A2 | 7/2006 |
| WO | 2006084281 A1 | 8/2006 |
| WO | 2006091905 A1 | 8/2006 |
| WO | 2006125548 A1 | 11/2006 |
| WO | 2007025043 A2 | 3/2007 |
| WO | 2007046747 A1 | 4/2007 |
| WO | 2008005542 A2 | 1/2008 |
| WO | 2008049923 A1 | 5/2008 |
| WO | 2008055959 A1 | 5/2008 |
| WO | 2008100447 A2 | 8/2008 |
| WO | 2008104077 A1 | 9/2008 |
| WO | 2008139293 A1 | 11/2008 |
| WO | 2009068617 A1 | 6/2009 |
| WO | 2009121919 A1 | 10/2009 |
| WO | 2010026214 A1 | 3/2010 |
| WO | 2010092123 A1 | 8/2010 |
| WO | 2010092125 A1 | 8/2010 |
| WO | 2010112437 A1 | 10/2010 |
| WO | 2011018495 A1 | 2/2011 |

OTHER PUBLICATIONS

Bagli, Jehan et al; Chemistry and Positive Inotropic Effect of Pelrinone and related Derivates. A Novel Class of 2-Methylpyrimidones as Inotropic Agents; Journal of Medicinal Chemistry (1988) vol. 31 pp. 814-823.

Barger, Steven, W; Role of Cyclic GMP in the Regulation of Neuronal Calcium and Survival by Secreted Forms of Beta-Amyloid Precursor; Journal of Neurochemistry (1995) vol. 64, No. 5, pp. 2087-2096.

Bernabeu, R., et al; Hippocampal cGMP and cAMP are Differentially Involved in Memory Processing of Inhibitors Avoidance Learning; Neuroreport (1996) vol. 7, No. 2 pp. 585-588.

Byrn, Stephen, R; Solid State Chemistry of Drugs (1999) vol. 2, No. 10, pp. 232-247.

Caligiuri, Maureen, et al; A ProTeome-Wide CDK/CRK-Specific Kinase inhibitor Promotes Tumor Cell Death in the Absence of Cell Cycle Progression; Chemistry & Biology (2005) vol. 12 pp. 1103-1115.

Chem Abstracts Service, Database Accession No. ALB-H01677136, Database Chemcats, 2007, XP002556399.

Cheng, C. C. et al; Potential Purine Antagonists VII. Synthesis of 6-Alkylpyrazolo-[3,4-d]pyrimidinesn Potential Purine Antagonist VII; Gazz. Chim. Ital., (1958) vol. 23, pp. 191-200.

Ciba Geigy AG, "Nucleosides and oligonucleotides and 2'-ether groups," Data Supplied from the espacenet database, Publication Date: Nov. 30, 1994; English Abstract of EPO 626 387.

DeNinno et al. "The discovery of potent, selective, and orally bioavailable PDE9 . . . ", Bioorganic & Medicinal Chemistry Letters, 2009, vol. 19, pp. 2537-2541.

Doerwald et al., "Side reactions in organic synthesis," A Guide to Successful Synthesis Design, 2005, 4 pages.

Ebert et al., "Scopolamine model of demential: electroencephalogram findings and cognitive performance," Europ J of Clinical Investigation, 1998, vol. 28, No. 11, pp. 944-949.

Farlow, Martin, R; Pharmacokinetic Profiles of Currect Therapies for Alzheimer's Disease: Implications for Switching to Galantamine; Clinical Therapeutics (2001) vol. 23, Suppl. A, pp. A13-A-24.

Fawcett, Lindsay et al; "Molecular Cloning and Characterization of a Distinct Human . . . ", Proc. Natl. Acad. Science, 2000, vol. 97, No. 7, pp. 3702-3707.

Fischer, Douglas A., et al; "Isolation and Characterization of PDE9A, A Novel . . . ", J. of Biological Chemistry, 1998, vol. 273, No. 25, pp. 15559-15564.

Fisher, Douglas A, et al; "Isolation and Characterization of PDE8A, A Novel . . . ", Biochemical and Biophysical Research Communications, 1998, vol. 246, pp. 570-577.

Francis et al; Cortical Pyramidal Neurone Loss May Cause Glutamatergic Hypoativity and Cognitive Impairment in Alzheimer's Disease: investigative and Therapeutic Perspectives; Journal of Neurochemistry (1993) vol. 60, No. 5, pp. 1589-1604.

Francis, Paul T; "Glutamatergic Systems in Alzheimer's Disease" International Journal of Geriatic Psychiatry (2003) vol. 18, pp. S15-S21.

Francis, Sharron H., et al; "Characterization of a Novel cGMP Binding Protein form Rat Lung . . . ", J. of Biological Chemistry, vol. 255, No. 2, pp. 620-626. (1980).

Fujhishige et al; Cloning and Characterization of a Novel Human Phosphodiesterase That Hydrolyzes Both cAMP and cGMP (PDE10A); Journal of Bilogical Chemistry (1999) vol. 274, No. 26, pp. 18438-18445.

Gielen, Hieke et al; A Novel Approach to Amidines from Esters; Tetrahedron Letters (2002) vol. 43 pp. 419-421.

(56) References Cited

OTHER PUBLICATIONS

Gillespie et al; Characterization of a Bovine Cone Photoreceptor Phosphodiesterase Purified by Cyclic Cyclic GMP-Sepharose Chromatography; J. of Biological Chemistry (1988) vol. 263, No. 17, pp. 8133-8141.
Gompper, Rudolf et al; Substituted Dithiocarboxylic Acids and Ketene Thioacetals; Institute for Organic Chemistry Technology (1962) vol. 95, pp. 2861-2870. German & English Translation.
Guipponi, Michel et al; Identification and Characterization of a Novel Cyclic Nucleotide Phosphodiesterase Gene (PDE9A) that Maps to 21q22.3: Alternative Splicing of mRNA Transcripts, Genomic Structure and Sequence; Hum Genet (1998) vol. 103, pp. 386-392.
Harb, A.-F. A., et al; Pyrazoles as Building Blocks in Heterocyclic Synthesis: Synthesis of Some Ne Substituted 1-Triazinylpyrazolo[3,4-d]pyrimidine and 1-Triazinylpyrazolo[3,4-b]pyridine Derivates; Chemical Papers (2005) vol. 59, No. 3, pp. 187-195.
Hendrix et al; "6-cyclymethyl-and 6-alkylmethyl-Substituted Pyrazolopyrimidines," Publication Date: Nov. 18, 2004, Data Supplied from the espacenet database Worlwide; English Abstract of WO 2004099211.
Hendrix et al; "Use of Pyrazolopyrimidine Against Cardiovascular Disease," Publication Date: Nov. 30, 2006, Data Supplied from the espacenet database Worldwide; English Abstract or WO 20060125548.
Hetman, J. M., et al; Cloning and Characterization of PDE7B, a cAMP-Specific Phosphodiesterase; Proc, Natl. Acad. Science (2000) vol. 97, No. 1, pp. 472-476.
http://www.nlm.nih.gov/medlineplus/ency/article/000746.htm, last accessed Jul. 15, 2010.
Huettner et al; Primary Culture of Identified Neurons from the Visual Cortex of Postnatal Rats; Journal of Neuroscience (1986) vol. 6, No. 10, pp. 3044-3060.
Hung et al., "A high-yielding synthesis of monalkylhydrazines," Journal of Organic Chemistry, 1981, vol. 46, pp. 5413-5414.
International Search Report for PCT/EP2008/066350 dated Feb. 23, 2009.
International Search Report for PCT/EP2009/053907 dated May 26, 2009.
International Search Report for PCT/EP2010/054050 dated May 27, 2010.
International Search Report for PCT/EP2010/061735 dated Sep. 24, 2010.
International Search Report for PCT/EP2004/006477 dated Oct. 27, 2004.
International Search Report for PCT/EP2004/014872 dated May 19, 2005.
International Search Report of PCT/EP2003/08880 dated Apr. 16, 2004.
International Search Report of PCT/EP2003/08923 dated Dec. 15, 2003.
International Search Report of PCT/EP2003/08979 dated Nov. 25, 2003.
International Search Report of PCT/EP2004/004412 dated Jul. 14, 2004.
International Search Report of PCT/EP2004/004455 dated Sep. 17, 2004.
Loughney, Kate, et al; Isolation and Characterization of cDNAs Corresponsing to Two human Calcium, Calmodulin-regulated, 3',5'-Cyclic Nucleotide Phosphodiesterases; The Journal of Biological Chemistry (1996) vol. 271, No. 2, pp. 796-806.
Loughney, Kate, et al; Isolation and Characterization of cDNAs Encoding PDE5A, a Human cGMP-Bing, cGMP-Specific 3',5'-cyclic Nucleotide Phosphodiesterase; Gene (1998) vol. 216, pp. 139-147.
Lugnier, Claire; Cyclic Nucleotide Phosphodiesterase (PDE) Superfamily: A New Target for the Development of Specific Therapeutic Agents; Pharmacology & Therapeutics; (2006) vol. 109, pp. 366-398.
Markwalder, J. A. et al; Synthesis and Biological Evaluation of 1-Aryl-4,5-dihydro-1H-pyrazolo[3,4-d]pyrimidin-4-one Inhibitors of Cyclin-Dependent Kinases; J. of Med Chemistry (2004) vol. 47, pp. 5894-5911.
Martins, Timothy, J., et al; Purification and Characterization of a Cyclic GMP-stimulated Cyclic Nucleotide Phosphodiesterase from Bovine Tissues; The Journal of Biological Chemistry (1982) vol. 257, No. 4, pp. 1973-1979.
Merriam-Webster's Collegiate Dictionary, published 1998 by Merriam-Webster Inc. p. 924.
Miki, Takashi, et al; Characterization of the cDNA and Gene Encoding Human PDE3B, the cGIP1 Isoform of the Human Cyclic GMP-Inhibited Cyclic Nucleotide Phosphodiesterase Family; Genomics (1996) vol. 36, pp. 476-485.
Miyashita, A., et al; Studies on Pyrazolo[3,4-d]pyrimidine Derivatives XVIII Facile Preparation of 1H-Pyrazolo[3,4-d] Pyrimidin-4(5H)-Ones; Heterocycles (1990) vol. 31, No. 7, pp. 1309-1314.
Murashima, Seiko., et al; Characterization of Particulate Cyclic Nucleotide Phosphodiesterases from Bovine Brain: Purification of a Distinct cGMP-Stimulated Isoenzyme; Biochemistry (1990) vol. 29, No. 22, pp. 5285-5292.
Obernolte, Rena, et al; The cDNA of a Human Lymphocyte Cyclic AMP Phosphodiesterase (PDE IV) Reveals a Multigene Family; Gene (1993) vol. 129, pp. 239-247.
Podraza, Kenneth F.; Reductive Cyclization of Ketoesters Utilizing Sodium Cyanoborohydride: Synthesis of ?- and ?-Lactones; J. Heterocyclic Chem (1987) vol. 24. pp. 293.
Prickaerts et al; Possible Role of Nitric Oxide-Cyclic GMP Pathway in Object Recognition Memory: Effects of 7 Nitroindazole and Zaprinast; Europ J of Pharmacology (1997) vol. 337, No. 2-3, pp. 125-136.
Prickaerts, J. et al; Effects of Two Selective Phosphodiesterase Type 5 Inhibitors, Sildenafil and Vardenafil, on Object Recognition Memory and Hippocampal Cyclic GMP Levels in the Rat, Neuroscience (2002) vol. 113, No. 2, pp. 351-361.
Puzzo, Daniela, et al; Amyloid-b Peptide Inhibits Activation of the Nitric Oxide/cGMP/cAMP-Responsive Element-Binding Protein Pathway During Hippocampal Synaptic Plasticity; The Journal of Neuroscience (2005) vol. 25, No. 29, pp. 6887-6897.
Reddy, K. Hemender et al; Versatile Synthesis of 6-Alkyl/Aryl-1H-Pyrazolo[3,4-d]Pyrimidin-4[5M]-Ones; Indian Journal of Chemistry (1992) vol. 31B, pp. 163-166.
Reid I. A.; Role of Phosphodiesterase Isozymes in the Control of Renin Secretion: Effects of Selective Enzyme Inhibitors; Current Pharmaceutical Design (1999) vol. 5, No. 9, pp. 725-735.
Related U.S. Appl. No. 12/855,129, filed Aug. 12, 2010.
Related U.S. Appl. No. 12/935,686, filed Sep. 30, 2010.
Related U.S. Appl. No. 13/062,625, filed Mar. 7, 2011.
Related U.S. Appl. No. 13/099,064, filed May 2, 2011.
Rentero, Carles, et al; Identification and Distribution of Different mRNA Variants Produced by Differential Splicing in the Human Phosphodiesterase 9A Gene; Biochemical and Biophysical Research Communications (2003) vol. 301 pp. 686-692.
Reymann, Klaus, et al; The Late Maintenance of Hippocampal LTP: Requirements, Phases, 'Synaptic Tagging', 'Late-Associativity' and Implications; Neuropharmacology (2007) vol. 52, pp. 24-40.
Roenn, Magnus et al; Palladium (II)-Catalyzed Cyclization Using Molecular Oxygen as Reoxidant; Tetrahedron Letters (1995) vol. 36, No. 42, pp. 7749-7752.
Rosman, Guy, J., et al; Isolation and Characterization of Human cDNSs Encoding a cGMP-Stimulated 3',5'-Cyclic Nucleotide Phosphodiesterase; Gene (1997) vol. 191, pp. 89-95.
Schmidt, Richard, R. et al; Pyrazolo[3, 4-d]Pyrimidin-Nucleoside; Chemische Berichte (1977) vol. 110, pp. 2445-2455.
Schmidt, von P., et al; Heilmittelchemische Studien in der Heterocyclischen Reihe; Helvetica Chimica Acta (1962) vol. 62, No. 189, pp. 1620-1627.
Schousboe, Arne et al; Role of Ca++ and Other Second Messengers in Excitatory Amino Acid Receptor Mediated Neuogeneration: Clinical Perspective; Clinical Neuroscience (1997) vol. 4, pp. 194-198.

(56) References Cited

OTHER PUBLICATIONS

Skipper, Howard, E., et al; Structure-Activity Relationships Observed on Screening a Series of Pyrazolopyrimidines Against Experimental Neoplasms; Cancer Research (1957) vol. 17, pp. 579-596.

Soderling, Scott, H. et al; Identification and Characterization of a Novel Family of Cyclic Nucleotide Phosphodiesterases; The Journal of Biological Chemistry (1998) vol. 273, No. 25, pp. 15553-15558.

Soderling, Scott, H. et al; Regulation of cAMP and cGMP signalling: New Phosphodiesterases and New Functions; Current Opinion in Cell Biology (2000) vol. 12, pp. 174-179.

Thomson Innovation Record View, Publication Date: Apr. 18, 1963; English Abstract of DE 1147234B.

Thomson Innovation Record View, Publication Date: Aug. 15, 1965; English Abstract of CH 396 923.

Thomson Innovation Record View, Publication Date: May 22, 1963; English Abstract of DE 1149013B.

Timberlake, J.W. et al; Preparative Procedures: Chemistry of Hydrazo-, Azo-, and Azoxy Groups; Patai (1975) Chapter 4, pp. 69-107.

U.S. Appl. No. 12/545,175, filed Aug. 21, 2009, Inventor: Matthias Eckhardt.

U.S. Appl. No. 12/892,310, filed Sep. 28, 2010. Inventor: Dirk Weber.

U.S. Appl. No. 12/892,326, filed Sep. 28, 2010. Inventor: Dirk Weber.

U.S. Appl. No. 12/894,385, filed Sep. 30, 2010. Inventor: Peter Schneider.

U.S. Appl. No. 13/079,424, filed Apr. 4, 2011. Inventor: Matthias Eckhardt.

U.S. Appl. No. 13/369,596, filed Feb. 9, 2012. Inventor: Niklas Heine.

U.S. Appl. No. 13/369,623, filed Feb. 9, 2012. Inventor: Niklas Heine.

Ugarkar, Bheemarao, et al; Synthesis and antiviral/Antitumor Activities of Certain Pyrazolo[3,4-d]pyrimidine-4 (5H)-selone Nucleosides and Related compounds; Journal of Medicinal Chemistry (1984) vol. 27, No. 8, pp. 1026-1030.

Ulrich, Joachim; Crystallization; Kirk-Othmer Encyclopedia of Chem Techn (2002) 7 pages.

Van Der Staay, F. Josef., et al; The Novel Selective PDE9 Inhibitor BAY 73/6691 Improves Learning and Memory in Rodents; Neuropharmacology (2008) vol. 55, pp. 908-916.

Van Staveren, W. C. G., et al; Cloning and localization of the cGMP-specific Phosphodiesterase Type 9 in the Rat Brain; Journal of Neurocytology (2002) vol. 31, pp. 729-741.

Vippagunta, Sudha, R., et al; Crystalline Solids; Advanced Drug Delivery Reviews (2001) vol. 48, pp. 3-26.

Wang, Huanchen, et al; Insight Into Binding of Phosphodiesterase-9-A Selective Inhibitors by Crystal Structures and Mutagenesis; Journal of Medicinal Chemistry (2009) pp. 1-6.

Wang, Peng., et al; Identification and Characterization of a New Human Type 9 cGMP-specific Phosphodiesterase-Splice Variant (PDE9A5) Different Tissue Distribution and Subcellular Localization of PDE9A Variants; Gene (2003) vol. 314, pp. 15-27.

Weeber, Edwin, et al; Molecular Genetics of Human Cognition; Molecular Interventions (2002) vol. 2, No. 6, pp. 376-391.

Wei, Ji-Ye, et al; Molecular and Pharmacological Analysis of Cyclic Nucloeotide-Gated Channel Function in the Central Nervous System; Progress in Neurobiology (1998) vol. 56, pp. 37-64.

West, Anthony, R; Solid Solutions; Department of Chemistry, Univesity of Aberdeen (1988) vol. 10 3 pages.

Wunder, Frank et al; Characterization of the First Potent and Selective PDE9 Inhibitor Using a cGMP Reporter Cell Line; Molecular Pharmacology (2005) vol. 68, No. 6 pp. 1775-1781.

Penning, etal., Synthesis and the biological evaluation of the 1,5-Diaiylpyrazole Class of Cyclooxygenase-2 Inhibitors: Identification of 4-[5-(4-Methylphenyl)-3-(triflouromethyl)-1H-pyrazol-1-yl]benzenesulfonamide (SC-58635, Celecoxib), 1997, vol. 40, 1347-1365.

\* cited by examiner

COMPOUNDS FOR THE TREATMENT OF CNS DISORDERS

The invention relates to novel cycloalkyl- or cycloalkenyl-substituted pyrazolopyrimidinones. The new compounds shall be used for the manufacture of medicaments, in particular medicaments for improving perception, concentration, learning and/or memory in patients in need thereof, for example patients suffering from Alzheimer's disease.

Chemically, the compounds are characterised as pyrazolopyrimidinones with a cycloalkyl-moiety directly bound to the 1 position of the pyrazolopyrimidinone and a second substituent in the 6 position which is bound via an optionally substituted methylene-bridge. Further aspects of the present invention refer to a process for the manufacture of the compounds and their use as/for producing medicaments.

BACKGROUND OF THE INVENTION

The inhibition of phosphodiesterase 9A (PDE9A) is one of the currents concepts to find new access paths to the treatment of cognitive impairments due to CNS disorders like Alzheimer's Disease or due to any other neurodegenerative process of the brain. With the present invention, new compounds are presented that follow this concept.

Phosphodiesterase 9A is one member of the wide family of phosphodiesterases. These kinds of enzymes modulate the levels of the cyclic nucleotides 5'-3' cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural proteins, transcription factors). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., Prog. Neurobiol., 1998, 56, 37-64). The phosphodiesterases (PDE) are a control mechanism for controlling the activity of cAMP and cGMP and thus in turn for the corresponding physiological processes. PDEs hydrolyse the cyclic monophosphates to the inactive monophosphates AMP and GMP. Currently, 11 PDE families have been defined on the basis of the sequence homology of the corresponding genes. Individual PDE genes within a family are differentiated by letters (e.g. PDE1A and PDE1B). If different splice variants within a gene also occur, this is then indicated by an additional numbering after the letters (e.g. PDE1A1).

Human PDE9A was cloned and sequenced in 1998. The amino acid identity with other PDEs does not exceed 34% (PDE8A) and is never less than 28% (PDE5A). With a Michaelis-Menten constant (Km) of 170 nanomolar (nM), PDE9A has high affinity for cGMP. In addition, PDE9A is selective for cGMP (Km for cAMP=230 micromolar (μM). PDE9A has no cGMP binding domain, suggesting that the enzyme activity is not regulated by cGMP. It was shown in a Western blot analysis that PDE9A is expressed in humans inter alia in testes, brain, small intestine, skeletal muscle, heart, lung, thymus and spleen. The highest expression was found in the brain, small intestine, kidney, prostate, colon, and spleen (Fisher et al., J. Biol. Chem., 1998, 273 (25), 15559-15564; Wang et al., Gene, 2003, 314, 15-27). The gene for human PDE9A is located on chromosome 21q22.3 and comprises 21 exons. 4 alternative splice variants of PDE9A have been identified (Guipponi et al., Hum. Genet., 1998, 103, 386-392). Classical PDE inhibitors do not inhibit human PDE9A. Thus, IBMX, dipyridamole, SKF94120, rolipram and vinpocetine show no inhibition on the isolated enzyme in concentrations of up to 100 micromolar (μM). An IC50 of 35 micromolar (μM) has been demonstrated for zaprinast (Fisher et al., J. Biol. Chem., 1998, 273 (25), 15559-15564).

Murine PDE9A was cloned and sequenced in 1998 by Soderling et al. (J. Biol. Chem., 1998, 273 (19), 15553-15558). This has, like the human form, high affinity for cGMP with a Km of 70 nanomolar (nM). Particularly high expression was found in the mouse kidney, brain, lung and liver. Murine PDE9A is not inhibited by IBMX in concentrations below 200 micromolar either; the 1050 for zaprinast is 29 micromolar (Soderling et al., J. Biol. Chem., 1998, 273 (19), 15553-15558). It has been found that PDE9A is strongly expressed in some regions of the rat brain. These include olfactory bulb, hippocampus, cortex, basal ganglia and basal forebrain (Andreeva et al., J. Neurosci., 2001, 21 (22), 9068-9076). The hippocampus, cortex and basal forebrain in particular play an important role in learning and memory processes. As already mentioned above, PDE9A is distinguished by having particularly high affinity for cGMP. PDE9A is therefore active even at low physiological concentrations, in contrast to PDE2A (Km=10 micromolar (μM); Martins et al., J. Biol. Chem., 1982, 257, 1973-1979), PDE5A (Km=4 micromolar (μM); Francis et al., J. Biol. Chem., 1980, 255, 620-626), PDE6A (Km=17 micromolar; Gillespie and Beavo, J. Biol. Chem., 1988, 263 (17), 8133-8141) and PDE11A (Km=0.52 micromolar; Fawcett et al., Proc. Nat. Acad. Sci., 2000, 97 (7), 3702-3707). In contrast to PDE2A (Murashima et al., Biochemistry, 1990, 29, 5285-5292), the catalytic activity of PDE9A is not increased by cGMP because it has no GAF domain (cGMP-binding domain via which the PDE activity is allosterically increased) (Beavo et al., Current Opinion in Cell Biology, 2000, 12, 174-179). PDE9A inhibitors may therefore lead to an increase in the baseline cGMP concentration.

This outline will make it evident that PDE9A engages into specific physiological processes in a characteristic and unique manner, which distinguish the role of PDE9A characteristically from any of the other PDE family members.

WO04018474 discloses phenyl-substituted pyrazolopyrimidinones comprising inter alia an unsubstituted cycloalkyl moiety in the 1 position of the pyrazolopyrimidine.

WO04026876 discloses alkyl-substituted pyrazolopyrimidinones comprising inter alia an unsubstituted cycloalkyl moiety in the 1 position of the pyrazolopyrimidine.

WO04096811 disclose heterocyclic bicycles as PDE9 inhibitors for the treatment of diabetes, including type 1 and type 2 diabetes, hyperglycemia, dyslipidemia, impaired glucose tolerance, metabolic syndrome, and/or cardiovascular disease.

U.S. Pat. No. 6,479,463 discloses nucleosidanaloga for antiviral use.

OBJECTIVE OF THE INVENTION

It will be evident that changes in the substitution pattern of pyrazolopyrimidinones may result in interesting changes concerning biological activity, respectively changes in the affinity towards different target enzymes.

Therefore it is an objective of the present invention to provide compounds that effectively modulate PDE9A for the purpose of the development of a medicament, in particular in view of diseases, the treatment of which is accessible via PDE9A modulation.

It is another objective of the present invention to provide compounds that are useful for the manufacture of a medicament for the treatment of CNS disorders.

Yet another objective of the present invention is to provide compounds which show a favourable side effect profile.

Another objective of the present invention is to provide compounds that have a favourable selectively profile in favour for PDE9A inhibition over other PDE family members and other pharmacological targets and by this may provide therapeutic advantage.

Yet another objective is to provide such a medicament not only for treatment but also for prevention or modification of the corresponding disease.

DETAILED DESCRIPTION OF THE PRESENT INVENTION

The compounds of the present invention are characterised by general formula I:

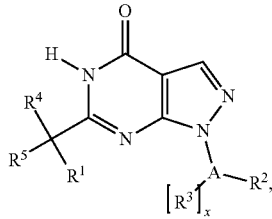

(I)

with the following definitions:

$\overline{A}$ is defined via the following definitions $A^i$, whereby the index i describes the order of preference, ascending from preferably (i.e. $A^1$) to more preferably (i.e. $A^2$) and so on:

$A^1$ $\overline{A}$ being a $C_3$-$C_8$-cycloalkyl group or a $C_4$-$C_8$-cycloalkenyl group, whereby the members of $C_3$-$C_8$-cycloalkyl group being selected from the group of cyclopropyl, cyclobutyl, cyclopentyl, cyclohexyl, cycloheptyl and cyclooctyl; and the members of the $C_4$-$C_8$-cycloalkenyl group, being selected from cyclobutenyl, cyclopentenyl, cyclohexenyl, cycloheptenyl, cyclooctenyl, cyclopentadienyl, cyclohexadienyl, cycloheptadienyl, cyclooctadienyl, cycloheptatrienyl, cyclooctatrienyl, cyclooctatetraenyl.

$A^2$ $\overline{A}$ being a $C_3$-$C_8$-cycloalkyl group or a $C_4$-$C_8$-cycloalkenyl group, whereby the members of $C_3$-$C_8$-cycloalkyl group being selected from the group of cyclopropyl, cyclobutyl, cyclopentyl, cyclohexyl, cycloheptyl and cyclooctyl; and the members of the $C_4$-$C_8$-cycloalkenyl group, being selected from cyclobutenyl, cyclopentenyl, cyclohexenyl, cycloheptenyl, cyclooctenyl.

In each of the definitions, $A^1$, $A^2$, $\overline{A}$ may be either only the $C_3$-$C_8$-cycloalkyl group ($A^{1a}$, $A^{2a}$) or only the $C_4$-$C_8$-cycloalkenyl group ($A^{1b}$, $A^{2b}$).

$A^3$ $\overline{A}$ being a $C_3$-$C_8$-cycloalkyl group, whereby the members of $C_3$-$C_8$-cycloalkyl group being selected from the group of cyclopropyl, cyclobutyl, cyclopentyl, cyclohexyl, cycloheptyl and cyclooctyl.

$A^4$ $\overline{A}$ being a $C_5$-$C_6$-cycloalkyl group the members of which being selected from the group of cyclopentyl and cyclohexyl.

$A^5$ $\overline{A}$ being cyclohexyl, preferably cyclohex-1-yl with at least one of $R^2$ or $R^3$ being attached to the 4-position of said cyclohex-1-yl, more preferably cyclohex-1-yl with $R^2$ and one $R^3$ being attached to the 4-position of said cyclohex-1-yl and no further $R^3$ substituent being attached to said cyclohex-1-yl (i.e. x=1).

$R^1$ is defined via the following definitions $R^{1,j}$ whereby the index j describes the order of preference, ascending from preferably (i.e. $R^{1.1}$) to more preferably (i.e. $R^{1.2}$), and so on. The definition $R^{1.0.1}$ is an independently preferred embodiment:

$R^{1.1}$ $R^1$ being a substituent selected from the group of $C_{1-8}$-alkyl-, $C_{2-8}$-alkenyl-, $C_{2-8}$-alkynyl-, $R^{10}$—S—$C_{1-3}$-alkyl-, $R^{10}$—O—$C_{1-3}$-alkyl-, $C_{3-7}$-cycloalkyl-, $C_{3-7}$-cycloalkyl-$C_{1-6}$-alkyl-, $C_{3-7}$-cycloalkyl-$C_{2-6}$-alkenyl-, $C_{3-7}$-cycloalkyl-$C_{2-6}$-alkynyl-, $C_{3-8}$-heterocycloalkyl-, $C_{3-8}$-heterocycloalkyl-$C_{1-6}$-alkyl-, $C_{3-8}$-heterocycloalkyl-$C_{2-6}$-alkenyl-, $C_{3-8}$-heterocycloalkyl-$C_{2-6}$-alkynyl-, aryl, aryl-$C_{1-6}$-alkyl-, aryl-$C_{2-6}$-alkenyl-, aryl-$C_{2-6}$-alkynyl-, heteroaryl, heteroaryl-$C_{1-6}$-alkyl-, heteroaryl-$C_{2-6}$-alkenyl- and heteroaryl-$C_{2-6}$-alkynyl-, where the above mentioned members may optionally be substituted independently of one another by one or more substituents selected from the group $R^{1.1.S1}$ which consists of fluorine, chlorine, bromine, iodine, oxo, whereby this oxo group preferably is only a substituent for a cycloalkyl group or a heterocycloalkyl group, HO—, NC—, $O_2N$—, $F_3C$—, $HF_2C$—, $FH_2C$—, $F_3C$—$CH_2$—, $F_3C$—O—, $HF_2C$—O—, HO—$C_{1-6}$-alkyl-, $R^{10}$—O—$C_{1-6}$-alkyl-, $R^{10}$—S—$C_{1-6}$-alkyl-, $C_{1-6}$-alkyl-, $C_{3-7}$-cycloalkyl-, $C_{3-7}$-cycloalkyl-$C_{1-6}$-alkyl-, $C_{3-7}$-cycloalkyl-O—, $C_{3-7}$-cycloalkyl-$C_{1-6}$-alkyl-O—, aryl, aryl-$C_{1-6}$-alkyl-, heteroaryl, heteroaryl-$C_{1-6}$-alkyl-, heteroaryl-O—, heteroaryl-$C_{1-6}$-alkyl-O—, $C_{3-8}$-heterocycloalkyl-, $C_{3-8}$-heterocycloalkyl-$C_{1-6}$-alkyl-, $C_{3-8}$-heterocycloalkyl-O— with $C_{3-8}$-heterocycloalkyl being bound to O via one of its ring C-atoms, $C_{3-8}$-heterocycloalkyl-$C_{1-6}$-alkyl-O— with $C_{3-8}$-heterocycloalkyl being bound to the $C_{1-6}$-alkyl- via one of its ring-C-atoms, $(R^{10})_2N$—, $(R^{10})_2N$—$C_{1-6}$-alkyl-, $R^{10}$—O—, $R^{10}$—S—, $R^{10}$—CO—, $R^{10}O$—CO—, $(R^{10})_2N$—CO—, $(R^{10})_2N$—CO—$C_{1-6}$-alkyl-, $R^{10}$—CO—$(R^{10})N$—, $R^{10}$—CO—$(R^{10})N$—$C_{1-6}$-alkyl-, $R^{10}$—CO—O—, $R^{10}O$—CO—O—, $R^{10}O$—CO—O—$C_{1-6}$-alkyl-, $R^{10}O$—CO—$(R^{10})N$—, $R^{10}O$—CO—$(R^{10})N$—$C_{1-6}$-alkyl-, $(R^{10})_2N$—CO—O—, $(R^{10})_2N$—CO—O—$C_{1-6}$-alkyl-, $(R^{10})_2N$—CO—$(R^{10})N$—, $(R^{10})_2N$—CO—$(R^{10})N$—$C_{1-6}$-alkyl-, $R^{10}$—$SO_2$—) $(R^{10})N$—, $R^{10}$—$SO_2$—$(R^{10})N$—$C_{1-6}$-alkyl-, $(R^{10})_2N$—$SO_2$—$(R^{10})N$—$C_{1-6}$-alkyl-, $(R^{10})_2N$—$SO_2$—, $(R^{10})_2N$—$SO_2$—$C_{1-6}$-alkyl-, and $C_{1-6}$-alkyl-$SO_2$—;

whereby any of the $C_{3-7}$-cycloalkyl-, $C_{3-8}$-heterocycloalkyl-, aryl-, heteroaryl-groups of aforementioned group $R^{1.1.S1}$ may optionally be substituted by a member of the group $R^{1.1.S2}$ which consists of fluorine, chlorine, bromine, HO—, NC—, $O_2N$—, $F_3C$—, $HF_2C$—, $FH_2C$—, $F_3C$—$CH_2$—, $F_3C$—O—, $HF_2C$—O—, $C_{3-8}$-heterocycloalkyl-, $R^{10}$—O—$C_{1-6}$-alkyl-, $R^{10}$—S—$C_{1-6}$-alkyl-, $C_{1-6}$-alkyl-, $(R^{10})_2N$—, $(R^{10})_2N$—$C_{1-6}$-alkyl-, $R^{10}$—O—, $R^{10}$—S—, $R^{10}$—CO—, $R^{10}O$—CO—, $(R^{10})_2N$—CO—, $(R^{10})_2N$—CO—$C_{1-6}$-alkyl-, $R^{10}$—CO—$(R^{10})N$—, $R^{10}$—CO—$(R^{10})$N—$C_{1-6}$-alkyl-, $R^{10}$—CO—O—, $R^{10}O$—CO—O—, $R^{10}O$—CO—O—$C_{1-6}$-alkyl-, $R^{10}O$—CO—$(R^{10})N$—, $R^{10}O$—CO—) $(R^{10})N$—$C_{1-6}$-alkyl-, $(R^{10})_2N$—CO—O—, $(R^{10})_2N$—CO—$(R^{10})N$—, $(R^{10})_2N$—$SO_2$—$(R^{10})N$—, $(R^{10})_2N$—CO—O—$C_{1-6}$-alkyl-, $(R^{10})_2N$—CO—$(R^{10})N$—$C_{1-6}$-alkyl-, $R^{10}$—$SO_2$—$(R^{10})N$—, $R^{10}$—$SO_2$—$(R^{10})N$—$C_{1-6}$-alkyl-, $(R^{10})_2N$—$SO_2$—$(R^{10})N$—$C_{1-6}$-alkyl-, $(R^{10})_2N$—$SO_2$—, $(R^{10})_2N$—$SO_2$—$C_{1-6}$-alkyl-, and $C_{1-6}$-alkyl-$SO_2$—.

$R^{1.2}$ $R^1$ being a substituent selected from the group of $C_{1-8}$-alkyl-, $C_{3-7}$-cycloalkyl-, $C_{3-7}$-cycloalkyl-$C_{1-3}$-alkyl-, $C_{3-8}$-heterocycloalkyl-, $C_{3-8}$-heterocycloalkyl-$C_{1-6}$-alkyl-, aryl, aryl-$C_{1-6}$-alkyl-, heteroaryl and heteroaryl-$C_{1-6}$-alkyl-, where the above mentioned members may optionally be substituted independently of one another by one or more substituents selected from the group $R^{1.2.S1}$ which consists of fluorine, chlorine, bromine, iodine, oxo, whereby this oxo group preferably is only a substituent for a heterocycloalkyl group, HO—, NC—, $O_2N$—, $F_3C$—, $HF_2C$—, $FH_2C$—, $F_3C$—$CH_2$—, $F_3C$—O—, $HF_2C$—O—, $R^{10}O$—$C_{1-6}$-alkyl-, $C_{1-6}$-alkyl-, $C_{3-7}$-cycloalkyl-, $C_{3-7}$-cycloalkyl-$C_{1-6}$-alkyl-, aryl, aryl-$C_{1-6}$-alkyl-, heteroaryl, heteroaryl-$C_{1-6}$-alkyl-, $C_{3-8}$-heterocycloalkyl-, $C_{3-8}$-heterocycloalkyl-$C_{1-6}$-alkyl-, tetrahydrofuranyl-O—, tetrahydropyranyl-O—, piperidinyl-O— with piperidinyl being bound to O via one of its ring C-atoms, pyrrolidinyl-O— with pyrrolidinyl being bound to O via one of its ring C-atoms, $(R^{10})_2N$—, $(R^{10})_2N$—$C_{1-6}$-alkyl-, $R^{10}$—O—, $(R^{10})_2N$—CO—, $(R^{10})_2N$—CO—$C_{1-6}$-alkyl-, $R^{10}$—) CO—$(R^{10})N$—, $R^{10}$—CO—$(R^{10})N$—$C_{1-6}$-alkyl-, $R^{10}O$—CO—O—, $R^{10}O$—CO—$(R^{10})N$—, and $(R^{10})_2N$—CO—O—;

whereby any of the $C_{3-7}$-cycloalkyl-, $C_{3-8}$-heterocycloalkyl-, aryl, heteroaryl, tetrahydrofuranyl, tetrahydropyranyl, piperidinyl, $(R^{10})_2N$—CO—$C_{1-6}$-alkyl-, pyrrolidinyl-groups of the aforementioned group $R^{1.2.S1}$ may optionally be substituted by a member of the group $R^{1.2.S2}$ which consists of fluorine, chlorine, bromine, NC—, $O_2N$—, $F_3C$—, $HF_2C$—, $FH_2C$—, $F_3C$—$CH_2$—, $F_3C$—O—, $HF_2C$—O—, $C_{3-8}$-heterocycloalkyl-, $R^{10}$—O—$C_{1-6}$-alkyl-, $C_{1-6}$-alkyl-, $R^{10}$—O—, $R^{10}$—CO—, $R^{10}O$—CO—, and $(R^{10})_2N$—CO—. Preferably piperidinyl or pyrrolidinyl are substituted by $R^{10}$—CO—.

$R^{1.3}$ $R^1$ being a substituent selected from the group of phenyl, 2-, 3- and 4-pyridyl, pyrimidinyl, pyrazolyl, thiazolyl, cyclopropyl, cyclobutyl, cyclopentyl, cyclohexyl, cycloheptyl, cyclopentylmethyl, ethyl, propyl, 1- and 2-butyl, 1-, 2- and 3-pentyl, tetrahydrofuranyl and tetrahydropyranyl, where these groups may optionally be substituted by one or more substituents selected from the group $R^{1.3.S1}$ which consists of fluorine, chlorine, bromine, iodine, oxo, whereby this oxo group is only a substituent for tetrahydrofuranyl and tetrahydropyranyl, HO—, NC—, $C_{1-6}$-alkyl-O—, $C_{1-6}$-alkyl-, $C_{3-7}$-cycloalkyl-, $C_{3-7}$-cycloalkyl-O—, $C_{3-7}$-cycloalkyl-$C_{1-3}$-alkyl-O—, $CF_3O$—, $CF_3$—, $C_{3-8}$-heterocycloalkyl-, $C_{3-8}$-heterocycloalkyl-$C_{1-6}$-alkyl-, HO—$C_{1-6}$-alkyl-, pyrazolyl, pyridyl, pyrimidinyl, $(R^{10})_2N$—CO—$C_{1-6}$-alkyl-, and phenyl, whereby the pyridyl and phenyl group of the aforementioned group $R^{1.3.S1}$ may optionally be substituted by a member of the group $R^{1.3.S2}$ which consists of fluorine, chlorine, $H_3C$—, $F_3C$—, $CH_3O$—, $F_3C$—O—, $H_2NCO$—, NC—, morpholinyl and benzyl-O—.

$R^{1.4}$ $R^1$ being a substituent selected from the group of phenyl, 2-, 3- and 4-pyridyl, cyclopropyl, cyclobutyl, cyclopentyl, cyclohexyl, ethyl, 1- and 2-propyl, 1- and 2-butyl, 1-, 2- and 3-pentyl, tetrahydrofuranyl and tetrahydropyranyl, where these groups may optionally be substituted by one or more substituents selected from the group $R^{1.4.S1}$ which consists of fluorine, chlorine, bromine, iodine, oxo, whereby this oxo group is only a substituent for tetrahydrofuranyl and tetrahydropyranyl, NC—, $C_{1-6}$-alkyl-O—, $C_{1-6}$-alkyl-, $CF_3O$—, $F_3C$—, pyridyl, $(R^{10})_2N$—CO-methyl-, N-morpholinyl-$C_{1-6}$-alkyl-, pyrazolyl and phenyl, whereby the pyridyl, pyrazolyl and phenyl group of the aforementioned group $R^{1.4.S1}$ may optionally be substituted by a member of the group $R^{1.4.S2}$ which consists of fluorine, chlorine, $H_3C$—, $F_3C$—, $CH_3O$—, $H_2NCO$— and NC—.

$R^{1.5}$ $R^1$ being a substituent selected from the group of phenyl, 2-, 3- and 4-pyridyl, whereby said phenyl or 2-, 3- and 4-pyridyl optionally may be substituted by $C_{1-6}$-alkyl-O—, $C_{1-6}$-alkyl-, $C_{3-7}$-cycloalkyl-, $C_{3-7}$-cycloalkyl-O—.

$R^{1.0.1}$ $R^1$ being aryl or heteroaryl, with said aryl being phenyl, and said heteroaryl being selected from the group of 2-, 3- and 4-pyridyl, pyrimidinyl, pyrazolyl, thiazolyl, preferably phenyl and pyridyl, whereby said aryl and each of said heteroaryl being substituted by one member of the group $R^{1.0.1.S1}$ which consists of phenyl, oxadiazolyl, triazolyl, pyrazolyl, furanyl, pyrrolyl, pyridazinyl, pyrimidinyl, and 2-, 3- and 4-pyridyl, whereby preferably said aryl or heteroaryl is ar-1-yl or heteroar-1-yl and the member of the group $R^{1.0.1.S1}$ being attached to said ar-1-yl or heteroar-1-yl at the 2-position thereof, and more preferred the group $R^{1.0.1.S1}$ consists of oxadiazolyl, triazolyl, pyrazolyl, furanyl, pyrrolyl, pyridazinyl, pyrimidinyl, and 2-, 3- and 4-pyridyl, whereby preferably said aryl or heteroaryl is ar-1-yl or heteroar-1-yl and the member of the group $R^{1.0.1.S1}$ being attached to said ar-1-yl or heteroar-1-yl at the 2-position thereof, and whereby said aryl and said heteroaryl and/or the member of said group $R^{1.0.1.S1}$ optionally may be substituted by one or more members of the group $R^{1.0.1.S2}$ which consists of fluorine, chlorine, $H_3C$—, $F_3C$—, $CH_3O$—, $H_2NCO$—, N-morpholinyl, and NC—, preferably $R^{1.0.1.S2}$ consists of fluorine, $H_3C$—, $F_3C$—, $CH_3O$— and NC—.

$R^2$ is a mandatory substituent and different from H (i.e. hydrogen). It is defined via the following definitions $R^{2.k}$ whereby the index k describes the order of preference, ascending from preferably (i.e. $R^{2.1}$) to more preferably (i.e. $R^{2.2}$), and so on:

$R^{2.1}$ $R^2$ being a substituent selected from the group of fluorine, NC—, $F_3C$—, $HF_2C$—, $FH_2C$—, $F_3C$—$CH_2$—, carboxy-, $C_{1-6}$-alkyl-, $C_{2-6}$-alkenyl-, $C_{2-6}$-alkynyl-, $R^{10}$—S—, $R^{10}$—S—$C_{1-3}$-alkyl-, $C_{3-7}$-cycloalkyl-, $C_{3-7}$-cycloalkyl-$C_{1-6}$-alkyl-, $C_{3-7}$-cycloalkyl-$C_{2-6}$-alkenyl-, $C_{3-7}$-cycloalkyl-$C_{2-6}$-alkynyl-, $C_{3-8}$-heterocycloalkyl-, $C_{3-8}$-heterocycloalkyl-$C_{1-6}$-alkyl-, $C_{3-8}$-heterocycloalkyl-$C_{2-6}$-alkenyl-, $C_{3-8}$-heterocycloalkyl-$C_{2-6}$-alkynyl-, aryl, aryl-$C_{1-6}$-alkyl-, aryl-$C_{2-6}$-alkenyl-, aryl-$C_{2-6}$-alkynyl-, heteroaryl-, heteroaryl-$C_{1-6}$-alkyl-, heteroaryl-$C_{2-6}$-alkenyl-, heteroaryl-$C_{2-6}$-alkynyl-, $R^{10}$—O—, $R^{10}$—O—$C_{1-3}$-alkyl-, $(R^{10})_2N$—, $R^{10}O$—CO—, $(R^{10})_2N$—CO—, $R^{10}$—CO—$(R^{10})N$—, $R^{10}$—CO—, $(R^{10})_2N$—CO—$(R^{10})N$—, $R^{10}$—O—CO—$(R^{10})N$—, $R^{10}$—$SO_2$—$(R^{10})N$—, and $C_{1-6}$-alkyl-$SO_2$—, where the above mentioned members $C_{1-6}$-alkyl-, $C_{2-6}$-alkenyl-, $C_{2-6}$-alkynyl-, $R^{10}$—S—, $R^{10}$—S—$C_{1-3}$-alkyl-, $C_{3-7}$-cycloalkyl-, $C_{3-7}$-cycloalkyl-$C_{1-6}$-alkyl-, $C_{3-7}$-cycloalkyl-$C_{2-6}$-alkenyl-, $C_{3-7}$-cycloalkyl-$C_{2-6}$-alkynyl-, $C_{3-8}$-heterocycloalkyl-, $C_{3-8}$-heterocycloalkyl-$C_{1-6}$-alkyl-, $C_{3-8}$-heterocycloalkyl-$C_{2-6}$-alkenyl-, $C_{3-8}$-heterocycloalkyl-$C_{2-6}$-alkynyl-, aryl, aryl-$C_{1-6}$-alkyl-, aryl-$C_{2-6}$-alkenyl-, aryl-$C_{2-6}$-alkynyl-, heteroaryl-, heteroaryl-$C_{1-6}$-alkyl-, heteroaryl-$C_{2-6}$-alkenyl-, heteroaryl-$C_{2-6}$-alkynyl-, $R^{10}$—O—, $R^{10}$—O—$C_{1-3}$-alkyl-, $(R^{10})_2N$—, $R^{10}O$—CO—, $(R^{10})_2N$—CO—, $R^{10}$—CO—$(R^{10})N$—, $R^{10}$—CO—, $(R^{10})_2N$—CO—$(R^{10})$N—, $R^{10}$—O—CO—$(R^{10})N$—, $R^{10}$—$SO_2$—$(R^{10})N$—, and $C_{1-6}$-alkyl-$SO_2$— may optionally be substituted independently of one another by one or more substituents selected from the group $R^{2.1.S1}$ which consists of fluorine, chlorine, bromine, NC—, $O_2N$—, $F_3C$—, $HF_2C$—, $FH_2C$—, $F_3C$—$CH_2$—, HO—$C_{1-6}$-alkyl-, $C_{1-6}$-alkyl-O—, $C_{1-6}$-alkyl-O—$C_{1-6}$-alkyl-, $C_{1-6}$-alkyl-, $(R^{10})_2N$—, $(R^{10})_2N$—$C_{1-3}$-alkyl-, and $(R^{10})_2N$—CO—, or $R^{2.1}$ and $R^{3.1}$ together form a $C_{2-6}$-alkylene bridge, wherein one or two $CH_2$ groups of the $C_{2-6}$-alkylene bridge may be replaced independently of one another by O, S, SO, $SO_2$, $N(R^{10})$ or $N-C(O)-R^{10}$ in such a way that in each case two O or S atoms or an O and an S atom are not joined together directly.

$R^{2.2}$ $R^2$ being a substituent selected from the group of
fluorine, NC—, $F_3C$—, $HF_2C$—, $FH_2C$—, $F_3C-CH_2$—, $C_{1-6}$-alkyl-, $C_{2-6}$-alkenyl-, $C_{2-6}$-alkynyl-, $R^{10}-S$—, $R^{10}-S-C_{1-3}$-alkyl-, $C_{3-7}$-cycloalkyl-, $C_{3-7}$-cycloalkyl-$C_{1-6}$-alkyl-, $C_{3-8}$-heterocycloalkyl-, $C_{3-8}$-heterocycloalkyl-$C_{1-6}$-alkyl-, aryl, aryl-$C_{1-6}$-alkyl-, heteroaryl-, heteroaryl-$C_{1-6}$-alkyl-, $R^{10}-O$—, $R^{10}-O-C_{1-3}$-alkyl-, $(R^{10})_2N$—, $R^{10}O-CO$—, $(R^{10})_2N-CO$—, $R^{10}-CO-(R^{10})N$—, $R^{10}-CO$—, $(R^{10})_2N-CO-(R^{10})N$— and $R^{10}-O-CO-(R^{10})N$—, where the above mentioned members $C_{1-6}$-alkyl-, $C_{2-6}$-alkenyl-, $C_{2-6}$-alkynyl-, $R^{10}-S$—, $R^{10}-S-C_{1-3}$-alkyl-, $C_{3-7}$-cycloalkyl-, $C_{3-7}$-cycloalkyl-$C_{1-6}$-alkyl-, $C_{3-8}$-heterocycloalkyl-, $C_{3-8}$-heterocycloalkyl-$C_{1-6}$-alkyl-, aryl, aryl-$C_{1-6}$-alkyl-, heteroaryl-, heteroaryl-$C_{1-6}$-alkyl-, $R^{10}-O$—, $R^{10}-O-C_{1-3}$-alkyl-, $(R^{10})_2N$—, $R^{10}O-CO$—, $(R^{10})_2N-CO$—, $R^{10}-CO-(R^{10})N$—, $R^{10}-CO$—, $(R^{10})_2N-CO-(R^{10})N$— and $R^{10}-O-CO-(R^{10})N$— may optionally be substituted independently of one another by one or more substituents selected from the group $R^{2.2.S1}$ which consists of fluorine, chlorine, bromine, NC—, $O_2N$—, $F_3C$—, $HF_2C$—, $FH_2C$—, $F_3C-CH_2$—, $HO-C_{1-6}$-alkyl-, $C_{1-6}$-alkyl-O—, $C_{1-6}$-alkyl-O-$C_{1-6}$-alkyl-, $C_{1-6}$-alkyl-, $(R^{10})_2N$—, $(R^{10})_2N-C_{1-3}$-alkyl-, and $(R^{10})_2N-CO$—, $R^{2.3}$ $R^2$ being a substituent selected from the group of fluorine, $F_3C$—, $C_{1-6}$-alkyl-, aryl, HO—, $C_{1-6}$-alkyl-O—, $C_{1-6}$-alkyl-O-$C_{2-3}$-alkyl-, $(R^{10})_2N$—, $(R^{10})_2N-CO$—, $R^{10}-CO-(R^{10})N$—, $(R^{10})_2N-CO-(R^{10})N$— and $R^{10}-O-CO-(R^{10})N$—, where the above mentioned members $C_{1-6}$-alkyl-, aryl, HO—, $C_{1-6}$-alkyl-O—, $C_{1-6}$-alkyl-O-$C_{2-3}$-alkyl-, $(R^{10})_2N$—, $(R^{10})_2N-CO$—, $R^{10}-CO-(R^{10})N$—, $(R^{10})_2N-CO-(R^{10})N$— and $R^{10}-O-)CO-(R^{10})N$— may optionally be substituted independently of one another by one or more substituents selected from the group $R^{2.3.S1}$ which consists of fluorine, chlorine, bromine, NC—, $C_{1-3}$-alkyl-, and $F_3C$—, $R^{2.4}$ $R^2$ being a substituent selected from the group of fluorine, methyl, HO—, $CH_3-O$—, phenyl, $H_2N$—, $C_{1-6}$-alkyl-O-CO-(H)N—, $C_{1-6}$-alkyl-CO-(H)N— and phenyl-CO-(H)N—, where the above mentioned members methyl, $CH_3-O$—, phenyl, $H_2N$—, $C_{1-6}$-alkyl-O-CO-(H)N—, $C_{1-6}$-alkyl-CO-(H)N—, phenyl-CO-(H)N— may optionally be substituted independently of one another by one or more fluorine, $R^{2.5}$ $R^2$ being fluorine $R^3$ is defined by the following definitions $R^{3.1}$ whereby the index l describes the order of preference, ascending from preferably (i.e. $R^{3.1}$) to more preferably (i.e. $R^{3.2}$), and so on:

$R^{3.1}$ $R^3$ independently of any other $R^3$ being a substituent selected from
fluorine, NC—, $F_3C$—, $HF_2C$—, $FH_2C$—, $F_3C-CH_2$—, $C_{1-6}$-alkyl-, $C_{2-6}$-alkenyl-, $C_{2-6}$-alkynyl-, $R^{10}-S$—, $R^{10}-S-C_{1-3}$-alkyl-, $C_{3-7}$-cycloalkyl-, $C_{3-7}$-cycloalkyl-$C_{1-6}$-alkyl-, $C_{3-8}$-heterocycloalkyl-, aryl, aryl-$C_{1-6}$-alkyl-, heteroaryl-, heteroaryl-$C_{1-6}$-alkyl-, $R^{10}-O$—, $R^{10}-O-C_{1-3}$-alkyl-, $(R^{10})_2N$—, $(R^{10})_2N-CO$—, $R^{10}-CO-(R^{10})N$—, $(R^{10})_2N-CO-(R^{10})N$—, and $R^{10}-O-CO-(R^{10})N$—, where the above mentioned members $C_{1-6}$-alkyl-, $C_{2-6}$-alkenyl-, $C_{2-6}$-alkynyl-, $R^{10}-S$—, $R^{10}-S-C_{1-3}$-alkyl-, $C_{3-7}$-cycloalkyl-, $C_{3-7}$-cycloalkyl-$C_{1-6}$-alkyl-, $C_{3-8}$-heterocycloalkyl-, aryl, aryl-$C_{1-6}$-alkyl-, heteroaryl-, heteroaryl-$C_{1-6}$-alkyl-, $R^{10}-O$—, $R^{10}-O-C_{1-3}$-alkyl-, $(R^{10})_2N$—, $(R^{10})_2N-CO$—, $R^{10}-CO-(R^{10})N$—, $(R^{10})_2N-CO-(R^{10})N$—, and $R^{10}-O-CO-(R^{10})N$— may optionally be substituted independently of one another by one or more substituents selected from the group $R^{3.1.S1}$ which consists of fluorine, chlorine, bromine, NC—, $O_2N$—, $F_3C$—, $HF_2C$—, $FH_2C$—, $F_3C-CH_2$—, HO—, $HO-C_{1-6}$-alkyl-, $C_{1-6}$-alkyl-O—, $C_{1-6}$-alkyl-O-$C_{1-6}$-alkyl-, $C_{1-6}$-alkyl-, $(R^{10})_2N$—, $(R^{10})_2N-C_{1-3}$-alkyl-, and $(R^{10})_2N-CO$—, $R^{3.2}$ $R^3$ independently of any other $R^3$ being a substituent selected from
fluorine, $F_3C$—, $HF_2C$—, $FH_2C$—, $F_3C-CH_2$—, methyl, ethyl, methoxy-, pyridyl, pyridylmethyl-, phenyl and benzyl, where the above mentioned members $F_3C-CH_2$—, methyl, ethyl, methoxy-, pyridyl, pyridylmethyl-, phenyl and benzyl may optionally be substituted independently of one another by one fluorine, $R^{3.3}$ $R^3$ independently of any other $R^3$ being a substituent selected from
fluorine, $F_3C$—, $HF_2C$—, $FH_2C$—, $F_3C-CH_2$— and methyl, $R^{3.4}$ $R^3$ being fluorine.

$R^{4/5}$ is defined by the following definitions $R^{4/5.m}$ whereby the index m describes the order of preference, ascending from preferably (i.e. $R^{4/5.1}$) to more preferably (i.e. $R^{4/5.2}$), and so on:

$R^{4/5.1}$ $R^4$ and $R^5$ being independently of one another a substituent (substituents) selected from H—, fluorine, $F_3C$—, $HF_2C$—, $FH_2C$—, and $C_{1-3}$-alkyl-, or $R^{4.1}$ and $R^{5.1}$ together with the carbon atom to which they are bound form a 3- to 6-membered cycloalkyl group, where the above mentioned members including the 3- to 6-membered cycloalkyl group formed by $R^{4.1}$ and $R^{5.1}$ may optionally be substituted independently of one another by one or more substituents selected from the group $R^{4/5.1.S1}$ which consists of fluorine, HO—, NC—, $O_2N$—, $F_3C$—, $HF_2C$—, $FH_2C$—, $F_3C-CH_2$—, $HO-C_{1-6}$-alkyl-, $CH_3-O-C_{1-6}$-alkyl-, $C_{1-6}$-alkyl-, $C_{1-6}$-alkyl-O— and $(C_{1-6}$-alkyl-$)_2N-CO$—.

$R^{4/5.2}$ $R^4$ and $R^5$ being independently of one another substituent (substituents) selected from H and fluorine, preferably $R^4$ and $R^5$ both being H.

$R^{4/5.3}$ $R^4$ and $R^5$ being H.

$R^{10}$ is defined by the following definitions $R^{10.n}$ whereby the index n describes the order of preference, ascending from preferably (i.e. $R^{10.1}$) to more preferably (i.e. $R^{10.2}$), and so on:

$R^{10.1}$ $R^{10}$ independently from any other potential $R^{10}$ being a substituent selected from
H, $F_3C-CH_2$—, $C_{1-6}$-alkyl-, $C_{2-6}$-alkenyl-, $C_{3-7}$-cycloalkyl-, $C_{3-7}$-cycloalkyl-$C_{1-3}$-alkyl-, $C_{3-8}$-heterocycloalkyl-, $C_{3-8}$-heterocycloalkyl-$C_{1-6}$-alkyl-, aryl, aryl-$C_{1-3}$-alkyl-, heteroaryl, and heteroaryl-$C_{1-3}$-alkyl-, and in case where two $R^{10}$ groups both are bound to the same nitrogen atom they may together with said nitrogen atom form a 3 to 7 membered heterocycloalkyl ring, and wherein one of the —$CH_2$-groups of the heterocyclic ring formed may be replaced by —O—, —S—, —NH—, $N(C_{3-8}$-cycloalkyl), —$N(C_{3-8}$-cycloalkyl-$C_{1-4}$-alkyl)- or —$N(C_{1-4}$-alkyl)- and where the above mentioned members $F_3C-CH_2$—, $C_{1-6}$-alkyl-, $C_{2-6}$-alkenyl-, $C_{3-7}$-cycloalkyl-, $C_{3-7}$-cycloalkyl-$C_{1-3}$-alkyl-, $C_{3-8}$-heterocycloalkyl-, $C_{3-8}$-heterocycloalkyl-$C_{1-6}$-alkyl-, aryl, aryl-$C_{1-3}$-alkyl-, heteroaryl, and heteroaryl-$C_{1-3}$-alkyl- and in case where two $R^{10}$ groups both are bound to the same nitrogen atom they may together with said nitrogen atom form a 3 to 7 membered heterocycloalkyl ring as defined above may optionally be substituted independently of one another by one or more substituents selected from the group $R^{10.1.S1}$ which consists of fluorine, chlorine, bromine, HO—, NC—, $O_2N$—, $F_3C$—, $HF_2C$—, $FH_2C$—, $F_3C$—$CH_2$—, HO—$C_{1-6}$-alkyl, $CH_3$—O—$C_{1-6}$-alkyl-, $C_{1-6}$-alkyl- and $C_{1-6}$-alkyl-O—.

$R^{10.2}$ $R^{10}$ independently from any other potential $R^{10}$ being a substituent selected from the group of H—, $C_{1-6}$-alkyl-, $C_{3-7}$-cycloalkyl-, $C_{3-7}$-cycloalkyl-$C_{1-3}$-alkyl-, aryl and heteroaryl, and in case where two $R^{10}$ groups both are bound to the same nitrogen atom they may together with said nitrogen atom form a 3 to 7 membered heterocycloalkyl ring, and wherein one of the —$CH_2$-groups of the heterocyclic ring formed may be replaced by —O—, —NH—, —N($C_{3-6}$-cycloalkyl)-, —N($C_{3-6}$-cycloalkyl-$C_{1-4}$-alkyl)- or —N($C_{1-4}$-alkyl)- and where the above mentioned members $C_{1-6}$-alkyl-, $C_{3-7}$-cycloalkyl-, $C_{3-7}$-cycloalkyl-$C_{1-3}$-alkyl-, aryl and heteroaryl and in case where two $R^{10}$ groups both are bound to the same nitrogen atom they may together with said nitrogen atom form a 3 to 7 membered heterocycloalkyl ring as defined above may optionally be substituted independently of one another by one or more substituents selected from the group $R^{10.2.S1}$ which consists of fluorine, NC—, $F_3C$—, $HF_2C$—, $FH_2C$—, $F_3C$—$CH_2$—, $CH_3$—O—$C_{1-6}$-alkyl-, $C_{1-6}$-alkyl-, and $C_{1-6}$-alkyl-O—.

$R^{10.3}$ $R^{10}$ independently from any other potential $R^{10}$ being a substituent selected from the group of H—, $C_{1-6}$-alkyl-, $C_{3-7}$-cycloalkyl-, aryl and heteroaryl where the above mentioned members $C_{1-6}$-alkyl-, $C_{3-7}$-cycloalkyl-, aryl and heteroaryl may optionally be substituted independently of one another by one or more substituents selected from the group $R^{10.3.S1}$ which consists of fluorine, $F_3C$—, $HF_2C$—, $FH_2C$—, $F_3C$—$CH_2$—, $CH_3$—O—$C_{1-6}$-alkyl-, $C_{1-6}$-alkyl-, and $C_{1-6}$-alkyl-O—.

$R^{10.4}$ $R^{10}$ independently from any other potential $R^{10}$ being a substituent selected from the group of H—, $C_{1-6}$-alkyl-, phenyl and pyridyl;

where the above mentioned members $C_{1-6}$-alkyl-, phenyl, pyridyl may optionally be substituted independently of one another by one or more substituents selected from the group $R^{10.4.S1}$ which consists of fluorine, $F_3C$—, $HF_2C$—, $FH_2C$—, $F_3C$—$CH_2$—, $CH_3$—O—$C_{1-6}$-alkyl-, $C_{1-6}$-alkyl-, and $C_{1-6}$-alkyl-O—.

$R^{10.5}$ $R^{10}$ independently from any other potential $R^{10}$ being a substituent selected from the group of H—, methyl, ethyl and tert.-butyl, where the above mentioned members methyl, ethyl and tert.-butyl may optionally be substituted independently of one another by one or more substituents selected from the group consisting of fluorine.

x independently from each other x being 0, 1, 2, 3, 4, preferably being 0, 1, 2, more preferably being 0 or 1. In case x being 0, there is a H at the appropriate position.

The letters i, j, k, l, m, n in $A^i$, $R^{1,j}$, $R^{2,k}$ etc. are indices, each of which shall have the meaning of an integer figure: 1, 2, 3, etc.

Thus, each set of ($A^i$, $R^{1,j}$ $R^{2,k}$ $R^{3,l}R^{4/5,m}$ $R^{10,n}$), in which the letters i, j, k, l, m, n are defined by figures, represents a characterised, individual (generic) embodiment of a compound according to general formula I, whereby x is as hereinbefore described, namely 0, 1, 2, 3, 4, preferably 0, 1, 2, more preferably 0 or 1. The specific definitions of the substituents $A^i$, $R^{1,j}$, $R^{2,k}$, $R^{3,l}$, $R^{4/5,m}$, $R^{10,n}$ have herein been defined.

It will be evident that the term ($A^i R^{1,j} R^{2,k} R^{3,l} R^{4/5,m} R^{10,n}$) represents the complete plurality of embodiments for a given x of the subject matter of formula I if all indices i, j, k, l, m, and n are considered.

All individual embodiments ($A^i R^{1,j} R^{2,k} R^{3,l} R^{4/5,m} R^{10,n}$) described by the term in brackets shall be comprised by the present invention.

The following matrices 1 and 2 shows such embodiments of the inventions that are considered preferred (in the order from less preferred to most preferred, the preference of the embodiments ascending from top to down. This means that the embodiment, which is presented by the matrix element in the last row is the most preferred embodiment):

A compound characterised by general formula (I), in which the substituents are defined as and of the following matrix elements ($A^i R^{1,j} R^{2,k} R^{3,l} R^{4/5,m} R^{10,n}$):

| matrix 1: | |
|---|---|
| Matrix element No. | set of definitions of substituents |
| M1-01 | ($A^1R^{1.1}R^{2.1}R^{3.1}R^{4/5.1}R^{10.1}$) |
| M1-02 | ($A^2R^{1.1}R^{2.1}R^{3.1}R^{4/5.1}R^{10.1}$) |
| M1-03 | ($A^3R^{1.1}R^{2.1}R^{3.1}R^{4/5.1}R^{10.1}$) |
| M1-04 | ($A^4R^{1.1}R^{2.1}R^{3.1}R^{4/5.1}R^{10.1}$) |
| M1-05 | ($A^4R^{1.2}R^{2.3}R^{3.2}R^{4/5.2}R^{10.2}$) |
| M1-06 | ($A^4R^{1.2}R^{2.3}R^{3.2}R^{4/5.2}R^{10.4}$) |
| M1-07 | ($A^4R^{1.2}R^{2.3}R^{3.3}R^{4/5.2}R^{10.2}$) |
| M1-08 | ($A^4R^{1.2}R^{2.3}R^{3.3}R^{4/5.2}R^{10.4}$) |
| M1-09 | ($A^4R^{1.2}R^{2.4}R^{3.3}R^{4/5.2}R^{10.3}$) |
| M1-10 | ($A^4R^{1.2}R^{2.4}R^{3.3}R^{4/5.2}R^{10.4}$) |
| M1-11 | ($A^4R^{1.2}R^{2.5}R^{3.3}R^{4/5.2}R^{10.4}$) |
| M1-12 | ($A^4R^{1.2}R^{2.5}R^{3.3}R^{4/5.2}R^{10.5}$) |
| M1-13 | ($A^4R^{1.3}R^{2.3}R^{3.2}R^{4/5.2}R^{10.2}$) |
| M1-14 | ($A^4R^{1.3}R^{2.3}R^{3.2}R^{4/5.2}R^{10.4}$) |
| M1-15 | ($A^4R^{1.3}R^{2.3}R^{3.3}R^{4/5.2}R^{10.2}$) |
| M1-16 | ($A^4R^{1.3}R^{2.3}R^{3.3}R^{4/5.2}R^{10.4}$) |
| M1-17 | ($A^4R^{1.3}R^{2.4}R^{3.3}R^{4/5.2}R^{10.4}$) |
| M1-18 | ($A^4R^{1.3}R^{2.5}R^{3.3}R^{4/5.2}R^{10.4}$) |
| M1-19 | ($A^4R^{1.3}R^{2.5}R^{3.4}R^{4/5.2}R^{10.4}$) |
| M1-20 | ($A^4R^{1.4}R^{2.3}R^{3.2}R^{4/5.2}R^{10.2}$) |
| M1-21 | ($A^4R^{1.4}R^{2.3}R^{3.2}R^{4/5.2}R^{10.4}$) |
| M1-22 | ($A^4R^{1.4}R^{2.3}R^{3.3}R^{4/5.2}R^{10.2}$) |
| M1-23 | ($A^4R^{1.4}R^{2.3}R^{3.3}R^{4/5.2}R^{10.4}$) |
| M1-24 | ($A^4R^{1.4}R^{2.4}R^{3.3}R^{4/5.2}R^{10.4}$) |
| M1-25 | ($A^4R^{1.4}R^{2.5}R^{3.3}R^{4/5.2}R^{10.4}$) |
| M1-26 | ($A^4R^{1.4}R^{2.5}R^{3.4}R^{4/5.2}R^{10.4}$) |
| M1-27 | ($A^5R^{1.1}R^{2.5}R^{3.4}R^{4/5.2}R^{10.4}$) |
| M1-28 | ($A^5R^{1.1}R^{2.5}R^{3.4}R^{4/5.2}R^{10.5}$) |
| M1-29 | ($A^5R^{1.2}R^{2.5}R^{3.4}R^{4/5.2}R^{10.4}$) |
| M1-30 | ($A^5R^{1.2}R^{2.5}R^{3.4}R^{4/5.2}R^{10.5}$) |
| M1-31 | ($A^5R^{1.3}R^{2.5}R^{3.4}R^{4/5.2}R^{10.4}$) |
| M1-32 | ($A^5R^{1.4}R^{2.5}R^{3.4}R^{4/5.2}R^{10.4}$) |
| M1-33 | ($A^5R^{1.5}R^{2.5}R^{3.4}R^{4/5.2}$) | whereby for each embodiments x being 0, 1, 2, 3, 4, preferably being 0, 1 or 2, more preferably 0 or 1 or only 1.

Another aspect of the invention concerns a compound characterised by general formula (I), in which the substituents are defined as and of the following matrix elements ($A^i R^{1,j} R^{2,k} R^{3,l} R^{4/5,m} R^{10,n}$):

| matrix 2: | |
|---|---|
| Matrix element No. | set of definitions of substituents |
| M2-01 | ($A^1R^{1.0.1}R^{2.4}R^{3.3}R^{4/5.2}$) |
| M2-02 | ($A^1R^{1.0.1}R^{2.5}R^{3.4}R^{4/5.2}$) |

-continued matrix 2:

| Matrix element No. | set of definitions of substituents |
|---|---|
| M2-03 | $(A^2R^{1.0.1}R^{2.4}R^{3.3}R^{4/5.2})$ |
| M2-04 | $(A^2R^{1.0.1}R^{2.5}R^{3.4}R^{4/5.2})$ |
| M2-05 | $(A^3R^{1.0.1}R^{2.4}R^{3.3}R^{4/5.2})$ |
| M2-06 | $(A^3R^{1.0.1}R^{2.5}R^{3.4}R^{4/5.2})$ |
| M2-07 | $(A^4R^{1.0.1}R^{2.4}R^{3.3}R^{4/5.2})$ |
| M2-08 | $(A^4R^{1.0.1}R^{2.5}R^{3.4}R^{4/5.2})$ |
| M2-09 | $(A^5R^{1.0.1}R^{2.4}R^{3.3}R^{4/5.2})$ |
| M2-10 | $(A^5R^{1.0.1}R^{2.5}R^{3.4}R^{4/5.2})$ | whereby for each embodiments x being 0, 1, 2, 3, 4, preferably being 0, 1 or 2, more preferably 0 or 1 or only 1.

In case one substituent $A^i$, $R^{1.j}$, $R^{2.k}$, $R^{3.l}$, $R^{4/5.m}$, $R^{10.n}$ is not defined in any of the elements of the matrices 1 or 2, it shall be $A^4$, preferably $A^5$ for $A^i$, $R^{1.4}$, preferably $R^{1.5}$ for $R^{i.j}$, $R^{2.4}$, preferably $R^{2.5}$ for $R^{2.k}$, $R^{3.4}$, preferably $R^{3.5}$ for $R^{3.l}$, $R^{4/5.2}$, preferably $R^{4/5.3}$ for $R^{4/5.m}$ and $R^{10.4}$, preferably $R^{10.5}$ for $R^{10.n}$.

All embodiments of the invention as herein described include salts of the compounds of the invention, preferably pharmaceutically acceptable salts of the compounds of the invention.

In order to illustrate the meaning of the aforementioned matrix elements, the following examples shall be given:

Matrix element M1-01 $(A^1R^{1.1}R^{2.1}R^{3.1}R^{4/5.1}R^{10.1})$ represents a compound according to general formula I

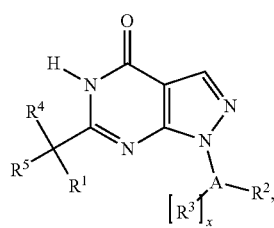

(I)

with

A being a substituent selected from the group of $A^1$ being a $C_3$-$C_8$-cycloalkyl group or a $C_4$-$C_8$-cycloalkenyl group, whereby the members of $C_3$-$C_8$-cycloalkyl group being selected from the group of cyclopropyl, cyclobutyl, cyclopentyl, cyclohexyl, cycloheptyl and cyclooctyl, and the members of the $C_4$-$C_8$-cycloalkenyl group, being selected from cyclobutenyl, cyclopentenyl, cyclohexenyl, cycloheptenyl, cyclooctenyl, cyclopentadienyl, cyclohexadienyl, cycloheptadienyl, cyclooctadienyl, cycloheptatrienyl, cyclooctatrienyl, cyclooctatetraenyl;

$R^1$ being a substituent selected from the group of $R^{1.1}$ being $C_{1-8}$-alkyl-, $C_{2-8}$-alkenyl-, $C_{2-8}$-alkynyl-, $R^{10}$—S—$C_{1-3}$-alkyl, $R^{10}$—O—$C_{1-3}$alkyl-, $C_{3-7}$-cycloalkyl-, $C_{3-7}$-cycloalkyl-$C_{1-6}$-alkyl-, $C_{3-7}$-cycloalkyl-$C_{2-6}$-alkenyl-, $C_{3-7}$-cycloalkyl-$C_{2-6}$-alkynyl-, $C_{3-8}$-heterocycloalkyl-, $C_{3-8}$-heterocycloalkyl-$C_{1-6}$-alkyl-, $C_{3-8}$-heterocycloalkyl-$C_{2-6}$-alkenyl-, $C_{3-8}$-heterocycloalkyl-$C_{2-6}$-alkynyl-, aryl, aryl-$C_{1-6}$-alkyl-, aryl-$C_{2-6}$-alkenyl-, aryl-$C_{2-6}$-alkynyl-, heteroaryl, heteroaryl-$C_{1-6}$-alkyl-, heteroaryl-$C_{2-6}$-alkenyl- and heteroaryl-$C_{2-6}$-alkynyl-, where the above mentioned members may optionally be substituted independently of one another by one or more substituents selected from the group $R^{1.1.S1}$ which consists of fluorine, chlorine, bromine, iodine, oxo, whereby this oxo group preferably is only a substituent for a cycloalkyl group or a heterocycloalkyl group, HO—, NC—, $O_2N$—, $F_3C$—, $HF_2C$—, $FH_2C$—, $F_3C$—$CH_2$—, $F_3C$—O—, $HF_2C$—O—, HO—$C_{1-6}$-alkyl-, $R^{10}$—O—$C_{1-6}$-alkyl-, $R^{10}$—S—$C_{1-6}$-alkyl-, $C_{1-6}$-alkyl-, $C_{3-7}$-cycloalkyl-, $C_{3-7}$-cycloalkyl-$C_{1-6}$-alkyl-, $C_{3-7}$-cycloalkyl-O—, $C_{3-7}$-cycloalkyl-$C_{1-6}$-alkyl-O—, aryl, aryl-$C_{1-6}$-alkyl-, heteroaryl, heteroaryl-$C_{1-6}$-alkyl-, heteroaryl-O—, heteroaryl-$C_{1-6}$-alkyl-O—, $C_{3-8}$-heterocycloalkyl-, $C_{3-8}$-heterocycloalkyl-$C_{1-6}$-alkyl-, $C_{3-8}$-heterocycloalkyl-O— with $C_{3-8}$-heterocycloalkyl being bound to O via one of its ring C-atoms, $C_{3-8}$-heterocycloalkyl-$C_{1-6}$-alkyl-O— with $C_{3-8}$-heterocycloalkyl being bound to the $C_{1-6}$-alkyl- via one of its ring-C-atoms, $(R^{10})_2N$—, $(R^{10})_2N$—$C_{1-6}$-alkyl-, $R^{10}$—CO—, $R^{10}$O—CO—, $(R^{10})_2N$—CO—, $(R^{10})_2N$—CO—$C_{1-6}$-alkyl-, $R^{10}$—CO—$(R^{10})N$—, $R^{10}$—CO—$(R^{10})N$—$C_{1-6}$-alkyl-, $R^{10}$—CO—O—, $R^{10}$O—CO—O—, $R^{10}$O—CO—$(R^{10})N$—, $R^{10}$O—CO—$(R^{10})N$—$C_{1-6}$-alkyl-, $(R^{10})_2N$—CO—O—, $(R^{10})_2N$—CO—O—$C_{1-6}$-alkyl-, $(R^{10})_2N$—CO—$(R^{10})N$—$C_{1-6}$-alkyl-, $R^{10}$—$SO_2$—$(R^{10})N$—, $R^{10}$—$SO_2$—$(R^{10})N$—$C_{1-6}$-alkyl-, $(R^{10})_2N$—$SO_2$—$(R^{10})N$—$C_{1-6}$-alkyl-, $(R^{10})_2N$—$SO_2$—, $(R^{10})_2N$—$SO_2$—$C_{1-6}$-alkyl-, and $C_{1-6}$-alkyl-$SO_2$—, whereby any of the $C_{3-7}$-cycloalkyl-, $C_{3-8}$-heterocycloalkyl-, aryl-, heteroaryl-groups of aforementioned group $R^{1.1.S1}$ may optionally be substituted by a member of the group $R^{1.1.S2}$ which consists of fluorine, chlorine, bromine, HO—, NC—, $O_2N$—, $F_3C$—, $HF_2C$—, $FH_2C$—, $F_3C$—$CH_2$—, $F_3C$—O—, $HF_2C$—O—, $C_{3-8}$-heterocycloalkyl-, $R^{10}$—S—$C_{1-6}$-alkyl-, $(R^{10})_2N$—, $(R^{10})_2N$—$C_{1-6}$-alkyl-, $R^{10}$—S—, $R^{10}$—CO—, $R^{10}$O—CO—, $(R^{10})_2N$—CO—, $(R^{10})_2N$—CO—$C_{1-6}$-alkyl-, $R^{10}$—CO—$(R^{10})N$—, $R^{10}$—CO—$(R^{10})N$—$C_{1-6}$-alkyl-, $R^{10}$—CO—O—, $R^{10}$O—CO—O—, $R^{10}$O—CO—$(R^{10})N$—, $R^{10}$O—CO—$(R^{10})N$—$C_{1-6}$-alkyl-, $(R^{10})_2N$—CO—O—, $(R^{10})_2N$—CO—$(R^{10})N$—, $(R^{10})_2N$—$SO_2$—$(R^{10})N$—, $(R^{10})_2N$—CO—O—$C_{1-6}$-alkyl-, $(R^{10})_2N$—CO—$(R^{10})N$—$C_{1-6}$-alkyl-, $R^{10}$—$SO_2$—$(R^{10})N$—, $R^{10}$—$SO_2$—$(R^{10})N$—$C_{1-6}$-alkyl-, $(R^{10})_2N$—$SO_2$—$(R^{10})N$—$C_{1-6}$-alkyl-, $(R^{10})_2N$—$SO_2$—, $(R^{10})_2N$—$SO_2$—$C_{1-6}$-alkyl-, and $C_{1-6}$-alkyl-$SO_2$—;

$R^2$ being a substituent selected from the group of $R^{21}$ being fluorine, NC—, $F_3C$—, $HF_2C$—, $FH_2C$—, $F_3C$—$CH_2$—, carboxy-, $C_{1-6}$-alkyl-, $C_{2-6}$-alkenyl-, $C_{2-6}$-alkynyl-, $R^{10}$—S—, $R^{10}$—S—$C_{1-3}$-alkyl-, $C_{3-7}$-cycloalkyl-$C_{1-6}$-alkyl-, $C_{3-7}$-cycloalkyl-$C_{2-6}$-alkenyl-, $C_{3-7}$-cycloalkyl-$C_{2-6}$-alkynyl-, $C_{3-8}$-heterocycloalkyl-, $C_{3-8}$-heterocycloalkyl-$C_{1-6}$-alkyl-, $C_{3-8}$-heterocycloalkyl-$C_{2-6}$-alkenyl-, $C_{3-8}$-heterocycloalkyl-$C_{2-6}$-alkynyl-, aryl, aryl-$C_{2-6}$-alkenyl-, aryl-$C_{2-6}$-alkynyl-, heteroaryl-, heteroaryl-$C_{1-6}$-alkyl-, heteroaryl-$C_{2-6}$-alkenyl-, heteroaryl-$C_{2-6}$-alkynyl-, $R^{10}$—O—$C_{1-3}$-alkyl-, $(R^{10})_2N$—, $R^{10}$O—CO—, $(R^{10})_2N$—CO—, $R^{10}$—CO—$(R^{10})N$—, $R^{10}$—CO—, $(R^{10})_2N$—CO—$(R^{10})N$—, $R^{10}$—O—CO—) $(R^{10})N$—, $R^{10}$—$SO_2$—$(R^{10})N$—, and $C_{1-6}$-alkyl-$SO_2$—, where the above mentioned members $C_{1-6}$-alkyl-, $C_{2-6}$-alkenyl-, $C_{2-6}$-alkynyl-, $C_{3-7}$-cycloalkyl-$C_{1-6}$-alkyl-, $C_{3-7}$-cycloalkyl-$C_{2-6}$-alkenyl-, $C_{3-7}$-cycloalkyl-$C_{2-6}$-alkynyl-, $C_{3-8}$-heterocycloalkyl-, $C_{3-8}$-heterocycloalkyl-$C_{1-6}$-alkyl-, $C_{3-8}$-heterocycloalkyl-$C_{2-6}$-alkenyl-, $C_{3-8}$-heterocycloalkyl-$C_{2-6}$-alkynyl-, aryl, aryl-$C_{1-6}$-alkyl-, aryl-$C_{2-6}$-alkenyl-, aryl-$C_{2-6}$-alkynyl-, heteroaryl, heteroaryl-$C_{1-6}$-alkyl-, heteroaryl-$C_{2-6}$-alkenyl-, heteroaryl-$C_{2-6}$-alkynyl-, $R^{10}$—O—, $R^{10}$—O—$C_{1-3}$-alkyl-, $(R^{10})_2N$—, $R^{10}$O—CO—, $(R^{10})_2N$—CO—, $R^{10}$—CO—$(R^{10})N$—, $R^{10}$—CO—, $(R^{10})_2N$—CO—$(R^{10})N$—, $R^{10}$—O—CO—$(R^{10})N$—, $R^{10}$—$SO_2$—$(R^{10})N$—, and $C_{1-6}$-alkyl-$SO_2$— may optionally be substituted independently of one another by one or more substituents selected from the group $R^{2.1.S1}$ which consists of fluorine, chlorine, bromine, NC—, $O_2N$—, $F_3C$—, $HF_2C$—, $FH_2C$—, $F_3C$—$CH_2$—, HO—$C_{1-6}$-alkyl-, $C_{1-6}$-alkyl-O—, $C_{1-6}$-alkyl-O—$C_{1-6}$-alkyl-, $C_{1-6}$-alkyl-, $(R^{10})_2N$—, $(R^{10})_2N$—$C_{1-3}$-alkyl-, and $(R^{10})_2N$—CO—, or $R^{2.1}$ and $R^{3.1}$ together form a $C_{2-6}$-alkylene bridge, wherein one or two $CH_2$ groups of the $C_{2-6}$-alkylene bridge may be replaced independently of one another by O, S, SO, $SO_2$, $N(R^{10})$ or N—C(O)—$R^{10}$ in such a way that in each case two O or S atoms or an O and an S atom are not joined together directly;

$R^3$ independently of any other $R^3$ being a substituent selected from the group of $R^{3.1}$ being fluorine, NC—, $F_3C$—, $HF_2C$—, $FH_2C$—, $F_3C$—$CH_2$—, $C_{2-6}$-alkenyl-, $C_{2-6}$-alkynyl-, $C_{3-7}$-cycloalkyl-$C_{1-6}$-alkyl-, $C_{3-8}$-heterocycloalkyl-, aryl, aryl-$C_{1-6}$-alkyl-, heteroaryl-, heteroaryl-$C_{1-6}$-alkyl-, $R^{10}$—O—, $R^{10}$—O—$C_{1-3}$-alkyl-, $(R^{10})_2N$—, $(R^{10})_2N$—CO—, $R^{10}$—CO—$(R^{10})N$—, $(R^{10})_2N$—CO—$(R^{10})N$—, and $R^{10}$—O—CO—$(R^{10})N$—, where the above mentioned members $C_{1-6}$-alkyl-, $C_{2-6}$-alkenyl-, $C_{2-6}$-alkynyl-, $R^{10}$—S—, $R^{10}$—S—$C_{1-3}$-alkyl-, $C_{3-7}$-cycloalkyl-, $C_{3-7}$-cycloalkyl-$C_{1-6}$-alkyl-, $C_{3-8}$-heterocycloalkyl-, aryl, aryl-$C_{1-6}$-alkyl-, heteroaryl-, heteroaryl-$C_{1-6}$-alkyl-, $R^{10}$—O—, $R^{10}$—O—$C_{1-3}$-alkyl-, $(R^{10})_2N$—, $(R^{10})_2N$—CO—, $R^{10}$—CO—$(R^{10})N$—, $(R^{10})_2N$—CO—$(R^{10})N$—, and $R^{10}$—O—CO—$(R^{10})N$—may optionally be substituted independently of one another by one or more substituents selected from the group $R^{3.1.S1}$ which consists of fluorine, chlorine, bromine, NC—, $O_2N$—, $F_3C$—, $HF_2C$—, $FH_2C$—, $F_3C$—$CH_2$—, HO—, HO—$C_{1-6}$-alkyl-, $C_{1-6}$-alkyl-O—$C_{1-6}$-alkyl-, $(R^{10})_2N$—, $(R^{10})_2N$—$C_{1-3}$-alkyl-, and $(R^{10})_2N$—CO—;

$R^4$ and $R^5$ being independently of one another a substituent selected from the group of $R^{4/5.1}$ being H—, fluorine, $F_3C$—, $HF_2C$—, $FH_2C$—, and $C_{1-3}$-alkyl-, or $R^{4.1}$ and $R^{5.1}$ together with the carbon atom to which they are bound form a 3- to 6-membered cycloalkyl group, where the above mentioned members including the 3- to 6-membered cycloalkyl group formed by $R^{4.1}$ and $R^{5.1}$ may optionally be substituted independently of one another by one or more substituents selected from the group $R^{4/5.1.S1}$ which consists of fluorine, HO—, NC—, $O_2N$—, $F_3C$—, $HF_2C$—, $FH_2C$—, $F_3C$—$CH_2$—, HO—$C_{1-6}$-alkyl-, $CH_3$—O—$C_{1-6}$-alkyl-, $C_{1-6}$-alkyl-, $C_{1-6}$-alkyl-O— and $(C_{1-6}$-alkyl-$)_2N$—CO—;

$R^{10}$ independently from any other potential $R^{10}$ being a substituent being selected from the group of $R^{10.1}$ being H, $F_3C$—$CH_2$—, $C_{1-6}$-alkyl-, $C_{2-6}$-alkenyl-, $C_{3-7}$-cycloalkyl-, $C_{3-7}$-cycloalkyl-$C_{1-3}$-alkyl-, $C_{3-8}$-heterocycloalkyl-, $C_{3-8}$-heterocycloalkyl-$C_{1-6}$-alkyl-, aryl, aryl-$C_{1-3}$-alkyl-, heteroaryl, and heteroaryl-$C_{1-3}$-alkyl-, and in case where two $R^{10}$ groups both are bound to the same nitrogen atom they may together with said nitrogen atom form a 3 to 7 membered heterocycloalkyl ring, and wherein one of the —$CH_2$-groups of the heterocyclic ring formed may be replaced by —O—, —S—, —NH—, $N(C_{3-6}$-cycloalkyl)-, —$N(C_{3-6}$-cycloalkyl-$C_{1-4}$-alkyl)- or —$N(C_{1-4}$-alkyl)- and where the above mentioned members $F_3C$—$CH_2$—, $C_{1-6}$-alkyl-, $C_{2-6}$-alkenyl-, $C_{3-7}$-cycloalkyl-, $C_{3-7}$-cycloalkyl-$C_{1-3}$-alkyl-, $C_{3-8}$-heterocycloalkyl-, $C_{3-8}$-heterocycloalkyl-$C_{1-6}$-alkyl-, aryl, aryl-$C_{1-3}$-alkyl-, heteroaryl, and heteroaryl-$C_{1-3}$-alkyl- and in case where two $R^{10}$ groups both are bound to the same nitrogen atom they may together with said nitrogen atom form a 3 to 7 membered heterocycloalkyl ring as defined above may optionally be substituted independently of one another by one or more substituents selected from the group $R^{10.1.S1}$ which consists of fluorine, chlorine, bromine, HO—, NC—, $O_2N$—, $F_3C$—, $HF_2C$—, $FH_2C$—, $F_3C$—$CH_2$—, HO—$C_{1-6}$-alkyl, $CH_3$—O—$C_{1-6}$-alkyl-, $C_{1-6}$-alkyl- and $C_{1-6}$-alkyl-O—;

x being 0, 1, 2, 3, 4, preferably being 0, 1 or 2, more preferably 0 or 1 or only 1;

and salts, preferably pharmaceutically acceptable salts thereof.

Matrix element M1-19 ($A^4R^{1.3}R^{2.5}R^{3.4}R^{4/5.2}R^{10.4}$) represents a compound according to general formula I with $\overline{A}$ being a substituent selected from the group of $A^4$ being a $C_5$-$C_6$-cycloalkyl group the members of which being selected from the group of cyclopentyl and cyclohexyl;

$R^1$ being a substituent selected from the group of $R^{1.3}$ being phenyl, 2-, 3- and 4-pyridyl, pyrimidinyl, pyrazolyl, thiazolyl, cyclopropyl, cyclobutyl, cyclopentyl, cyclohexyl, cycloheptyl, cyclopentylmethyl, ethyl, propyl, 1- and 2-butyl, 1-, 2- and 3-pentyl, tetrahydrofuranyl and tetrahydropyranyl, where these groups may optionally be substituted by one or more substituents selected from the group $R^{1.3.S1}$ which consists of fluorine, chlorine, bromine, iodine, oxo, whereby this oxo group is only a substituent for tetrahydrofuranyl and tetrahydropyranyl, HO—, NC—, $C_{1-6}$-alkyl-O—, $C_{1-6}$-alkyl-, $C_{3-7}$-cycloalkyl-, $C_{3-7}$-cycloalkyl-O—, $C_{3-7}$-cycloalkyl-$C_{1-3}$-alkyl-O—, $CF_3O$—, $CF_3$—, $C_{3-8}$-heterocycloalkyl-, $C_{3-8}$-heterocycloalkyl-$C_{1-6}$-alkyl-, HO—$C_{1-6}$-alkyl-, pyrazolyl, pyridyl, pyrimidinyl, $(R^{10})_2N$—CO—$C_{1-6}$-alkyl-, and phenyl, whereby the pyridyl and phenyl group of the aforementioned group $R^{1.3.S1}$ may optionally be substituted by a member of the group $R^{1.3.S2}$ which consists of fluorine, chlorine, $H_3C$—, $F_3C$—, $CH_3O$—, $F_3C$—O—, $H_2NCO$—, NC—, morpholinyl and benzyl-O—;

$R^2$ being a substituent of the group of $R^{2.5}$ being fluorine;

$R^3$ independently of any other $R^3$ being a substituent of the group of $R^{3.4}$ being fluorine;

$R^4$ and $R^5$ being independently of one another a substituent selected from the group of $R^{4/5.2}$ being H and fluorine, preferably $R^4$ and $R^5$ both being H;

$R^{10}$ independently of any other $R^{10}$ being a substituent of the group of $R^{10.4}$ being H—, $C_{1-6}$-alkyl-, phenyl and pyridyl;

x being 0, 1, 2, 3, 4, preferably being 0, 1 or 2, more preferably 0 or 1 or only 1;

and salts, preferably pharmaceutically acceptable salts thereof.

In a specific embodiment of the latter matrix element M1-19 $R^{10}$ independently of any other $R^{10}$ preferably is H—, $C_{1-6}$-alkyl-.

Matrix element M1-26 ($A^4R^{1.4}R^{2.5}R^{3.4}R^{4/5.2}R^{10.4}$) represents a compound according to general formula I with $\overline{A}$ being a substituent selected from the group of $A^4$ being a $C_5$-$C_6$-cycloalkyl group the members of which being selected from the group of cyclopentyl and cyclohexyl;

$R^1$ being a substituent selected from the group of $R^{1.4}$ being phenyl, 2-, 3- and 4-pyridyl, cyclopropyl, cyclobutyl, cyclopentyl, cyclohexyl, ethyl, 1- and 2-propyl, 1- and 2-butyl, 1-, 2- and 3-pentyl, tetrahydrofuranyl and tetrahydropyranyl, where these groups may optionally be substituted by one or more substituents selected from the group $R^{1.4.S1}$ which consists of fluorine, chlorine, bromine, iodine, oxo, whereby this oxo group is only a substituent for tetrahydrofuranyl and tetrahydropyranyl, NC—, $C_{1-6}$-alkyl-O—, $C_{1-6}$-alkyl-, $CF_3O$—, $F_3C$—, pyridyl, $(R^{10})_2N$—CO-methyl-, N-morpholinyl-$C_{1-6}$-alkyl-, pyrazolyl and phenyl, whereby the pyridyl, pyrazolyl and phenyl group of the aforementioned group $R^{1.4.S1}$ may optionally be substituted by a member of the group $R^{1.4.S2}$ which consists of fluorine, chlorine, $H_3C—$, $F_3C—$, $CH_3O—$, $H_2NCO—$ and NC—;

$R^2$ being a substituent of the group of $R^{2.5}$ being fluorine;

$R^3$ independently of any other $R^3$ being a substituent of the group of $R^{3.4}$ being fluorine;

$R^4$ and $R^5$ being independently of one another a substituent selected from the group of $R^{4/5.2}$ being H and fluorine, preferably $R^4$ and $R^5$ both being H;

$R^{10}$ independently of any other $R^{10}$ being a substituent of the group of $R^{10.4}$ being H—, $C_{1-6}$-alkyl-, phenyl and pyridyl;

x being 0, 1, 2, 3, 4, preferably being 0, 1 or 2, more preferably 0 or 1 or only 1;

and salts, preferably pharmaceutically acceptable salts thereof.

Matrix element M2-01 ($A^1R^{1.0.1}R^{2.4}R^{3.3}R^{4/5.2}$) represents a compound according to general formula I with $\overline{A}$ being a substituent selected from the group of $A^1$ being a $C_3$-$C_8$-cycloalkyl group or a $C_4$-$C_8$-cycloalkenyl group, whereby the members of $C_3$-$C_8$-cycloalkyl group being selected from the group of cyclopropyl, cyclobutyl, cyclopentyl, cyclohexyl, cycloheptyl and cyclooctyl, and the members of the $C_4$-$C_8$-cycloalkenyl group, being selected from cyclobutenyl, cyclopentenyl, cyclohexenyl, cycloheptenyl, cyclooctenyl, cyclopentadienyl, cyclohexadienyl, cycloheptadienyl, cyclooctadienyl, cycloheptatrienyl, cyclooctatrienyl, cyclooctatetraenyl;

$R^1$ being defined as outlined for $R^{1.0.1}$, namely $R^1$ being aryl or heteroaryl, with said aryl being phenyl, and said heteroaryl being selected from the group of 2-, 3- and 4-pyridyl, pyrimidinyl, pyrazolyl, thiazolyl, preferably phenyl and pyridyl, whereby said aryl and each of said heteroaryl being substituted by one member of the group $R^{1.0.1.S1}$ which consists of phenyl, oxadiazolyl, triazolyl, pyrazolyl, furanyl, pyrrolyl, pyridazinyl, pyrimidinyl, and 2-, 3- and 4-pyridyl, whereby preferably said aryl or heteroaryl is ar-1-yl or heteroar-1-yl and the member of the group $R^{1.0.1.S1}$ being attached to said ar-1-yl or heteroar-1-yl at the 2-position thereof, and more preferred the group $R^{1.0.1.S1}$ consists of oxadiazolyl, triazolyl, pyrazolyl, furanyl, pyrrolyl, pyridazinyl, pyrimidinyl, and 2-, 3- and 4-pyridyl, whereby preferably said aryl or heteroaryl is ar-1-yl or heteroar-1-yl and the member of the group $R^{1.0.1.S1}$ being attached to said ar-1-yl or heteroar-1-yl at the 2-position thereof, and whereby said aryl and said heteroaryl and/or the member of said group $R^{1.0.1.S1}$ optionally may be substituted by one or more members of the group $R^{1.0.1.S2}$ which consists of fluorine, chlorine, $H_3C—$, $F_3C—$, $CH_3O—$, $H_2NCO—$, N-morpholinyl, and NC—, preferably $R^{1.0.1.S2}$ consists of fluorine, $H_3C—$, $F_3C—$, $CH_3O—$ and NC—;

$R^2$ being a substituent selected from the group of $R^{2.4}$ being fluorine, methyl, HO—, $CH_3$—O—, phenyl, $H_2N—$, $C_{1-6}$-alkyl-O—CO—(H)N—, $C_{1-6}$-alkyl-CO—(H)N— and phenyl-CO—(H)N—, where the above mentioned members methyl, $CH_3$—O—, phenyl, $H_2N—$, $C_{1-6}$-alkyl-O—CO—(H)N—, $C_{1-6}$-alkyl-CO—(H)N—, phenyl-CO—(H)N— may optionally be substituted independently of one another by one or more fluorine;

$R^3$ independently of any other $R^3$ being a substituent selected from the group of $R^{3.3}$ being fluorine, $F_3C—$, $HF_2C—$, $FH_2C—$, $F_3C—CH_2—$ and methyl;

$R^4$ and $R^5$ being independently of one another a substituent selected from the group of $R^{4/5.2}$ being H and fluorine, preferably $R^4$ and $R^5$ both being H;

x being 0, 1, 2, 3, 4, preferably being 0, 1 or 2, more preferably 0 or 1 or only 1;

and salts, preferably pharmaceutically acceptable salts thereof.

Matrix element M2-07 ($A^4R^{1.0.1}R^{2.4}R^{3.3}R^{4/5.2}$) represents a compound according to general formula I with $\overline{A}$ being a substituent selected from the group of $A^4$ being a $C_5$-$C_6$-cycloalkyl group the members of which being selected from the group of cyclopentyl and cyclohexyl;

$R^1$ being defined as outlined for $R^{1.0.1}$, namely $R^1$ being aryl or heteroaryl, with said aryl being phenyl, and said heteroaryl being selected from the group of 2-, 3- and 4-pyridyl, pyrimidinyl, pyrazolyl, thiazolyl, preferably phenyl and pyridyl, whereby said aryl and each of said heteroaryl being substituted by one member of the group $R^{1.0.1.S1}$ which consists of phenyl, oxadiazolyl, triazolyl, pyrazolyl, furanyl, pyrrolyl, pyridazinyl, pyrimidinyl, and 2-, 3- and 4-pyridyl, whereby preferably said aryl or heteroaryl is ar-1-yl or heteroar-1-yl and the member of the group $R^{1.0.1.S1}$ being attached to said ar-1-yl or heteroar-1-yl at the 2-position thereof, and more preferred the group $R^{1.0.1.S1}$ consists of oxadiazolyl, triazolyl, pyrazolyl, furanyl, pyrrolyl, pyridazinyl, pyrimidinyl, and 2-, 3- and 4-pyridyl, whereby preferably said aryl or heteroaryl is ar-1-yl or heteroar-1-yl and the member of the group $R^{1.0.1.S1}$ being attached to said ar-1-yl or heteroar-1-yl at the 2-position thereof, and whereby said aryl and said heteroaryl and/or the member of said group $R^{1.0.1.S1}$ optionally may be substituted by one or more members of the group $R^{1.0.1.S2}$ which consists of fluorine, chlorine, $H_3C—$, $F_3C—$, $CH_3O—$, $H_2NCO—$, N-morpholinyl, and NC—, preferably $R^{1.0.1.S2}$ consists of fluorine, $H_3C—$, $F_3C—$, $CH_3O—$ and NC—;

$R^2$ being a substituent selected from the group of $R^{2.4}$ being fluorine, methyl, HO—, $CH_3$—O—, phenyl, $H_2N—$, $C_{1-6}$-alkyl-O—CO—(H)N—, $C_{1-6}$-alkyl-CO—(H)N— and phenyl-CO—(H)N—, where the above mentioned members methyl, $CH_3$—O—, phenyl, $H_2N—$, $C_{1-6}$-alkyl-O—CO—(H)N—, $C_{1-16}$-alkyl-CO—(H)N—, phenyl-CO—(H)N— may optionally be substituted independently of one another by one or more fluorine;

$R^3$ independently of any other $R^3$ being a substituent selected from the group of $R^{3.3}$ being fluorine, $F_3C—$, $HF_2C—$, $FH_2C—$, $F_3C—CH_2—$ and methyl;

$R^4$ and $R^5$ being independently of one another a substituent selected from the group of $R^{4/5.2}$ being H and fluorine, preferably $R^4$ and $R^5$ both being H;

x being 0, 1, 2, 3, 4, preferably being 0, 1 or 2, more preferably 0 or 1 or only 1;

and salts, preferably pharmaceutically acceptable salts thereof.

The same principle applies for any other matrix element.

A first set of specific embodiments of the invention relates to all embodiments as hereinbefore described, provided that the compound according to general formula (I) is not a compound according to the general formula (Id1):

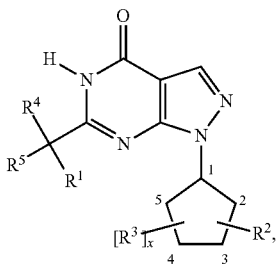

(Id1)

in which
- the figures 1, 2, 3, 4 and 5 at the cyclopentylring label the corresponding ring C atom and
- if neither $R^2$ nor $R^3$ is bound at the cyclopentylring C atom labelled by the figure 2 (i.e. at this position there is a $CH_2$-group); then none of $R^2$ or $R^3$ are bound to the cyclopentylring C atom labelled by the figure 3 by a $CH_2$-group that is integral part of said $R^2$ or $R^3$ or
- if neither $R^2$ nor $R^3$ is bound at the cyclopentylring C atom labelled by the figure 5 (i.e. at this position there is a $CH_2$-group); then none of $R^2$ or $R^3$ are bound to the cyclopentylring C atom labelled by the figure 4 by a $CH_2$-group that is integral part of said $R^2$ or $R^3$ and
- the remaining definitions for $R^1$, $R^2$, $R^3$, $R^4$, $R^5$ and x are the same as described in said appropriate generic definition of compounds according to general formula (I).

A second set of specific embodiments of the invention relates to all embodiments as described above the first set of specific embodiment, provided that the compound according to general formula (I) is not a compound according to the general formula (Id2):

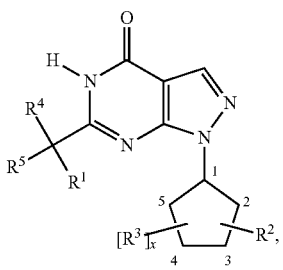

(Id2)

in which
- the figures 1, 2, 3, 4 and 5 at the cyclopentylring label the corresponding ring C atom;
- one or both of the cyclopentylring C atoms labelled by the figure 2 and 5 are unsubstituted (i.e. $CH_2$-groups);
- none of $R^2$ or $R^3$ are bound to the cyclopentylring C atoms labelled by the figure 3 and 4 by a $CH_2$-group that is integral part of said $R^2$ or $R^3$; and
- the remaining definitions are the same as hereinbefore and herein below described.

A third set of specific embodiments of the invention relates to all embodiments as described above the first and second set of specific embodiments, provided that the compound is not a compound according to general formula (I)

in which $\overline{A}$ is cyclopentyl, $R^2$ and $R^3$ are bound to those carbon atoms of $\overline{A}$

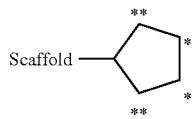

indicated by * via a —$CH_2$-group of said substituents $R^2$ or $R^3$ if at one or both of the positions indicated by ** are —$CH_2$— groups.

Specifically Preferred Compounds

Each of the compounds presented in the following table is specifically and individually preferred. The listed compounds are described in detail in the section "Exemplary embodiments". The following list presents the specific compounds of the invention as neutral compounds without stereochemical properties. The example numbers are identical with the numbering according to the section "Exemplary embodiments". More specific information can be found in the section "Exemplary embodiments".

Table of preferred specific embodiments as exemplified

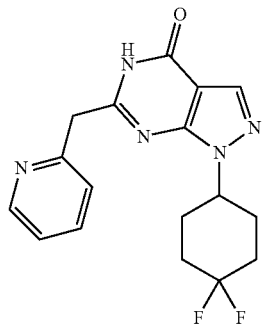

Example 1

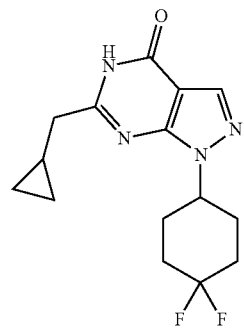 [SMILES: O=c1[nH]c(CC2CC2)nc2c1cnn2C1CCC(F)(F)CC1]

Example 2

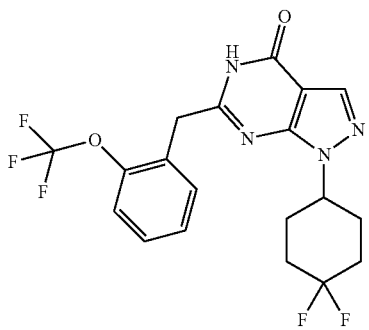 [SMILES: O=c1[nH]c(Cc2ccccc2OC(F)(F)F)nc2c1cnn2C1CCC(F)(F)CC1]

Example 3

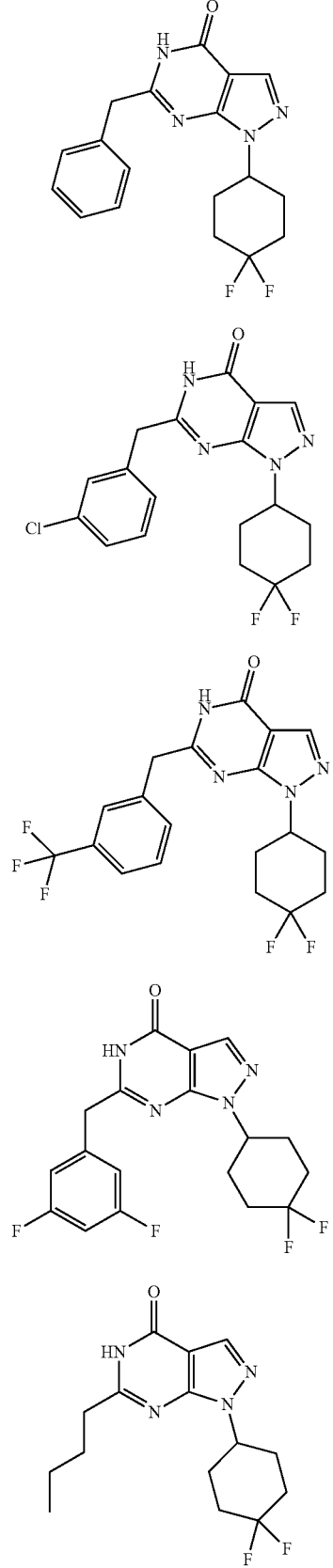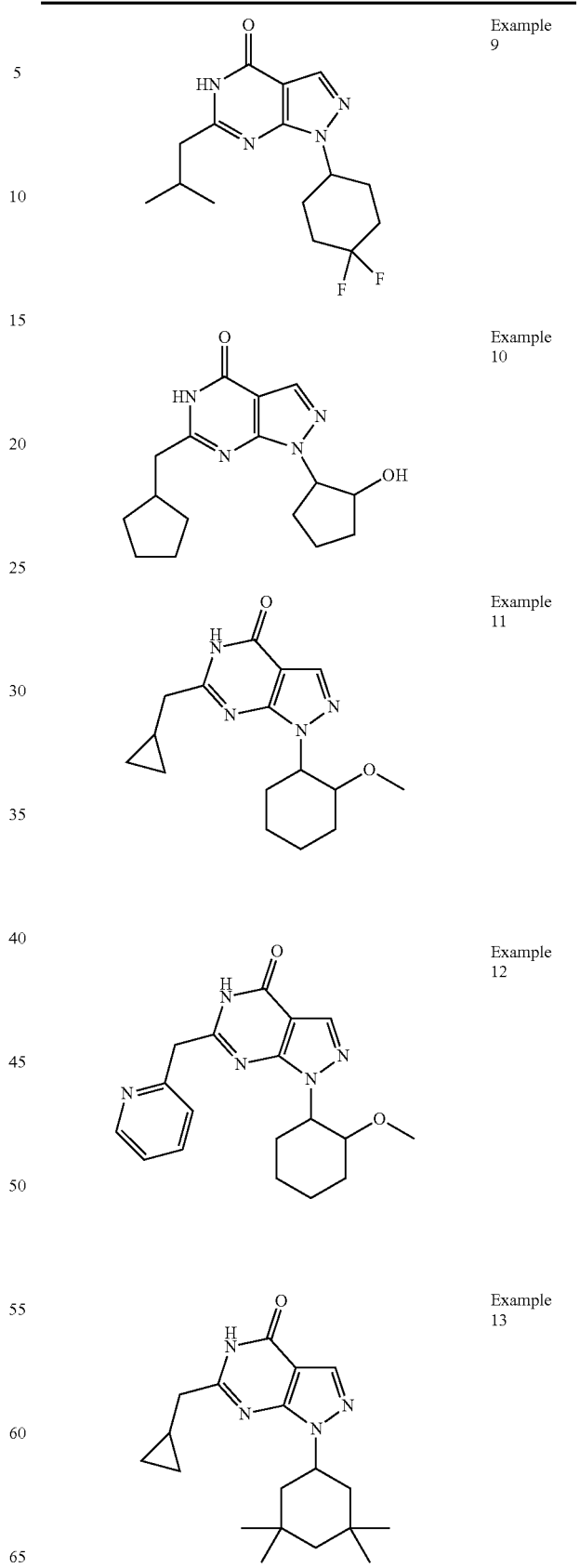

| | |
|---|---|
| 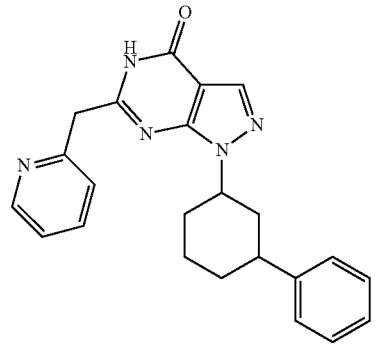 [SMILES: O=c1[nH]c(Cc2ccccn2)nc2c1cnn2C1CCCC(c2ccccc2)C1] Example 14 | 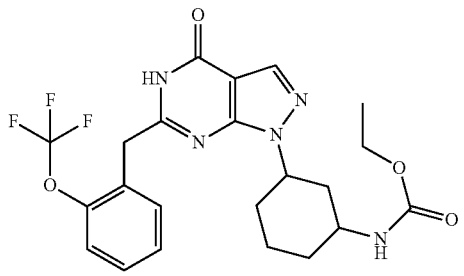 Example 19 |
| 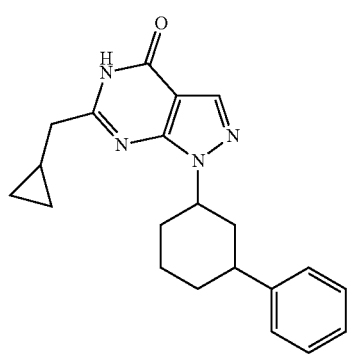 [SMILES: O=c1[nH]c(CC2CC2)nc2c1cnn2C1CCCC(c2ccccc2)C1] Example 15 | 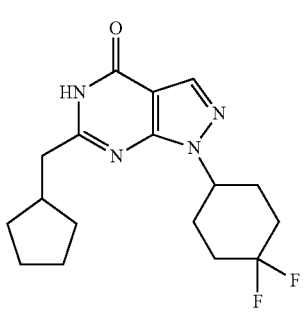 Example 20 |
| 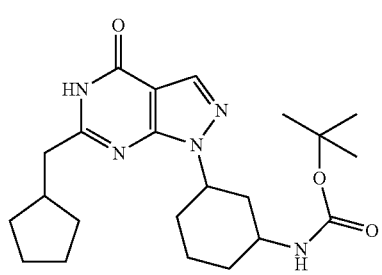 [SMILES: CC(C)(C)OC(=O)NC1CCCC(n2ncc3c(=O)[nH]c(CC4CCCC4)nc32)C1] Example 16 | 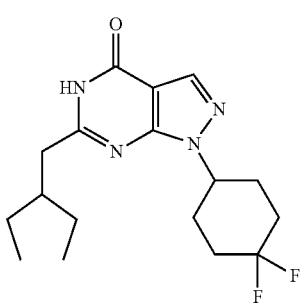 Example 21 |
| 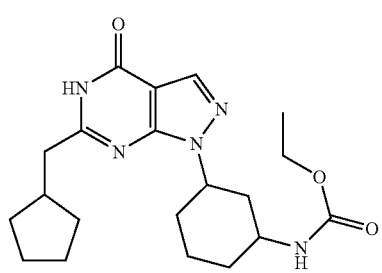 [SMILES: CCOC(=O)NC1CCCC(n2ncc3c(=O)[nH]c(CC4CCCC4)nc32)C1] Example 17 | 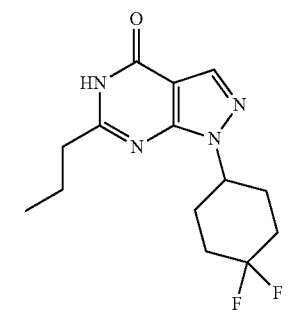 Example 22 |
| 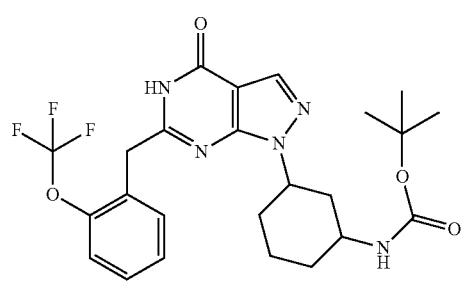 [SMILES: CC(C)(C)OC(=O)NC1CCCC(n2ncc3c(=O)[nH]c(Cc4ccccc4OC(F)(F)F)nc32)C1] Example 18 | 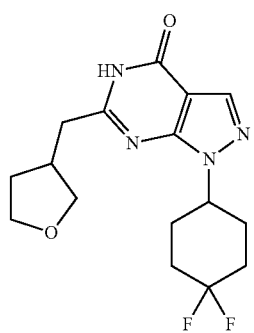 [SMILES: O=c1[nH]c(CC2CCOC2)nc2c1cnn2C1CCC(F)(F)CC1] Example 23 |

-continued
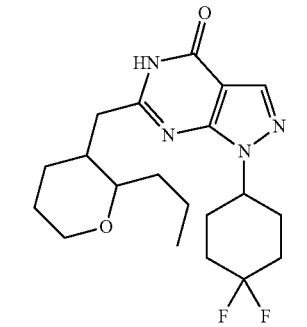 [SMILES: CCCC1OCCCC1Cc1nc2c(cnn2C2CCC(F)(F)CC2)c(=O)[nH]1]
Example 24
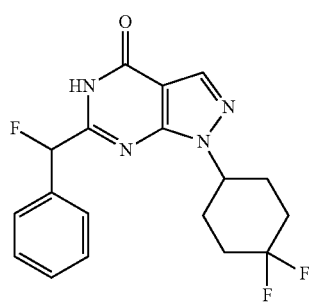 [SMILES: O=c1[nH]c(C(F)c2ccccc2)nc2c1cnn2C1CCC(F)(F)CC1]
Example 25
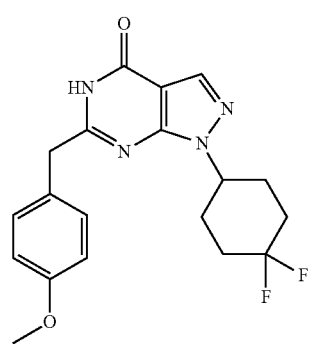 [SMILES: COc1ccc(Cc2nc3c(cnn3C3CCC(F)(F)CC3)c(=O)[nH]2)cc1]
Example 26
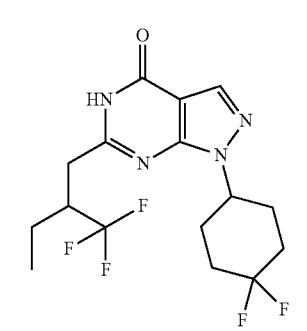 [SMILES: CCC(Cc1nc2c(cnn2C2CCC(F)(F)CC2)c(=O)[nH]1)C(F)(F)F]
Example 27
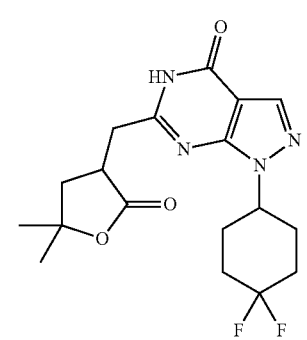 [SMILES: CC1(C)CC(Cc2nc3c(cnn3C3CCC(F)(F)CC3)c(=O)[nH]2)C(=O)O1]
Example 28
-continued
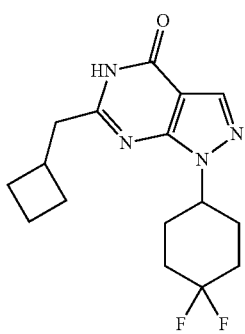 [SMILES: O=c1[nH]c(CC2CCC2)nc2c1cnn2C1CCC(F)(F)CC1]
Example 29
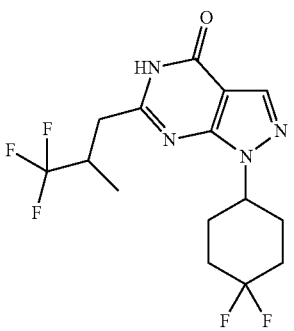 [SMILES: CC(Cc1nc2c(cnn2C2CCC(F)(F)CC2)c(=O)[nH]1)C(F)(F)F]
Example 30
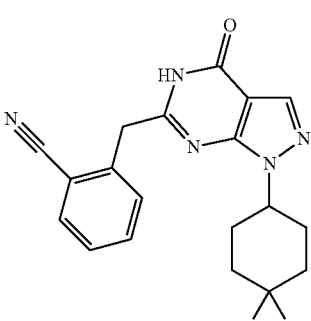
Example 31
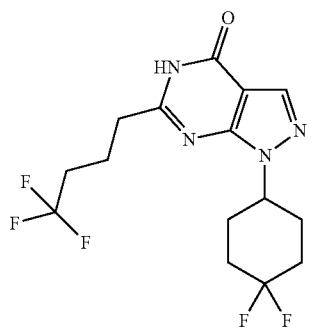 [SMILES: O=c1[nH]c(CCCC(F)(F)F)nc2c1cnn2C1CCC(F)(F)CC1]
Example 32

-continued
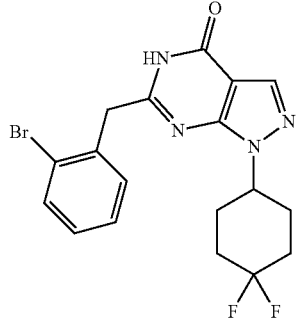 [SMILES: O=c1[nH]c(Cc2ccccc2Br)nc2c1cnn2C1CCC(F)(F)CC1]
Example 33
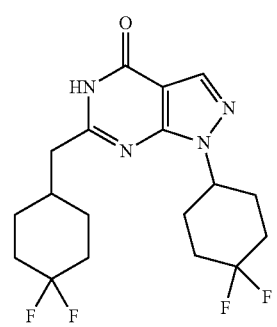 [SMILES: O=c1[nH]c(CC2CCC(F)(F)CC2)nc2c1cnn2C1CCC(F)(F)CC1]
Example 34
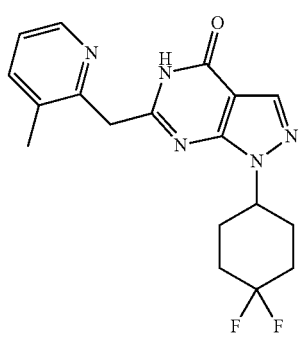 [SMILES: Cc1cccnc1Cc1nc2c(cnn2C2CCC(F)(F)CC2)c(=O)[nH]1]
Example 35
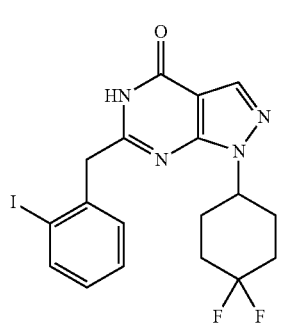 [SMILES: O=c1[nH]c(Cc2ccccc2I)nc2c1cnn2C1CCC(F)(F)CC1]
Example 36
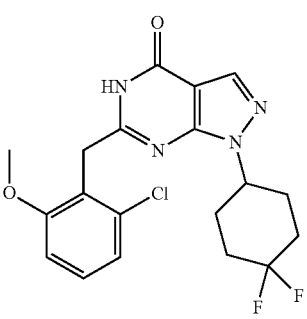 [SMILES: COc1cccc(Cl)c1Cc1nc2c(cnn2C2CCC(F)(F)CC2)c(=O)[nH]1]
Example 37
-continued
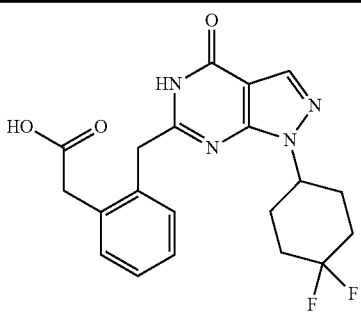
Example 38
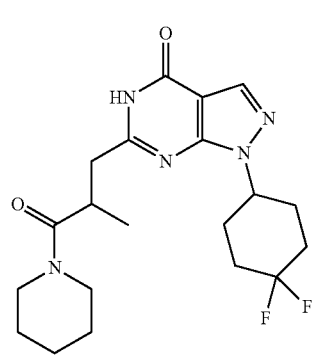 [SMILES: CC(Cc1nc2c(cnn2C2CCC(F)(F)CC2)c(=O)[nH]1)C(=O)N1CCCCC1]
Example 39
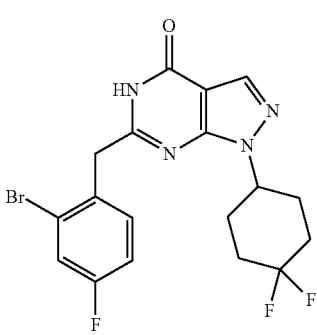 [SMILES: O=c1[nH]c(Cc2ccc(F)cc2Br)nc2c1cnn2C1CCC(F)(F)CC1]
Example 44
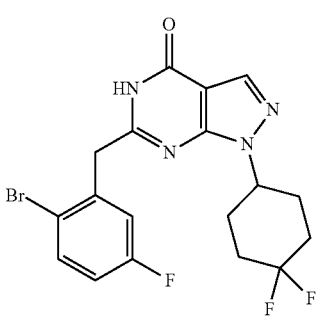 [SMILES: O=c1[nH]c(Cc2cc(F)ccc2Br)nc2c1cnn2C1CCC(F)(F)CC1]
Example 45
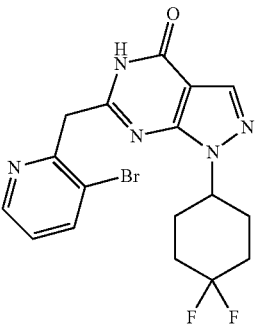 [SMILES: O=c1[nH]c(Cc2ncccc2Br)nc2c1cnn2C1CCC(F)(F)CC1]
Example 46

| | |
|---|---|
| 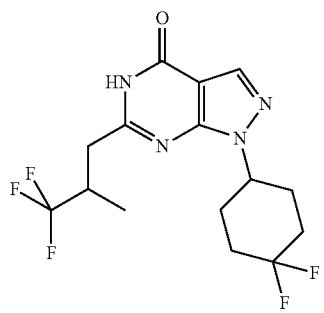 [SMILES: CC(Cc1nc2c(cnn2C2CCC(F)(F)CC2)c(=O)[nH]1)C(F)(F)F] | Example 47 & 48 |
| 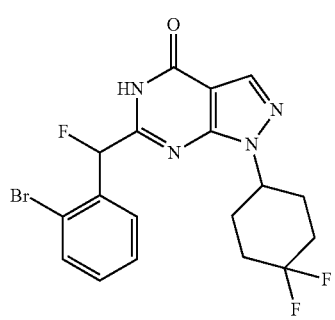 [SMILES: O=c1[nH]c(C(F)c2ccccc2Br)nc2c1cnn2C1CCC(F)(F)CC1] | Example 48-2 |
| 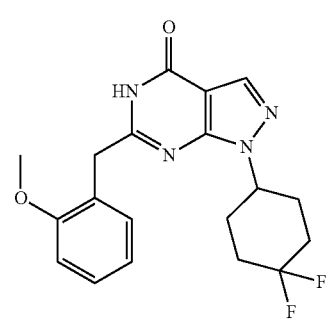 [SMILES: COc1ccccc1Cc1nc2c(cnn2C2CCC(F)(F)CC2)c(=O)[nH]1] | Example 48-3 |
| 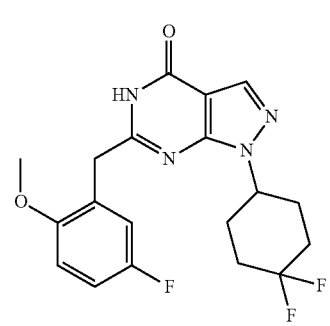 [SMILES: COc1ccc(F)cc1Cc1nc2c(cnn2C2CCC(F)(F)CC2)c(=O)[nH]1] | Example 48-4 |
| 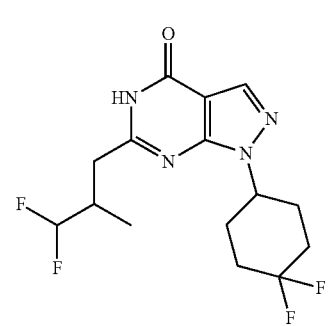 [SMILES: CC(Cc1nc2c(cnn2C2CCC(F)(F)CC2)c(=O)[nH]1)C(F)F] | Example 48-5 |
| 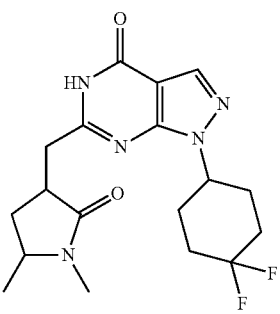 [SMILES: CC1CC(Cc2nc3c(cnn3C3CCC(F)(F)CC3)c(=O)[nH]2)C(=O)N1C] | Example 48-6 |
| 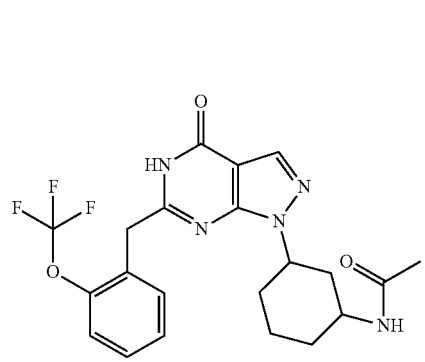 [SMILES: CC(=O)NC1CCCC(n2ncc3c(=O)[nH]c(Cc4ccccc4OC(F)(F)F)nc32)C1] | Example 49 |
| 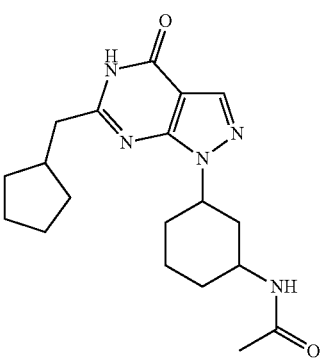 [SMILES: CC(=O)NC1CCCC(n2ncc3c(=O)[nH]c(CC4CCCC4)nc32)C1] | Example 50 |
| 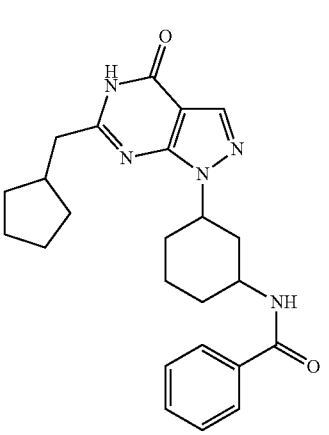 [SMILES: O=C(NC1CCCC(n2ncc3c(=O)[nH]c(CC4CCCC4)nc32)C1)c1ccccc1] | Example 51 |

| | |
|---|---|
| 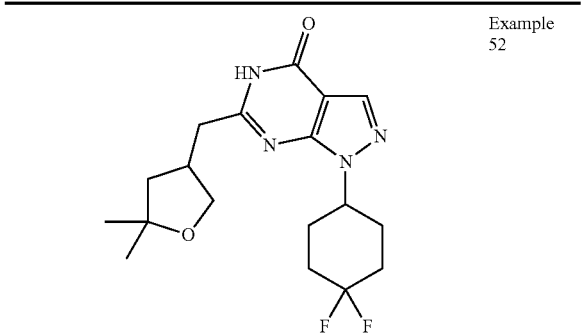 Example 52 | 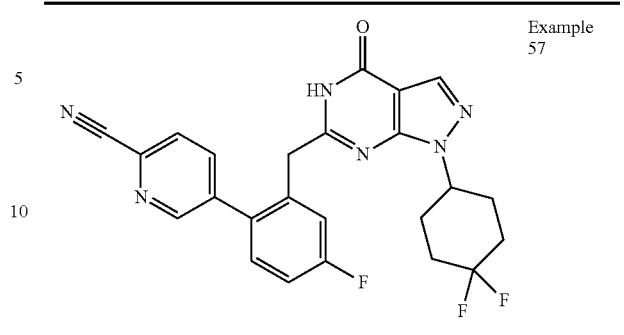 Example 57 |
| 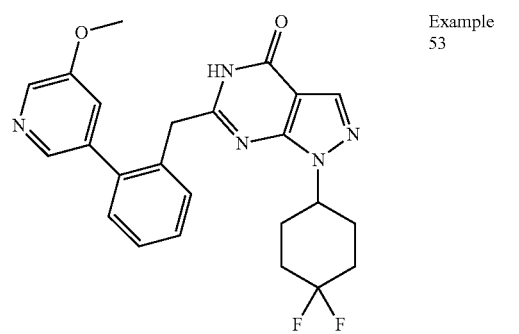 Example 53 | 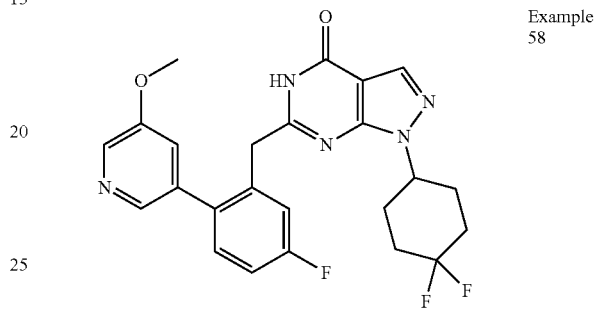 Example 58 |
| 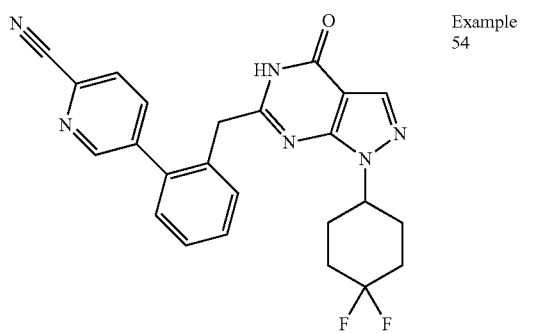 Example 54 | 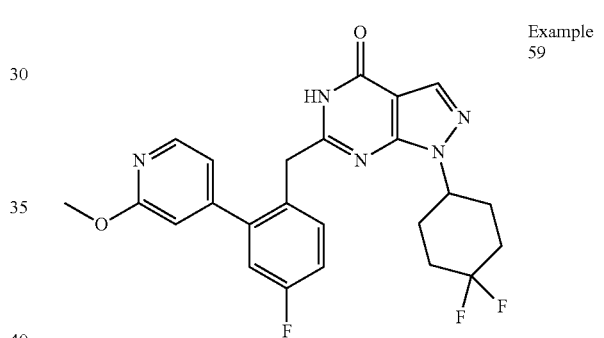 Example 59 |
| 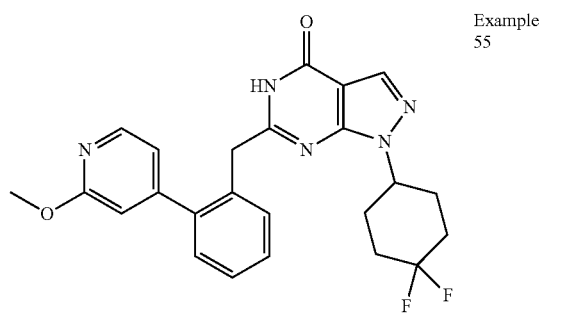 Example 55 | 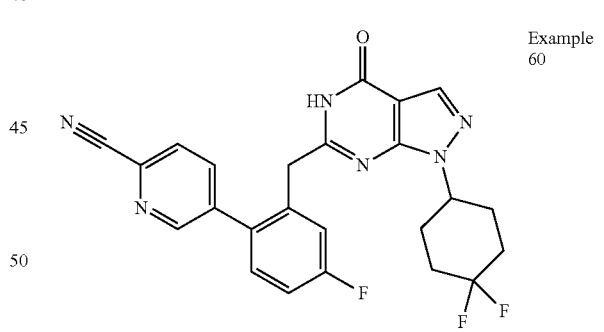 Example 60 |
| 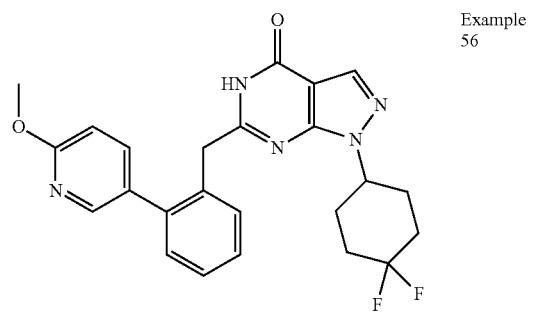 Example 56 | 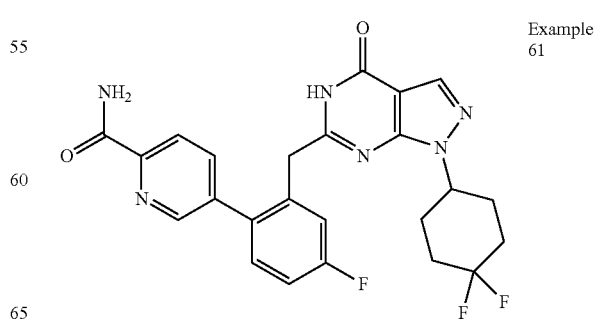 Example 61 |

| | |
|---|---|
| 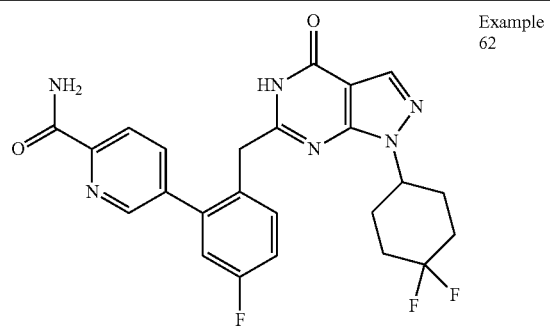 Example 62 | 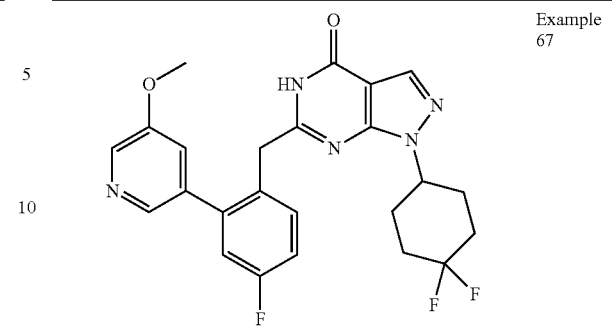 Example 67 |
| 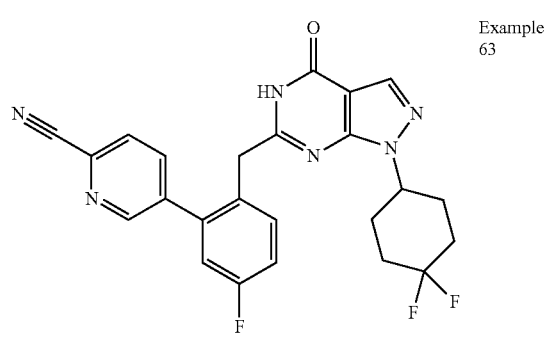 Example 63 | 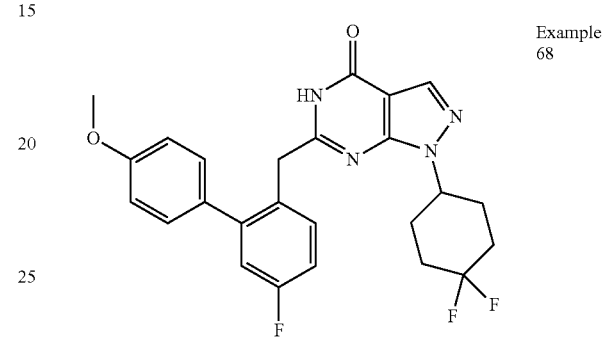 Example 68 |
| 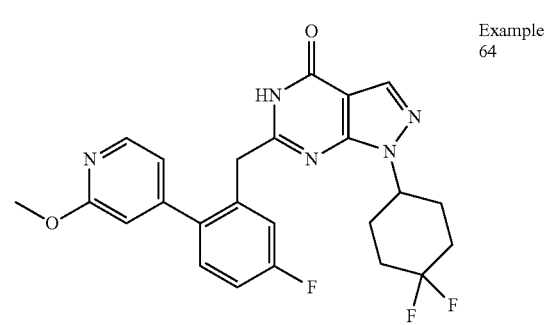 Example 64 | 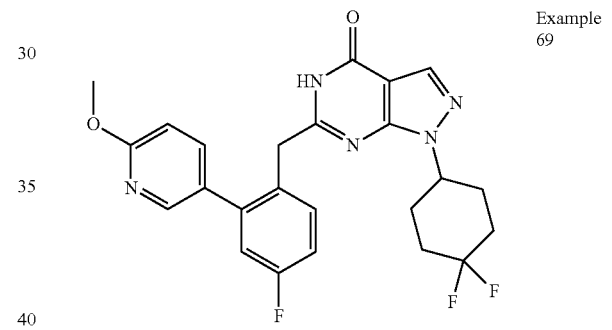 Example 69 |
| 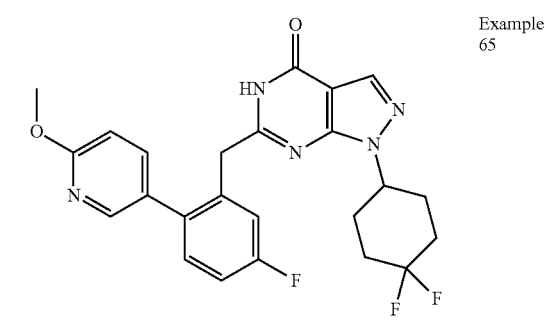 Example 65 | 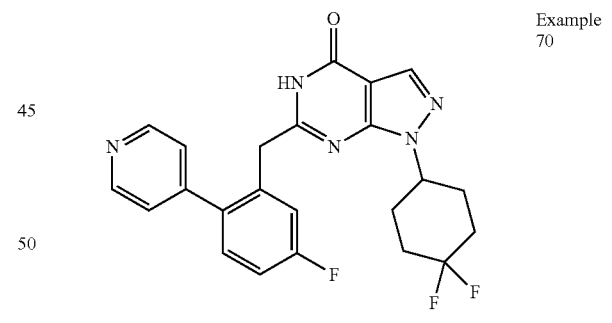 Example 70 |
| 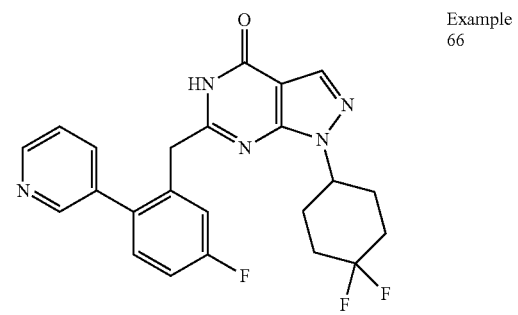 Example 66 | 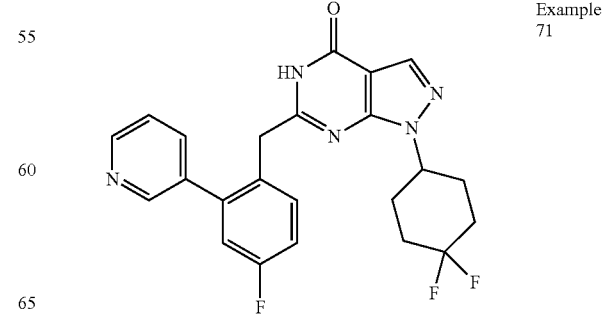 Example 71 |

-continued
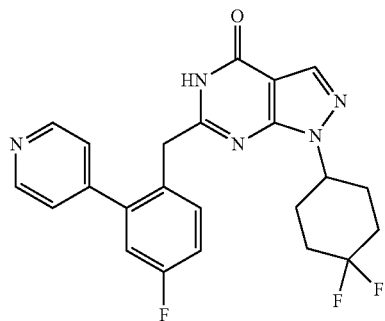 [SMILES: O=c1[nH]c(Cc2ccc(F)cc2-c2ccncc2)nc2c1cnn2C1CCC(F)(F)CC1]
Example 72
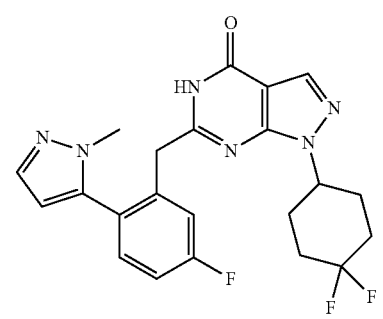 [SMILES: Cn1nccc1-c1ccc(F)cc1Cc1nc2c(cnn2C2CCC(F)(F)CC2)c(=O)[nH]1]
Example 72-2
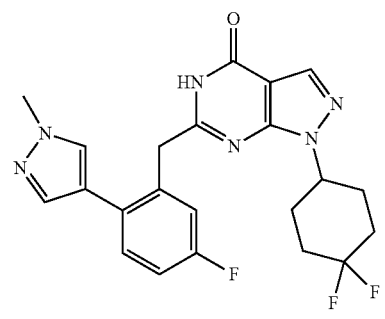 [SMILES: Cn1cc(-c2ccc(F)cc2Cc2nc3c(cnn3C3CCC(F)(F)CC3)c(=O)[nH]2)cn1]
Example 72-3
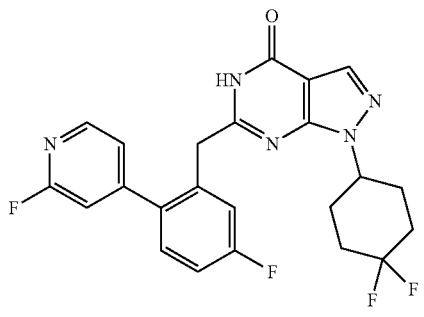 [SMILES: O=c1[nH]c(Cc2cc(F)ccc2-c2ccnc(F)c2)nc2c1cnn2C1CCC(F)(F)CC1]
Example 72-4
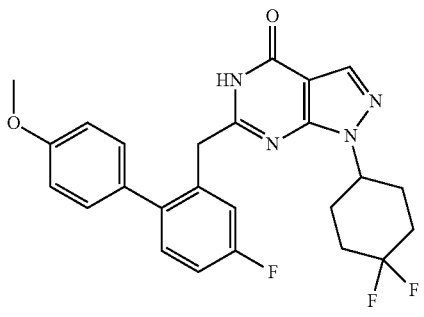 [SMILES: COc1ccc(-c2ccc(F)cc2Cc2nc3c(cnn3C3CCC(F)(F)CC3)c(=O)[nH]2)cc1]
Example 72-5
-continued
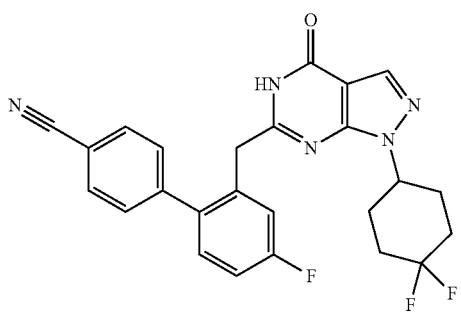 [SMILES: N#Cc1ccc(-c2ccc(F)cc2Cc2nc3c(cnn3C3CCC(F)(F)CC3)c(=O)[nH]2)cc1]
Example 72-6
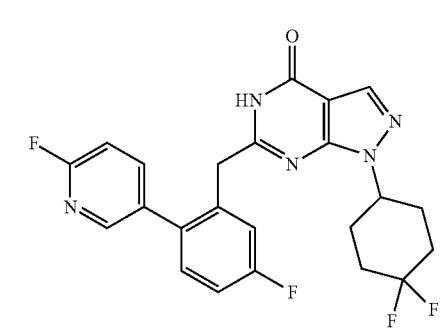
Example 72-7
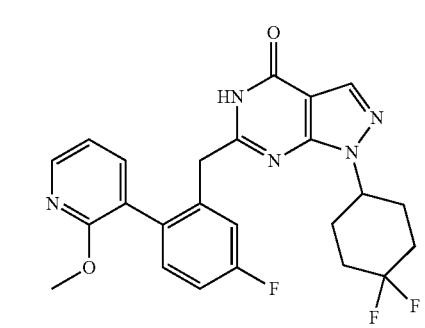 [SMILES: COc1ncccc1-c1ccc(F)cc1Cc1nc2c(cnn2C2CCC(F)(F)CC2)c(=O)[nH]1]
Example 72-8
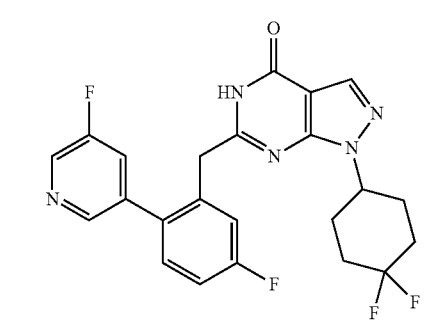 [SMILES: O=c1[nH]c(Cc2cc(F)ccc2-c2cncc(F)c2)nc2c1cnn2C1CCC(F)(F)CC1]
Example 72-9
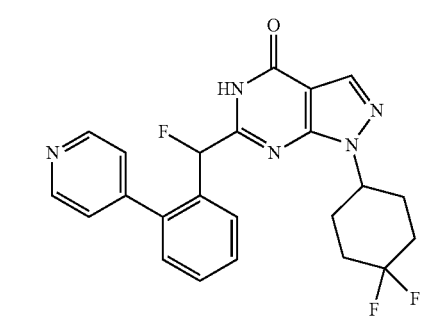 [SMILES: O=c1[nH]c(C(F)c2ccccc2-c2ccncc2)nc2c1cnn2C1CCC(F)(F)CC1]
Example 72-10

-continued
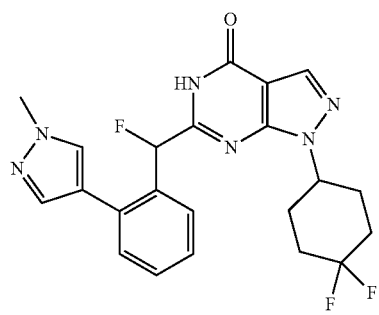 [SMILES: Cn1cc(-c2ccccc2C(F)c2nc3c(cnn3C3CCC(F)(F)CC3)c(=O)[nH]2)cn1]
Example 72-11
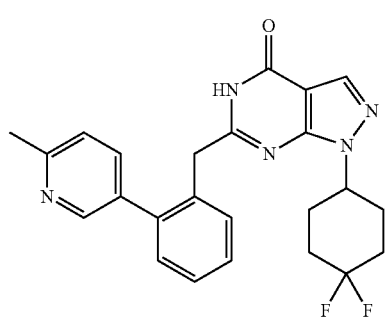 [SMILES: Cc1ccc(-c2ccccc2Cc2nc3c(cnn3C3CCC(F)(F)CC3)c(=O)[nH]2)cn1]
Example 73
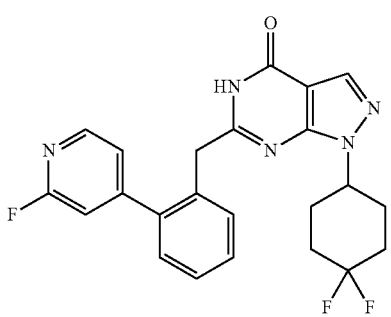 [SMILES: O=c1[nH]c(Cc2ccccc2-c2ccnc(F)c2)nc2c1cnn2C1CCC(F)(F)CC1]
Example 74
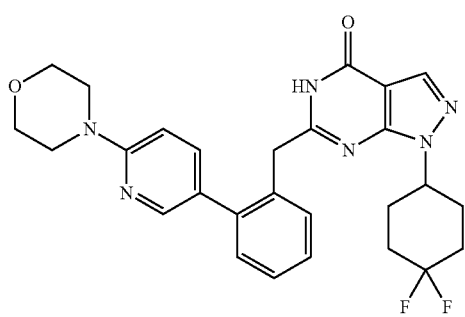 [SMILES: O=c1[nH]c(Cc2ccccc2-c2ccc(N3CCOCC3)nc2)nc2c1cnn2C1CCC(F)(F)CC1]
Example 75
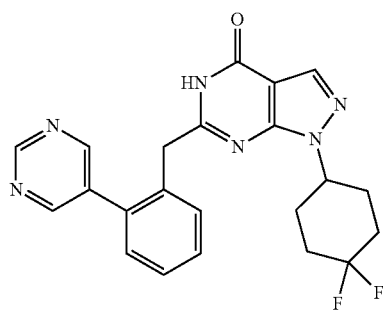 [SMILES: O=c1[nH]c(Cc2ccccc2-c2cncnc2)nc2c1cnn2C1CCC(F)(F)CC1]
Example 76
-continued
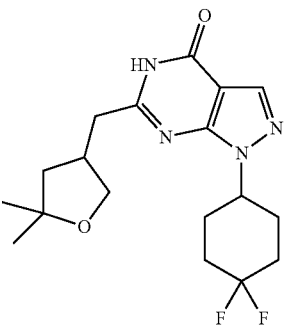 [SMILES: CC1(C)CC(Cc2nc3c(cnn3C3CCC(F)(F)CC3)c(=O)[nH]2)CO1]
Example 77
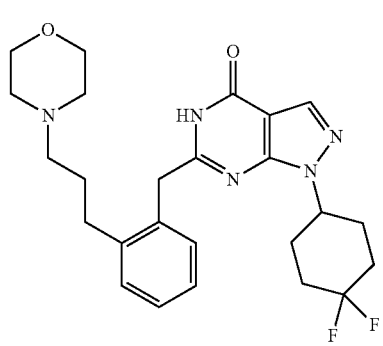 [SMILES: O=c1[nH]c(Cc2ccccc2CCCN2CCOCC2)nc2c1cnn2C1CCC(F)(F)CC1]
Example 78
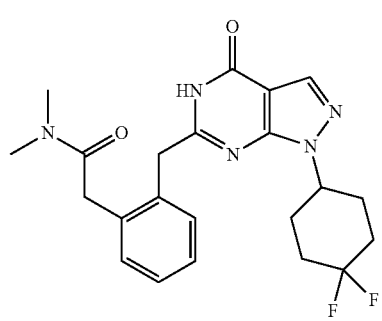 [SMILES: CN(C)C(=O)Cc1ccccc1Cc1nc2c(cnn2C2CCC(F)(F)CC2)c(=O)[nH]1]
Example 79
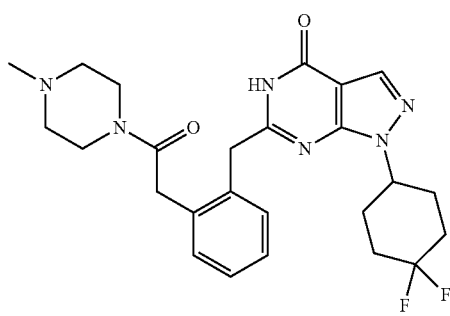 [SMILES: CN1CCN(C(=O)Cc2ccccc2Cc2nc3c(cnn3C3CCC(F)(F)CC3)c(=O)[nH]2)CC1]
Example 80
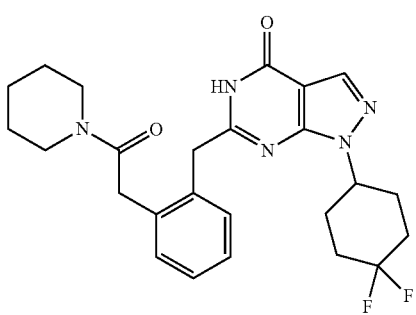 [SMILES: O=C(Cc1ccccc1Cc1nc2c(cnn2C2CCC(F)(F)CC2)c(=O)[nH]1)N1CCCCC1]
Example 81

37
-continued
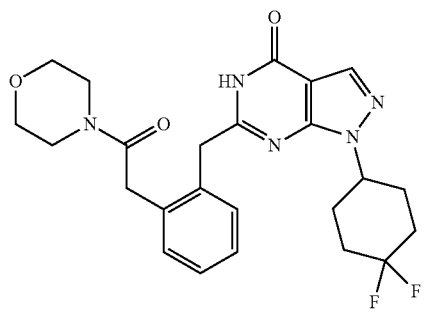 [SMILES: O=C(Cc1ccccc1Cc1nc2c(cnn2C2CCC(F)(F)CC2)c(=O)[nH]1)N1CCOCC1]
Example 82
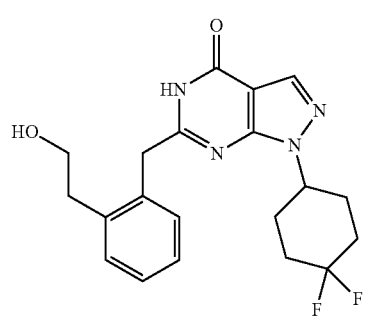 [SMILES: O=c1[nH]c(Cc2ccccc2CCO)nc2c1cnn2C1CCC(F)(F)CC1]
Example 83
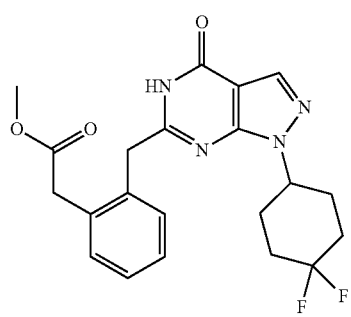 [SMILES: COC(=O)Cc1ccccc1Cc1nc2c(cnn2C2CCC(F)(F)CC2)c(=O)[nH]1]
Example 84
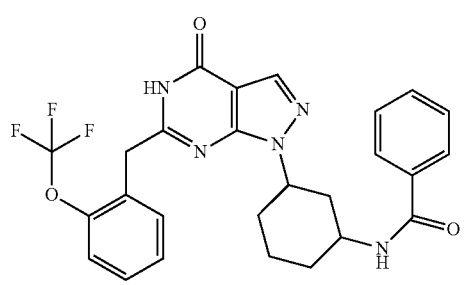 [SMILES: O=C(NC1CCCC(n2ncc3c(=O)[nH]c(Cc4ccccc4OC(F)(F)F)nc32)C1)c1ccccc1]
Example 85
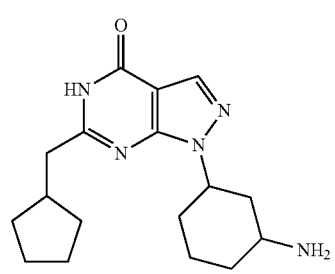 [SMILES: NC1CCCC(n2ncc3c(=O)[nH]c(CC4CCCC4)nc32)C1]
Example 86
38
-continued
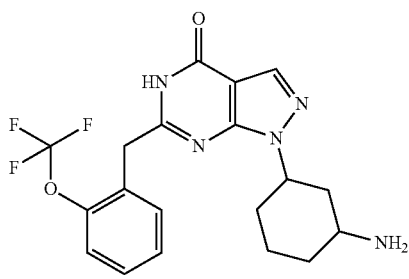 [SMILES: NC1CCCC(n2ncc3c(=O)[nH]c(Cc4ccccc4OC(F)(F)F)nc32)C1]
Example 87
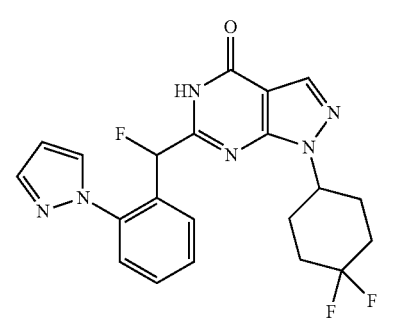 [SMILES: O=c1[nH]c(C(F)c2ccccc2-n2cccn2)nc2c1cnn2C1CCC(F)(F)CC1]
Example 88
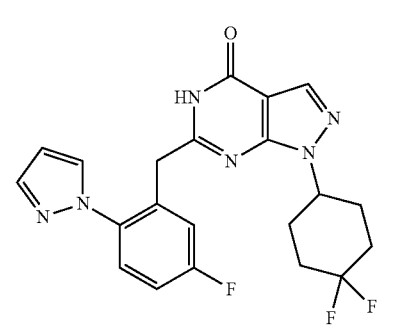 [SMILES: O=c1[nH]c(Cc2cc(F)ccc2-n2cccn2)nc2c1cnn2C1CCC(F)(F)CC1]
Example 89
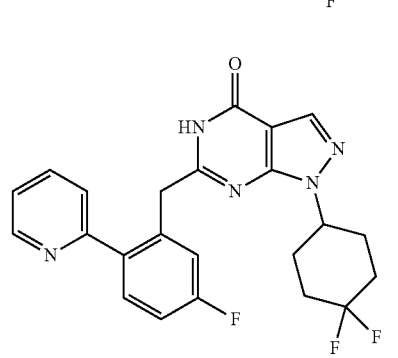
Example 90
Example 91

| | |
|---|---|
| 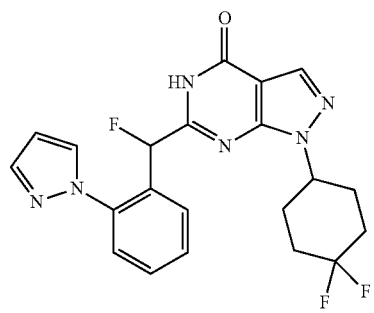 [SMILES: O=c1[nH]c(C(F)c2ccccc2-n2cccn2)nc2c1cnn2C1CCC(F)(F)CC1] | Example 92 |
| 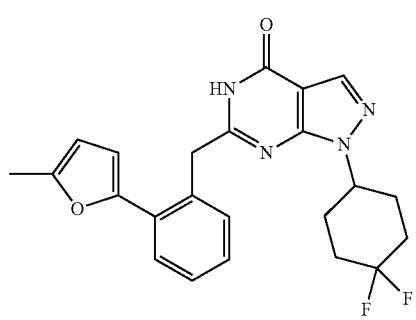 [SMILES: Cc1ccc(-c2ccccc2Cc2nc3c(cnn3C3CCC(F)(F)CC3)c(=O)[nH]2)o1] | Example 93 |
| 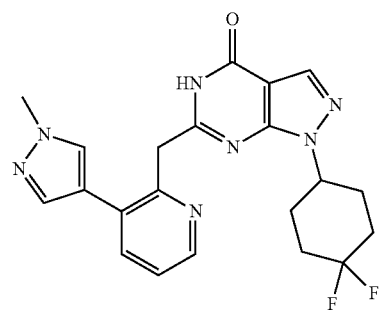 [SMILES: Cn1cc(-c2cccnc2Cc2nc3c(cnn3C3CCC(F)(F)CC3)c(=O)[nH]2)cn1] | Example 94 |
| 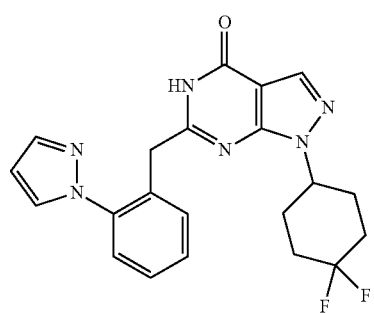 [SMILES: O=c1[nH]c(Cc2ccccc2-n2cccn2)nc2c1cnn2C1CCC(F)(F)CC1] | Example 95 |
| 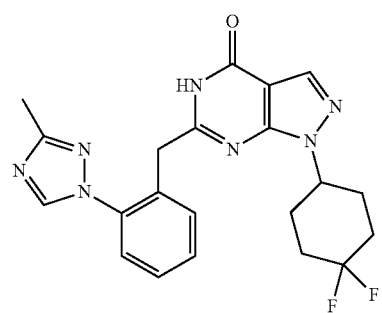 [SMILES: Cc1ncn(-c2ccccc2Cc2nc3c(cnn3C3CCC(F)(F)CC3)c(=O)[nH]2)n1] | Example 95-1 |
| 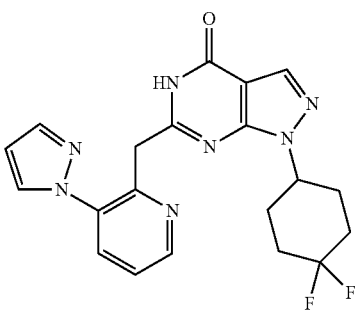 [SMILES: O=c1[nH]c(Cc2ncccc2-n2cccn2)nc2c1cnn2C1CCC(F)(F)CC1] | Example 96 |
| 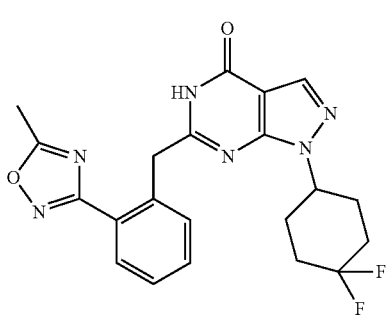 [SMILES: Cc1nc(-c2ccccc2Cc2nc3c(cnn3C3CCC(F)(F)CC3)c(=O)[nH]2)no1] | Example 97 |
| 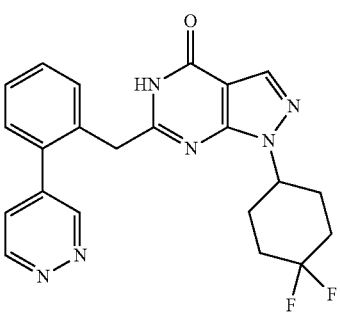 [SMILES: O=c1[nH]c(Cc2ccccc2-c2ccnnc2)nc2c1cnn2C1CCC(F)(F)CC1] | Example 98 |
| 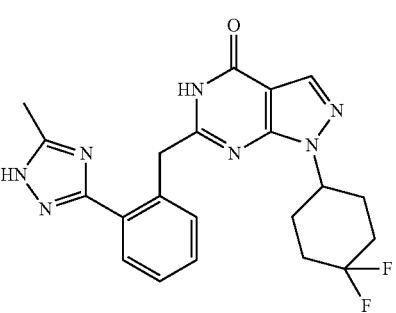 [SMILES: Cc1nc(-c2ccccc2Cc2nc3c(cnn3C3CCC(F)(F)CC3)c(=O)[nH]2)n[nH]1] | Example 99 |
| 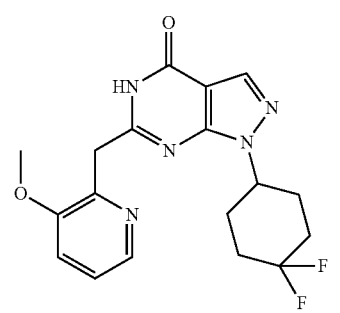 [SMILES: COc1cccnc1Cc1nc2c(cnn2C2CCC(F)(F)CC2)c(=O)[nH]1] | Example 100 |

| | |
|---|---|
| 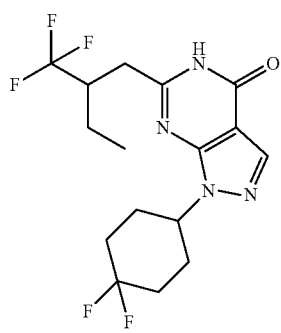 [SMILES: CCC(Cc1nc2c(cnn2C2CCC(F)(F)CC2)c(=O)[nH]1)C(F)(F)F] | Examples 101 & 102 |
| 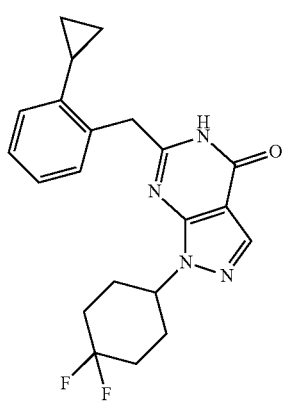 [SMILES: O=c1[nH]c(Cc2ccccc2C2CC2)nc2c1cnn2C1CCC(F)(F)CC1] | Example 103 |
| 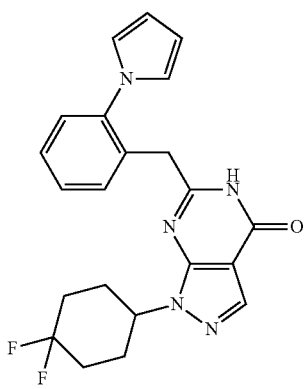 [SMILES: O=c1[nH]c(Cc2ccccc2-n2cccc2)nc2c1cnn2C1CCC(F)(F)CC1] | Example 104 |
| 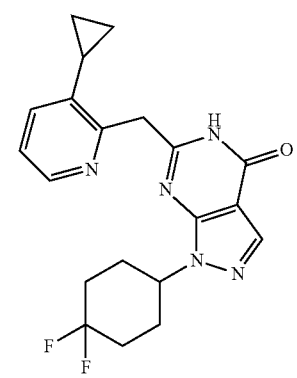 | Example 105 |
| 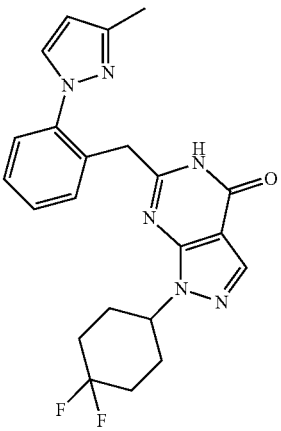 [SMILES: Cc1ccn(-c2ccccc2Cc2nc3c(cnn3C3CCC(F)(F)CC3)c(=O)[nH]2)n1] | Example 106 |
| 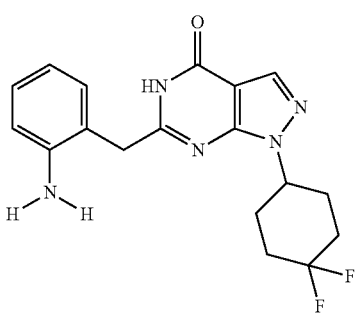 [SMILES: Nc1ccccc1Cc1nc2c(cnn2C2CCC(F)(F)CC2)c(=O)[nH]1] | Example 107 |
| 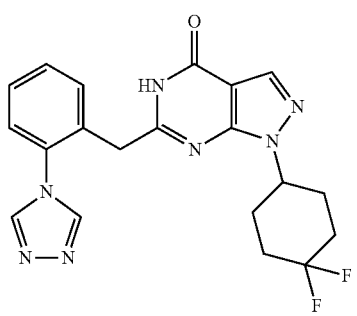 [SMILES: O=c1[nH]c(Cc2ccccc2-n2cnnc2)nc2c1cnn2C1CCC(F)(F)CC1] | Example 108 |
| 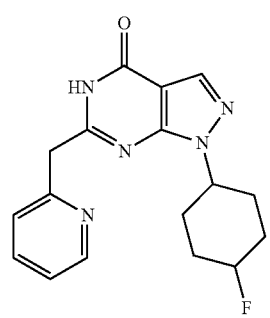 [SMILES: O=c1[nH]c(Cc2ccccn2)nc2c1cnn2C1CCC(F)CC1] | Example 109 |

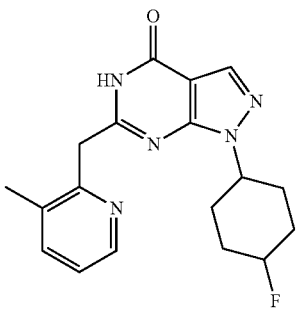 [SMILES: Cc1cccnc1Cc1nc2c(cnn2C2CCC(F)CC2)c(=O)[nH]1]

Example 110

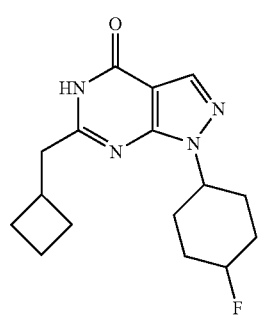 [SMILES: O=c1[nH]c(CC2CCC2)nc2c1cnn2C1CCC(F)CC1]

Example 111

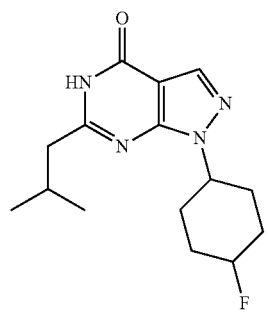 [SMILES: CC(C)Cc1nc2c(cnn2C2CCC(F)CC2)c(=O)[nH]1]

Example 112

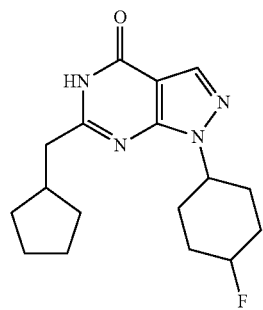 [SMILES: O=c1[nH]c(CC2CCCC2)nc2c1cnn2C1CCC(F)CC1]

Example 113

Beside the neutral compounds without stereochemical properties another preferred embodiment of the invention are compounds as listed in the above table of preferred specific embodiments in the form of salts, preferably pharmaceutically acceptable salts thereof.

Another preferred embodiment of the invention are the stereochemical isomers of the compounds according to the one as listed in the above table of preferred specific embodiments and salts, preferably the pharmaceutically acceptable salts thereof.

The compounds of preference according to the present invention may be structural part of a solvate form, in particular a hydrate form.

USED TERMS AND DEFINITIONS

Terms not specifically defined herein should be given the meanings that would be given to them by a person skilled in the art in light of the disclosure and the context. Examples include that specific substituents or atoms are presented with their 1 or 2 letter code, like H for hydrogen, N for nitrogen, C for carbon, O for oxygen, S for sulphur and the like. As used in the specification and unless specified to the contrary, the following terms have the meaning indicated and the following conventions are adhered to.

In the groups, radicals, or moieties defined below, the number of carbon atoms is often specified preceding the group, for example, $C_{1-6}$ alkyl means an alkyl group or alkyl radical having 1 to 6 carbon atoms. In general, for groups comprising two or more subgroups, the last named group is the radical attachment point, for example, "thioalkyl" means a monovalent radical of the formula HS-alkyl-. A hyphen may indicate a bond. Sometimes a term of a substituent starts or ends with a minus sign or hyphen, i.e.—. This sign emphasises the attachment point or bond of said substituent to another part of the molecule. In cases such an information is not needed the hyphen may not be used. Unless otherwise specified below, conventional definitions of terms control and conventional stable atom valences are presumed and achieved in all formulas and groups.

In general, all "tautomeric forms and isomeric forms and mixtures", whether individual geometric isomers or optical isomers or racemic or non-racemic mixtures of isomers, of a chemical structure or compound are intended, unless the specific stereochemistry or isomeric form is specifically indicated in the compound name or structure.

The term "substituted" as used herein explicitly or implicitly, means that any one or more hydrogen(s) on the designated atom is replaced with a member of the indicated group of substituents, provided that the designated atom's normal valence is not exceeded. The substitution shall result in a stable compound. "Stable" in this context preferably means a compound that from a pharmaceutical point of view is chemically and physically sufficiently stable in order to be used as an active pharmaceutical ingredient of a pharmaceutical composition.

If a substituent is not defined, it shall be hydrogen.

By the term "optionally substituted" is meant that either the corresponding group is substituted or is not.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salt(s)" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric acid, hydrobromic acid, sulfuric acid, sulfamic acid, phosphoric acid, nitric acid, and the like; and the salts prepared from organic acids such as acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isothionic acid, and the like. As the compounds of the present invention may have both, acid as well as basic groups, those compounds may therefore be present as internal salts too.

The pharmaceutically acceptable salts of the present invention can be synthesized from the parent compound which contains a basic or acidic moiety by conventional chemical methods. Generally, such salts can be prepared by reacting the free acid or base form of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

"Prodrugs" are considered compounds that release an active parent drug of the present invention in vivo when such prodrug is administered to a mammalian subject. Prodrugs according to the present invention are prepared by modifying functional groups present in the compound in such a way that these modifications are retransformed to the original functional groups under physiological conditions. Prodrugs include compounds of the present invention wherein a hydroxy, amino, or sulfhydryl group is bound to any group that, when the prodrug of the present invention is administered to a mammalian subject, is retransformed to free said hydroxyl, amino, or sulfhydryl group. Examples of prodrugs include, but are not limited to, acetate, formate and benzoate derivatives of alcohol and amine functional groups in the compounds of the present invention.

"Metabolites" are considered as derivatives of the compounds according to the present invention that are formed in vivo. Active metabolites are such metabolites that cause a pharmacological effect. It will be appreciated that metabolites of the compounds according to the present inventions are subject to the present invention as well, in particular active metabolites.

Some of the compounds may form "solvates". For the purposes of the invention the term "solvates" refers to those forms of the compounds which form, in the solid or liquid state, a complex by coordination with solvent molecules. Hydrates are a specific form of solvates in which the coordination takes place with water.

It will be evident that the atoms within the compounds according to the present invention may exist in form of different isotopes. Therefore specific isotopes are not mentioned individually, but are considered to be comprised by the definitions as used herein. For example, the term hydrogen shall comprise deuterium as well or the genius as defined herein shall comprise compounds of the invention in which one atom is enriched by a specific isotope (isotopically labelled compound) etc.

"Scaffold": The scaffold of the compounds according to the present invention is represented by the following core structure, the numeration of which is indicated in bold (pyrazolopyrimdin-4-one representation):

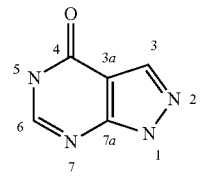

It will be evident for the skilled person in the art, that this scaffold can be described by its tautomeric "enol" form (enol-representation):

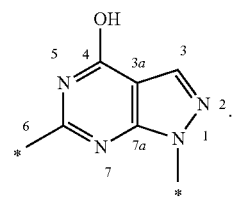

In the context of the present invention both structural representations of the scaffold shall be considered the subject of the present invention, even if only one of the two representatives is presented. It is believed that for the majority of compounds under ambient conditions and therewith under conditions which are the relevant conditions for a pharmaceutical composition comprising said compounds, the equilibrium of the tautomeric forms lies on the side of the pyrazolopyrimidin-4-one representation, which therefore is the preferred presentation of the compounds of the present invention (pyrazolopyrimdin-4-one-derivatives or more precisely pyrazolo[3,4-d]pyrimidin-4-one derivatives).

"Bonds": If within a chemical formula of a ring system or a defined group a substituent is directly linked to an atom or a group like "RyR" in below formula this shall mean that the substituent is attached to the corresponding atom. If however from another substituent like RxR a bond is not specifically linked to an atom of the ring system but drawn towards the centre of the ring or group this means that this substituent "RxR" may be linked to any meaningful atom of the ring system/group unless stated otherwise.

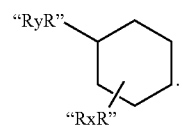

A hyphen (-) or a hyphen followed by an asterisk (-*) stands for the bond through which a substituent is bound to the corresponding remaining part of the molecule/scaffold. In cases in that the hyphen alone does not indicate the attachment point(s) sufficiently clear, the asterisk is added to the hyphen in order to determine the point of attachment of said bond with the corresponding main part of the molecule/scaffold.

In general, the bond to one of the herein defined heterocycloalkyl or heteroaryl groups may be effected via a C atom or optionally an N atom.

The term "aryl" used in this application denotes a phenyl, biphenyl, indanyl, indenyl, 1,2,3,4-tetrahydronaphthyl or naphthyl group. This definition applies for the use of "aryl" in any context within the present description in the absence of a further definition.

The term "$C_{1-n}$-alkyl" denotes a saturated, branched or unbranched hydrocarbon group with 1 to n C atoms, wherein n is a figure selected from the group of 2, 3, 4, 5, 6, 7, 8, 9, or 10, preferably from the group of 2, 3, 4, 5, or 6, more preferably from the group of 2, 3, or 4. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl etc. As will be evident from the context, such $C_{1-n}$-alkyl group optionally can be substituted.

This definition applies for the use of "alkyl" in any reasonable context within the present description in the absence of a further definition.

In cases in which the term "$C_{1-n}$-alkyl" is used in the middle of two other groups/substituents, like for example in "$C_{1-n}$-cycloalkyl-$C_{1-n}$-alkyl-O—", this means that the "$C_{1-n}$-alkyl"-moiety bridges said two other groups. In the present example it bridges the $C_{1-n}$-cycloalkyl with the oxygen like in "cyclopropyl-methyl-oxy-". It will be evident, that in such cases "$C_{1-n}$-alkyl" has the meaning of a "$C_{1-n}$-alkylene" spacer like methylene, ethylene etc. The groups that are bridged by "$C_{1-n}$-alkyl" may be bound to "$C_{1-n}$-alkyl" at any position thereof. Preferably the right hand group is located at the distal right hand end of the alkyl group (the C-atom numbered n, the n-position) and the left hand group at the distal left hand side of the alkyl group (the C-atom numbered 1, the 1-position). The same applies for other substituents.

The term "$C_{2-n}$-alkenyl" denotes a branched or unbranched hydrocarbon group with 2 to n C atoms and at least one C=C group (i.e. carbon-carbon double bond), wherein n preferably has a value selected from the group of 3, 4, 5, 6, 7, or 8, more preferably 3, 4, 5, or 6, more preferably 3 or 4. Examples of such groups include ethenyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc. As will be evident from the context, such $C_{2-n}$-alkenyl group optionally can be substituted.

This definition applies for the use of "alkenyl" in any reasonable context within the present description in the absence of a further definition if no other definition.

In cases in which the term "$C_{2-n}$-alkenyl" is used in the middle of two other groups/substituents, the analogue definition as for $C_{1-n}$-alkyl applies.

The term "$C_{2-n}$-alkynyl" denotes a branched or unbranched hydrocarbon group with 2 to n C atoms and at least one C≡C group (i.e. a carbon-carbon triple bond), wherein n preferably has a value selected from the group of 3, 4, 5, 6, 7, or 8, more preferably 3, 4, 5, or 6, more preferably 3 or 4. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. As will be evident from the context, such $C_{2-n}$-alkynyl group optionally can be substituted.

This definition applies for the use "alkynyl" in any reasonable context within the present description in the absence of a further definition.

In cases in which the term "$C_{2-n}$-alkynyl" is used in the middle of two other groups/substituents, the analogue definition as for $C_{1-n}$-alkyl applies.

The term "$C_{3-n}$-cycloalkyl" denotes a saturated monocyclic group with 3 to n C ring atoms with no heteroatoms within the ringsystem. n preferably has a value of 4 to 8 (=4, 5, 6, 7, or 8), more preferably 4 to 7, more preferably such $C_{3-n}$-cycloalkyl is 5 or 6 membered. Examples of such groups include cyclopropyl, cyclobutyl, cyclopentyl, cyclohexyl, cycloheptyl etc. This definition applies for "cycloalkyl" in any reasonable context within the present description in the absence of a further definition.

The term "$C_{4-n}$-cycloalkenyl" denotes an unsaturated, preferably a partly unsaturated, but in any case a not aromatic monocyclic group with 4 to n C ring atoms with no heteroatoms within the ringsystem. n preferably has a value of 4, 5, 6, 7 or 8, more preferably 4, 5, 6 or 7, more preferably $C_{4-n}$-cycloalkenyl is 5 or 6 membered. Examples of such groups include cyclobutenyl, cyclopentenyl, cyclohexenyl, cycloheptenyl etc. There may be one double bond in case of 4, 5, 6, 7 and 8 membered ring systems, two double bonds in 5, 6, 7 and 8 membered ring systems, three double bonds in 7 and 8 membered ring systems and four double bonds in a 8 membered group. This definition applies for the use "cycloalkenyl" in any context within the present description in the absence of a further definition.

The term "halogen" denotes an atom selected from F, Cl, Br, and I.

The term "heteroaryl" used in this application denotes a heterocyclic, mono- or bicyclic aromatic ring system which includes within the ring system itself in addition to at least one C atom one or more heteroatom(s) independently selected from N, O, and/or S. A monocyclic ring system preferably consists of 5 to 6 ring members, a bicyclic ring system preferably consists of 8 to 10 ring members. Preferred are heteroaryls with up to 3 heteroatoms, more preferred up to 2 heteroatoms, more preferred with 1 heteroatom. Preferred heteroatom is N. Examples of such moieties are benzimidazolyl, benzisoxazolyl, benzo[1,4]-oxazinyl, benzoxazol-2-onyl, benzofuranyl, benzoisothiazolyl, 1,3-benzodioxolyl, benzothiadiazolyl, benzothiazolyl, benzothienyl, benzoxadiazolyl, benzoxazolyl, chromanyl, chromenyl, chromonyl, cinnolinyl, 2,3-dihydrobenzo[1,4]dioxinyl, 2,3-dihydrobenzofuranyl, 3,4-dihydrobenzo[1,4]oxazinyl, 2,3-dihydroindolyl, 1,3-dihydroisobenzofuranyl, 2,3-dihydroisoindolyl, 6,7-dihydropyrrolizinyl, dihydroquinolin-2-onyl, dihydroquinolin-4-onyl, furanyl, imidazo[1,2-a]pyrazinyl, imidazo[1,2-a]pyridyl, imidazolyl, imidazopyridyl, imidazo[4,5-d]thiazolyl, indazolyl, indolizinyl, indolyl, isobenzofuranyl, isobenzothienyl, isochromanyl, isochromenyl, isoindoyl, isoquinolin-2-onyl, isoquinolinyl, isothiazolyl, isoxazolyl, naphthyridinyl, 1,2,4-oxadiazoyl, 1,3,4-oxadiazoyl, 1,2,5-oxadiazoyl, oxazolopyridyl, oxazolyl, 2-oxo-2,3-dihydrobenzimidazolyl, 2-oxo-2,3-dihydroindolyl, 1-oxoindanyl, phthalazinyl, pteridinyl, purinyl, pyrazinyl, pyrazolo[1,5-a]pyridyl, pyrazolo[1,5-a]pyrimidinyl, pyrazolyl, pyridazinyl, pyridopyrimidinyl, pyridyl (pyridinyl), pyridyl-N-oxide, pyrimidinyl, pyrimidopyrimidinyl, pyrrolopyridyl, pyrrolopyrimidinyl, pyrrolyl, quinazolinyl, quinolin-4-onyl, quinolinyl, quinoxalinyl, 1,2,3,4-tetrahydroquinolinyl, 1,2,3,4-tetrahydroisoquinolinyl, tetrazolyl, 1,2,4-thiadiazolyl, 1,3,4-thiadiazolyl, 1,2,5-thiadiazolyl, thiazolyl, thieno[2,3-d]imidazolyl, thieno[3,2-b]pyrrolyl, thieno[3,2-b]thiophenyl, thienyl, triazinyl, or triazolyl.

Preferred heteroaryl groups are furanyl, isoxazolyl, pyrazolyl, pyridyl, pyrimidinyl, thienyl, and thiazolyl.

More preferred heteroaryl groups are oxadiazolyl, triazolyl, pyrazolyl, furanyl, pyrrolyl, pyridazinyl, pyrimidinyl, and pyridyl, more preferred is pyrazolyl and pyridyl.

The definition pyrazole includes the isomers 1H-, 3H- and 4H-pyrazole. Preferably pyrazolyl denotes 1H-pyrazolyl.

The definition imidazole includes the isomers 1H-, 2H- and 4H-imidazole. A preferred definition of imidazolyl is 1H-imidazolyl.

The definition triazole includes the isomers 1H-, 3H- and 4H-[1,2,4]-triazole as well as 1H-, 2H- and 4H-[1,2,3]-triazole. The definition triazolyl therefore includes 1H-[1,2,4]-triazol-1-, -3- and -5-yl, 3H-[1,2,4]-triazol-3- and -5-yl, 4H-[1,2,4]-triazol-3-, -4- and -5-yl, 1H-[1,2,3]-triazol-1-, -4- and -5-yl, 2H-[1,2,3]-triazol-2-, -4- and -5-yl as well as 4H-[1,2,3]-triazol-4- and -5-yl.

The term tetrazole includes the isomers 1H-, 2H- and 5H-tetrazole. The definition tetrazolyl therefore includes 1H-tetrazol-1- and -5-yl, 2H-tetrazol-2- and -5-yl and 5H-tetrazol-5-yl.

The definition indole includes the isomers 1H- and 3H-indole. The term indolyl preferably denotes 1H-indol-1-yl.

The term isoindole includes the isomers 1H- and 2H-isoindole.

This definition applies for "heteroaryl" in any reasonable context within the present description in the absence of a further definition, in particular with regard to the preferred and most preferred representatives of the above definition.

The term "heterocycloalkyl" within the context of the present invention denotes a saturated 3 to 8 membered, preferably 5-, 6- or 7-membered ring system or a 5-12 membered bicyclic ring system, which include 1, 2, 3 or 4 heteroatoms, selected from N, O, and/or S. Preferred are 1, 2, or 3 heteroatoms. The preferred number of carbon atoms is 3 to 8 with 1, 2, 3 or 4 heteroatoms selected from N, O, and/or S. Such heterocycloalkyl groups are addressed as $C_{3-8}$-heterocycloalkyl.

Preferred are saturated heterocycloalkyl rings with 5, 6, 7 or 8 ring atoms, of which 1 or 2 are heteroatoms and the remaining are C-atoms.

Wherever $C_{3-8}$-heterocycloalkyl-substituents are mentioned, the preferred embodiments thereof are 5-, 6-,- or 7-membered cycles, more preferably monocycles. They include 1, 2, 3, or 4 heteroatoms, selected from N, O, and/or S, whereby 1 or 2 such heteroatoms are preferred, more preferably 1 such heteroatom. In case of a nitrogen containing heterocycloalkyl ring system, the nitrogen may be the atom by which the heterocycloalkyl ring is attached to the main body of the compound in total. In another embodiment the nitrogen may saturate its third valence (two binding sites are occupied within the ring system) by binding another radical. Preferred example for heterocycloalkyl include morpholinyl, piperidinyl, piperazinyl, thiomorpholinyl, oxathianyl, dithianyl, dioxanyl, pyrrolidinyl, tetrahydrofuranyl, dioxolanyl, oxathiolanyl, imidazolidinyl, tetrahydropyranyl, pyrrolinyl, tetrahydrothienyl, oxazolidinyl, homopiperazinyl, homopiperidinyl, homomorpholinyl, homothiomorpholinyl, azetidinyl, 1,3-diazacyclohexyl or pyrazolidinyl group.

This definition applies for "heterocycloalkyl" in any reasonable context within the present description in the absence of a further specific definition.

The term "oxo" denotes an oxygen atom as substituent that is bonded by a double bond, preferably it is bonded to a C-atom. In case oxo is used as a substituent, the oxo formally replaces two hydrogen atoms of the corresponding C-atom of the unsubstituted compound.

The following schemes shall illustrate a process to manufacture the compounds of the present invention by way of example:

Scheme 1

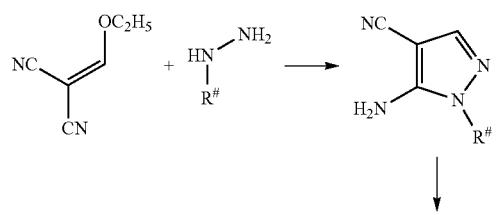

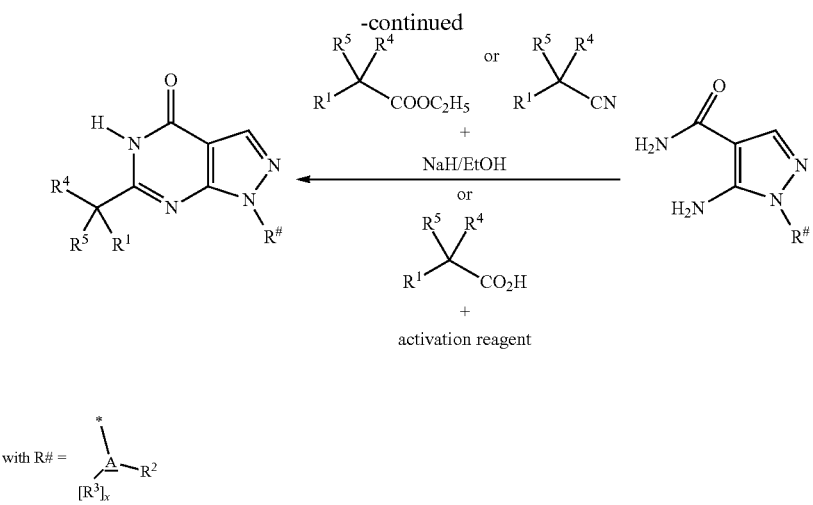

Scheme 1: In a first step 2-ethoxymethylene-malononitrile is condensed with mono-substituted hydrazines by heating in an appropriate solvent like ethanol in the presence of a base (e.g. triethylamine) to form 5-amino-1H-pyrazole-4-carbonitriles. These compounds are converted in a second step to the corresponding amides, e.g. by treatment of an ethanolic solution with ammonia (25% in water) and hydrogen peroxide (35% in water). In a third step, heating with carboxylic esters under basic conditions (e.g sodium hydride in ethanol) or carboxylic acids with an activation reagent (e.g. polyphosphoric acid) leads to pyrazolo[3,4-d]pyrimidin-4-ones as final products [cf., for example, A. Miyashita et al., *Heterocycles* 1990, 31, 1309ff].

The mono-substituted hydrazine derivatives, that are used in step 1 of scheme 1 can be prepared either by nucleophilic displacement on the corresponding mesylate derivative (scheme 2a) or by reduction of the hydrazone intermediate as depicted in scheme 2b [cf., for example, J. W. Timberlake et al., "*Chemistry of Hydrazo-, Azo-, and Azoxy Groups*"; Patai, S., Ed.; 1975, Chapter 4; S. C. Hung et al., *Journal of organic Chemistry* 1981, 46, 5413-5414].

Scheme 2a

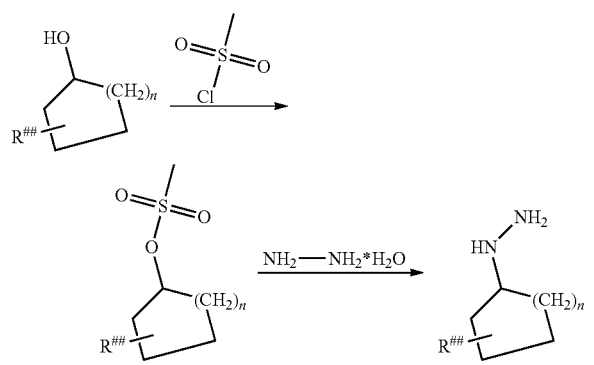

$R^{\#\#} = R^2$ and optionally $R^3$
$n = 1, 2, 3$

Scheme 2b

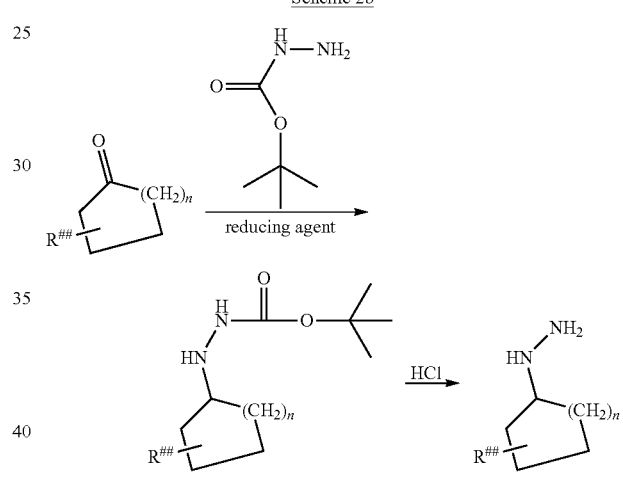

$R^{\#\#} = R^2$ and optionally $R^3$
$n = 1, 2, 3$

Scheme 3 illustrates an alternative method to prepare the final compounds: in these exemplified manufacturing method 5-amino-1H-pyrazole-4-carboxylic acid amides are condensed in a first step with an appropriate ester derivative followed in a second step by alkylation with suitable electrophiles.

Scheme 3

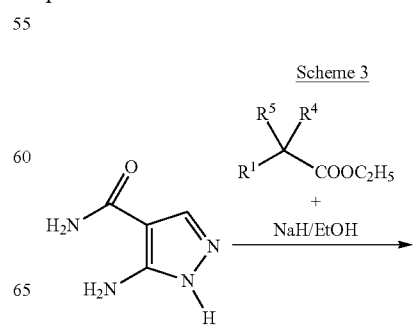

-continued

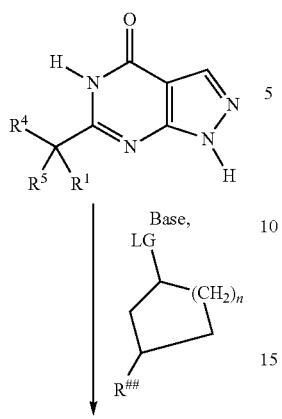

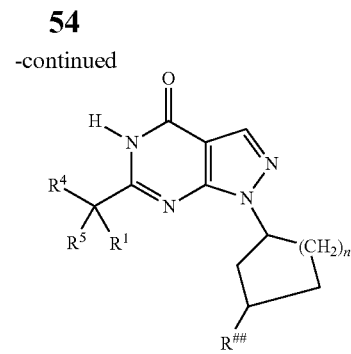

$R^{\#\#} = R^2$ or $R^3$
LG = Br—, Cl—, I—, CH$_3$—SO$_2$—O—, p-toluenesulphonyl-
n = 1, 2
Base = N(C$_2$H$_5$)$_3$, KOtBu, NaH Scheme 4 illustrates alternative methods to prepare the final compounds: in the exemplified manufacturing methods 5-amino-1H-pyrazole-4-carboxylic acid amides are condensed in a first step with (2-bromo-phenyl)-acetic acid ester derivatives followed in a second step by substitution of the bromine atom by an aromatic or heteroaromatic residue e.g. using Suzuki or Ullmann type reaction conditions.

Scheme 4

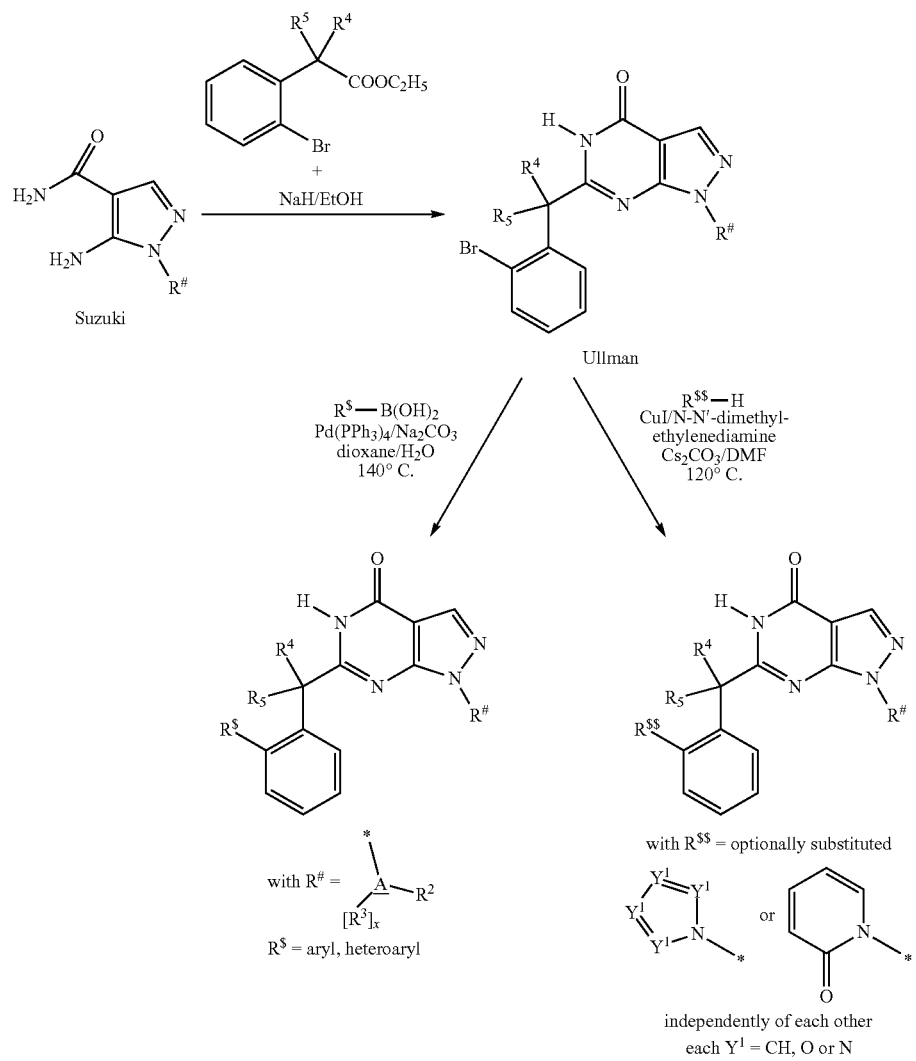

Scheme 5 illustrates an alternative method to prepare the final compounds: in the exemplified manufacturing method 5-amino-1H-pyrazole-4-carboxylic acid amides are condensed in a first step with (2-cyano-phenyl)-acetic acid ester derivatives followed in a second step by transformation of the nitrile group into a 5-membered heteroaromatic group.

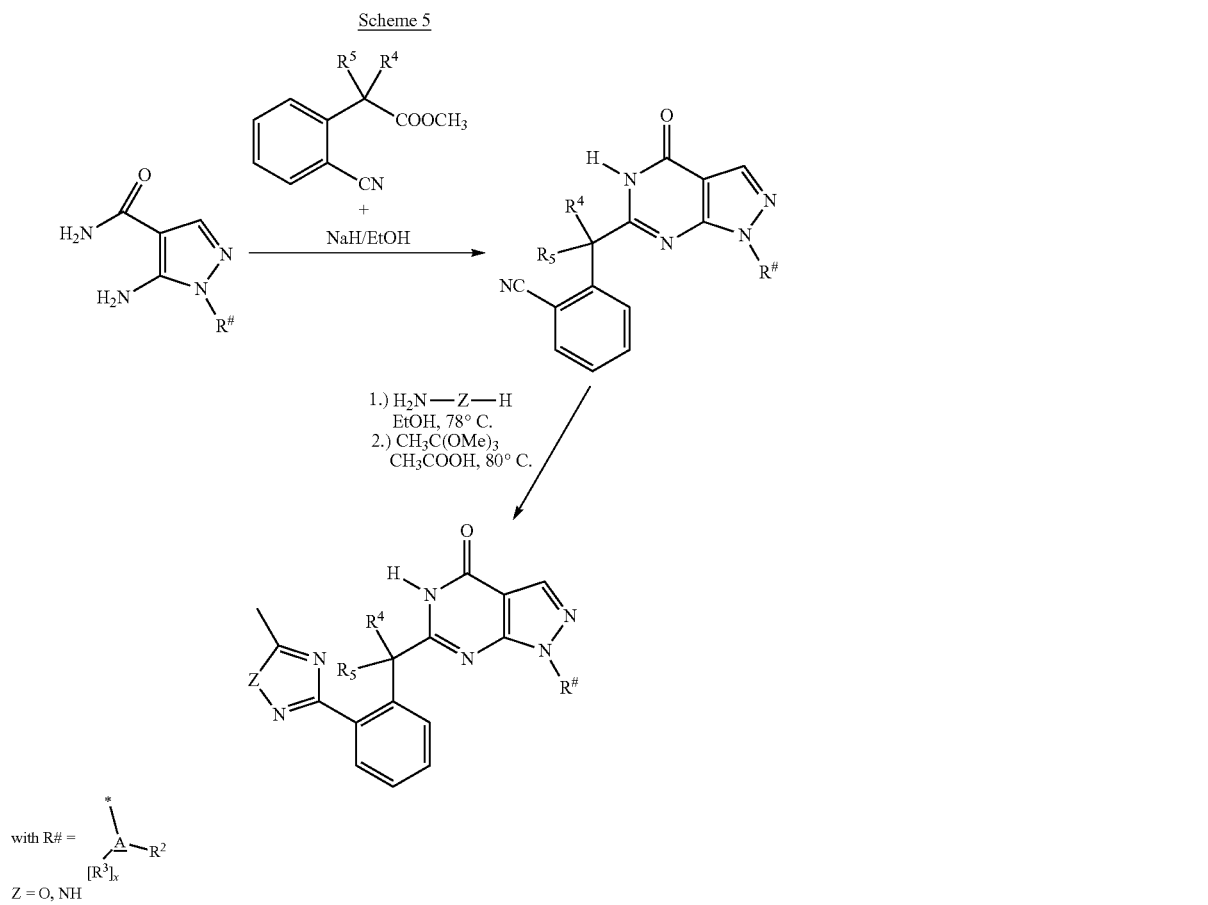

Further alternative processes for preparing pyrazolo[3,4-d]pyrimidin-4-ones are known in the art and can likewise be employed for synthesizing the compounds of the invention (see, for example: P. Schmidt et al., *Helvetica Chimica Acta* 1962, 189, 1620ff.).

Further information also can be found in WO04099210 (in particular page 9, last paragraph to page 14, line 8, incorporated by reference).

The compounds of the invention show a valuable range of pharmacological effects which could not have been predicted. They are characterised in particular by inhibition of PDE9A.

Preferably the compounds according to the present invention show a high selectivity profile in view of inhibiting or modulating specific members within the PDE9 family or other PDE families, with a clear preference (selectivity) towards PDE9A inhibition.

The compounds of the present invention are supposed to show a favourable safety profile for the purpose of treatment.

The compounds of the present invention are supposed to show a favourable profile with respect to metabolic stability over a certain period of time for the purpose of treatment.

The compounds of the present invention are supposed to show a favourable profile with respect to bioavailability for the purpose of treatment.

Method of Treatment

The present invention refers to compounds, which are considered effective and selective inhibitors of phosphodiesterase 9A and can be used for the development of medicaments. Such medicaments shall preferably be used for the treatment of diseases in which the inhibition of PDE9A can evolve a therapeutic, prophylactic or disease modifying effect. Preferably the medicaments shall be used to improve perception, concentration, cognition, learning or memory, like those occurring in particular in situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

Another aspect of the present invention concerns the treatment of a disease which is accessible by PDE9A modulation, in particular sleep disorders like insomnia or narcolepsy, bipolar disorder, metabolic syndrome, obesity, diabetes mellitus, including type 1 or type 2 diabetes, hyperglycemia, dyslipidemia, impaired glucose tolerance, or a disease of the testes, brain, small intestine, skeletal muscle, heart, lung, thymus or spleen.

Thus the medical aspect of the present invention can be summarised in that it is considered that a compound according to any of the genius embodiments of the invention as outlined herein or a compound selected from the group of the specifically disclosed final compounds of the examples is used as a medicament.

Such a medicament preferably is for the treatment of a CNS disease.

In an alternative use, the medicament is for the treatment of a CNS disease, the treatment of which is accessible by the inhibition of PDE9.

In an alternative use, the medicament is for the treatment of a disease that is accessible by the inhibition of PDE9.

In an alternative use, the medicament is for the treatment, amelioration and/or prevention of cognitive impairment being related to perception, concentration, cognition, learning or memory.

In an alternative use, the medicament is for the treatment amelioration and/or prevention of cognitive impairment being related to age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

In an alternative use, the medicament is for the treatment of Alzheimer's disease.

In an alternative use, the medicament is for the treatment of sleep disorders, bipolar disorder, metabolic syndrome, obesity, diabetis mellitus, hyperglycemia, dyslipidemia, impaired glucose tolerance, or a disease of the testes, brain, small intestine, skeletal muscle, heart, lung, thymus or spleen.

Pharmaceutical Compositions

Medicaments for administration comprise a compound according to the present invention in a therapeutically effective amount. By "therapeutically effective amount" it is meant that if the medicament is applied via the appropriate regimen adapted to the patient's condition, the amount of said compound of formula (I) will be sufficient to effectively treat, to prevent or to decelerate the progression of the corresponding disease, or otherwise to ameliorate the estate of a patient suffering from such a disease. It may be the case that the "therapeutically effective amount" in a mono-therapy will differ from the "therapeutically effective amount" in a combination therapy with another medicament.

The dose range of the compounds of general formula (I) applicable per day is usually from 0.1 to 5000 mg, preferably 0.1 to 1000 mg, preferably from 2 to 500 mg, more preferably from 5 to 250 mg, most preferably from 10 to 100 mg. A dosage unit (e.g. a tablet) preferably contains between 2 and 250 mg, particularly preferably between 10 and 100 mg of the compounds according to the invention.

The actual pharmaceutically effective amount or therapeutic dosage will of course depend on factors known by those skilled in the art such as age, weight, gender or other condition of the patient, route of administration, severity of disease, and the like.

The compounds according to the invention may be administered by oral, parenteral (intravenous, intramuscular etc.), intranasal, sublingual, inhalative, intrathecal, topical or rectal route. Suitable preparations for administering the compounds according to the present invention include for example patches, tablets, capsules, pills, pellets, dragees, powders, troches, suppositories, liquid preparations such as solutions, suspensions, emulsions, drops, syrups, elixirs, or gaseous preparations such as aerosols, sprays and the like. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

The dosage of the compounds according to the invention is naturally highly dependent on the method of administration and the complaint which is being treated. When administered by inhalation the compounds of formula (I) are characterised by a high potency even at doses in the microgram range. The compounds of formula (I) may also be used effectively above the microgram range. The dosage may then be in the gram range, for example.

Combinations with Other Active Substances

In another aspect the present invention relates to the above mentioned pharmaceutical formulations as such which are characterised in that they contain a compound according to the present invention.

A further aspect of the present invention refers to a combination of each of the compounds of the present invention, preferably at least one compound according to the present invention with another compound selected from the group of for example beta-secretase inhibitors; gamma-secretase inhibitors; gamma-secretase modulators; amyloid aggregation inhibitors such as e.g. alzhemed; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having AR lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5 and/or PDE10 inhibitors, GABAA receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; metabotropic glutamate receptor 5 positive modulators; metabotropic glutamate receptor 2 antagonists, and other substances that modulate receptors or enzymes in a manner such that the efficacy and/or safety of the compounds according to the invention is increased and/or unwanted side effects are reduced.

This invention further relates to pharmaceutical compositions containing one or more, preferably one active substance. At least one active substance is selected from the compounds according to the invention and/or the corresponding salts thereof. Preferably the compositno comprises only one such active compound. In case of more than one active compound the other one can be selected from the aforementioned group of combination partners such as alzhemed, vitamin E, ginkolide, donepezil, rivastigmine, tacrine, galantamine, memantine, ibutamoren mesylate, capromorelin, minocyclin and/or rifampicin. Optionally the compositon comprises further ingreideints such as inert carriers and/or diluents.

The compounds according to the invention may also be used in combination with immunotherapies such as e.g. active immunisation with Abeta or parts thereof or passive immunisation with humanised anti-Abeta antibodies or antibody-fragments for the treatment of the above mentioned diseases and conditions.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e the compounds of the present invention are provided in one dosage form and one or more of the above mentioned combination partners is provided in another dosage form. These two dosage forms may be equal dosage forms, for example a co-administration of two tablets, one containing a therapeutically effective amount of the compound of the present invention and one containing a therapeutically effective amount of the above mentioned combination partner. It is also possible to combine different administration forms, if desired. Any type of suitable administration forms may be provided.

The compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above mentioned combination partners is expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.). It is preferred that the compounds of the invention be administered either three or fewer times, more preferably once or twice daily.

EXAMPLES

Pharmaceutical Compositions

The following examples propose pharmaceutical formulations that may illustrate the present invention without restricting its scope:

The term "active substance" denotes one or more compounds according to the invention including the salts thereof.

Example A

Tablets containing 100 mg of active substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Example B

Tablets containing 150 mg of active substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Example C

Hard gelatine capsules containing 150 mg of active substance 1 capsule contains:

| | |
|---|---|
| active substance | 150.0 mg |
| corn starch (dried) | approx. 80.0 mg |
| lactose (e.g. granulated) | approx. 87.0 mg |
| magnesium stearate | 3.0 mg |
| | approx. 320.0 mg |

Capsule shell: size 1 hard gelatine capsule.

Example D

Suppositories containing 150 mg of active substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Example E

Ampoules containing 10 mg active substance

Composition:

| | |
|---|---|
| active substance | 10.0 mg |
| 0.01N hydrochloric acid | q.s. |
| double-distilled water | ad 2.0 mL |

Example F

Ampoules containing 50 mg of active substance

Composition:

| | |
|---|---|
| active substance | 50.0 mg |
| 0.01N hydrochloric acid | q.s. |
| double-distilled water | ad 10.0 mL |

The preparation of any the above mentioned formulations can be done following standard procedures.

Biological Assay

The in vitro effect of the compounds of the invention can be shown with the following biological assays.

PDE9A2 Assay Protocol:

The PDE9A2 enzymatic activity assay was run as scintillation proximity assay (SPA), in general according to the protocol of the manufacturer (Amersham Biosciences, product number: TRKQ 7100).

As enzyme source, lysate (PBS with 1% Triton X-100 supplemented with protease inhibitors, cell debris removed by centrifugation at 13.000 rpm for 30 min) of SF 9 cell expressing the human PDE9A2 was used. The total protein amount included in the assay varied upon infection and production efficacy of the SF9 cells and lay in the range of 0.1-100 ng.

In general, the assay conditions were as follows:
total assay volume: 40 microliter
protein amount: 0.1-50 ng
substrate concentration (cGMP): 20 nanomolar; ~1 mCi/l
incubation time: 60 min at room temperature
final DMSO concentration: 0.2-1

The assays were run in 384-well format. The test reagents as well as the enzyme and the substrate were diluted in assay buffer. The assay buffer contained 50 mM Tris, 8.3 mM $MgCl_2$, 1.7 mM EGTA, 0.1% BSA, 0.05% Tween 20; the pH of assay buffer was adjusted to 7.5. The reaction was stopped by applying a PDE9 specific inhibitor (e.g. compounds according to WO04099210 or WO04099211) in excess.

Determination of % Inhibition:

The activity of the positive control (minus the negative control=background) is set to 100% and activity in the presence of test compound is expressed relative to these 100%. Within this setting, an inhibition above 100% might be possible due to the nature of the variation of the positive control within the assay. In the following inhibition of PDE 9A2 is presented for a concentration at 10 μM, if not indicated otherwise.

Determination of $IC_{50}$:

$IC_{50}$ can be calculated with GraphPadPrism or other suited software setting the positive control as 100 and the negative control as 0. For calculation of $IC_{50}$ dilutions of the test compounds (substrates) are to be selected and tested following the aforementioned protocol.

Data

In the following, % inhibition data will illustrate that the compounds according to the present invention are suited to inhibit PDE9 and thus provide useful pharmacological properties. The examples are not meant to be limiting. The table also provides $IC_{50}$ values. The values are presented as being within a nanomolar range (nM), i.e. within the range of either 1 nanomolar to 100 nanomolar or within the range of 101 nanomolar to 1200 nanomolar. The specific $IC_{50}$ value is within said range. The example number refer to the final examples as outlined in the section "Exemplary embodiments".

All data are measured according to the procedure described herein.

| Example No. | % Inhibition* | IC50 range (nM) |
|---|---|---|
| 1 | 98 | 1-100 |
| 2 | 101 | 1-100 |
| 3 | 94 | 1-100 |
| 4 | 100 | 1-100 |
| 5 | 98 | 1-100 |
| 6 | 98 | 1-100 |
| 7 | 96 | 1-100 |
| 8 | 98 | 1-100 |
| 9 | 97 | 1-100 |
| 10 | 102 | 1-100 |
| 11 | 89 | 101-1500 |
| 12 | 83 | 101-1500 |
| 13 | 98 | 101-1500 |
| 14 | 94 | 101-1500 |
| 15 | 93 | 101-1500 |
| 16 | 104 | 1-100 |
| 17 | 103 | 1-100 |
| 18 | 100 | 1-100 |
| 19 | 100 | 1-100 |
| 20 | 104 | 1-100 |
| 21 | 103 | 1-100 |
| 22 | 104 | 1-100 |
| 23 | 100 | 101-1500 |
| 24 | 98 | 101-1500 |
| 25 | 103 | 1-100 |
| 26 | 100 | 1-100 |
| 27 | 104 | 1-100 |
| 28 | 91 | 101-1500 |
| 30 | 98 | 1-100 |
| 31 | 99 | 1-100 |
| 32 | 98 | 1-100 |
| 33 | 98 | 1-100 |
| 34 | 96 | 101-1500 |
| 35 | 94 | 1-100 |
| 36 | 99 | 1-100 |
| 37 | 97 | 1-100 |
| 38 | 85 | 101-1500 |
| 39 | 84 | 101-1500 |
| 44 | 92 | 101-1500 |
| 45 | 97 | 1-100 |
| 46 | 98 | 1-100 |
| 47 | 98 | 1-100 |
| 48 | 96 | 101-1500 |
| 48-2 | 92 | 101-1500 |
| 48-3 | 95 | 1-100 |
| 48-4 | 99 | 1-100 |
| 48-5 | 93 | 101-1500 |
| 48-6 | 87 | 101-1500 |
| 49 | 99 | 1-100 |
| 50 | 95 | 101-1500 |
| 51 | 98 | 101-1500 |
| 52 | 98 | 1-100 |
| 53 | 100 | 1-100 |
| 54 | 102 | 1-100 |
| 55 | 100 | 1-100 |
| 56 | 99 | 1-100 |
| 57 | 101 | 1-100 |
| 58 | 101 | 1-100 |
| 59 | 95 | 101-1500 |
| 60 | 101 | 1-100 |
| 61 | 99 | 1-100 |
| 62 | 100 | 1-100 |
| 63 | 93 | 101-1500 |
| 64 | 97 | 1-100 |
| 65 | 101 | 1-100 |
| 66 | 100 | 1-100 |
| 67 | 99 | 1-100 |
| 68 | 96 | 101-1500 |
| 69 | 97 | 101-1500 |
| 70 | 100 | 1-100 |
| 71 | 98 | 1-100 |
| 72 | 97 | 101-1500 |
| 72-2 | 98 | 1-100 |
| 72-3 | 98 | 1-100 |
| 72-4 | 101 | 1-100 |
| 72-5 | 99 | 1-100 |
| 72-6 | 96 at 1 μM | 1-100 |
| 72-7 | 100 | 1-100 |
| 72-8 | 98 | 1-100 |
| 72-9 | 100 | 1-100 |
| 72-10 | 52 at 3.3 μM | 101-1500 |
| 72-11 | 84 | 1-100 |
| 73 | 98 | 1-100 |
| 74 | 98 | 1-100 |
| 75 | 101 | 1-100 |
| 76 | 99 | 1-100 |
| 77 | 100 | 1-100 |
| 78 | 97 | 1-100 |
| 79 | 95 | 101-1500 |
| 80 | 91 | 101-1500 |
| 81 | 95 | 101-1500 |
| 82 | 91 | 101-1500 |
| 83 | 88 | 101-1500 |
| 84 | 81 | 101-1500 |
| 85 | 94 | 101-1500 |
| 86 | 77 | 101-1500 |
| 87 | 81 | 101-1500 |
| 88 | 93 | 101-1500 |
| 89 | 98 | 1-100 |
| 90 | 97 | 1-100 |
| 91 | 95 | 1-100 |
| 92 | 93 | 101-1500 |
| 93 | 94 | 1-100 |
| 94 | 98 | 1-100 |
| 95 | 97 | 1-100 |
| 95-1 | 111 | 1-100 |
| 96 | 93 | 1-100 |
| 97 | 100 | 1-100 |
| 98 | 100 | 1-100 |
| 99 | 100 | 1-100 |
| 100 | 95 | 101-1500 |
| 101 | 100 | 1-100 |
| 102 | 96 | 101-1500 |
| 103 | 96 at 3.3 μM | 1-100 |
| 104 | 97 | 1-100 |
| 105 | 97 | 101-1500 |
| 106 | 83 | 1-100 |
| 107 | 100 | 1-100 |
| 108 | 99 | 1-100 |
| 109 | 93 | |
| 110 | 95 | |
| 111 | 74 | 1-100 |
| 112 | 97 | 1-100 |
| 113 | 98 | 1-100 |

*inhibition of PDE 9A2 at 10 μM, if not indicated otherwise

In Vivo Effect:

The in vivo effect of the compounds of this invention can be tested in the Novel Object Recognition test according to the procedure of Prickaerts et al. (*Neuroscience* 2002, 113, 351-361).

For further information concerning biological testing of the compounds of the present invention see also *Neuropharmacology* 2008, 55, 908-918.

Beside the inhibition property toward the target PE9, compounds according to the present invention may provide further pharmacokinetic properties of advantage. Among such properties may be a beneficial selectivity profile in view of the target, beneficial safety features, balanced metabolism, bioavailability, high fraction absorbed, blood brain transport properties, low risk of causing drug-drug interaction, balanced clearance, high mean residence time (mrt), favourable exposure in the effect compartment and so on.

Chemical Manufacture

ABBREVIATIONS

APCI Atmospheric Pressure Chemical Ionization
$CO_2$ (sc) supercritical carbon dioxide
DMSO dimethyl sulphoxide
DEA diethylamine
DIBAH diisobutylaluminiumhydride
DIPEA diisopropylethylamine
DMF dimethylformamide
EI electron ionization (in MS)
ESI electrospray ionization (in MS)
Exm. Example
Fp melting point
h hour(s)
HPLC high performance liquid chromatography
HPLC-MS coupled high performance liquid chromatography-mass spectroscopy
GC-MS gas chromatography with mass spectrometric detection
MPLC medium pressure liquid chromatography
min minutes
MS mass spectroscopy
$R_f$ retention factor
$R_t$ retention time (in HPLC)
TBTU O-(Benzotriazol-1-yl)-N,N,N',N'-tetramethyluroniumtetrafluorborat
TEA triethylamine
TFA trifluoroacetic acid
THF tetrahydrofuran
TLC thin-layer chromatography LC-MS Methods:

Method 1 (M1)

MS apparatus type: Waters Micromass ZQ; HPLC apparatus type: Waters Alliance 2695, Waters 2996 diode array detector; column: Varian Microsorb 100 C18, 30×4.6 mm, 3.0 µm; eluent A: water+0.13% TFA, eluent B: acetonitrile; gradient: 0.0 min 5% B→0.18 min 5% B→2.0 min 98% B→2.2 min 98% B→2.3 min 5% B→2.5 min 5% B; flow rate: 3.5 mL/min; UV detection: 210-380 nm.

Method 1E Hydro (M1Eh)

Instrument: LC/MS ThermoFinnigan. Hplc Surveyor DAD, MSQ Quadrupole; column: Synergi Hydro-RP80A, 4 um, 4.60×100 mm; eluent A: 90% water+10% acetonitrile+ammonium formate 10 mM; eluent B=ACN 90%+10% $H_2O$+$NH_4COOH$ 10 mM; gradient: A(100) for 1.5 min, then to B (100) in 10 min for 1.5 min; flow rate: 1.2 mL/min; UV Detection: 254 nm; Ion source: APCI.

Method A (MA)

Instrument: HPLC/MS ThermoFinnigan. HPLC Surveyor DAD, LCQduo Ion trap.; column: Sunryse MS-C18, 5 um, 4.6×100 mm; eluent A: water+20 mM ammonium formate; eluent B: acetonitrile+20 mM ammonium formate; gradient: NB (95:5) for 1 min, then to A/B (5:95) in 7 min for 1.5 min; flow rate: 0.85 mL/min; UV detection: 254 nm; ion source: ESI.

Method 1D (M1D)

Instrument:HPLC-MS ThermoFinnigan. HPLC Surveyor DAD, MSQ Quadrupole; column: Sunryse MS-C18, 5 um, 4.6×100 mm; eluent A: 90% water+10% acetonitrile+ammonium formate 10 mM; eluent B: acetonitrile 90%+10% water+ammonium formate 10 mM; gradient: A (100) for 1 min, then to B (100) in 7 min for 1 min; flow rate: 1.2 mL/min; UV detection: 254 nm; ion source: APCI.

Method 1E (M1E)

Instrument: HPLC-MS ThermoFinnigan. HPLC Surveyor DAD, MSQ Quadrupole; column: Symmetry C8, 5 µm, 3×150 mm; eluent A: 90% water+10% acetonitrile+ammonium formate 10 mM; eluent B: acetonitrile 90%+10% $H_2O$+ammonium formate 10 mM; gradient: A (100) for 1.5 min, then to B (100) in 10 min for 1.5 min; flow rate: 1.2 mL/min; UV detection: 254 nm; ion source: APCI.

Method 1E Fusion (M1Ef)

Instrument: HPLC-MS ThermoFinnigan. HPLC Surveyor DAD, MSQ Quadrupole; column: Synergi Fusion-RP80A, 4 µm, 4.60×100 mm; eluent A: 90% water+10% acetonitrile+ammonium formate 10 mM; eluent B: acetonitrile 90%+10% $H_2O$+ammonium formate 10 mM; gradient: A (100%) for 1.5 min, then to B (100%) in 10 min for 1.5 min; flow rate: 1.2 mL/min; UV detection: 254 nm; ion source: APCI.

Method 1F (M1F)

Instrument: HPLC-MS ThermoFinnigan. HPLC Surveyor DAD, Surveyor MSQ single quadrupole; column: Eclipse XDB-C18, 3.5 µm, 4.6×100 mm; eluent A: 90% water+10% acetonitrile+$NH_4COOH$ 10 mM; eluent B: acetonitrile 90%+10% water+$NH_4COOH$ 10 mM; gradient: A (100) for 1.5 min, then to B (100) in 10 min for 3 min; flow rate: 1.2 mL/min; UV detection: 254 nm; ion source: APCI.

Method 2F (M2F)

Instrument: HPLC-MS ThermoFinnigan. HPLC Surveyor DAD, Finnigan LCQduo Ion trap; column: Symmetry-C18, 5 um, 3×150 mm; eluent A: 95% water+5% acetonitrile+formic acid 0.1%; eluent B: acetonitrile 95%+5% water+formic acid 0.1%; gradient: NB (95/5) for 1.5 min, then to NB (5/95) in 10 min for 1.5 min; flow rate: 1 mL/min; UV detection: 254 nm; ion source: ESI.

Method 2L (M2L)

Instrument: HPLC-MS ThermoFinnigan. HPLC Surveyor DAD, Finnigan LCQduo Ion trap;
column: Symmetry Shield, 5 um, 4.6×150 mm; eluent A: 90% water+10% acetonitrile+formic acid 0.1%; eluent B: acetonitrile 90%+10% water+formic acid 0.1%; flow rate: 0.85 mL/min; UV detection: 254 nm; ion source: ESI.

Method 2M (M2M)

Instrument: HPLC-MS ThermoFinnigan. HPLC Surveyor DAD, Finnigan LCQduo Ion trap; column: Symmetry Shield RPB, 5 um, 4.6×150 mm; eluent A: 90% water+10% acetonitrile+formic acid 0.1%; eluent B: acetonitrile 90%+10% water+formic acid 0.1%; gradient: NB (90/10) for 1.5 min, then to NB (10/90) in 10 min for 2 min; flow rate: 1.2 mL/min; UV detection: 254 nm; ion source: APCI.

Method Grad_C8_acidic (MGC8a)

Instrument: HPLC-MS Waters. HPLC Alliance 2695 DAD, ZQ Quadrupole; column: Xterra MS-C8, 3.5 µm, 4.6× 50 mm; eluent A: water+0.1% TFA+10% acetonitrile; eluent B: acetonitrile; gradient:NB (80:20), then to NB (10:90) in 3.25 min for 0.75 min; flow rate: 1.3 mL/min; UV detection: 254 nm; ion source: ESI.

Method Grad_C18_acidic (MGC18a)

Instrument: HPLC-MS Waters. HPLC Alliance 2695 DAD, ZQ Quadrupole; column: Sunfire MS-C18, 3.5 µm, 4.6×50 mm; eluent A: water+0.1% TFA+10% acetonitrile; eluent B: acetonitrile; gradient:NB (80:20), then to NB (10:90) in 3.25 min for 0.75 min; flow rate: 1.3 mL/min; UV detection: 254 nm; ion source: ESI.

Method Grad_90_10_C8 acidic (MG90C8a)

Instrument: HPLC-MS Waters. HPLC Alliance 2695 DAD, ZQ Quadrupole; column: Xterra MS-C8, 3.5 µm, 4.6×50 mm; eluent A: water+0.1% TFA+10% acetonitrile; eluent B: acetonitrile; gradient: A (100%), then to NB (10:90) in 3.25 min for 0.75 min; flow rate: 1.3 mL/min; UV detection: 254 nm; ion source: ESI.

Method Grad_90_10_C18 acidic (MG90C18a)

Instrument: HPLC-MS Waters. HPLC Alliance 2695 DAD, ZQ Quadrupole; column: Xterra MS-C18, 3.5 µm, 4.6×50 mm; eluent A: water+0.1% TFA+10% acetonitrile; eluent B: acetonitrile; gradient: A (100), then to NB (10:90) in 3.25 min for 0.75 min; flow rate: 1.3 mL/min; UV detection: 254 nm; ion source: ESI.

Method Grad_C8_$NH_4COOH$ (MGC8N)

Instrument: HPLC-MS Waters. HPLC Alliance 2695 DAD, ZQ Quadrupole. Column: Xterra MS-C8, 3.5 µm, 4.6×50 mm; eluent A: water+ammonium formate 5 mM+10% acetonitrile; eluent B: acetonitrile; gradient: A 100%, then to NB (10:90) in 3.25 min for 0.75 min; flow rate: 1.3 mL/min; UV detection: 254 nm; ion source: ESI.

Method 2 (M2)

MS apparatus type: Waters Micromass ZQ; HPLC apparatus type: Waters Alliance 2695, Waters 2996 diode array detector; column: Varian Microsorb 100 C18, 30×4.6 mm, 3.0 µm; eluent A: water+0.13% TFA, eluent B: methanol; gradient: 0.00 min 5% B→0.35 min 5% B→3.95 min 100% B→4.45 min 100% B→4.55 min 5% B→4.90 min 5% B; flow rate: 2.4 mL/min; UV detection: 210-380 nm.

Chiral HPLC Methods

Instrument: Agilent 1100. Column: Chiralpak AS-H Daicel, 4.6 µm, 4.6×250 mm;

Method Chiral 1: eluent: hexane/ethanol 97/3 (isocratic); flow rate: 1.0 mL/min; UV detection: 254 nm.

Method Chiral 2: eluent: hexane/ethanol 98/2 (isocratic); flow rate: 1.0 mL/min; UV detection: 254 nm.

Instrument: Agilent 1100. Column: Chiralpak AD-H Daicel, 4.6 µm, 4.6×250 mm;

Method Chiral 3: eluent: hexane/methanol+DEA 85/15 (isocratic); flow rate: 4.0 mL/min; UV Detection: 254 nm.

Instrument: Berger "Analytix" Column: Chiralpak IC Daicel, 5 µm, 4.6 mm×250 mm;

Method Chiral 4: eluent: $CO_2$ (sc)/25% isopropanol/0.2% DEA (isocratic); flow rate: 4 mL/min; Temp: 40° C.; Backpressure: 100 bar; UV Detection: 210/220/254 nm.

Instrument: Berger Multigram II. Column: 2× Chiralpak IC Daicel, 5 µm, 20 mm×250 mm;

Method Chiral 5: eluent: $CO_2$ (sc)/25% isopropanol/0.2% DEA (isocratic); flow rate: 50 mL/min; Temp: 40° C.; Pressure 100 bar; UV Detection 220 nm.

GC/MS Methods

Method 3A (M3A)

Instrument: GC/MS Finnigan. Trace GC, MSQ quadrupole; Column: DB-5MS, 25 m×0.25 mm×0.25 µm; Carrier Gas: Helium, 1 mL/min constant flow. Oven program: 50° C. (hold 1 minute) to 100° C. in 10° C./min, to 200° C. in 20° C./min, to 300° C. in 30° C./min; detection: Trace MSQ, quadrupole Ion source: IE Scan range: 50-450 uma.

Method 3A.1 (M3A.1)

Instrument: GC/MS Finnigan Thermo Scientific. Trace GC Ultra, DSQ II single quadrupole. Column: DB-5MS UI, 25 m×0.25 mm×0.25 µm; carrier gas: helium, 1 mL/min constant flow; oven program: 50° C. (hold 1 minute), to 100° C. in 10° C./min, to 200° C. in 20° C./min, to 300° C. in 30° C./min eluent, detection: trace DSQ, single quadrupole.

Microwave Heating:

Microwave Apparatus Types:

Discover® CEM instruments, equipped with 10 and 35 mL vessels;

Microwave apparatus type: Biotage Initiator Sixty.

General Comment Concerning the Presentation of the Structures

Some compounds have one or more chiral centres. The depicted structure will not necessarily show all the possible stereochemical realisation of the compound but only one. However, in such cases the depicted structure is complemented by a term like "cis-racemic mixture" in order to pin point to the other stereochemical options.

An example is given for Example 8B, below. The presented structural formula is

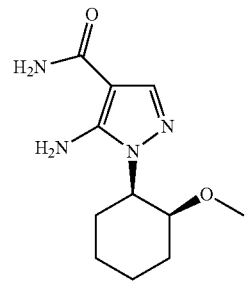 [SMILES: CO[C@H]1CCCC[C@H]1n1ncc(C(N)=O)c1N]

Cis-Racemic Mixture

The added term "cis-racemic mixture" points to the second stereochemical option:

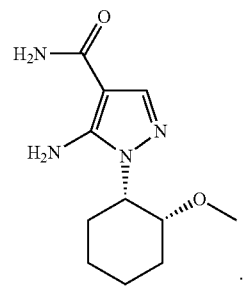 [SMILES: CO[C@@H]1CCCC[C@@H]1n1ncc(C(N)=O)c1N]

This principle applies to other depicted structures as well.

Synthesis

In the following the manufacture of compounds which exemplify the present invention is described. In case the process of manufacture of a specific compound has not been disclosed literally, the skilled person in the art will find a description of analogue procedures, which he can follow in principle, within this description or in the art. At some places in the following description it is said, the examples can be prepared in analogy to another example. If reference should be made to such an "analogue process" the reactions conditions are about the same, even if molar ratios of reagents and educts might to be adjusted. It also will be evident that starting materials within a described process can be varied chemically to achieve the same results, i.e. if a condensation reaction of an ester is described, in that the alcoholic component is a leaving group but not subject of the product, this alcoholic component may vary without significant changes of the procedure as such.

Starting materials are numbers by a figure followed by a letter (e.g. Example 1A), the exemplary embodiments of the invention are numbered by a figure (e.g. Example 1).

Starting Compounds:

Example 1A

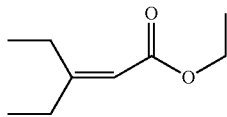

75.0 g (215 mmol) carbethoxymethylene triphenylphosphorane were suspended in 225 mL toluene. 100 mL (948 mmol) 3-pentanone and 5.50 g (45.0 mmol) benzoic acid were added. The reaction mixture was heated to 80° C. and stirred 2 days. After cooling to room temperature the reaction mixture was filtered and the filtrate was concentrated under reduced pressure. The residue was purified by vacuum distillation (30 mbar and 130° C. bath temperature, main fraction: 88° C.). 8.4 g (25%) of the product were obtained as an oil.

HPLC-MS (M1): $R_t$=1.71 min

Example 1B

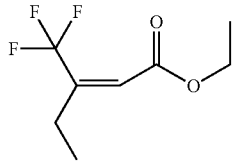

A solution of 70.0 g (201 mmol) carbethoxymethylene triphenylphosphorane in 300 mL diethyl ether was cooled to 0° C. and 25.0 g (198 mmol) 1,1,1-trifluorobutanone were added. The solution was warmed to room temperature and stirred over night. The reaction mixture was filtered and the filtrate was concentrated under reduced pressure. The residue was purified by vacuum distillation (170 mbar and 130° C. bath temperature, main fraction: 95-96° C.). 29.0 g (75%) of the product were obtained as an oil.

HPLC-MS (M1): $R_t$=1.77 min
MS (ESI pos): m/z=196 (M+H)$^+$

Example 1C

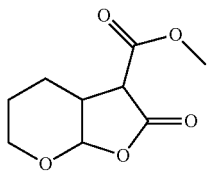

Under a nitrogen atmosphere 5.43 mL (59.4 mmol) 3,4-dihydro-2H-pyran, 23.2 g (149 mmol) potassium methyl malonate and 200 mL acetonintrile were combined and 65.2 g (119 mmol) ceric (IV) ammonium nitrate were added. The flask with the reaction mixture was immersed in an ultrasonic bath for 2 h at 0° C. The reaction mixture was filtered and the filtrate was evaporated under reduced pressure. The residue was partitioned between dichloromethane and water and the aqueous phase extracted with dichloromethane. The organic layer was dried and evaporated under reduced pressure. The residue was purified by filtration over silica gel (eluent: dichloromethane). 5.50 g (46%) of the product were obtained.

MS (ESI pos): m/z=201 (M+H)$^+$

Example 1D

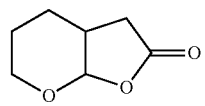

5.50 g (27.5 mmol) of example 1C were dissolved in 50 mL dimethylformamide and 1 mL water and heated to reflux for 7 h. After cooling to room temperature the reaction mixture was evaporated under reduced pressure. 3.40 g (78%) of the product were obtained.

HPLC-MS (M1): $R_t$=0.56 min
MS (ESI pos): m/z=143 (M+H)$^+$

Example 1E

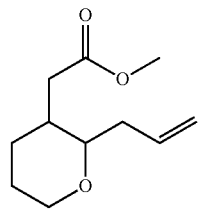

To 5.00 mL dichloromethane, 1.66 mL (12.7 mmol) titanium(IV)-chloride solution (1 mol/L in dichlormethane) and a solution of 900 mg (6.33 mmol) of example 1D and 1.44 g (12.7 mmol) allyltrimethylsilane in 95.0 mL dichloromethane were added at −78° C. The reaction mixture was stirred for 4 h, then warmed to room temperature. After stirring 1 h at room temperature the reaction mixture was cooled to 0° C. and 3.00 mL (76.0 mmol) methanol were added and the mixture stirred over night at room temperature. 1.40 mL (76.0 mmol) water were added. The reaction mixture was extracted three times with water and the organic layer was dried and evaporated under reduced pressure. 1.06 g (84%) of the product were obtained (as mixture of stereoisomers).

HPLC-MS (M1): $R_t$=1.34 min
MS (ESI pos): m/z=199 (M+H)$^+$

Example 1F

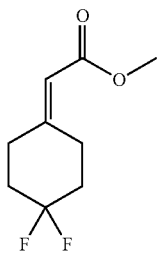

400 mg (10.0 mmol) NaH suspended in 30 mL THF were cooled to 5° C. and 1.30 mL (9.00 mmol) methyl-2-(dimethoxyphosphoryl)acetate were added. The reaction mixture was stirred for 1 h at this temperature. 1.00 g (7.50 mmol) 4,4-difluorocyclohexanone was added to the mixture. The reaction mixture was warmed to room temperature and stirred over night at ambient temperature. The mixture was hydrolysed with water and THF and concentrated under reduced pressure. The product was obtained as an oil.

Example 2A

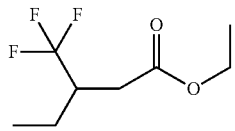

Racemic Mixture 29.0 g (148 mmol) of example 1B were combined with 2.0 g Pd/C (10%) and hydrogenated at room temperature (6 h, 15 psi). The reaction mixture was filtered and washed with diethyl ether. The solvent was evaporated under reduced pressure (500 mbar, 40° C. bath temperature). 27.6 g (94%) of the product were obtained as a liquid.

HPLC-MS (M1): $R_t$=1.65 min

Example 2B

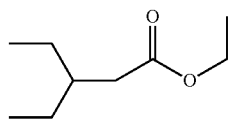

4.70 g (30 mmol) of example 1A were dissolved in 10 mL methanol, 400 mg Pd/C 10% was added, and the mixture hydrogenated at room temperature (8 h, 15 psi). The reaction mixture was filtered and washed with methanol. The solvent was evaporated by reduced pressure. 4.00 g (84%) was obtained as an oil.

HPLC-MS (M1): $R_t$=1.72 min
MS (ESI pos): m/z=159 (M+H)$^+$

Example 2C

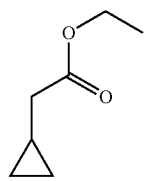

A solution of 10.0 g (100 mmol) of cyclopropyl acetic acid in 40 mL ethanol were cooled to 0° C. and 11 mL (152 mmol) thionylchloride were added. The reaction mixture was heated to 50° C. over night. After cooling to room temperature the solvent was removed under reduced pressure. The residue was dissolved in ethyl acetate and filtered over 30 g basic aluminium oxide. The filtrate was evaporated under reduced pressure. 8.0 g (62%) of the product were obtained.

HPLC-MS (M1): $R_t$=1.29 min

The following examples were synthesized in analogy to the preparation of example 2C, using the corresponding acids as starting materials.

| | structure | starting material | $R_t$ | MS (ESI or EI pos, m/z) |
|---|---|---|---|---|
| Exm. 2D | ![structure] | ![starting material] | 1.53 min (M1) | 201 (ESI M + H)$^+$ |
| Exm. 2E | ![structure] | ![starting material] | 1.65 min (M1) | 157/58 (ESI M + H)$^+$ HPLC-MS |

-continued

| | structure | starting material | $R_t$ | MS (ESI or EI pos, m/z) |
|---|---|---|---|---|
| Exm. 2F | ethyl 2-(2-(trifluoromethoxy)phenyl)acetate | 2-(2-(trifluoromethoxy)phenyl)acetic acid | 1.69 min (M1) | 249/50 (ESI M + H)+ |
| Exm. 2G | ethyl 2-(3-(trifluoromethyl)phenyl)acetate | 2-(3-(trifluoromethyl)phenyl)acetic acid | 1.63 min (M1) | |
| Exm. 2H racemic mixture | ethyl 2-fluoro-2-phenylacetate | 2-fluoro-2-phenylacetic acid | | 133 (ESI M + H)+ |
| Exm. 2I | ethyl 2-(tetrahydrofuran-3-yl)acetate | 2-(tetrahydrofuran-3-yl)acetic acid  Sunshine Chemlab, Inc., Richmond, CA, USA. | | 159 (ESI M + H)+ |
| Exm. 2J | ethyl 2-(2-bromophenyl)acetate | 2-(2-bromophenyl)acetic acid | 1.62 min (M1) | 243/245 (Br) (ESI M + H)+ |
| Exm. 2K | ethyl 5,5,5-trifluoropentanoate | 5,5,5-trifluoropentanoic acid | | 184 (ESI M + H)+ |

-continued

| | structure | starting material | $R_t$ | MS (ESI or EI pos, m/z) |
|---|---|---|---|---|
| Exm. 2KA | ethyl 2-(2-iodophenyl)acetate | 2-(2-iodophenyl)acetic acid | 1.64 min (M1) | 291 (ESI M + H)+ |
| Exm. 2KB | ethyl 2-(2-methoxy-6-nitrophenyl)acetate | 2-(2-methoxy-6-nitrophenyl)acetic acid Sinova Inc., Bethesda, MD, USA | 1.47 min (M1) | 194 (ESI M − ethanol + H)+ |
| Exm. 2KC | diethyl 2,2'-(1,3-phenylene)diacetate | 2,2'-(1,3-phenylene)diacetic acid | 1.57 min (M1) | 251 (ESI M + H)+ |
| Exm. 2KD | ethyl 5,5,5-trifluoropentanoate | 5,5,5-trifluoropentanoic acid | | |
| Exm. 2KE | ethyl 2-(2-bromo-4-fluorophenyl)acetate | 2-(2-bromo-4-fluorophenyl)acetic acid | 1.60 min (M1) | 261/263 (Br) (ESI M + H)+ |
| Exm. 2KF | ethyl 2-(2-bromo-5-fluorophenyl)acetate | 2-(2-bromo-5-fluorophenyl)acetic acid | 1.59 min (M1) | 261/263 (Br) (ESI M + H)+ |

| structure | starting material | $R_t$ | MS (ESI or EI pos, m/z) |
|---|---|---|---|
| Exm. 2KG racemic mixture | | 1.23 min (M1) | 258 (EI, M⁺) |
| Exm. 2KH | | 1.44 min (M1) | 195 (ESI, M + H)⁺ |
| Exm. 2KI | | 1.12 min (M1) | 213 (ESI, M + H)⁺ |

Example 2L

Example 2M

Racemic Mixture 4.00 g (23.2 mmol) (5,5-Dimethyl-2-oxo-tetrahydro-furan-3-yl)-acetic acid were dissolved in 9 mL acetonitrile and 1 mL methanol and 14.0 mL (27.9 mmol) trimethylsilyldiazomethane (2 M in diethyl ether) were added drop wise. The reaction mixture was stirred at room temperature for 15 min, then acetic acid was added until the yellow colour disappeared. The solvent was removed under reduced pressure and the residue was purified by preparative HPLC. 3.14 g (72%) of the product were obtained.

MS (ESI pos): m/z=187 (M+H)⁺

Mixture of Stereoisomers 690 mg (3.48 mmol) of example 1E were dissolved in 10 mL methanol, 70 mg Pd/C 10% was added and the resulting mixture was hydrogenated at (4 h, 50 psi). The reaction mixture was filtered and washed with methanol. The solvent was evaporated under reduced pressure. 610 mg (88%) of the product were obtained.

MS (ESI pos): m/z=201 (M+H)⁺

Example 2N

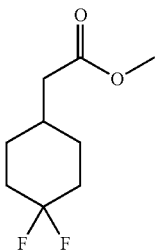

1.49 g (7.42 mmol) of example 1F were dissolved in 20 mL ethanol and 150 mg Pd/C 10% was added. The mixture was hydrogenated at room temperature (20 h, 50 psi). The reaction mixture was filtered and washed with ethanol. The solvent was evaporated under reduced pressure. 1.27 g (89%) of the product were obtained.

MS (ESI pos): m/z=193 (M+H)$^+$

Example 3A

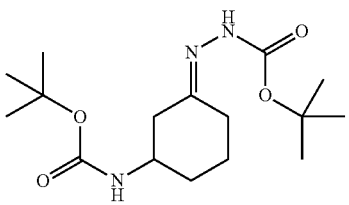 [SMILES: CC(C)(C)OC(=O)N/N=C1\CCCC(NC(=O)OC(C)(C)C)C1]

Racemic Mixture 5.00 g (23.5 mmol) t-butyl-3-oxocyclohexylcarbamate were dissolved in 70 mL ethanol and 3.10 g (23.5 mmol) t-butyl carbazate were added. The reaction mixture was stirred at room temperature for 2 h. The solvent was evaporated under reduced pressure. 8.85 g (98%) of the product were obtained.

HPLC-MS (M1): R$_t$=1.37 min
MS (ESI neg.): m/z=328 (M+H)$^+$

Example 4A

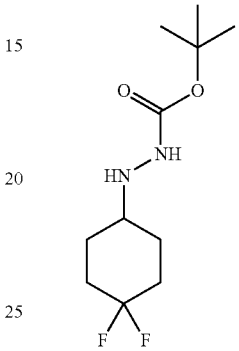

5.00 g (37.3 mmol) 4,4-difluorocyclohexanone were dissolved in 200 mL isopropanol and 5.30 g (40.1 mmol) t-butylcarbazate, 0.75 mL conc. acetic acid and PtO$_2$ were added. The reaction mixture was hydrogenated at room temperature (12 h, 50 psi). The reaction mixture was filtered and the solvent was evaporated under reduced pressure. 10.1 g (98%) of the product were obtained.

MS (ESI pos): m/z=251 (M+H)$^+$

The following examples were synthesized in analogy to the preparation of example 4A, using the corresponding ketons as starting materials.

| | structure | starting material | R$_t$ | MS (ESI pos, m/z) |
|---|---|---|---|---|
| Exm. 4B mixture of stereoisomers | 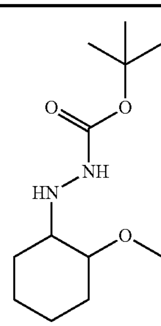 | | | 245 (M + H)$^+$ |
| Exm. 4C | 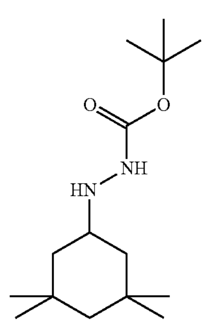 [SMILES: CC1(C)CC(NNC(=O)OC(C)(C)C)CC(C)(C)C1] | | 1.66 min (M1) | 215 (M − Isobutene + H)$^+$ |

| structure | starting material | $R_t$ | MS (ESI pos, m/z) |
|---|---|---|---|
| Exm. 4D mixture of stereoisomers 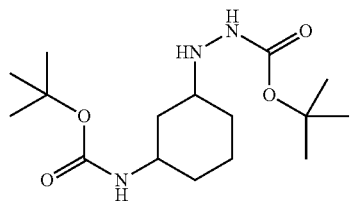 | 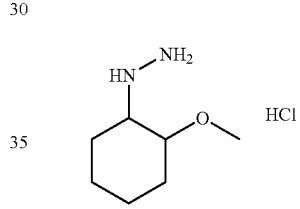 | 1.77 min (M1) | 291 (M + H)+ |

Example 4E

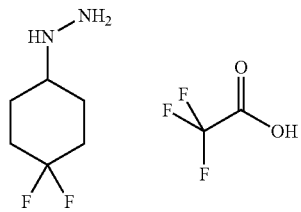 [SMILES: NNC1CCC(F)(F)CC1 ; O=C(O)C(F)(F)F]

Mixture of Stereoisomers 7.90 g (24.1 mmol) of example 3A were dissolved in 75 mL heptane and 26.5 mL (26.5 mmol) borane tetrahydrofuran complex solution in THF (1 mol/l) were added drop wise at 20° C. and stirred at room temperature for 14 h. The reaction mixture was cooled with an ice bath and a solution of 60 mL methanol and 6 mL water were added. The mixture was stirred 20 min at room temperature. The solvent was evaporated under reduced pressure. 7.90 g (quantitative) of the product were obtained.

Example 5A 4.00 g (16.0 mmol) of example 4A were dissolved in 40 mL dichlormethane and 5.50 mL (71.4 mmol) trifluoroacetic acid were added. The reaction mixture was stirred 12 h at room temperature. The solvent was evaporated under reduced pressure. 4.0 g (95%) of the product were obtained.

MS (ESI pos): m/z=151 (M+H)+

Example 5B

Mixture of Stereoisomers 3.05 g (12.5 mmol) of example 4B were dissolved in 10.0 mL (40.0 mmol) HCl in dioxane (4 mol/l). The reaction mixture was stirred 12 h at room temperature. The solvent was evaporated under reduced pressure. 2.71 g (quantitative) of the product were obtained.

MS (ESI pos): m/z=145 (M+H)+

The following examples were synthesized in analogy to the preparation of example 5B, using the corresponding hydrazinecarboxylic acid t-butyl esters as starting materials.

| structure | | Starting material | $R_t$ [min] | MS (ESI pos, m/z) |
|---|---|---|---|---|
| Exm. 5C 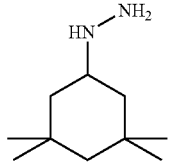 | ClH | Exm. 4C | | |

| structure | Starting material | $R_t$ [min] | MS (ESI pos, m/z) |
|---|---|---|---|
| Exm. 5D mixture of stereoisomers | ClH Exm. 4D | | 191 (M + H)⁺ |
| Exm. 5E mixture of stereoisomers | Exm. 4E | | |

Example 5F

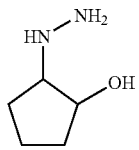

Mixture of Stereoisomers 1.50 mL (17.3 mmol) 1,2-epoxycyclopentane and 2.00 mL (41.1 mmol) hydrazine hydrate were dissolved in 5 mL of ethanol. The reaction mixture was heated to 85° C. and stirred 12 h. After cooling to room temperature the solvent was evaporated under reduced pressure. 2.00 g (100%) of the product were obtained.

MS (ESI pos): m/z=117 (M+H)+

Example 6A

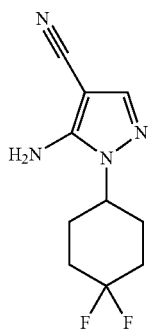

4.20 g (16.0 mmol) of example 5A were suspended with 2.15 g (17.6 mmol) of ethoxymethylenemalononitrile in 50 mL of ethanol and 6.70 mL (48.0 mmol) of triethylamine were added. The reaction mixture was heated to 50° C. for 2 h. After cooling to room temperature the solvent was removed under reduced pressure. The residue was suspended in dichloromethane. The suspension was filtered. 3.88 g (96%) of the product were obtained.

HPLC-MS (M1): $R_t$=1.19 min

MS (ESI pos): m/z=225 (M−H)⁻

The following examples were synthesized in analogy to the preparation of example 6A, using the corresponding hydrazines as starting materials.

| structure | Starting material | $R_t$ | MS (ESI pos, m/z) |
|---|---|---|---|
| Exm. 6B mixture of stereoisomers | Exm. 5B | | 221 (M + H)⁺ |
| Exm. 6C | Exm. 5C | 1.63 min (M1) | 247 (M + H)⁺ |
| Exm. 6D mixture of stereoisomers | Exm. 5D | 1.58 min (M1) | 267 (M + H)⁺ |
| Exm. 6E mixture of stereoisomers | Exm. 5E | 0.60 min (M1) | 206 (M + H)⁺ |

-continued

| structure | Starting material | $R_t$ | MS (ESI pos, m/z) |
|---|---|---|---|
| Exm. 6F mixture of stereo-isomers 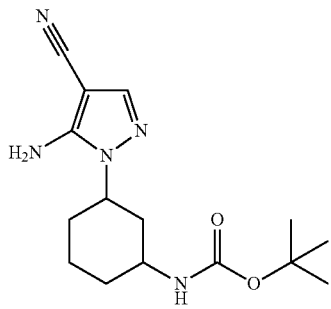 | Exm. 5F | 0.85 min (M1) | 193 (M+H)$^+$ |

Example 7A

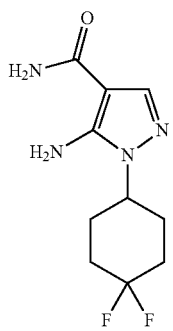 [SMILES: NC(=O)c1cnn(C2CCC(F)(F)CC2)c1N]

Mixture of Stereoisomers 4.00 g (19.5 mmol) of example 6E were suspended in 120 mL of tetrahydrofuran, and 4.9 g (22.4 mmol) di-t-butyl-dicarbamate were added. The reaction mixture was heated to 60° C. for 5 h. After cooling to room temperature the solvent was removed under reduced pressure. The residue was purified by preparative MPLC (SiO$_2$, eluent dichloromethane/methanol 9/1). 2.90 g (48%) of the product were obtained.

HPLC-MS (M1): $R_t$=1.28 min
MS (ESI pos): m/z=306 (M+H)$^+$

Example 8A (25% in water) were added over a period of 10 min. The reaction mixture was stirred at room temperature for 2 h. The solution was concentrated to a volume of 50 mL under reduced pressure. The residue was dissolved in dichloromethane and water. The organic layer was extracted with water and 40% Na$_2$S$_2$O$_3$ solution. The organic layer was dried, filtered and the filtrate was concentrated under reduced pressure. 2.44 g (68%) of the product were obtained.

HPLC-MS (M1): $R_t$=0.91 min
MS (ESI pos): m/z=245 (M+H)$^+$

The following examples were synthesized in analogy to the preparation of example 8A, using the corresponding pyrazoles as starting materials.

| | structure | Starting material | $R_t$ | MS (ESI pos, m/z) |
|---|---|---|---|---|
| Exm. 8B cis racemic mixture | 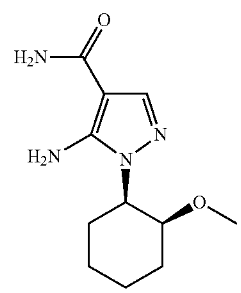 [SMILES: CO[C@H]1CCCC[C@H]1n1ncc(C(N)=O)c1N] | Exm. 6B | 0.89 min (M1) | 239 (M+H)$^+$ |
| Exm. 8C | 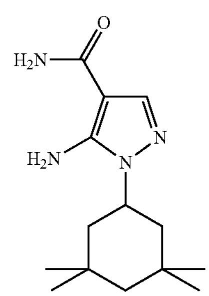 [SMILES: CC1(C)CC(n2ncc(C(N)=O)c2N)CC(C)(C)C1] | Exm. 6C | 1.37 min (M1) | 265 (M+H)$^+$ |
| Exm. 8D mixture of stereo-isomers | 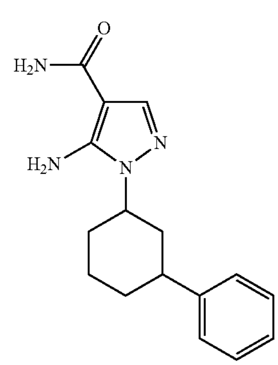 [SMILES: NC(=O)c1cnn(C2CCCC(c3ccccc3)C2)c1N] | Exm. 6D | 1.3 min (M1) | 285 (M+H)$^+$ |

3.88 g (14.6 mmol) of example 6A were dissolved in 40 mL of ethanol. At room temperature a solution of 35.0 mL (410 mmol) hydrogen peroxide (35% in water) in 20 mL ammonia

| structure | Starting material | $R_t$ | MS (ESI pos, m/z) |
|---|---|---|---|
| Exm. 8E mixture of stereo-isomers | Exm. 7A | 1.11 min (M1) | 324 (M+H)+ |
| Exm. 8F mixture of stereo-isomers | Exm. 6F | 0.59 min (M1) | 211 (M+H)+ |

Example 9A

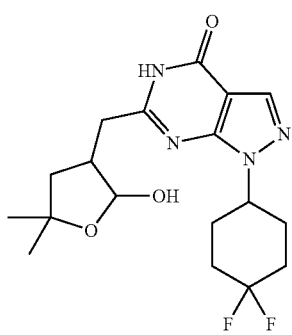 [SMILES: CC1(C)CC(Cc2nc3c(cnn3C3CCC(F)(F)CC3)c(=O)[nH]2)C(O)O1]

Mixture of Stereoisomers 110 mg (0.29 mmol) of example 28 were dissolved in 1 mL THF and cooled to −78° C. 1.30 mL (1.30 mmol) DIBAH (1M in THF) were added and the mixture stirred 5 h at −78° C. The reaction mixture was quenched with NH$_3$/MeOH and water was added. The mixture was extracted with dichloromethane. The organic layer was dried, filtered and evaporated under reduced pressure. 89.0 mg (80%) of the product were obtained.

HPLC-MS (Method1): $R_t$=1.17 min

MS (ESI pos): m/z=383 (M+H)+

Example 10A

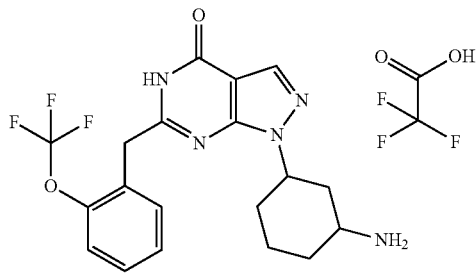 [SMILES: NC1CCCC(n2ncc3c(=O)[nH]c(Cc4ccccc4OC(F)(F)F)nc32)C1 ; O=C(O)C(F)(F)F]

Mixture of Stereoisomers 50.0 mg (0.10 mmol) of example 18 were dissolved in 1.50 mL dichloromethane and 0.30 mL trifluoroacetic acid were added. The mixture was stirred over night at room temperature. The reaction mixture was evaporated under reduced pressure and the residue was purified by preparative HPLC (eluent A: water+0.13% TFA, eluent B: acetonitrile). 37.0 mg (72%) of the product were obtained.

HPLC-MS (Method1): $R_t$=1.16 min

MS (ESI pos): m/z=408 (M+H)+

Example 11A

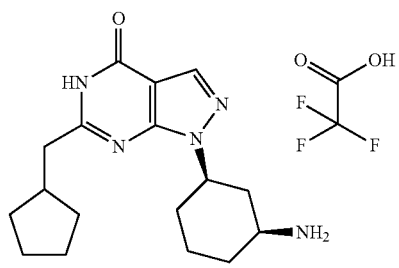 [SMILES: N[C@H]1CCC[C@@H](n2ncc3c(=O)[nH]c(CC4CCCC4)nc32)C1 ; O=C(O)C(F)(F)F]

Cis Racemic Mixture 77.5 mg (0.20 mmol) of example 17 were dissolved in 4.0 mL ethanol, 45.0 mg (0.80 mmol) potassium hydroxide were added and the mixture heated to reflux for 20 h. After cooling to room temperature the reaction mixture was evaporated under reduced pressure. The residue was dissolved in dichloromethane, water was added and the mixture was acidified with trifluoroacetic acid. The aqueous phase was evaporated under reduced pressure. The residue was purified by preparative HPLC (eluent A: water+0.13% TFA, eluent B: acetonitrile). 40.0 mg (47%) of the product were obtained.

HPLC-MS (Method1): $R_t$=1.04 min

MS (ESI pos): m/z=316 (M+H)+

Example 12A

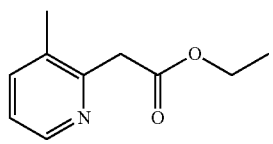

5.00 g (46.7 mmol) of 2,3-dimethylpyridine were dissolved in 70 mL THF. The mixture was cooled to 0° C. and 29.2 mL (46.7 mmol) n-butyllithium 6M solution in n-hexane were added and the mixture stirred for 30 min. The mixture was cooled to −60° C. and diethyl carbonate (5.66 mL, 46.7 mmol) dissolved in 25 mL THF was added. The reaction was allowed to warm to room temperature over night. After adding 5 mL HCl 4M the reaction mixture was evaporated under reduced pressure. The residue was dissolved in dichloromethane and was made basic with $K_2CO_3$. The organic layer was washed with saturated NaCl and evaporated at room temperature. The residue was purified over BIOTAGE SP1 with n-hexane:ethylacetate 1:1. 1.80 g (22%) of the product were obtained.

HPLC-MS (Method1E hydro): $R_t$=6.97 min
MS (APCI): m/z=180 (M+H)$^+$

The following examples were synthesized in analogy to the preparation of example 12A, using the corresponding bromide as starting materials.

| | structure | starting material | $R_t$ | MS (APCI pos, m/z) |
|---|---|---|---|---|
| Exm. 12AA | 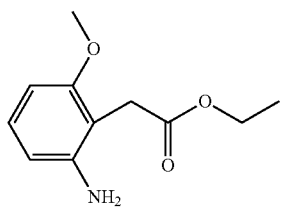 | 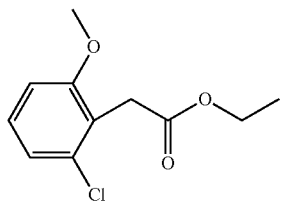 | 8.23 min (M1Eh) | 244/ 246 (Br) (M + H)$^+$ |

Example 13A

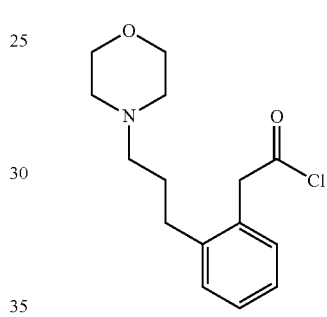

2.05 g (8.55 mmol) of Example 2 KB were dissolved in 40 mL ethanol. Pd/C was added and the mixture was hydrogenated for 2 h at room temperature and a pressure of 50 psi. The catalyst was filtered off and the solvent removed under reduced pressure to give 1.80 g (100%) of the product.

HPLC-MS (Method1): $R_t$=0.91 min
MS (ESI pos): m/z=210.1 (M+H)$^+$

Example 14A

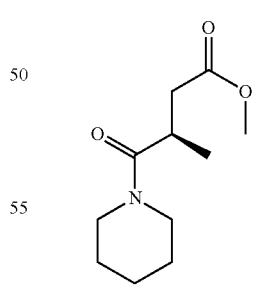

To 1.83 g (8.73 mmol) of Example 13A were added 60 mL ice cold 4M HCl and the mixture kept cool in a ice/salt bath. 1.14 g sodium nitrite in 13.5 mL ice water were added to the mixture. After stirring for 40 min, 1.90 g (19.2 mmol) copper (I)-chloride dissolved in 6 mL conc. HCl were added to the reaction. Then the reaction was allowed to warm to room temperature and stirred for 40 min. The aqueous solution was extracted with ethyl acetate. The organic layer was dried, neutralised with $K_2CO_3$, filtered and the solvent removed under reduced pressure. The residue was dissolved in dichloromethane and washed with water before the solvent of the organic fraction was removed under reduced pressure. The residue was taken up in ethyl acetate, the precipitate which was formed was filtered off and the filtrate was re-filtered through celite. The solvent was removed again to give 1.24 g (62%) of the product.

HPLC-MS (Method1): $R_t$=0.81 min
MS (ESI pos): m/z=230.9 (M+H)$^+$

Example 15A

To 590 mg (2.24 mmol) of 2-(2-(3-morpholinopropyl)phenyl)acetic acid in 3 mL thionylchloride was added one drop of DMF. The reaction mixture was stirred for 1 h at ambient temperature. Then the solvent was removed to give the desired product, which was used without further purification in the next step.

Example 16A 1.74 mL (13.7 mmol) (R)-4-methoxy-2-methyl-4-oxobutanoic acid were dissolved in 1 mL DMF and 7.03 mL (41.1 mmol) DIPEA and 4.83 g (15.1 mmol) TBTU were added and stirred 10 min at room temperature. Then 1.35 mL (13.7 mmol) piperidine were added and the reaction mixture was stirred for 3 h at room temperature. The solvent was removed under reduced pressure and the residue was purified by preparative HPLC (eluent A: water+0.13% TFA, eluent B: acetonitrile). 2.31 g (79%) of the product were obtained.
HPLC-MS (Method1): R$_t$=1.07 min
MS (ESI pos): m/z=213 (M+H)$^+$ Example 17A

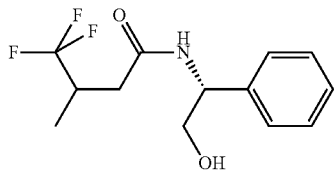

Diastereomer A

A solution of 3-(trifluoromethyl)butyric acid (10.0 g, 64.0 mmol) in DMF (100 mL) was treated with N-(3-dimethylaminopropyl)-N'-ethylcarbodiimide hydrochloride (14.7 g, 77.0 mmol), 4-dimethylamino pyridine (11.0 g, 89.7 mmol) and (R)-(−)-phenylglycinol (9.90 g, 70.5 mmol). The mixture was stirred at 20° C. for 16 h, then concentrated and treated with 10% citric acid in water (300 mL). The mixture was extracted with ethyl ether (2×200 mL) and the separated organic phase was washed with 10% NaHCO$_3$ (150 mL) and brine (150 mL). The organic phase was dried over Na$_2$SO$_4$ and evaporated to give 13.1 g of crude product as a solid.

Separation of diastereoisomers was achieved by flash chromatography on SiO$_2$ eluting with a mixture of ethyl acetate/hexane 6/4. 5.32 g (30%) of the title compound were obtained.

R$_f$: 0.23 (ethyl acetate/hexane 6/4)
HPLC-MS (1E hydro): R$_t$=6.97 min
MS (APCI pos): m/z=276 (M+H)$^+$.

Example 17B

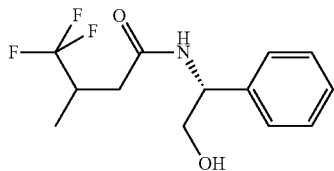

Diastereomer B 3.08 g (17.5%) of a solid were obtained as second product from flash chromatography of Example 17A.
R$_f$: 0.16 (ethyl acetate/hexane 6/4)
HPLC-MS (1E hydro): R$_t$=6.92 min
MS (APCI pos): m/z=276 (M+H)$^+$.

Example 18A

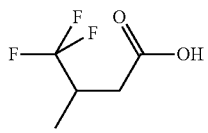

Enantiomer A

A solution of Example 17A (2.00 g, 7.26 mmol) in tetrahydrofuran (10 mL) was treated with H$_2$SO$_4$ (70% in water) (10 mL) and refluxed for 16 h. The mixture was cooled, basified to pH 14 with NaOH (32% in water), diluted with water (50 mL) and extracted with dichloromethane (2×50 mL). The resulting solution was acidified to pH 1 with 9N HCl, extracted with dichloromethane (3×50 mL) and the combined organic phases were dried. Evaporation of the solvent afforded 0.84 g (74.1%) of an oil.

HPLC-MS (1E hydro): R$_t$=1.73 min
MS (APCI neg): m/z=155 (M−H)$^-$
Chiral HPLC (Method Chiral 2): R$_t$=6.92 min ee: 99%

The following examples were synthesized in analogy to the preparation of example 18A, using the corresponding amide as starting material.

| | structure | starting material | R$_t$ [min] | MS (APCI neg, m/z) |
|---|---|---|---|---|
| Exm. 18B | 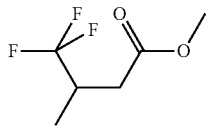 Enantiomer B | Exm. 17B | 1.30 (M1Eh) Chiral HPLC (Method Chiral 2): 6.49 ee: 98.6% | 155 (M − H)$^-$ |

Example 19A

Enantiomer A

To a stirred solution of example 18A (440 mg, 2.82 mmol) in dichloromethane (10 mL) and methanol (0.46 mL) under nitrogen atmosphere, 1.55 mL (3.1 mmol) trimethylsilyldiazomethane (2.0 M solution in diethyl ether) were added at 0° C. The reaction mixture was stirred keeping the temperature below 5° C. for 1 h. The solvent was removed (40° C., 0.33 bar) yielding 480 mg (100%) of an oil that was used in the next step without further purification.

GC (Method 3A): Rt=8.01 min
MS (m/z)=170 M$^+$

The following examples were synthesized in analogy to the preparation of example 19A, using the corresponding acid as starting material.

| | structure | starting material | GC R$_t$ | MS (m/z) |
|---|---|---|---|---|
| Exm. 19B |  Enantiomer B | Exm. 18B | 8.01 min (Method 3A) | 170 |

Example 20A

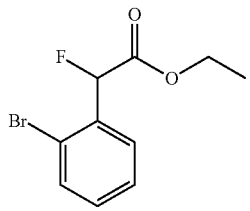

Racemic Mixture

A solution of 5.00 g (19.3 mmol) of example 2KG in 60 mL dichloromethane was cooled to −78° C. under a nitrogen atmosphere. 5.06 mL (38.6 mmol) diethylaminosulfur trifluoride were added and stirred for 1 h at −78° C. The mixture was slowly heated to room temperature and stirred for 12 h. The reaction mixture was cooled to 0° C. and diluted with ethyl acetate. Saturated NaHCO₃ solution was added. The organic layer was separated, washed with water and brine, dried and evaporated under reduced pressure. The residue was filtered through a pad of silica gel and concentrated under reduced pressure. 4.9 g (98%) of the product were obtained.

HPLC-MS (Method1): $R_t$=1.53 min
MS (ESI pos): m/z=278 (M+NH₄)⁺

Example 21A

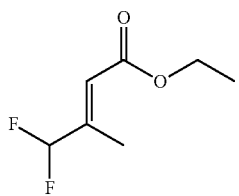

Cis/Trans Mixture

A solution of 18.8 g (54.1 mmol) carbethoxymethylene triphenylphosphorane in 100 mL diethyl ether were cooled to 0° C. and 5.30 g (56.4 mmol) of 1,1-difluoroacetone were added. The solution was warmed to room temperature and stirred over night. The reaction mixture was filtered and the filtrate was concentrated under reduced pressure. The residue was purified by vacuum distillation (100 mbar and 160° C. bath temperature). 7.1 g (76%) of the product were obtained.

HPLC-MS (Method 1): $R_t$=1.40/1.44 min (cis/trans isomers)
MS (ESI pos): m/z=164 M⁺

Example 22A

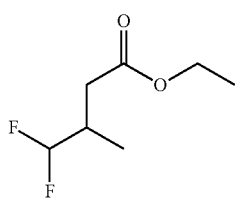

Racemic Mixture 500 mg (3.05 mmol) of example 21A were combined with 160 mg Pd/C (10%) and 15 mL methanol and hydrogenated at room temperature (24 h, 15 psi). The reaction mixture was filtered and the filtrate was evaporated under reduced pressure. 0.20 g (40%) of the product were obtained.

MS (ESI pos): m/z=166 M⁺

Example 23A

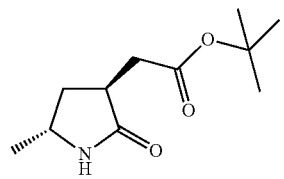

Under nitrogen atmosphere 10.0 g (32.5 mmol) of (3S,5S)-(5-methanesulfonyloxy-methyl-2-oxo-pyrrolidin-3-yl)-acetic acid tert-butyl ester (see U.S. Pat. No. 5,576,444) and 1.29 g sodium borohydride in 40 mL DMSO were slowly heated to 85° C. within 3 h. The reaction mixture was cooled to room temperature and poured onto water and ethyl acetate. The organic layer was separated, dried and evaporated under reduced pressure. 5.6 g (81%) of the product were obtained.

MS (ESI pos): m/z=214 (M+H)⁺

Example 24A

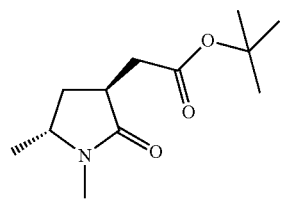 [SMILES: C[C@@H]1C[C@@H](CC(=O)OC(C)(C)C)C(=O)N1C]

284 mg (7.09 mmol) of sodium hydride (60% suspension in mineral oil) in 10 mL of DMF were cooled to 0° C. under nitrogen atmosphere. 1.26 g (5.91 mmol) of example 23A in 8 mL DMF were added. After 2 h, 1.10 mL (17.7 mmol) of methyliodide in 5 mL of DMF were added. The mixture was heated to room temperature and stirred over night. The reaction mixture was diluted with water and ethyl acetate. The phases were separated and the organic layer was dried and evaporated under reduced pressure. 0.89 g (66%) of the product were obtained. The product was used without further purification in the next step.

Example 25A

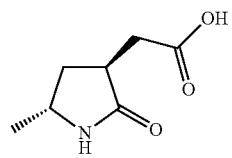

A solution of 3.20 g (14.1 mmol) of example 24A in 5 mL TFA (70% in dichloromethane) was stirred over night at room temperature. The mixture was evaporated under reduced pressure. The residue was purified by preparative HPLC (eluent A: water+0.13% TFA, eluent B: acetonitrile). The fractions containing the product were concentrated under reduced pressure and the residue was extracted with dichloromethane. The organic layer was dried and evaporated under reduced pressure. 0.80 mg (33%) of the product were obtained.

HPLC-MS (Method 1): $R_t$=0.62 min

Example 26A

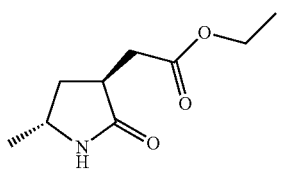

To a solution of 801 mg (4.68 mmol) of example 25A in 5 mL ethanol 0.41 mL (5.61 mmol) thionylchloride were added. The reaction mixture was stirred for 1 h at room temperature. The solvent was removed under reduced pressure. 656 mg (70%) of the product were obtained.

HPLC-MS (Method 1): $R_t$=1.00 min

Example 27A

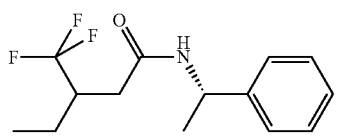

Diastereomer A

A solution of racemic 3-trifluoromethyl-pentanoic acid (8 g, 47 mmol), TBTU (16.6 g, 52 mmol) and diisopropylethylamine (24.1 mL, 141 mmol) in dimethylformamide (80 mL) was stirred at 20° C. for 1 h then (S)-(−)-1-phenylethylamine (10 g, 82 mmol) was added and the mixture was stirred for 16 h at 20° C. The solvent was removed and dichloromethane (200 mL) was added. The resulting mixture was washed with 10 citric acid aqueous solution (200 mL), K₂CO₃20% in water (100 mL) and dried over Na₂SO₄. Evaporation of the solvent gave a crude solid that was mixed with methanol (10 mL) and filtered through a pad of activated basic alumina. Separation of diastereoisomers was obtained by flash chromatography on SiO₂ eluting with a mixture of cyclohexane/ethyl acetate 85/15.

4.5 g (35.8%) of the title compound were obtained as a solid.

Rf: 0.25 (cyclohexane/ethyl acetate 85/15, stained with basic KMnO₄)

HPLC-MS (Method 1 E hydro): $R_t$: 9.35 min

MS (APCI pos): m/z=274 (M+H)⁺.

Chiral HPLC (Method Chiral 1): $R_t$: 5.58 min de: >99%

Example 27B

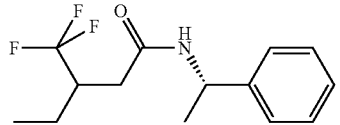

Diastereomer B 4.4 g (34.2%) of a solid were obtained as second product from flash chromatography of Example 1B.

Rf: 0.20 (cyclohexane/ethyl acetate 85/15, stained with basic KMnO₄)

HPLC-MS (Method 1 E hydro): $R_t$: 9.33 min

MS (APCI pos): m/z=274 (M+H)⁺.

Chiral HPLC (Method Chiral 1): $R_t$: 6.18 min de: >99%

Example 28A

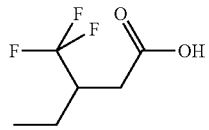

Enantiomer A

A solution of Example 1B (4.6 g, 17 mmol) in dioxane (15 mL) was treated with H₂SO₄ 70% in water (25 mL) and refluxed for 16 h. The mixture was cooled, basified to pH 14 with NaOH 32% in water, diluted with water (50 mL) and extracted with dichloromethane (2×200 mL). The resulting solution was acidified to pH 1 with 9N HCl, extracted with dichloromethane (3×500 mL). The combined organic phases were dried over Na₂SO₄. Evaporation of solvent afforded 2.47 g (86.3%) of the title compound.

Rf: 0.66 (dichloromethane/methanol 9/1, stained with Bromocresol Green) Chiral HPLC (Method Chiral 1): $R_t$ 5.58 min ee: >99

Example 28B

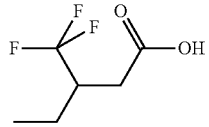

Enantiomer B

In analogy to the preparation of Example 1D, the title compound was obtained using Example 1C as starting material.

Yield: 80.3

Rf: 0.66 (dichloromethane/methanol 9/1, stained with Bromocresol Green)

Chiral HPLC (Method Chiral 1): $R_t$: 5.08 min ee: >99%

Example 29A

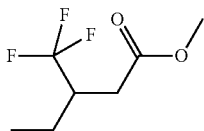
Enantiomer A

To a stirred solution of Example 28A (250 mg, 1.47 mmol) in dichloromethane (10 mL) and methanol (0.25 mL), under nitrogen atmosphere, trimethylsilyldiazomethane (2.0 M solution in diethyl ether) (2.1 mL, 4.19 mmol) was added dropwise at 0° C. The reaction mixture was stirred keeping the temperature below 5° C. for 1 h. The solvent was removed (40° C., 0.33 bar) yielding 250 mg (75.4%) of an oil that was used in the next step without further purification.

GC (Method 3A): $R_t$: 3.29 min

MS: m/z: 165 (M−19)$^+$, 155 (M−29)$^+$, 153 (M−31)$^+$

The following examples were synthesized in analogy to the preparation of Example 29A, using the corresponding acids as starting materials:

| structure | starting material: carboxylic acid | $R_t$ | MS m/z |
|---|---|---|---|
| Exm. 29B Enantiomer B <br> 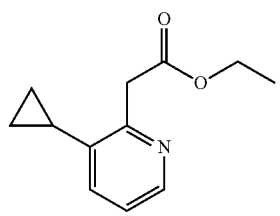 | Example 28B | 3.29 min (M3A) | 165 (M − 19)$^+$, 155 (M − 29)$^+$, 153 (M − 31)$^+$ [EI] |

Example 30A

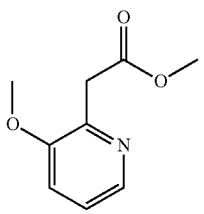

A mixture of (3-methoxy-2-pyridin-2-yl)acetonitrile (400 mg, 2.7 mmol) in 2 mL of methanol and 96% sulphuric acid (1.8 mL, 32 mmol) was heated in a microwave oven at 120° C. for 1 h. The mixture was cooled to 0° C., basified with solid NaHCO$_3$, diluted with water (2 mL) and extracted with dichloromethane. The organic phase was dried over sodium sulphate and evaporated to give 450 mg (92%) of the compound used in the next step without further purification.

HPLC-MS (Method Grad_C8_NH$_4$COOH): $R_t$: 1.92 min

MS (ESI pos): m/z=182 (M+H)$^+$

Example 31A

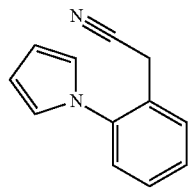 [SMILES: N#CCc1ccccc1-n1cccc1]

A Schlenk tube was charged with 244 mg (1 mmol) of Example 12AA, 192.37 mg (1.3 mmol) of potassium cyclopropyltrifluoroborate, 742.93 mg (3.5 mmol) of tri-potassium phosphate, 11.23 mg (0.05 mmol) of palladium(II)acetate, 28.04 mg (0.1 mmol) of tricyclohexylphosphine in toluene (4 ml) and water (200 µl) and heated to 100° C. for 24 hours. After cooling a solid was filtered and the filtrate was concentrated under reduced pressure. The residue was purified by flash chromatography on SiO$_2$ using n-hexane/ethyl acetate mixture of increasing polarity (from 100% n-hexane to 100% ethyl acetate) as eluant. 160 mg (78%) of the title compound were obtained.

GC-MS (Method 3A): $R_t$: 11.08 min

MS: 205 [M]$^+$.

Example 32A

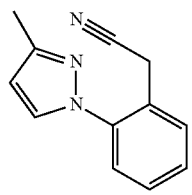

Under inert atmosphere a solution of 500 mg (3.78 mmol) of 2-Aminophenylacetonitrile and 1 mL (7.57 mmol) of 2,5-Dimethoxytetrahydrofuran in 5 mL of Acetic acid was heated to 60° C. for 2 hours. After cooling the reaction mixture was concentrated under reduced pressure. The residue was purified by flash chromatography on SiO$_2$ using cyclohexane/ethyl acetate mixture of increasing polarity (from 100% cyclohexane to 100% ethyl acetate) as eluant. 470 mg of the title compound (68%) were obtained.

GC-MS (Method 3A.1): $R_t$: 9.75 min

MS: 182 [M]$^+$.

Example 33A

A round bottom flask was charged under inert atmosphere with copper iodide (760 mg, 4 mmol), cesium carbonate (3.91 g, 12 mmol) then dimethylformamide (20 mL), previously degassed, was added followed by 2-Bromophenylacetonitrile (519 µL, 4 mmol), 3-Methylpyrazole (3.32 mL, 40 mmol) and N—N'-dimethylethylenediamine (425.86 µL, 4 mmol). The reaction mixture was heated to 120° C. for 2.5 hours. After cooling the reaction mixture was filtered through a Celite pad that was rinsed with dimethylformamide. The volume was reduced under reduced pressure, saturated ammonium chloride aqueous solution was added and extracted with ethyl acetate. The organic phase was washed with saturated aqueous $NH_4Cl$ solution, brine then dried over $Na_2SO_4$ and the solvent was removed under reduced pressure. The crude product was purified by flash chromatography on $SiO_2$ using cyclohexane/ethyl acetate mixture of increasing polarity (from 100% cyclohexane to 100% ethyl acetate) as eluant. The oil obtained was further purified by SPE cartridge Stratosphere "PL-THIOL MP" to remove copper salts. 300 mg of the title compound (38%) were obtained.

GC-MS (Method 3A.1): $R_t$: 10.47 min
MS: 197 $[M]^+$.

Example 35A

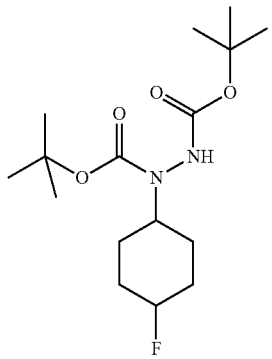 [SMILES: CC(C)(C)OC(=O)NN(C(=O)OC(C)(C)C)C1CCC(F)CC1]

Under inert atmosphere a solution of di-tert-butyl azodicarboxylate (4.67 g, 20.29 mmol) in tetrahydrofuran (20 mL) was added dropwise to a solution of 4-fluoro-cyclohexanol (1.70 g, 13.24 mmol) and triphenylphosphine (5.32 g, 20.29 mmol) in tetrahydrofuran (50 mL). After 4 hours at 25° C. the reaction mixture was concentrated under reduce pressure. The thick orange oil was purified by flash chromatography on $SiO_2$ using cyclohexane/ethyl acetate mixture of increasing polarity (from 100% cyclohexane to cyclohexane/ethyl acetate 70/30) as eluant. The solid was further purified by flash chromatography on $SiO_2$ using cyclohexane/ethyl acetate mixture of increasing polarity (from cyclohexane/ethylacetate 95/5 to cyclohexane/ethyl acetate 60/40) as eluant. The title compound was obtained as a solid (1.72 g, 39%).

GC-MS (Method 3A.1): $R_t$: 11.52 and 11.57 min
MS: 332 $[M]^+$.

Example 36A

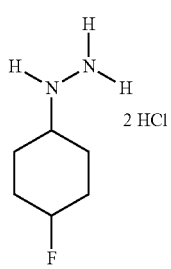

A solution of Example 35A (1.72 g, 5.17 mmol) in dry diethyl ether (35 mL) at 0°/5° C. was treated with gaseous HCl under vigorous stirring for 30 minutes. A solid was formed, the reaction mixture was stirred at 0°/5° C. for further 2 hours afterwards the solid was filtered and washed with diethyl ether under inert atmosphere. The solid was dried in a vacuum oven at 50° C. to give the title compound as a solid (0.78 g, 73%).

HPLC-MS (Method 1F): $R_t$: 0.92 min
MS (APCI pos): m/z=133 $(M+H)^+$

Example 37A

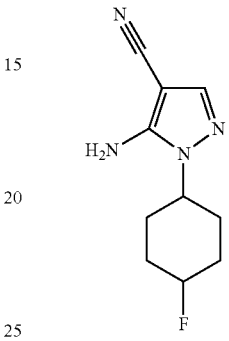

Under inert atmosphere triethylamine (2.12 mL, 15.2 mmol) and ethoxymethylenemalononitrile (0.52 g, 4.18 mmol) were added to a solution of Example 36A (0.78 g, 3.8 mmol) in absolute ethanol (10 mL) The reaction mixture was heated to 80° C. for 1 hour. After cooling to room temperature the reaction mixture was concentrated under reduce pressure. The red oil was vigorously stirred several times with diethyl ether. The solid obtained was filtered to give the title compound as a solid (0.85 g, 86%).

HPLC-MS (Method 1 E hydro): $R_t$: 6.97 min
MS (APCI neg): m/z=207 $(M+H)^-$

Example 38A

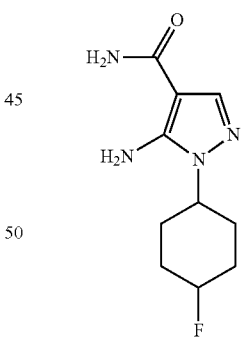

0.85 g (3.061 mmol) of Example 37A was dissolved in 20 mL of absolute ethanol. At 0°/5° C. a solution of 6.74 mL (78.37 mmol) hydrogen peroxide (35% in water) in 16.35 mL (117.56 mmol) ammonia (28% in water) was added dropwise. The reaction mixture was stirred at room temperature for 2 h. The solution was concentrated to a volume of 50 mL under reduced pressure. The solution was cooled to 0° C., a solid was filtered, washed thoroughly with water and dried in a vacuum oven at 50° C. to give the title compound as a solid (0.55 g, 79%).

HPLC-MS (Method 1E): $R_t$=5.25 min
MS (APCI pos): m/z=227 $(M+H)^+$

Example 39A

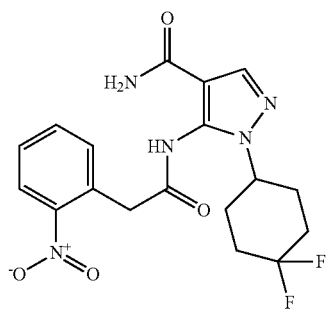

Under inert atmosphere a solution of (2-Nitro-phenyl)-acetyl chloride (817.2 mg, 4.1 mmol) in dry toluene (5 mL) was added dropwise to a suspension of Example 8A (250 mg, 1 mmol) and DMAP (6.25 mg, 0.05 mmol) in dry pyridine (10 mL). The reaction mixture was stirred at room temperature for 24 hours. The solvent was then removed under reduced pressure. The residue was dissolved in dichloromethane and washed with HCl 1N. During the extraction a solid was formed. It was filtered and dried, giving the title compound as a solid (304 mg, 73%).

HPLC-MS (Method 2M): $R_t$=8.50 min
MS (APCI pos): m/z=408 (M+H)$^+$

Example 40A

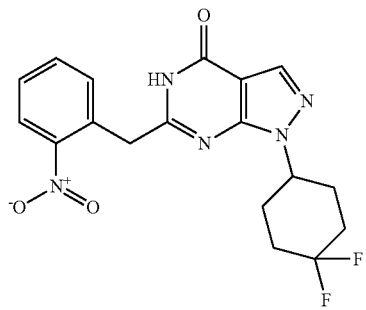

736.43 mg (18.4 mmol) of sodium hydride (60% suspension in mineral oil) were added to a suspension of Example 39A (300 mg, 0.74 mmol) in dry methanol (25 mL) and dry Toluene (15 mL). The reaction mixture was heated to 65° C. for 7 hours. The solvent was then removed under reduced pressure and the residue was taken up into H$_2$O (20 mL) and acidified with HCl 1N (20 mL) then extracted with dichloromethane (2×10 mL). The organic layer was dried over Na$_2$SO$_4$, filtered and the filtrate was concentrated under reduced pressure. The solid obtained was triturated with diethyl ether giving the title compound as a solid (205 mg, 71%).

HPLC-MS (Method 2M): $R_t$=8.50 min
MS (APCI pos): m/z=390 (M+H)$^+$

EXEMPLARY EMBODIMENTS

Example 1

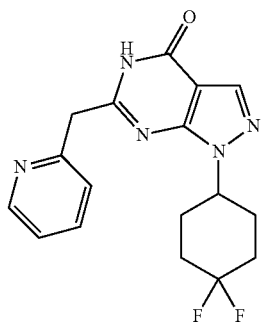 [SMILES: O=c1[nH]c(Cc2ccccn2)nc2c1cnn2C1CCC(F)(F)CC1]

100 mg (0.41 mmol) of example 8A were dissolved in 5 mL of absolute ethanol, 300 mg (1.82 mmol) of pyridine-2-yl-acetic acid ethyl ester, and 150 mg (3.75 mmol) of sodium hydride (60% suspension in mineral oil) were added. The reaction mixture was heated to 150° C. for 30 min in a microwave oven. Cooling to room temperature was followed by evaporation of the solvent under reduced pressure. The residue was purified by preparative HPLC (eluent A: water+ 0.13% TFA, eluent B: acetonitrile). 106 mg (75%) of the product were obtained as a solid.

HPLC-MS (Method1): $R_t$=0.98 min
MS (ESI pos): m/z=346 (M+H)$^+$

The following examples were synthesized in analogy to the preparation of example 1, using the corresponding pyrazoles and esters as starting materials

| | structure | starting material: pyrazole | starting material: ester | $R_t$ | MS (ESI pos/neg, m/z) |
|---|---|---|---|---|---|
| Exm. 2 | ![structure] | Exm. 8A | Exm. 2C | 1.32 min (M1) | 309 (M + H)$^+$ |

-continued

| structure | starting material: pyrazole | starting material: ester | $R_t$ | MS (ESI pos/neg, m/z) |
|---|---|---|---|---|
| Exm. 3 | Exm. 8A | Exm. 2F | 1.58 min (M1) | 427 (M − H)⁻ |
| Exm. 4 | Exm. 8A | | 1.44 min (M1) | 345 (M + H)⁺ |
| Exm. 5 | Exm. 8A | | 1.50 min (M1) | 377/379 (Cl) (M − H)⁻ |
| Exm. 6 | Exm. 8A | Exm. 2G | 1.55 min (M1) | 413 (M + H)⁺ |

-continued
| | structure | starting material: pyrazole | starting material: ester | R$_t$ | MS (ESI pos/neg, m/z) |
|---|---|---|---|---|---|
| Exm. 7 | 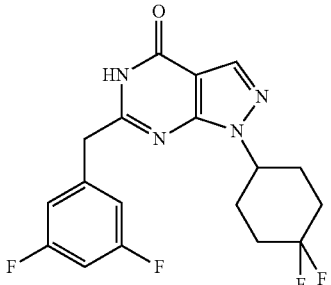 | Exm. 8A | Exm. 2D | 1.5 min (M1) | 381 (M + H)$^+$ |
| Exm. 8 | 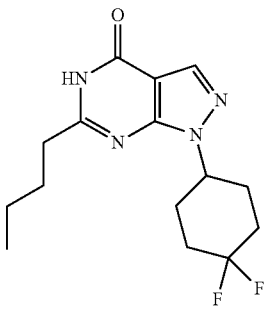 | Exm. 8A | | 1.43 min (M1) | 311 (M + H)$^+$ |
| Exm. 9 | 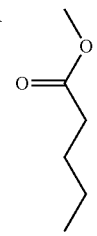 | Exm. 8A | | 1.39 min (M1) | 311 (M + H)$^+$ |
| Exm. 10 mixture of stereo-isomers | 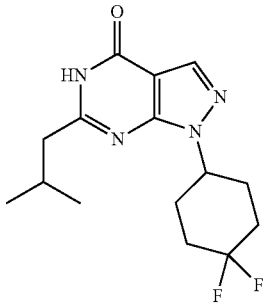 | Exm. 8F | Exm. 2E | 1.26 min (M1) | 303 (M + H)$^+$ |
| Exm. 11 cis racemic mixture | 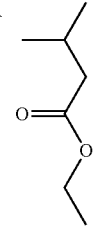 | Exm. 8B | Exm. 2C | 1.29 min (M1) | 303 (M + H)$^+$ |

-continued

| structure | starting material: pyrazole | starting material: ester | $R_t$ | MS (ESI pos/neg, m/z) |
|---|---|---|---|---|
| Exm. 12 cis racemic mixture | Exm. 8B | | 0.97 min (M1) | 340 (M + H)+ |
| Exm. 13 | Exm. 8C | Exm. 2C | 1.82 min (M1) | 329 (M + H)+ |
| Exm. 14 mixture of stereo-isomers | Exm. 8D | | 1.28 min (M1) | 386 (M + H)+ |
| Exm. 15 mixture of stereo-isomers | Exm. 8D | Exm. 2C | 1.70 min (M1) | 349 (M + H)+ |

| structure | starting material: pyrazole | starting material: ester | $R_t$ | MS (ESI pos/neg, m/z) |
|---|---|---|---|---|
| Exm. 16 mixture of stereo-isomers 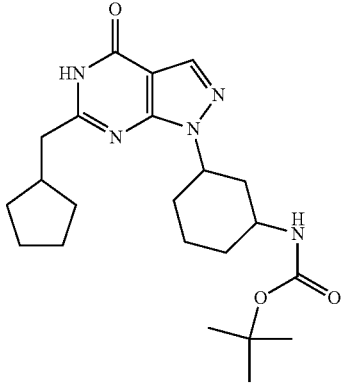 [SMILES: CC(C)(C)OC(=O)NC1CCCC(n2ncc3c(=O)[nH]c(CC4CCCC4)nc32)C1] | Exm. 8E | Exm. 2E | 1.59 min (M1) | 416 (M + H)+ |
| Exm. 17 mixture of stereo-isomers 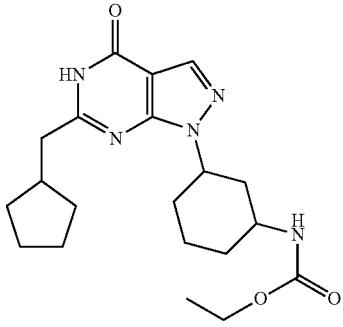 [SMILES: CCOC(=O)NC1CCCC(n2ncc3c(=O)[nH]c(CC4CCCC4)nc32)C1] | Exm. 8E | Exm. 2E | 1.40 min (M1) | 388 (M + H)+ |
| Exm. 18 mixture of stereo-isomers 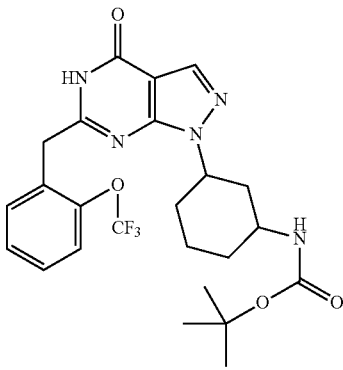 [SMILES: CC(C)(C)OC(=O)NC1CCCC(n2ncc3c(=O)[nH]c(Cc4ccccc4OC(F)(F)F)nc32)C1] | Exm. 8E | Exm. 2F | 1.6 min (M1) | 508 (M + H)+ |
| Exm. 19 mixture of stereo-isomers 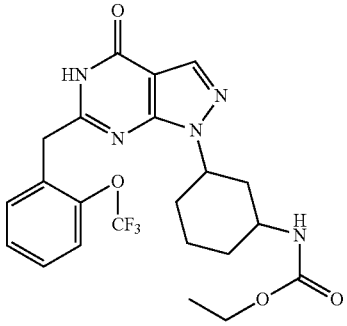 [SMILES: CCOC(=O)NC1CCCC(n2ncc3c(=O)[nH]c(Cc4ccccc4OC(F)(F)F)nc32)C1] | Exm. 8E | Exm. 2F | 1.46 min (M1) | 480 8M + H)+ |

-continued

| structure | starting material: pyrazole | starting material: ester | $R_t$ | MS (ESI pos/neg, m/z) |
|---|---|---|---|---|
| Exm. 20 | Exm. 8A | Exm. 2E | 1.52 min (M1) | 337 $(M+H)^+$ |
| Exm. 21 | Exm. 8A | Exm. 2B | 1.58 min (M1) | 339 $(M+H)^+$ |
| Exm. 22 | Exm. 8A | | 1.31 min (M1) | 297 $(M+H)^+$ |
| Exm. 23 | Exm. 8A | Exm. 2I | 1.21 min (M1) | 339 $(M+H)^+$ |

-continued

| structure | starting material: pyrazole | starting material: ester | R$_t$ | MS (ESI pos/neg, m/z) |
|---|---|---|---|---|
| Exm. 24 trans racemic mixture | Exm. 8A | Exm. 2M | 1.51 min (Method1) (the cis racemic mixture (R$_t$ = 1.53 min) was removed by chromatography) | 395 (M + H)$^+$ |
| Exm. 25 racemic mixture | Exm. 8A | Exm. 2H | 1.45 min (M1) | 363 (M + H)$^+$ |
| Exm. 26 | Exm. 8A | | 1.43 min (M1) | 375 (M + H)$^+$ |
| Exm. 27 racemic mixture | Exm. 8A | Exm. 2A | 1.54 min (M1) | 379 (M + H)+ |

-continued
| structure | starting material: pyrazole | starting material: ester | $R_t$ | MS (ESI pos/neg, m/z) |
|---|---|---|---|---|
| Exm. 28 racemic mixture 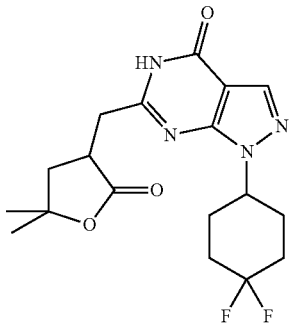 [SMILES: CC1(C)CC(Cc2nc3c(cnn3C3CCC(F)(F)CC3)c(=O)[nH]2)C(=O)O1] | Exm. 8A | Exm. 2K | 1.32 min (M1) | 381 (M + H)⁺ |
| Exm. 29 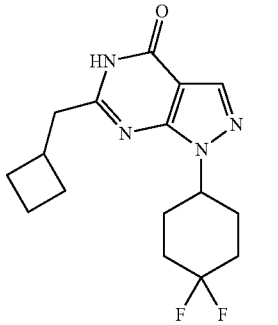 [SMILES: O=c1[nH]c(CC2CCC2)nc2c1cnn2C1CCC(F)(F)CC1] | Exm. 8A | 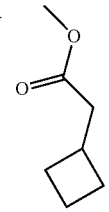 | 1.44 min (M1) | 323 (M + H)⁺ |
| Exm. 30 racemic mixture 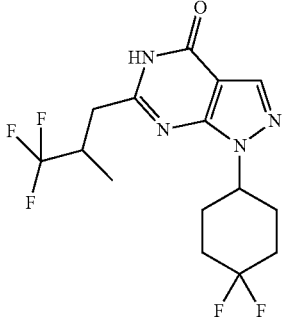 [SMILES: CC(Cc1nc2c(cnn2C2CCC(F)(F)CC2)c(=O)[nH]1)C(F)(F)F] | Exm. 8A | 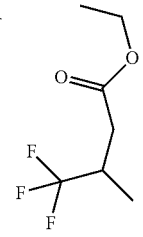 | 1.47 min (M1) | 365 (M + H)⁺ |
| Exm. 31 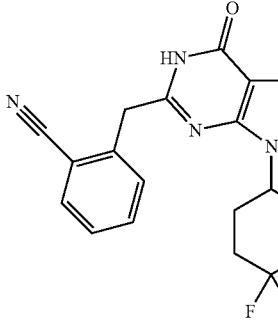 | Exm. 8A | 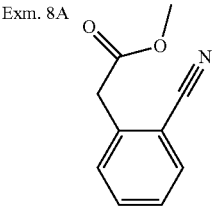 | 1.36 min (M1) | 370 (M + H)⁺ |

-continued
| structure | starting material: pyrazole | starting material: ester | $R_t$ | MS (ESI pos/neg, m/z) |
|---|---|---|---|---|
| Exm. 32 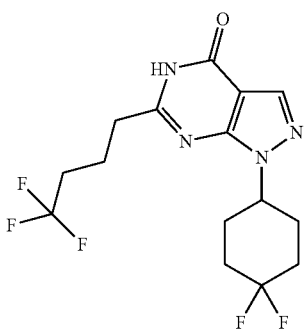 [SMILES: O=c1[nH]c(CCCC(F)(F)F)nc2c1cnn2C1CCC(F)(F)CC1] | Exm. 8A | Exm. 2K | 1.44 min (M1) | 365 $(M+H)^+$ |
| Exm. 33 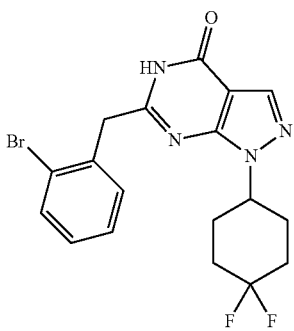 [SMILES: O=c1[nH]c(Cc2ccccc2Br)nc2c1cnn2C1CCC(F)(F)CC1] | Exm. 8A | Exm. 2J | 1.51 min (M1) | 423 $(M+H)^+$ |
| Exm. 34 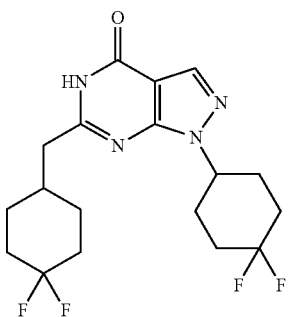 [SMILES: O=c1[nH]c(CC2CCC(F)(F)CC2)nc2c1cnn2C1CCC(F)(F)CC1] | Exm. 8A | Exm. 2N | 1.49 min (M1) | 387 $(M+H)^+$ |
| Exm. 35 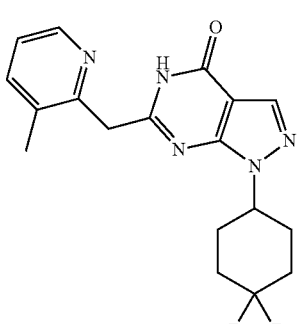 | Exm. 8A | Exm. 12A | 7.47 min (M1Eh) | 360 $(M+H)^+$ Ion Source: APCI |

-continued
| structure | starting material: pyrazole | starting material: ester | $R_t$ | MS (ESI pos/neg, m/z) |
|---|---|---|---|---|
| Exm. 36 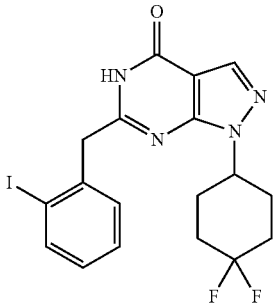 [SMILES: O=c1[nH]c(Cc2ccccc2I)nc2c1cnn2C1CCC(F)(F)CC1] | Exm. 8A | Exm. 2KA | 2.58 min (M1) | 471 (M + H)+ |
| Exm. 37 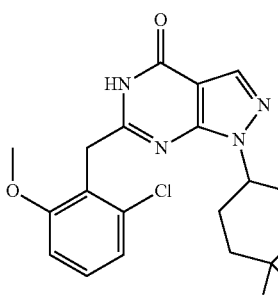 | Exm. 8A | Exm. 14A | 1.56 min (M1) | 409/411 (Cl) (M + H)+ |
| Exm. 38 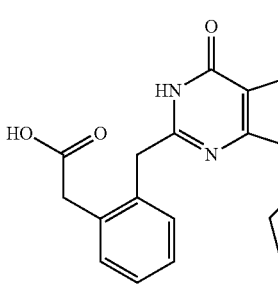 | Exm. 8A | Exm. 2KC | 1.31 min (M1) | 403 (M + H)+ |
| Exm. 39 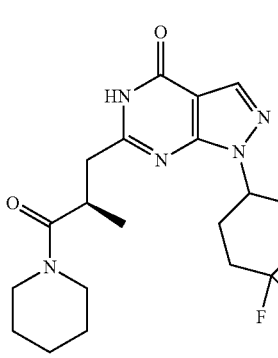 | Exm. 8A | Exm. 16A | 1.36 min (M1) | 408 (M + H)+ |

-continued

| structure | starting material: pyrazole | starting material: ester | $R_t$ | MS (ESI pos/neg, m/z) |
|---|---|---|---|---|
| Exm. 44 | Exm. 8A | Exm. 2KE | 1.54 min (M1) | 441/443 (Br) (M + H)+ |
| Exm. 45 | Exm. 8A | Exm. 2KF | 1.54 min (M1) | 441/443 (Br) (M + H)+ |
| Exm. 46 | Exm. 8A | Exm. 12AA | 8.75 min (M1Eh) | 424/426 (Br) (M + H)+ ion source: APCI |
| Exm. 47 enantiomer A | Exm. 8A | Exm. 19A | 9.47 min (M1Eh) | 365 (M + H)+ Ion Source APCI |

-continued

| structure | starting material: pyrazole | starting material: ester | $R_t$ | MS (ESI pos/neg, m/z) |
|---|---|---|---|---|
| Exm. 48 enantiomer B | Exm. 8A | Exm. 19B | 9.45 min (M1Eh) | 365 (M + H)+ Ion Source APCI |
| Exm. 48-2 racemic mixture | Exm. 8A | Exm. 20A | 1.54 min (Method 1) | 441/443 (Br) (M + H)+ |
| Exm. 48-3 | Exm. 8A | Exm. 2KH | 1.46 min (M1) | 375 (M + H)+ |
| Exm. 48-4 | Exm. 8A | Exm. 2KI | 1.50 min (M1) | 393 (M + H)+ |

-continued

| structure | starting material: pyrazole | starting material: ester | $R_t$ | MS (ESI pos/neg, m/z) |
|---|---|---|---|---|
| Exm. 48-5 racemic mixture | Exm. 8A | Exm. 22A | 3.14 min (M2) | 347 (M + H)+ |
| Exm. 48-6 diastereomeric mixture | Exm. 8A | Exm. 26A | 1.23 min (M1) | 380 (M + H)+ |

Example 49

Mixture of Stereoisomers

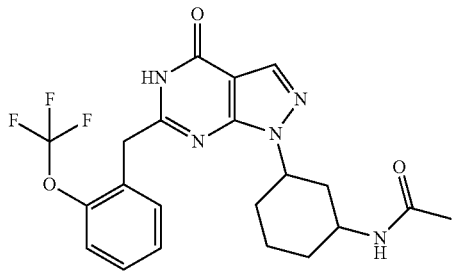 [SMILES: CC(=O)NC1CCCC(n2ncc3c(=O)[nH]c(Cc4ccccc4OC(F)(F)F)nc32)C1]

25.0 mg (0.08 mmol) of example 10A were dissolved in 2 mL of dichloromethane, 7.20 µL (0.10 mmol) acetylchloride and 13.3 µL (0.10 mmol) triethylamine were added and the reaction mixture stirred over night at room temperature. The reaction mixture was evaporated under reduced pressure. The residue was purified by preparative HPLC (eluent A: water+ 0.13% TFA, eluent B: acetonitrile). 2.50 mg (12%) of the product were obtained.

HPLC-MS (Method1): $R_t$=1.28 min

MS (ESI pos): m/z=450 (M+H)$^+$

The following examples were synthesized in analogy to the preparation of example 49, using the corresponding pyrazoles and acid chlorides as starting materials

| structure | starting material: pyrazole | starting material: acid chloride | $R_t$ | MS (ESI pos, m/z) |
|---|---|---|---|---|
| Exm. 50 cis racemic mixture | Exm. 11A | Cl—C(=O)—CH₃ | 1.17 min (M1) | 358 (M + H)+ |

| structure | starting material: pyrazole | starting material: acid chloride | $R_t$ | MS (ESI pos, m/z) |
|---|---|---|---|---|
| Exm. 51 cis racemic mixture 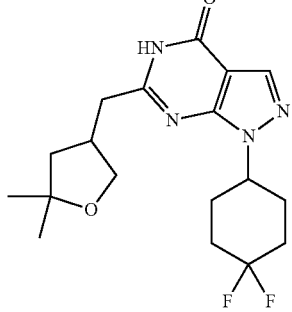 | Exm. 11A | 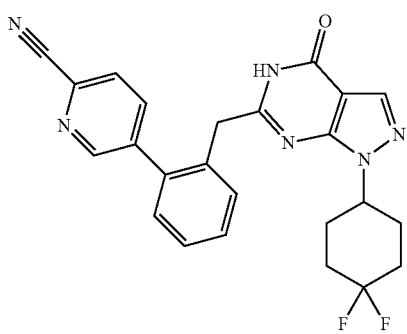 | 1.45 min (M1) | 420 (M + H)+ |

Example 52

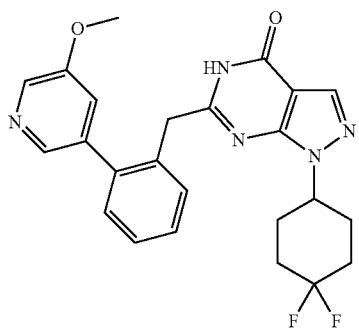 [SMILES: COc1cncc(-c2ccccc2Cc2nc3c(cnn3C3CCC(F)(F)CC3)c(=O)[nH]2)c1]

Racemic Mixture

To 100 mg (0.26 mmol) of example 9A, 0.17 mL (1.05 mmol) triethylsilane, 1 mL dichloromethane and 1 mL trifluoroacetic acid (with 5% water) were added. The reaction mixture was stirred 5 h at room temperature and then evaporated under reduced pressure. The residue was purified by preparative HPLC (eluent A: water+0.13% TFA, eluent B: acetonitrile). 32.0 mg (34%) of the product were obtained.

HPLC-MS (Method1): $R_t$=1.33 min
MS (ESI pos): m/z=367 (M+H)+

Example 53

The reaction was executed under an argon-atmosphere.

To 100 mg (0.24 mmol) of example 33 and 105 mg (0.69 mmol) 5-methoxy-3-pyridinylboronic acid, 5 mL dioxane, 300 µL (0.60 mmol) of an aqueous sodium carbonate solution (2 mol/L) and 20.0 mg (0.02 mmol) tetrakis-(triphenylphosphin)-palladium(0) were added. The reaction mixture was heated to 150° C. for 30 min in a microwave oven. After cooling to room temperature the reaction mixture was filtered and the filtrate was evaporated under reduced pressure. The residue was purified by preparative HPLC (eluent A: water+ 0.13% TFA, eluent B: acetonitrile). 90.0 mg (85%) of the product were obtained.

HPLC-MS (Method1): $R_t$=1.25 min
MS (ESI pos): m/z=452 (M+H)+

Example 54

The reaction was executed under an argon-atmosphere.

To 100 mg (0.24 mmol) of example 33 and 110 mg (0.48 mmol) 2-cyanopyridine-5-boronic acid pinacol ester, 5 mL dioxane, 300 µL (0.60 mmol) of an aqueous sodium carbonate solution (2 mol/L) and 20.0 mg (0.02 mmol) tetrakis-(triphenylphosphin)-palladium(0) were added. The reaction mixture was heated to 150° C. for 30 min in a microwave oven. After cooling to room temperature the reaction mixture was filtered and the filtrate was evaporated under reduced pressure. The residue was purified by preparative HPLC (eluent A: water+0.13% TFA, eluent B: acetonitrile). 72.0 mg (68%) of the product were obtained.

HPLC-MS (Method1): $R_t$=1.47 min
MS (ESI pos): m/z=447 (M+H)$^+$

The following examples were synthesized in analogy to the preparation of examples 53/54, using the corresponding boronic acids or boronic esters and bromides as starting materials

| | structure | starting material: bromide | starting material: boronic acid or -ester | $R_t$ | MS (ESI pos, m/z) |
|---|---|---|---|---|---|
| Exm. 55 | 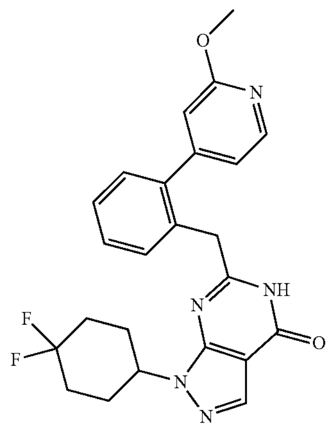 [SMILES: COc1cc(-c2ccccc2Cc2nc3c(cnn3C3CCC(F)(F)CC3)c(=O)[nH]2)ccn1] | Exm. 33 | | 1.45 min (M1) | 452 (M + H)$^+$ |
| Exm. 56 | 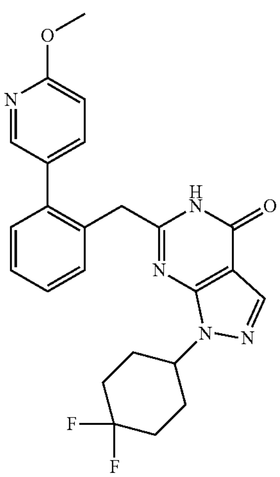 [SMILES: COc1ccc(-c2ccccc2Cc2nc3c(cnn3C3CCC(F)(F)CC3)c(=O)[nH]2)cn1] | Exm. 33 | | 1.51 min (M1) | 452 (M + H)$^+$ |
| Exm. 57 | 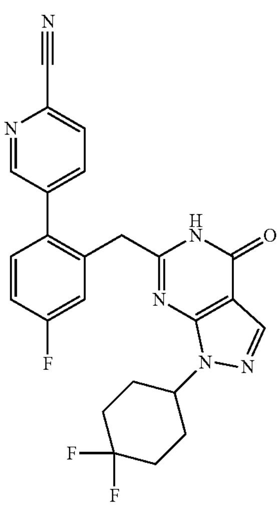 [SMILES: N#Cc1ccc(-c2ccc(F)cc2Cc2nc3c(cnn3C3CCC(F)(F)CC3)c(=O)[nH]2)cn1] | Exm. 45 | | 1.51 min (M1) | 465 (M + H)$^+$ |

-continued

| structure | starting material: bromide | starting material: boronic acid or -ester | $R_t$ | MS (ESI pos, m/z) |
|---|---|---|---|---|
| Exm. 58 | Exm. 45 | | 1.29 min (M1) | 470 (M + H)⁺ |
| Exm. 59 | Exm. 44 | | 1.51 min (M1) | 470 (M + H)⁺ |
| Exm. 60 | Exm. 45 | | 1.51 min (M1) | 465 (M + H)⁺ |

-continued

| | structure | starting material: bromide | starting material: boronic acid or -ester | $R_t$ | MS (ESI pos, m/z) |
|---|---|---|---|---|---|
| Exm. 61 | 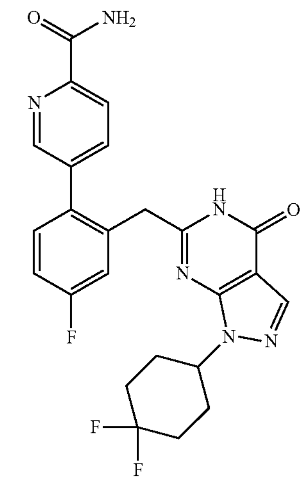 [SMILES: NC(=O)c1ccc(-c2ccc(F)cc2Cc2nc3c(cnn3C3CCC(F)(F)CC3)c(=O)[nH]2)cn1] | Exm. 45 | | 1.37 min (M1) | 483 (M + H)+ |
| Exm. 62 | 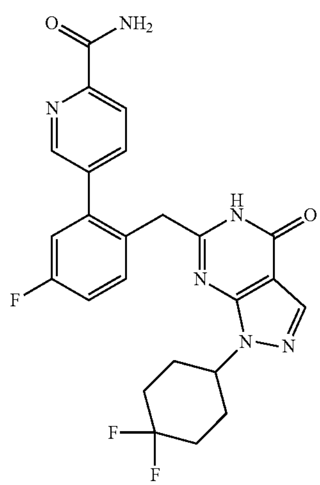 [SMILES: NC(=O)c1ccc(-c2cc(F)ccc2Cc2nc3c(cnn3C3CCC(F)(F)CC3)c(=O)[nH]2)cn1] | Exm. 44 | | 1.40 min (M1) | 483 (M + H)+ |
| Exm. 63 | 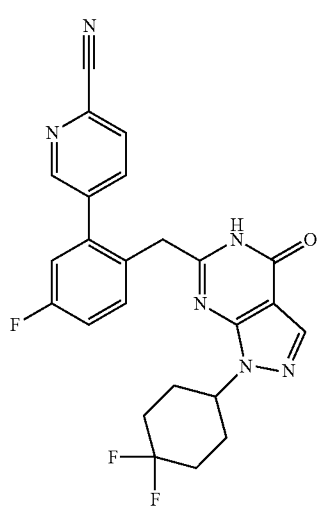 [SMILES: N#Cc1ccc(-c2cc(F)ccc2Cc2nc3c(cnn3C3CCC(F)(F)CC3)c(=O)[nH]2)cn1] | Exm. 44 | | 1.50 min (M1) | 465 (M + H)+ |

-continued

| structure | starting material: bromide | starting material: boronic acid or -ester | $R_t$ | MS (ESI pos, m/z) |
|---|---|---|---|---|
| Exm. 64 | Exm. 45 | | 1.47 min (M1) | 470 (M + H)+ |
| Exm. 65 | Exm. 45 | | 1.52 min (M1) | 470 (M + H)+ |
| Exm. 66 | Exm. 45 | | 1.24 min (M1) | 440 (M + H)+ |

| | structure | starting material: bromide | starting material: boronic acid or -ester | $R_t$ | MS (ESI pos, m/z) |
|---|---|---|---|---|---|
| Exm. 67 | 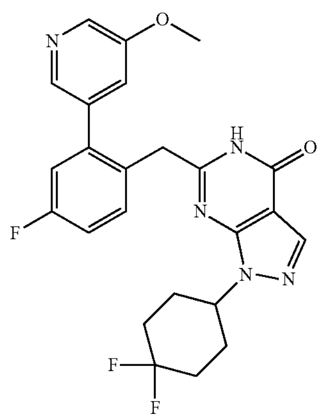 [SMILES: COc1cncc(-c2cc(F)ccc2Cc2nc3c(cnn3C3CCC(F)(F)CC3)c(=O)[nH]2)c1] | Exm. 44 | | 1.27 min (M1) | 470 (M + H)+ |
| Exm. 68 | 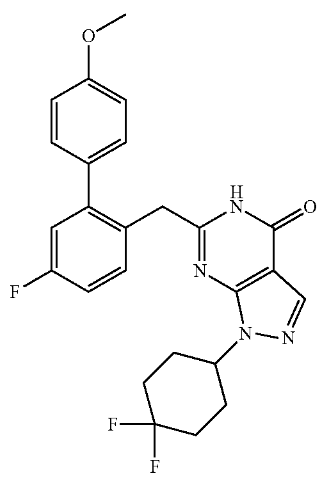 [SMILES: COc1ccc(-c2cc(F)ccc2Cc2nc3c(cnn3C3CCC(F)(F)CC3)c(=O)[nH]2)cc1] | Exm. 44 | | 1.63 min (M1) | 469 (M + H)+ |
| Exm. 69 | 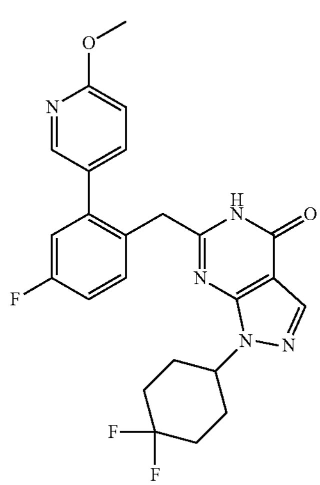 [SMILES: COc1ccc(-c2cc(F)ccc2Cc2nc3c(cnn3C3CCC(F)(F)CC3)c(=O)[nH]2)cn1] | Exm. 44 | | 1.52 min (M1) | 470 (M + H)+ |

-continued

| | structure | starting material: bromide | starting material: boronic acid or -ester | R$_t$ | MS (ESI pos, m/z) |
|---|---|---|---|---|---|
| Exm. 70 | 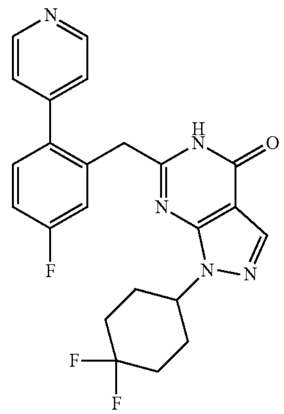 [SMILES: O=c1[nH]c(Cc2cc(F)ccc2-c2ccncc2)nc2c1cnn2C1CCC(F)(F)CC1] | Exm. 45 | | 1.23 min (M1) | 440 (M + H)$^+$ |
| Exm. 71 | 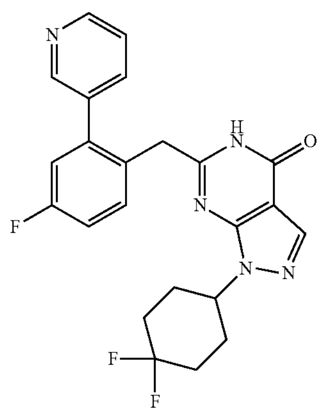 [SMILES: O=c1[nH]c(Cc2ccc(F)cc2-c2cccnc2)nc2c1cnn2C1CCC(F)(F)CC1] | Exm. 44 | | 1.21 min (M1) | 440 (M + H)$^+$ |
| Exm. 72 | 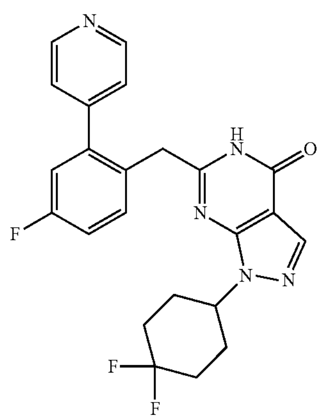 [SMILES: O=c1[nH]c(Cc2ccc(F)cc2-c2ccncc2)nc2c1cnn2C1CCC(F)(F)CC1] | Exm. 44 | | 1.22 min (M1) | 440 (M + H)$^+$ |
| Exm. 72-2 | 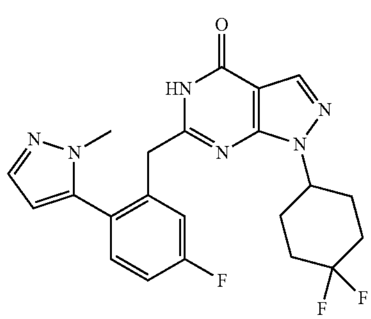 [SMILES: Cn1nccc1-c1ccc(F)cc1Cc1nc2c(cnn2C2CCC(F)(F)CC2)c(=O)[nH]1] | Exm. 45 | | 1.39 min (M1) | 443 (M + H)$^+$ |

| | structure | starting material: bromide | starting material: boronic acid or -ester | $R_t$ | MS (ESI pos, m/z) |
|---|---|---|---|---|---|
| Exm. 72-3 | 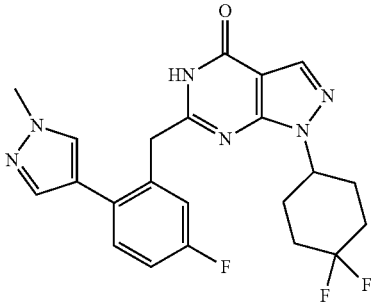 [SMILES: Cn1cc(-c2ccc(F)cc2Cc2nc3c(cnn3C3CCC(F)(F)CC3)c(=O)[nH]2)cn1] | Exm. 45 | 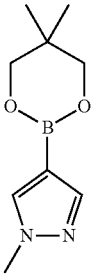 | 1.41 min (M1) | 443 (M + H)⁺ |
| Exm. 72-4 | 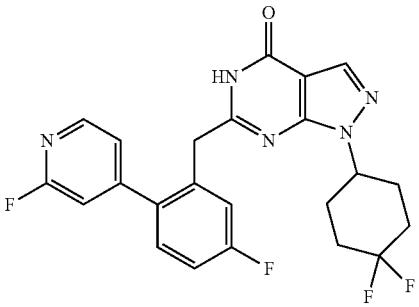 [SMILES: O=c1[nH]c(Cc2cc(F)ccc2-c2ccnc(F)c2)nc2c1cnn2C1CCC(F)(F)CC1] | Exm. 45 | 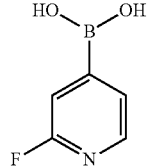 | 1.49 min (M1) | 458 (M + H)⁺ |
| Exm. 72-5 | 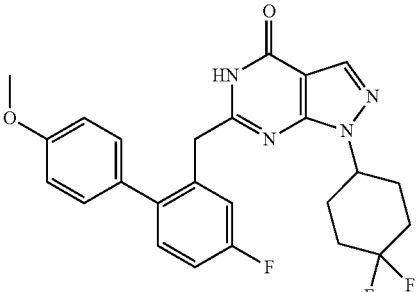 | Exm. 45 | 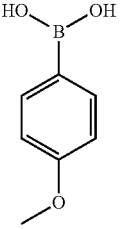 | 1.62 min (M1) | 469 (M + H)⁺ |
| Exm. 72-6 | 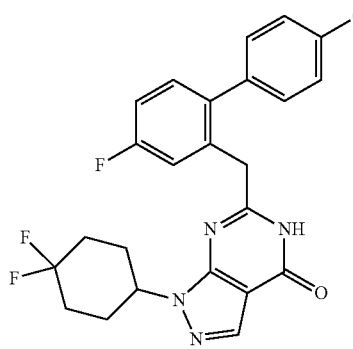 | Exm. 45 | 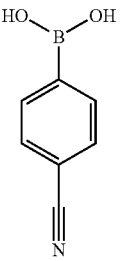 | 1.56 min (M1) | 464 (M + H)⁺ |

-continued

| | structure | starting material: bromide | starting material: boronic acid or -ester | $R_t$ | MS (ESI pos, m/z) |
|---|---|---|---|---|---|
| Exm. 72-7 | 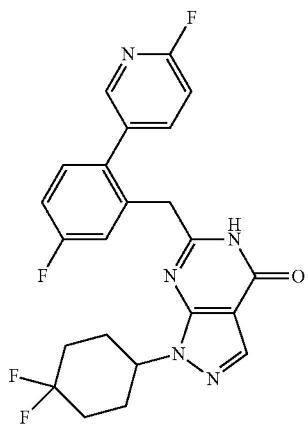 [SMILES: O=c1[nH]c(Cc2cc(F)ccc2-c2ccc(F)nc2)nc2c1cnn2C1CCC(F)(F)CC1] | Exm. 45 | | 1.51 min (M1) | 458 (M + H)+ |
| Exm. 72-8 | 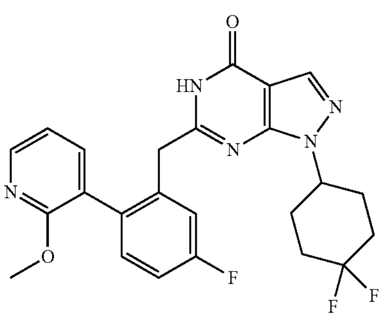 [SMILES: COc1ncccc1-c1ccc(F)cc1Cc1nc2c(cnn2C2CCC(F)(F)CC2)c(=O)[nH]1] | Exm. 45 | | 1.51 min (M1) | 470 (M + H)+ |
| Exm. 72-9 | 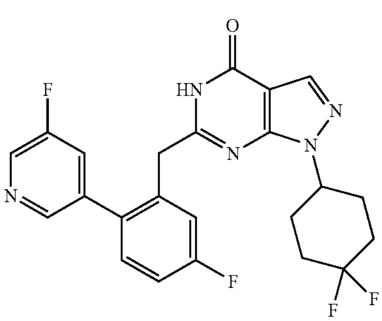 [SMILES: O=c1[nH]c(Cc2cc(F)ccc2-c2cncc(F)c2)nc2c1cnn2C1CCC(F)(F)CC1] | Exm. 45 | | 1.46 min (M1) | 458 (M + H)+ |

| | structure | starting material: bromide | starting material: boronic acid or -ester | $R_t$ | MS (ESI pos, m/z) |
|---|---|---|---|---|---|
| Exm. 72-10 racemic mixture | 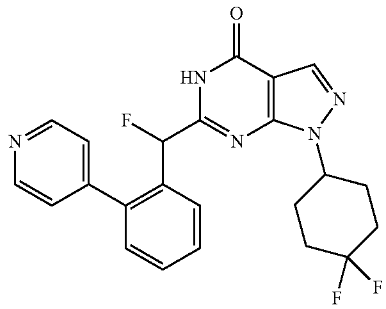 [SMILES: O=c1[nH]c(C(F)c2ccccc2-c2ccncc2)nc2c1cnn2C1CCC(F)(F)CC1] | Exm. 48-2 | | 1.23 min (M1) | 440 (M + H)+ |
| Exm. 72-11 racemic mixture | 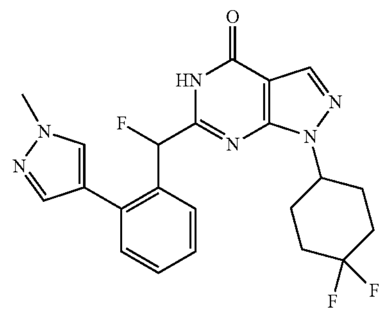 [SMILES: Cn1cc(-c2ccccc2C(F)c2nc3c(cnn3C3CCC(F)(F)CC3)c(=O)[nH]2)cn1] | Exm. 48-2 | | 1.43 min (M1) | 443 (M + H)+ |

Example 73

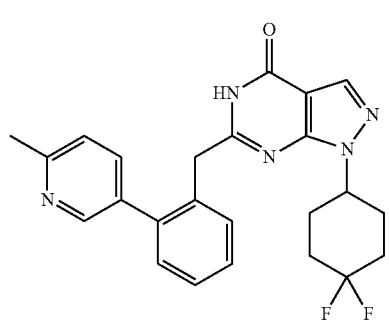 [SMILES: Cc1ccc(-c2ccccc2Cc2nc3c(cnn3C3CCC(F)(F)CC3)c(=O)[nH]2)cn1]

Example 74

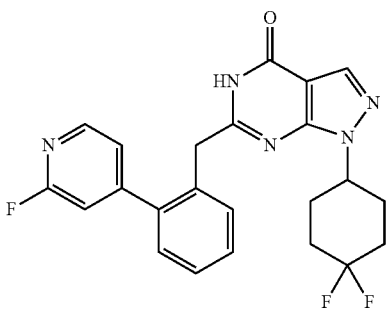 [SMILES: O=c1[nH]c(Cc2ccccc2-c2ccnc(F)c2)nc2c1cnn2C1CCC(F)(F)CC1]

The reaction was executed under an argon-atmosphere.

To 100 mg (0.24 mmol) of example 33 and 90.0 mg (0.66 mmol) 6-methylpyridin-3-ylboronic acid, 3 mL dioxane and 1 mL methanol, 140 μL (1 mmol) TEA and 15 mg (0.02 mmol) 1,1'-bis(diphenylphosphino)ferrocenedichloropalladium(II) were added. The reaction mixture was heated to 140° C. for 30 min in a microwave oven. After cooling to room temperature the reaction mixture was filtered and the filtrate was evaporated under reduced pressure. The residue was purified by preparative HPLC (eluent A: water+0.13% TFA, eluent B: acetonitrile). 33.2 mg (32%) of the product were obtained.

HPLC-MS (Method1): $R_t$=1.19 min

MS (ESI pos): m/z=436 (M+H)+

The reaction was executed under an argon-atmosphere.

To 100 mg (0.24 mmol) of example 33 and 70.0 mg (0.50 mmol) 2-fluoropyridin-4-ylboronic acid, 3 mL dioxane and 2 mL methanol, 350 μL (0.70 mmol) of a aqueous sodium carbonate solution (2 mol/L) and 18.0 mg (0.02 mmol) 1,1'-bis(diphenylphosphino)ferrocenedichloropalladium(II) were added. The reaction mixture was heated to 140° C. for 40 min in a microwave oven. After cooling to room temperature the reaction mixture was filtered and the filtrate was evaporated under reduced pressure. The residue was purified by preparative HPLC (eluent A: water+0.13% TFA, eluent B: acetonitrile). 47.4 mg (45.7%) of the product were obtained.

HPLC-MS (Method1): $R_t$=1.49 min

MS (ESI pos): m/z=440 (M+H)+

The following examples were synthesized in analogy to the preparation of example 74, using the corresponding boronic acids or boronic esters and bromides as starting materials

| | structure | starting material: bromide | starting material: boronic acid/-ester | $R_t$ | MS (ESI pos, m/z) |
|---|---|---|---|---|---|
| Exm. 75 | 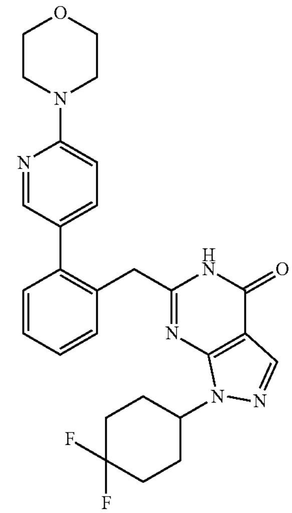 [SMILES: O=c1[nH]c(Cc2ccccc2-c2ccc(N3CCOCC3)nc2)nc2c1cnn2C1CCC(F)(F)CC1] | Exm. 33 | | 1.24 min (M1) | 507 (M + H)$^+$ |

Example 76

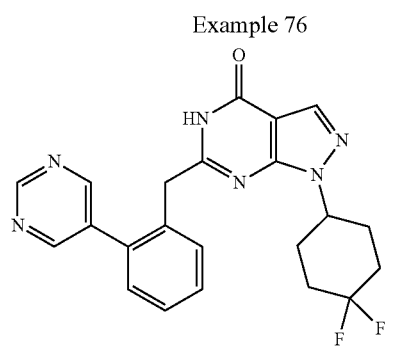

The reaction was executed under an argon-atmosphere.

To 100 mg (0.24 mmol) of example 33 and 60 mg (0.48 mmol) pyrimidin-5-ylboronic acid, 4 mL dioxane and 1 mL MeOH, 300 µL (0.60 mmol) of a aqueous sodium carbonate solution (2 mol/L) and 20.0 mg (0.02 mmol) tetrakis-(triphenylphosphin)-palladium(0) were added. The reaction mixture was heated to 140° C. for 30 min in a microwave oven. After cooling to room temperature the reaction mixture was filtered and the filtrate was evaporated under reduced pressure. The residue was purified by preparative HPLC (eluent A: water+0.13% TFA, eluent B: acetonitrile). 46.0 mg (46.1%) of the product were obtained.

HPLC-MS (Method1): $R_t$=1.29 min

MS (ESI pos): m/z=423 (M+H)$^+$

Example 77

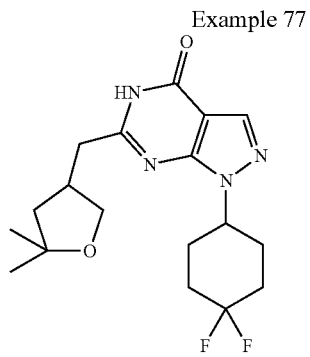

Enantiomer B

The title compound was obtained, using example 52 as starting material, by chiral HPLC separation with method Chiral 2. The product was the later eluting substance, 6.10 mg (24%).

Chiral HPLC (Method Chiral 3): $R_t$=2.26 min

HPLC-MS (Method 1): $R_t$=1.34 min

MS (ESI pos): m/z=367 (M+H)$^+$

Example 78

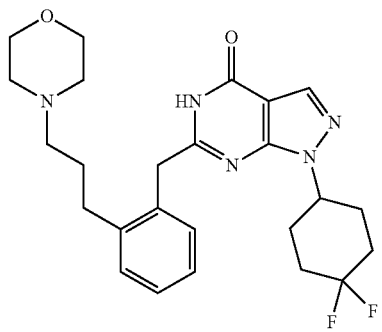 [SMILES: O=c1[nH]c(Cc2ccccc2CCCN2CCOCC2)nc2c1cnn2C1CCC(F)(F)CC1]

67.8 mg (0.25 mmol) of example 8A were dissolved in 8 mL pyridine, 300 mg (1.06 mmol) example 15A in 1.5 mL dichlormethane were added and the reaction mixture was stirred over night at room temperature. 6 mL methanol and one pellet of KOH were added and the solution was refluxed for 2 h. The reaction mixture was evaporated under reduced pressure. The residue was purified by preparative HPLC (eluent A: water+0.13% TFA, eluent B: acetonitrile). 13.9 mg (12%) of the product were obtained.

HPLC-MS (Method1): $R_t$=1.24 min

MS (ESI pos): m/z=472 (M+H)$^+$

Example 79

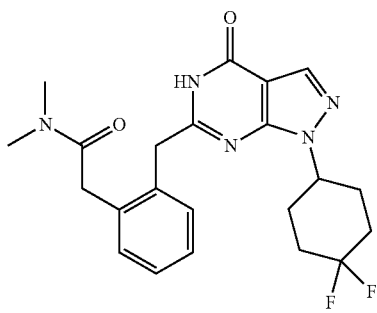 [SMILES: CN(C)C(=O)Cc1ccccc1Cc1nc2c(cnn2C2CCC(F)(F)CC2)c(=O)[nH]1]

80.0 mg (0.20 mmol) of example 38 were dissolved in 3 mL DMF and 121 µL (0.7 mmol) DIPEA and 21.1 µL (0.40 mmol) dimethylamine (2M in THF) and 67.1 mg (0.21 mmol) TBTU were added and stirred 2 h at room temperature. The reaction was made acidic with a mixture of acetonitrile, water and TFA. Then it was purified by preparative HPLC (eluent A: water+0.13% TFA, eluent B: acetonitrile). 38.0 mg (45%) of the product were obtained.

HPLC-MS (Method1): $R_t$=1.29 min

MS (ESI pos): m/z=430 (M+H)$^+$

The following examples were synthesized in analogy to the preparation of example 79, using the corresponding acids and amines as starting materials

| | structure | starting material: acid | starting material: amine | $R_t$ | MS (ESI pos, m/z) |
|---|---|---|---|---|---|
| Exm. 80 | 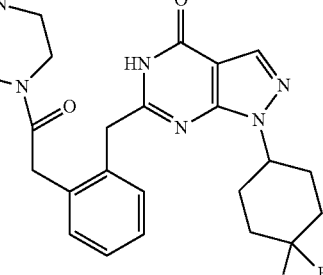 | Exm. 38 | 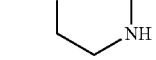 | 1.17 min (M1) | 485 (M + H)$^+$ |
| Exm. 81 | 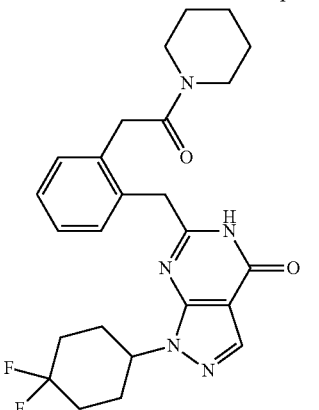 | Exm. 38 | 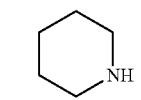 | 1.44 min (M1) | 470 (M + H)$^+$ |
| Exm. 82 | 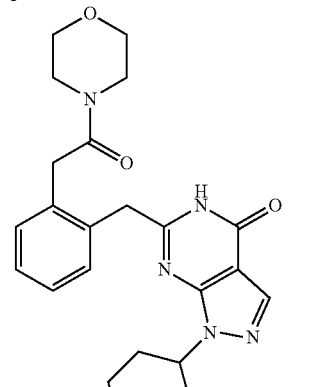 | Exm. 38 | 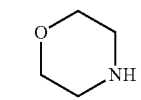 | 1.28 min (M1) | 472 (M + H)$^+$ |

Example 83

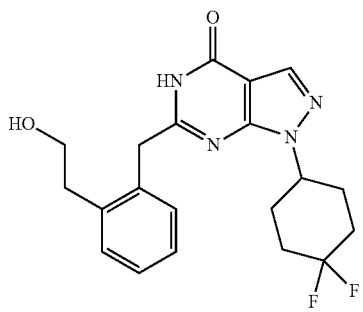 [SMILES: O=c1[nH]c(Cc2ccccc2CCO)nc2c1cnn2C1CCC(F)(F)CC1]

To 159 µL (0.16 mmol) lithiumaluminiumhydride 2 M in THF were added 33.0 mg (0.08 mmol) of example 38, dissolved in 1 mL THF at 0° C. and stirred for 5 min. The reaction mixture was quenched with a mixture of water and THF. After adding a few drops of 4N NaOH to the reaction, it was filtered over celite. The filtrate was washed three times with ethylacetate. The organic layer was dried and the solvent was removed under reduced pressure. The residue was dissolved in a mixture of acetonitrile, water and TFA. Then it was purified by preparative HPLC (eluent A: water+0.13% TFA, eluent B: acetonitrile). 15.0 mg (49%) of the product were obtained.

HPLC-MS (Method1): $R_t$=1.31 min
MS (ESI pos): m/z=389 (M+H)$^+$

Example 84

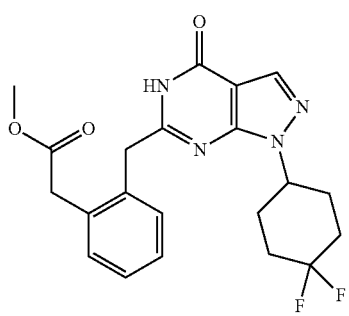 [SMILES: COC(=O)Cc1ccccc1Cc1nc2c(cnn2C2CCC(F)(F)CC2)c(=O)[nH]1]

60.0 mg (0.15 mmol) of example 38 were dissolved in 5 mL of a mixture consisting of acetonitrile/methanol (9:1). Then 0.09 mL (0.18 mmol) trimethylsilyldiazomethane were added. After stirring for 15 min at room temperature the reaction was quenched with a few drops of acetic acid. The solvent was removed under reduced pressure.

The residue was purified by preparative HPLC (eluent A: water+0.13% TFA, eluent B: acetonitrile). 37.0 mg (59%) of the product were obtained.

HPLC-MS (Method1): $R_t$=1.46 min
MS (ESI pos): m/z=417 (M+H)$^+$

Example 85

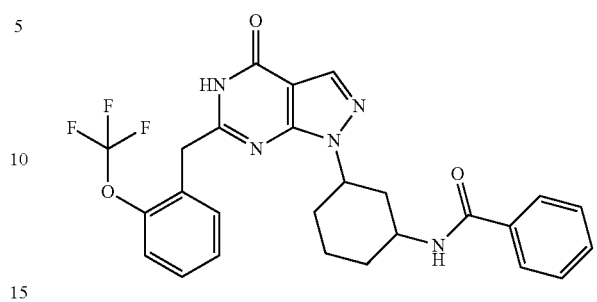

Mixture of Stereoisomers 28.0 mg (0.05 mmol) of example 10A were dissolved in 2 mL THF and 2 mL dichloromethane. Then 14.9 µL (0.11 mmol) TEA and 18.7 µL (0.16 mmol) benzoyl chloride were added. The reaction was stirred over night at room temperature. The solvent was removed under reduced pressure. The residue was dissolved in a mixture of acetonitrile, water and TFA and purified by preparative HPLC (eluent A: water+0.13% TFA, eluent B: acetonitrile). 7.5 mg (27%) of the product were obtained.

HPLC-MS (Method1): $R_t$=1.53 min
MS (ESI pos): m/z=512 (M+H)$^+$

Example 86

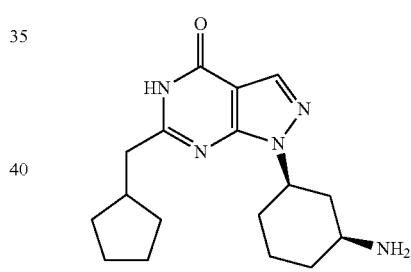

Cis Racemic Mixture
The synthesis of example 86 is described as example 11A.
HPLC-MS (Method1): $R_t$=1.04 min
MS (ESI pos): m/z=316 (M+H)$^+$

Example 87

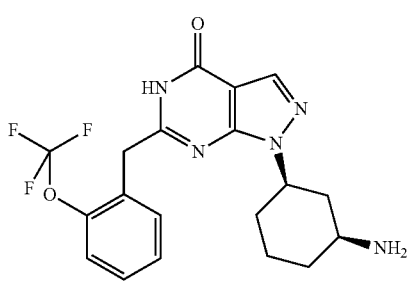 [SMILES: N[C@H]1CCC[C@@H](n2ncc3c(=O)[nH]c(Cc4ccccc4OC(F)(F)F)nc32)C1]

Cis Racemic Mixture
The synthesis of example 87 is described as example 10A.
HPLC-MS (Method1): $R_t$=1.16 min
MS (ESI pos): m/z=408 (M+H)$^+$ Example 88

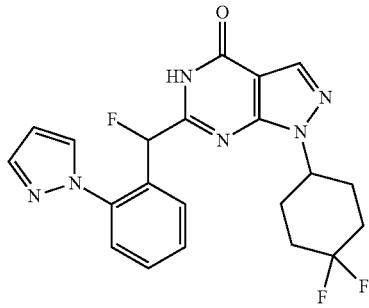 [SMILES: O=c1[nH]c(C(F)c2ccccc2-n2cccn2)nc2c1cnn2C1CCC(F)(F)CC1]

Racemic Mixture

A mixture of 148 mg (0.45 mmol) cesium carbonate, 9.32 mg (0.07 mmol) salicylaldoxime, 100 mg (0.23 mmol) of example 48-2 and 30.9 mg (0.45 mmol) pyrazole in 5 mL of acetonitrile were heated for 2 h at 82° C. under nitrogen using microwave heating. After cooling to room temperature the reaction mixture was diluted with dichloromethane. The precipitate was filtered off and the filtrate was evaporated under reduced pressure. The residue was taken up in dichloromethane and washed with water and brine. The organic layer was separated, dried and evaporated under reduced pressure. The residue was purified by preparative HPLC (eluent A: water+0.13% TFA, eluent B: acetonitrile). 40 mg (41%) of the product were obtained.

HPLC-MS (Method1): $R_t$=1.53 min
MS (ESI pos): m/z=429 (M+H)$^+$

The following example was synthesized in analogy to the preparation of example 88, using the corresponding starting materials Example 90

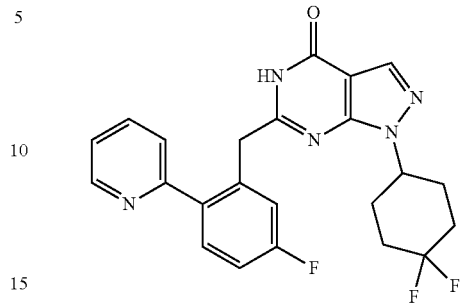

Step A:

2.00 mL (21.0 mmol) 2-bromo-pyridine and 5.07 mL (21.4 mmol) triisopropyl borate were dissolved in 40 mL THF under nitrogen. The mixture was cooled to −30° C. 13.5 mL (21.6 mmol) n-buthyllithium were added dropwise. After stirring for 1.5 h the mixture was allowed to warm to room temperature within 1 h. The precipitate was filtered off and dried to yield 4.1 g of solid material.

Step B:

To 100 mg (0.23 mmol) of example 45 and 235 mg of the product obtained in step A, 3 mL DMF, 289 mg (1.36 mmol) of potassium phosphate and 26.2 mg (0.02 mmol) tetrakis-(triphenylphosphin)-palladium(0) were added. The reaction mixture was heated to 140° C. for 45 min in a microwave oven. The mixture was evaporated under reduced pressure. The residue was taken up in dichloromethane and washed with water and brine. The organic layer was separated, dried and evaporated under reduced pressure. The residue was purified by preparative HPLC (eluent A: water+0.1% conc. ammonia, eluent B: methanol). 30 mg (30%) of the product were obtained.

HPLC-MS (Method1): $R_t$=1.39 min
MS (ESI pos): m/z=440 (M+H)$^+$

The following example was synthesized in analogy to the preparation of example 90, using the corresponding starting materials

|  | structure | starting material: bromide | starting material: amine | $R_t$ | MS (ESI pos, m/z) |
|---|---|---|---|---|---|
| Exm. 89 | ![structure] | Exm. 45 | ![amine] | 1.54 min (M1) | 429 (M + H)$^+$ |

| | structure | starting material: bromide | starting material: bromo-pyridine | $R_t$ | MS (ESI pos, m/z) |
|---|---|---|---|---|---|
| Exm. 91 | 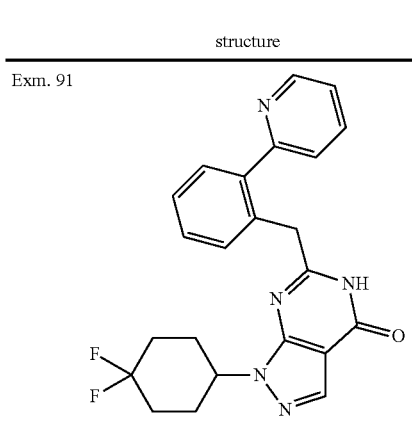 | Exm. 33 | | 3.12 min (M2) | 422 (M + H)$^+$ |

Example 92

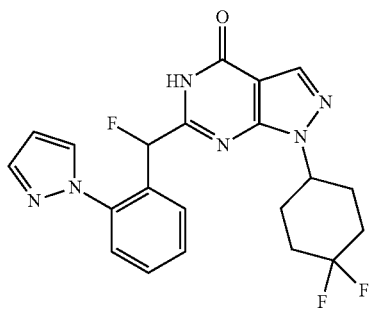

Enantiomer B

The enantiomers of 200 mg of example 88 were separated by preparative HPLC (Method Chiral 5). 72 mg (36%) of example 92 (Enantiomer B-S-Enantiomer) were obtained as the later eluting enantiomer.

Chiral HPLC (Method Chiral 4): $R_t$=4.98 min
HPLC-MS (Method 1): $R_t$=1.53 min
MS (ESI pos): m/z=429 (M+H)$^+$

Example 93

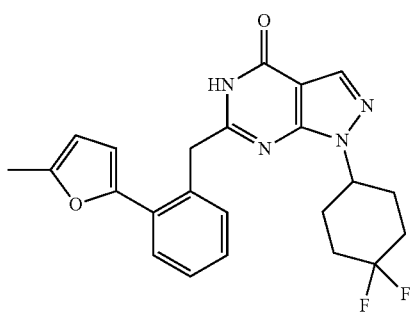 [SMILES: Cc1ccc(-c2ccccc2Cc2nc3c(cnn3C3CCC(F)(F)CC3)c(=O)[nH]2)o1]

A microwave vial was charged with Example 33 (99 mg, 0.23 mmol), 5-methylfuran-2-boronic acid (116.9 mg, 3.96 mmol), tetrakis(triphenylphosphine)palladium(0) (81.15 mg, 0.07 mmol) in Dioxane (1 mL) then 0.94 mL (1.87 mmol) of a 2M aqueous solution of Na$_2$CO$_3$ were added. The reaction mixture is heated to 130° C. for 40 min in a microwave oven. Cooling to 20° C. was followed by acidification with HCl 37% until acidic pH then extraction with dichloromethane (2×2 mL). The organic layer was dried over Na$_2$SO$_4$, filtered and the filtrate was concentrated under reduced pressure. The remaining residue was purified by flash chromatography on SiO$_2$ using n-hexane/ethyl acetate mixture of increasing polarity (from 100% n-hexane to 100% ethyl acetate) as eluant. The product obtained was further purified by preparative HPLC (eluent A: water+0.05% TFA, eluent B: acetonitrile). The title compound was obtained as a solid (32.2 mg, 32%).

HPLC-MS (Method 1E hydro): $R_t$: 10.37 min
MS (APCI pos): m/z=425 (M+H)$^+$

Example 94

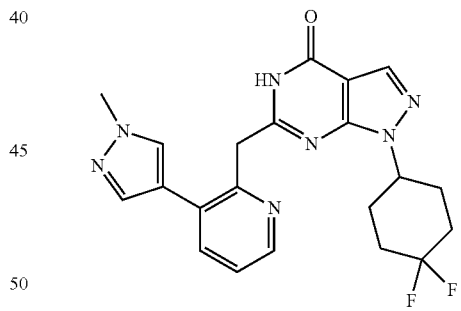

A microwave vial was charged with Example 46 (120 mg, 0.28 mmol), 1-methylfuran-4-84,4,5,5-tetramethyl-1,3,2-dioxaborolan-2-yl)-1H-pyrazole (235.4 mg, 1.13 mmol), dichlorobis(triphenylphosphine)palladium(II) (20 mg, 0.028 mmol) and 0.30 mL of a 2M solution of Cs$_2$CO$_3$ then dimethoxyethane (1 mL) and ethanol (0.5 mL) were added. The reaction mixture was heated to 130° C. for 2 h in a microwave oven. After cooling the solvent was removed under reduced pressure. The remaining residue was purified by flash chromatography on SiO$_2$ using n-hexane/ethyl acetate mixture of increasing polarity (from n-hexane/ethyl acetate 1/1 to 100% ethyl acetate) as eluant. The title compound was obtained as a solid (4 mg, 3%).

HPLC-MS (Method 1 E hydro): $R_t$: 7.52 min
MS (APCI pos): m/z=426 (M+H)$^+$

Example 95

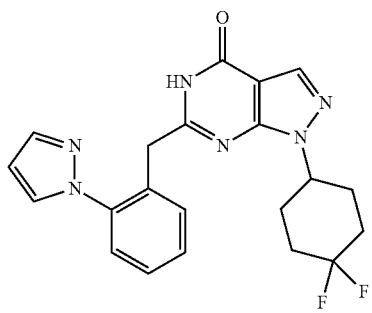 [SMILES: O=c1[nH]c(Cc2ccccc2-n2cccn2)nc2c1cnn2C1CCC(F)(F)CC1]

A vial was charged under inert atmosphere with Example 33 (184 mg, 0.44 mmol), pyrazole (296 mg, 4.35 mmol), copper iodide (82.79 mg, 0.44 mmol) and cesium carbonate (424.93 mg, 1.3 mmol). Dimethylformamide (5 mL), previously degassed, was then added, followed by N—N'-dimethylethylenediamine (46.28 µl, 0.44 mmol). The reaction mixture was heated to 120° C. for 3 hours. After cooling the reaction mixture was filtered through a Celite pad that was rinsed with dimethylformamide. The volume was reduced under reduced pressure, saturated ammonium chloride aqueous solution was added and extracted with ethyl acetate. The organic phase was washed with brine then dried over $Na_2SO_4$ and the solvent was removed under reduced pressure. The crude product was purified by flash chromatography on $SiO_2$ using n-hexane/ethyl acetate mixture of increasing polarity (from 100% n-hexane to 100% ethyl acetate then ethyl acetate/methanol 95/5) as eluant. The product obtained was further purified by SPE cartridge Stratosphere "PL-THIOL MP" to remove copper salts. The solid obtained was triturated with a diisopropylether/diethyl ether mixture (2:1) resulting in title compound as a solid (30 mg, 16%).

HPLC-MS (Method 1E hydro): $R_t$: 9.17 min
MS (APCI pos): m/z=411 (M+H)$^+$

The following example was synthesized in analogy to the preparation of example 95, using the corresponding starting materials

Example 96

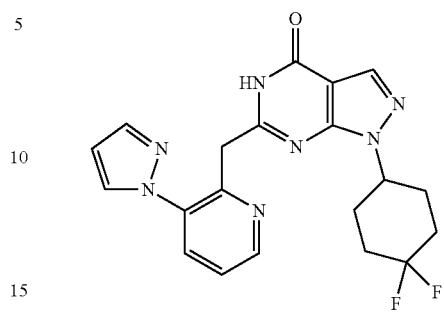

A Schlenk tube was charged under inert atmosphere with Example 46 (200 mg, 0.47 mmol), pyrazole (329 mg, 4.83 mmol), copper iodide (92.48 mg, 0.49 mmol) and cesium carbonate (473.09 mg, 1.45 mmol). Dioxane (5 mL), previously degassed, was then added, followed by N—N'-dimethylethylenediamine (51.70 µl; 0.49 mmol). The reaction mixture was heated to 120° C. overnight. A solid was filtered and washed thoroughly with dioxane. The solvent was removed under reduced pressure and the residue was dissolved in dichloromethane, washed with water and 10% citric acid aqueous solution. The phases were separated using a PHASE SEPARATOR cartridge. The solvent was removed under reduced pressure and the crude product was purified by flash chromatography on $SiO_2$ using n-hexane/ethyl acetate mixture of increasing polarity (from 100% to 100% ethyl acetate) as eluant. The product obtained was dissolved in dichloromethane and washed with 5% $NH_4Cl$ aqueous solution then it was further purified by preparative TLC (eluting with Dichloromethane/Methanol 90/10). The solid obtained was triturated with diethyl ether resulting in title compound as a solid (13.4 mg, 7%).

HPLC-MS (Method 1 E hydro): $R_t$: 7.93 min
MS (APCI pos): m/z=412 (M+H)$^+$

| | structure | starting material: bromide | starting material: | $R_t$ | MS (m/z) |
|---|---|---|---|---|---|
| Exm. 95-1 | 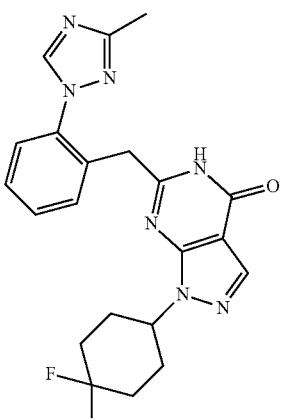 | Exm. 33 | 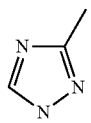 | 8.20 min (M1Eh) | 422 (M + H)$^+$ ion source: APCI |

Example 97

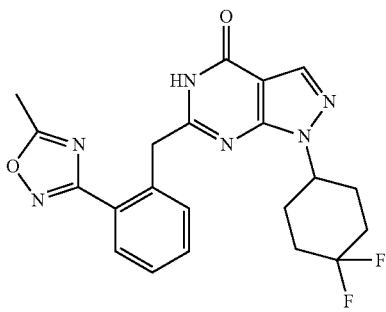 [SMILES: Cc1nc(-c2ccccc2Cc2nc3c(cnn3C3CCC(F)(F)CC3)c(=O)[nH]2)no1]

Example 31 (260 mg, 0.70 mmol) and hydroxylamine 50% in water (0.26 mL, 4.2 mmol) were mixed together in absolute ethanol (4 mL). The reaction mixture was refluxed for 11 hours. The solvent was then removed under reduced pressure to obtain 260 mg (0.65 mmol) of N-Hydroxy-2-[1-(4,4-Difluoro-cyclohexyl)-4-oxo-4,5-dihydro-1H-pyrazolo[3,4-d]pyrimidin-6-ylmethyl]-benzamidine as solid that was used as such in the next step.

N-Hydroxy-2-[1-(4,4-Difluro-cyclohexyl)-4-oxo-4,5-dihydro-1H-pyrazolo[3,4-d]pyrimidin-6-ylmethyl]-benzamidine (260 mg, 0.65 mmol) was suspended in trimethylorthoacetate (5 mL) and acetic acid (0.5 mL) was added afterwards. The mixture was heated to 100° C. for 2 hours. The mixture was cooled to room temperature and the solvent removed under reduced pressure. The solid obtained was purified by preparative HPLC (eluent A: water+0.05% TFA, eluent B: acetonitrile). The product obtained was further purified by preparative TLC using dichloromethane/methanol 95/5 as eluent. The title compound was obtained as a solid (25 mg, 9%).

HPLC-MS (Method 1E hydro): $R_t$: 9.35 min
MS (APCI pos): m/z=427 (M+H)$^+$

Example 98

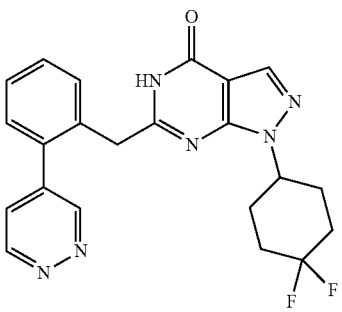 [SMILES: O=c1[nH]c(Cc2ccccc2-c2ccnnc2)nc2c1cnn2C1CCC(F)(F)CC1]

A vial was charged under inert atmosphere with Example 33 (150 mg, 0.35 mmol) and 4-(tributylstannyl)pyridazine (200 mg, 0.54 mmol) in toluene (3 mL), previously degassed, followed by tetrakis(triphenylphosphine)palladium(0) (60.95 mg, 0.052 mmol) and copper iodide (3.37 mg, 0.018 mmol). The reaction mixture was heated to 120° C. for 1 h in a microwave oven. The solvent was removed under reduced pressure. The residue was dissolved into 10% citric acid aqueous solution (2 mL) and extracted with dichloromethane (2×2 mL). The organic layer was dried over Na$_2$SO$_4$, filtered and the filtrate was concentrated under reduced pressure. The oil obtained was purified by SPE cartridge Stratosphere "PL-THIOL MP" and afterwards by flash chromatography on SiO$_2$ using n-hexane/ethyl acetate mixture of increasing polarity (from 100% n-hexane to 100% ethyl acetate then ethyl acetate/methanol 95/5) as eluant. The product obtained was further purified by SCX cartridge. The title compound was obtained as a solid (42 mg, 28%).

HPLC-MS (Method 1 E hydro): $R_t$: 7.68 min
MS (APCI pos): m/z=423 (M+H)$^+$

Example 99

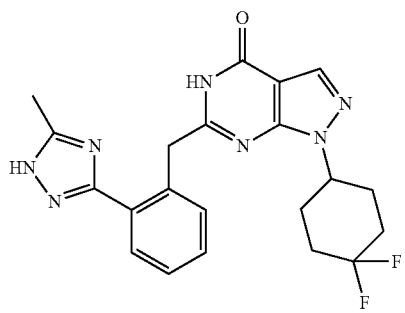 [SMILES: Cc1nc(-c2ccccc2Cc2nc3c(cnn3C3CCC(F)(F)CC3)c(=O)[nH]2)n[nH]1]

Example 31 (80 mg, 0.22 mmol) and hydrazine hydrate (0.64 mL, 13.86 mmol) were mixed together in absolute ethanol (4 mL) and heated to reflux for 7 hours. The solvent was then removed under reduced pressure to obtain 98 mg of N-Amino-2-[4-oxo-1-(tetrahydro-pyran-4-yl)-4,5-dihydro-1H-pyrazolo[3,4-d]pyrimidin-6-ylmethyl]-benzamidine as solid that was used as such in the next step.

Under inert atmosphere N-Amino-2-[4-oxo-1-(tetrahydro-pyran-4-yl)-4,5-dihydro-1H-pyrazolo[3,4-d]pyrimidin-6-ylmethyl]-benzamidine (95 mg, 0.24 mmol) was suspended in trimethylorthoacetate (6 mL) and acetic acid was added afterwards (0.6 mL). The mixture was heated to 80° C. for 30 min then cooled to room temperature and the solvent removed under reduced pressure. The solid obtained was purified by preparative HPLC (eluent A: water+0.05% TFA, eluent B: acetonitrile). The oil obtained was triturated with diethyl ether to give the title compound as a solid (21 mg, 20%).

HPLC-MS (Method 1 E hydro): $R_t$: 8.35 min
MS (APCI pos): m/z=426 (M+H)$^+$

Example 100

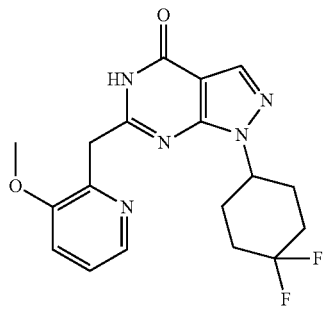 [SMILES: COc1cccnc1Cc1nc2c(cnn2C2CCC(F)(F)CC2)c(=O)[nH]1]

100 mg (0.41 mmol) of 8A were dissolved in absolute ethanol (2 mL), 65.51 mg (1.64 mmol) of sodium hydride (60% suspension in mineral oil) were added. The mixture was stirred for 10 minutes afterwards 296.74 mg (1.64 mmol) of Example 30A were added. The reaction mixture was heated to 150° C. for 1 hour in a microwave oven. Cooling to 20° C. was followed by evaporation of the solvent under reduced pressure. The residue was purified by flash chromatography on SiO$_2$ using dichloromethane/methanol of increasing polarity (from 100% dichloromethane to dichloromethane/methanol 96/4) as eluant. The solid obtained was triturated with diethyl ether to give the title compound as a solid (35 mg, 19%).

HPLC-MS (Method 1 E hydro): R$_t$=7.92 min

MS (APCI pos): m/z=376 (M+H)$^+$

The following examples were synthesized in analogy to the preparation of Example 100, using the corresponding esters or nitrile as starting materials:

| | structure | pyrazolyl-carboxamide | ester or nitrile | R$_t$ | MS (APCI pos, m/z) |
|---|---|---|---|---|---|
| Exm. 101 Enantiomer A | 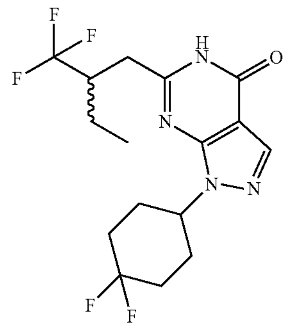 [SMILES: CCC(Cc1nc2c(cnn2C2CCC(F)(F)CC2)c(=O)[nH]1)C(F)(F)F] | Exm. 8A | Exm. 29A | 9.68 min (M1Eh) 13.97 min (Chiral 1) | 379 (M + H)$^+$ |
| Exm. 102 Enantiomer B | 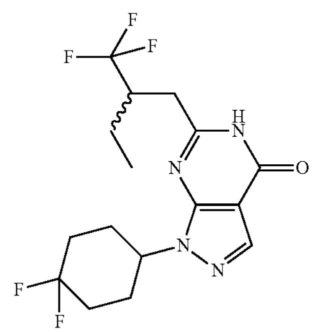 [SMILES: CCC(Cc1nc2c(cnn2C2CCC(F)(F)CC2)c(=O)[nH]1)C(F)(F)F] | Exm. 8A | Exm. 29B | 9.67 min (M1Eh) 13.77 min (Chiral 1) | 379 (M + H)$^+$ |
| Exm. 103 | 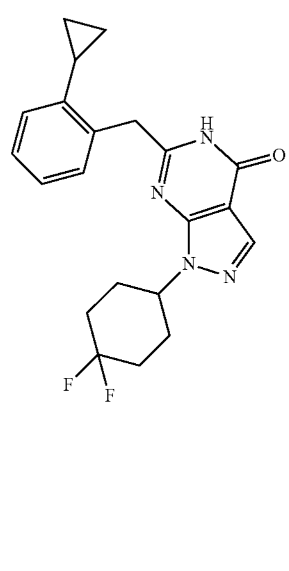 [SMILES: O=c1[nH]c(Cc2ccccc2C2CC2)nc2c1cnn2C1CCC(F)(F)CC1] | Exm. 8A | (may be prepared according to WO2007085557, page 63 example 56 a), incorporated by reference) | 9.95 min (M1Eh) | 385 (M + H)$^+$ |

-continued

| | structure | pyrazolyl-carboxamide | ester or nitrile | R$_t$ | MS (APCI pos, m/z) |
|---|---|---|---|---|---|
| Exm. 104 | 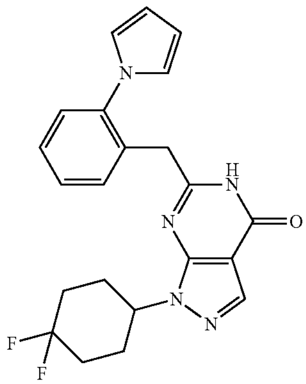 [SMILES: O=c1[nH]c(Cc2ccccc2-n2cccc2)nc2c1cnn2C1CCC(F)(F)CC1] | Exm. 8A | Exm. 32A | 11.69 min (M1Eh) | 410 (M + H)$^+$ |
| Exm. 105 | 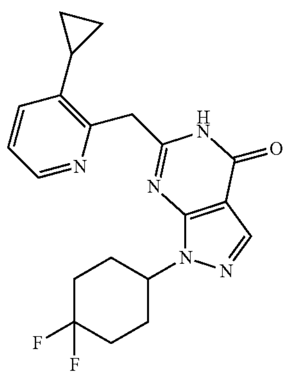 [SMILES: O=c1[nH]c(Cc2ncccc2C2CC2)nc2c1cnn2C1CCC(F)(F)CC1] | Exm. 8A | Exm. 31A | 8.88 min (M1Eh) | 386 (M + H)$^+$ |
| Exm. 106 | 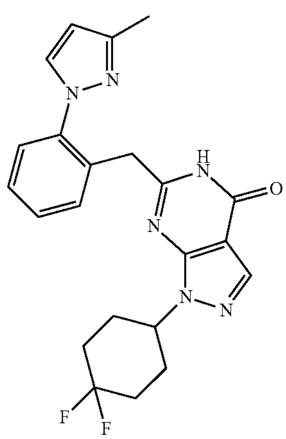 [SMILES: Cc1ccn(-c2ccccc2Cc2nc3c(cnn3C3CCC(F)(F)CC3)c(=O)[nH]2)n1] | Exm. 8A | Exm. 33A | 10.57 min (M2M) | 425 (M + H)$^+$ |

Example 107

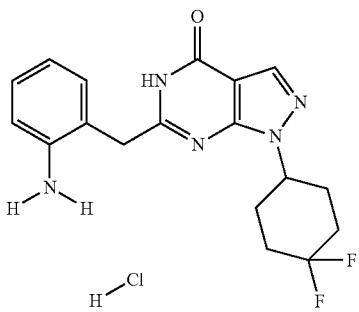 [SMILES: Nc1ccccc1Cc1nc2c(cnn2C2CCC(F)(F)CC2)c(=O)[nH]1 ; Cl]

40 mg of 5% Palladium on activated carbon wet and 48.12 µL (0.58 mmol) of HCl 37% were added to a suspension of Example 40A (205 mg, 0.53 mmol) in absolute ethanol (20 mL). The mixture was hydrogenated at 15 psi for 1 h. The reaction mixture was filtered on a Celite pad and the solvent removed under reduced pressure. The solid obtained was triturated with dichloromethane/methanol 1:1 mixture (5 mL). The solid hydrochloride was collected by filtration and washed with diethyl ether to give the title compound (196 mg, 94%).

HPLC-MS (Method 1 E hydro): $R_t$=8.47 min
MS (APCI pos): m/z=360 (M+H)$^+$

Example 108

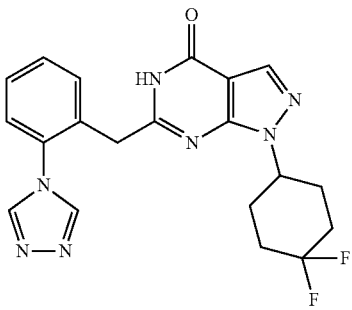 [SMILES: O=c1[nH]c(Cc2ccccc2-n2cnnc2)nc2c1cnn2C1CCC(F)(F)CC1]

To a suspension of Example 107 (188 mg, 0.48 mmol) in dry Toluene (10 mL), 196.2 µL (1.41 mmol) of triethylamine and 217.8 mg of p-Toluenesulfonic acid 102.17 mg (0.48 mmol) of 1,2-bis[(dimethylamino)methylene]hydrazine dihydrochloride were added. The reaction mixture is heated to reflux for 9 days. The solvent was then removed under reduced pressure. The residue was taken up into NaHCO$_3$ aqueous saturated solution and extracted with dichloromethane (2×20 mL). The organic layer was dried over Na$_2$SO$_4$, filtered and the filtrate was concentrated under reduced pressure. The residue was purified by preparative HPLC (eluent A: water+0.05% TFA, eluent B: acetonitrile). The oil obtained was further purified by flash chromatography on silica gel using cyclohexane/ethyl acetate mixture of increasing polarity (from 50% cyclohexane to 100% ethyl acetate then ethyl acetate/ethanol 90/10) as eluant. The residue obtained was triturated with diethyl ether to give the title compound as a solid (32 mg, 16%)

HPLC-MS (Method 1E hydro): $R_t$=7.15 min
MS (APCI pos): m/z=412 (M+H)+

Example 109

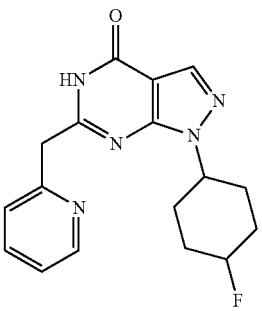 [SMILES: O=c1[nH]c(Cc2ccccn2)nc2c1cnn2C1CCC(F)CC1]

55 mg (0.24 mmol) of 38A were dissolved in absolute ethanol (2 mL), 29.17 mg (0.73 mmol) of sodium hydride (60% suspension in mineral oil) were added. The mixture was stirred for 10 minutes afterwards 151.20 µL (0.97 mmol) of ethyl-2-pyridylacetate were added. The reaction mixture was heated to 140° C. for 40 min in a microwave oven. Cooling to 20° C. was followed by evaporation of the solvent under reduced pressure. The residue was dissolved in citric acid 10% aqueous solution and extracted with dichloromethane 82×2 mL). After evaporation the residue was purified by preparative HPLC (eluent A: NH$_4$COOH 5 mM solution in water, eluent B: acetonitrile). After evaporation the solid was triturated with diethyl ether to give the title compound as a solid (40 mg, 50.3%).

HPLC-MS (Method 2F): $R_t$=7.31 min
MS (ESI pos): m/z=328 (M+H)$^+$

The following examples were synthesized in analogy to the preparation of Example 10, using the corresponding esters or nitrile as starting materials:

| | structure | pyrazolyl-carboxamide | ester | $R_t$ | MS (ESI-APCI, m/z) |
|---|---|---|---|---|---|
| Exm. 110 | 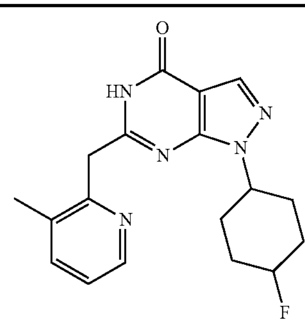 | Exm. 38A |  | 8.24 min (M1E) | 340 (M − H)$^−$ |

| | structure | pyrazolyl-carboxamide | ester | $R_t$ | MS (ESI-APCI, m/z) |
|---|---|---|---|---|---|
| Exm. 111 | 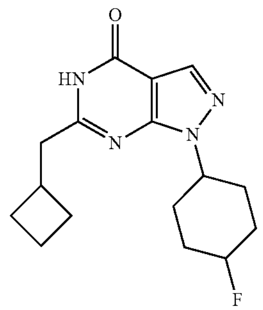 [SMILES: O=c1[nH]c(CC2CCC2)nc2c1cnn2C1CCC(F)CC1] | Exm. 38A | | 9.18 min (M1Eh) | 305 (M + H)+ |
| Exm. 112 | 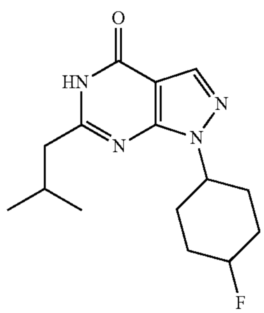 [SMILES: CC(C)Cc1nc2c(cnn2C2CCC(F)CC2)c(=O)[nH]1] | Exm. 38A | | 6.69 min (M2f) | 293 (M + H)+ |
| Exm. 113 | 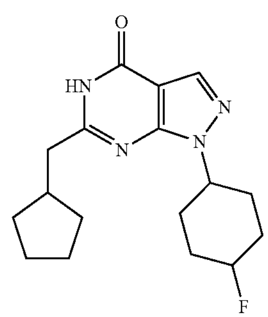 [SMILES: O=c1[nH]c(CC2CCCC2)nc2c1cnn2C1CCC(F)CC1] | Exm. 38A | | 7.54 min (M2F) | 319 (M + H)+ |

The invention claimed is:

1. A compound of formula (I)

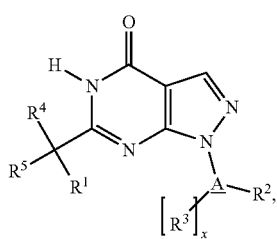

wherein

A is cyclohexyl;

$R^1$ is selected from the group consisting of phenyl, 2-, 3- and 4-pyridyl, cyclopropyl, cyclobutyl, cyclopentyl, cyclohexyl, ethyl, 1- and 2-propyl, 1- and 2-butyl, 1-, 2- and 3-pentyl, tetrahydrofuranyl and tetrahydropyranyl, wherein these $R^1$ groups may optionally be substituted by one or more substituents selected from the group $R^{1.1}$ which consists of fluorine, chlorine, bromine, iodine, NC—, $C_{1-6}$-alkyl-O—, $C_{1-6}$-alkyl-, $CF_3O$—, $F_3C$—, pyridyl, $(R^{10})_2N$—CO—$CH_2$—, N-morpholinyl-$C_{1-6}$-alkyl-, pyrazolyl and phenyl, and wherein if $R^1$ is tetrahydrofuranyl or tetrahydropyranyl, it may also be substituted with oxo, and wherein the pyridyl, pyrazolyl and phenyl group of the aforementioned group $R^{1.1}$ may optionally be substituted with a group selected from fluorine, chlorine, $H_3C$—, $F_3C$—, $CH_3O$—, $H_2NCO$— and NC—;

$R^2$ is fluorine;

$R^3$ is fluorine;

$R^4$ and $R^5$ are independently selected from H and fluorine;

$R^{10}$ independently of any other $R^{10}$ is selected from H—, $C_{1-6}$-alkyl-, phenyl and pyridyl; and x is 1;

and salts thereof.

2. The compound according to claim 1 selected from the group consisting of
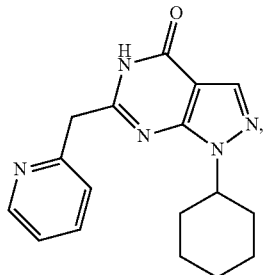
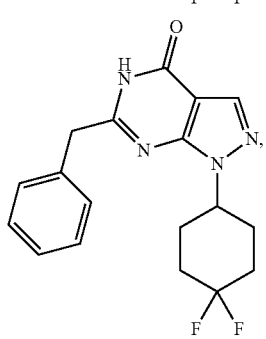
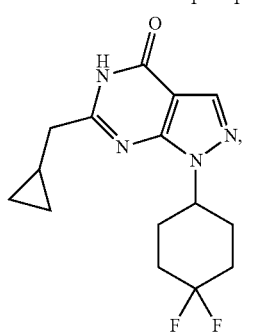
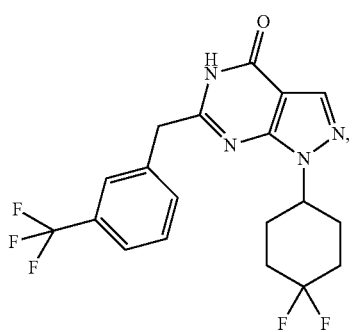
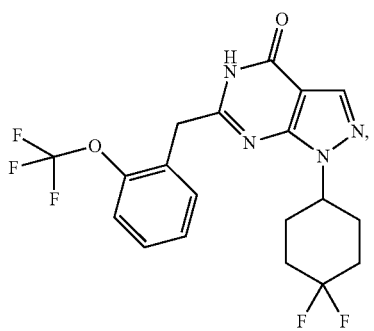
-continued
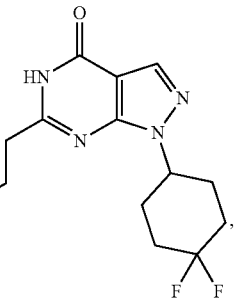
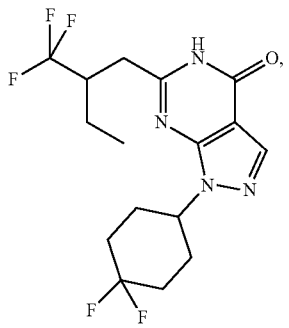
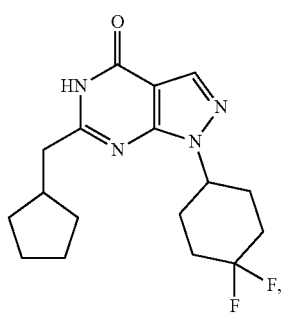
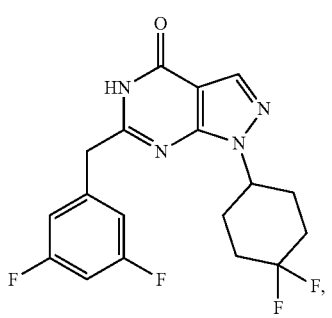
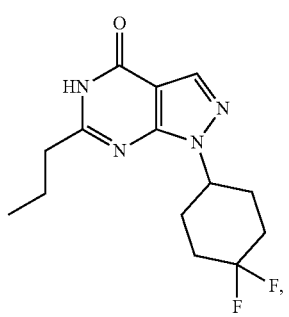

171
-continued
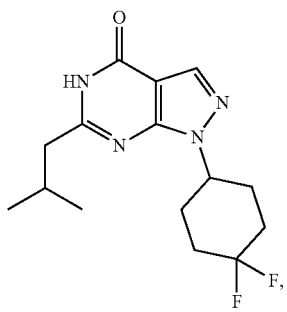
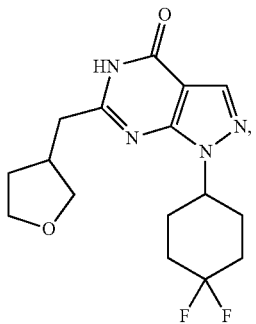
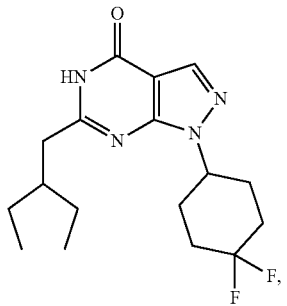
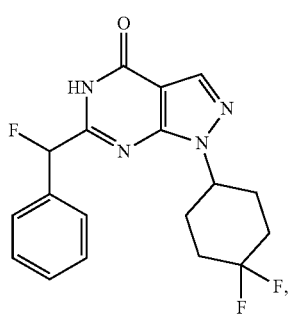
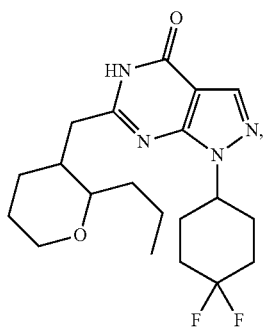
172
-continued
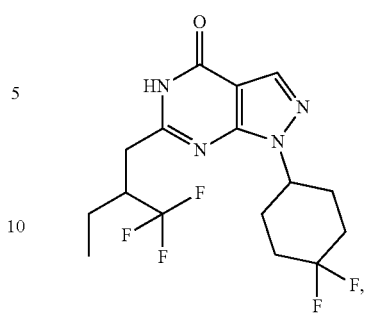
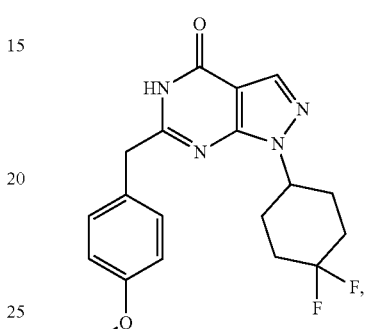
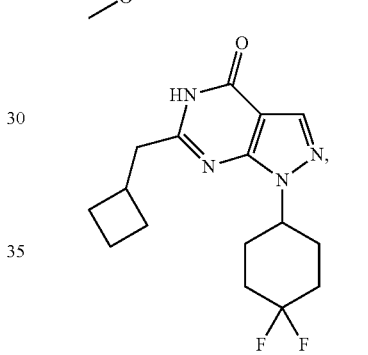
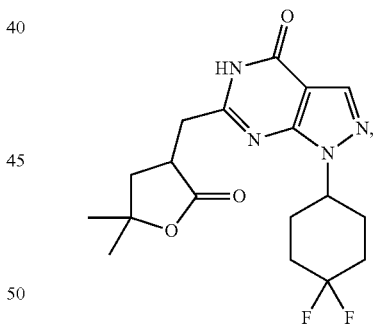
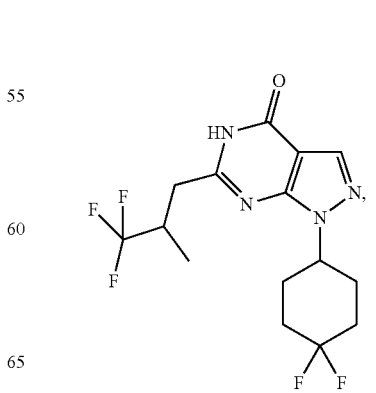

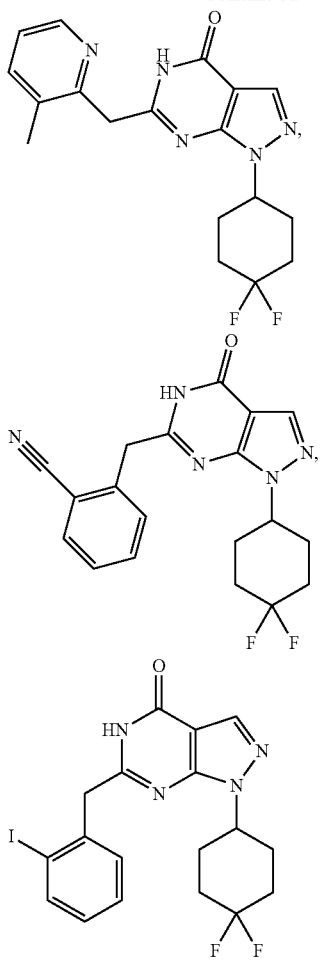
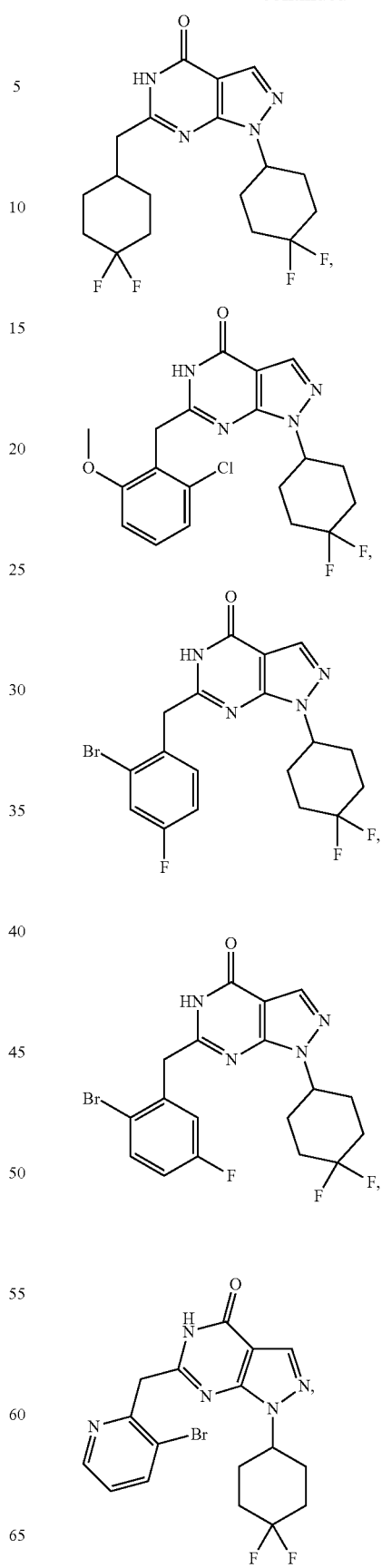

175
-continued
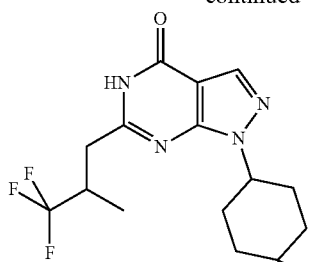
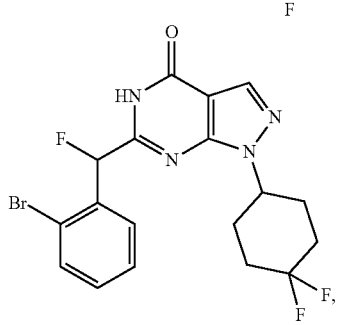
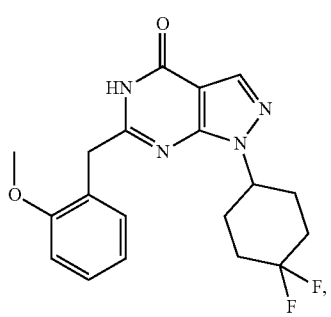
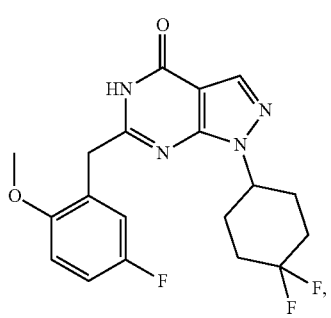
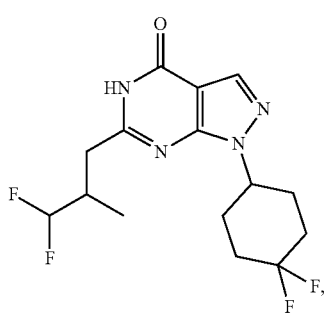
176
-continued
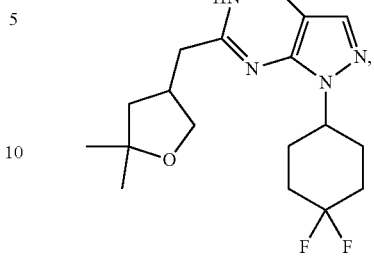
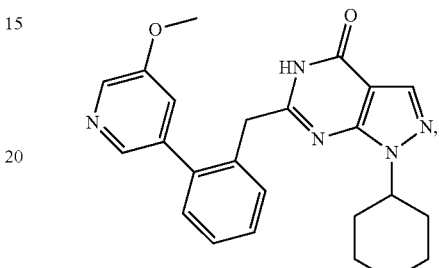
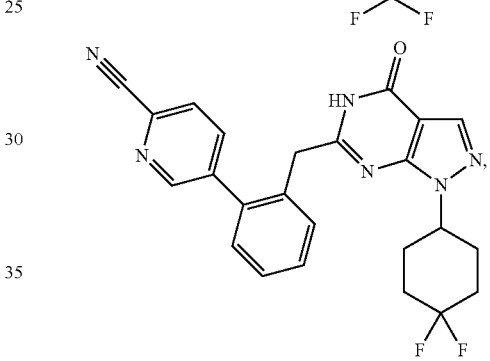
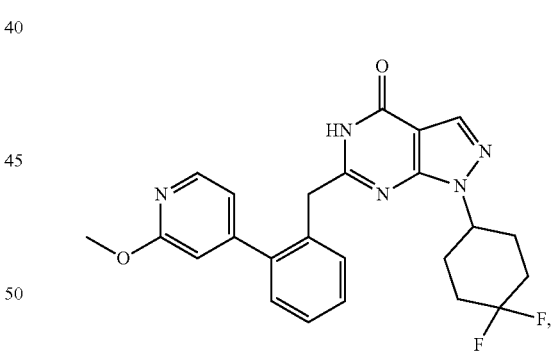
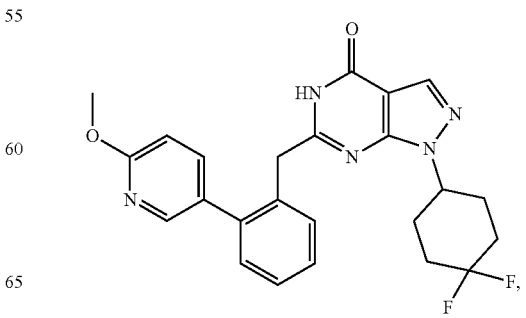

177
-continued
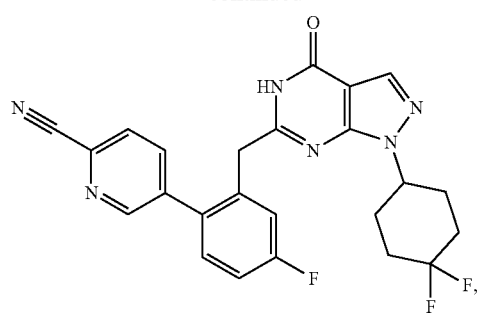
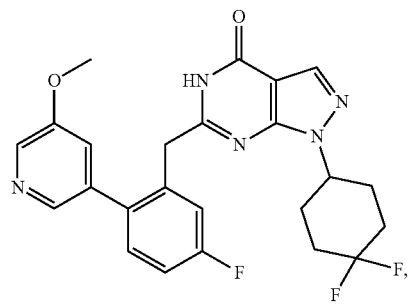
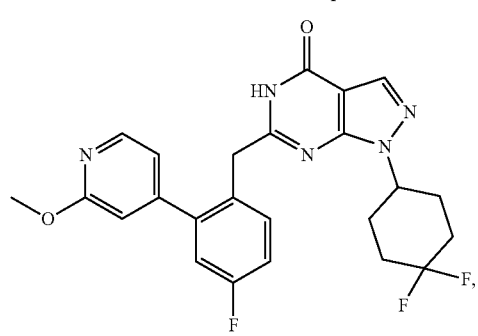
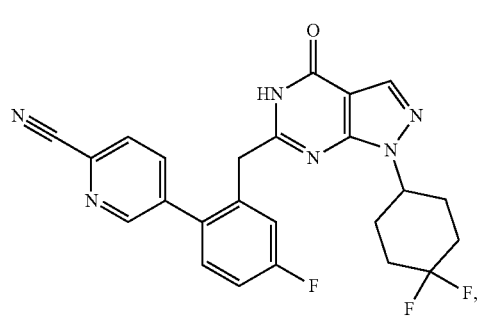
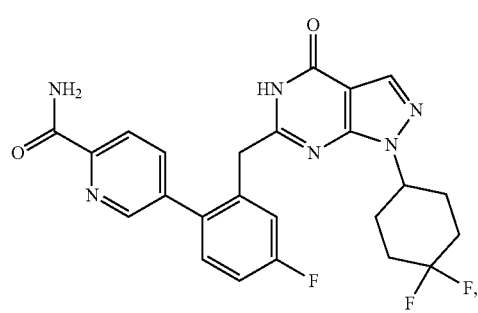
178
-continued
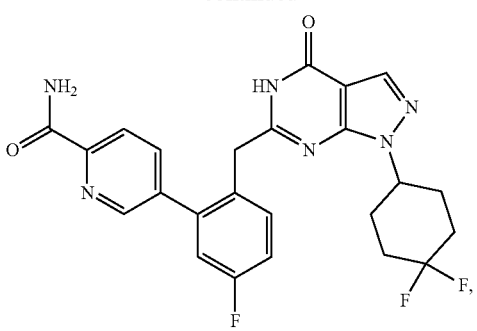
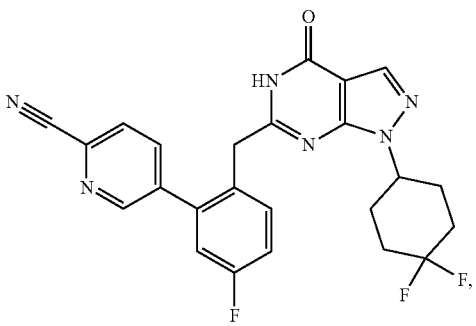
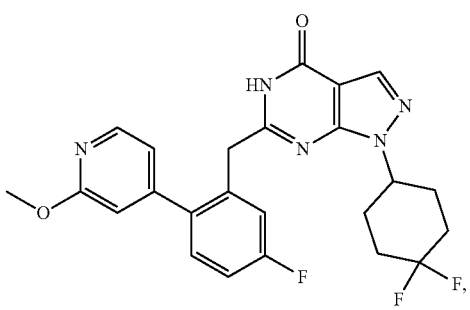
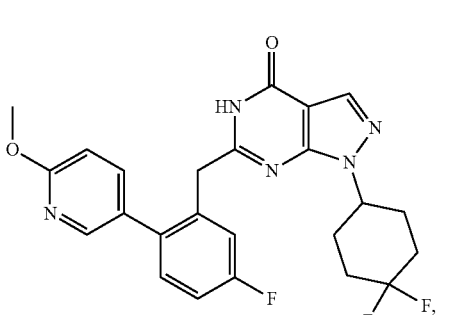
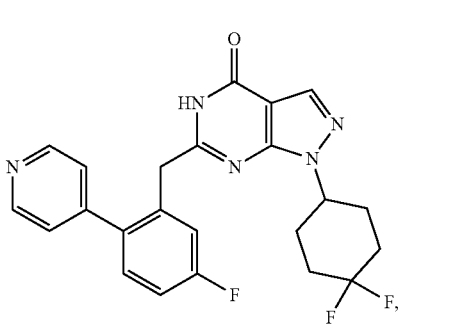

179
-continued
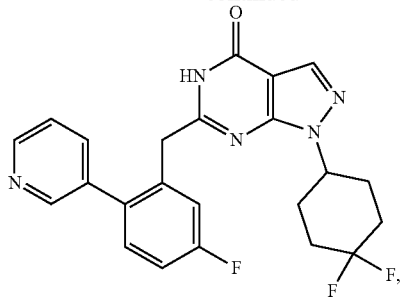
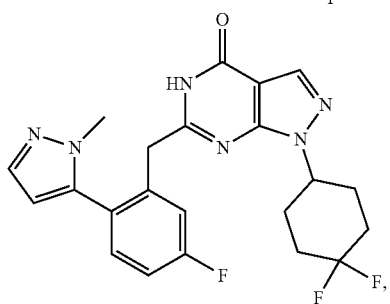
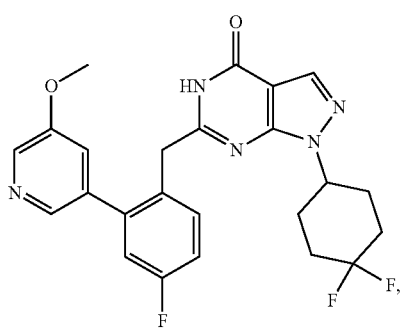
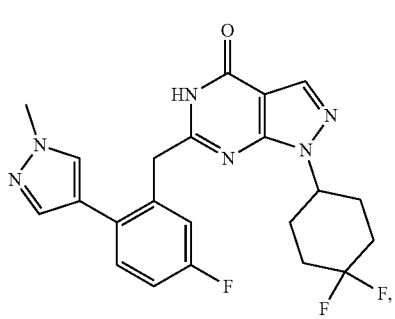
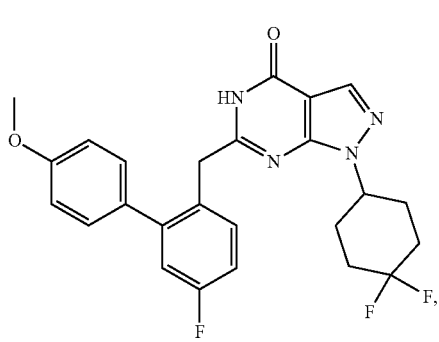
180
-continued
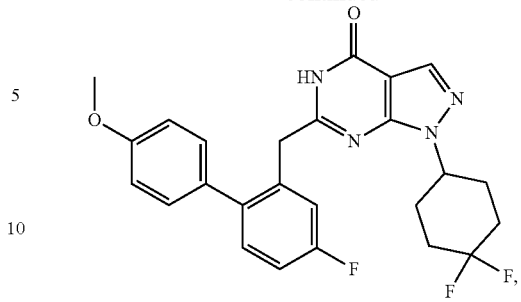
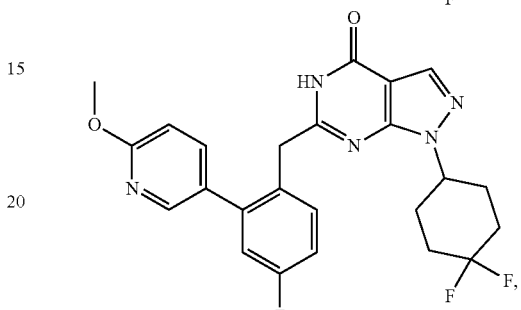
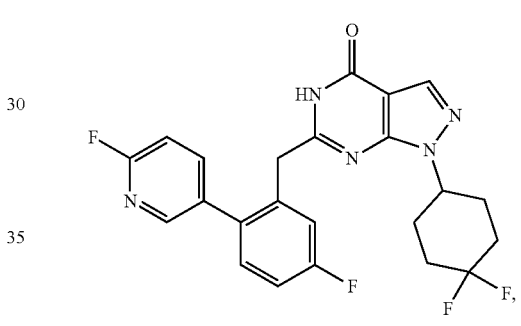
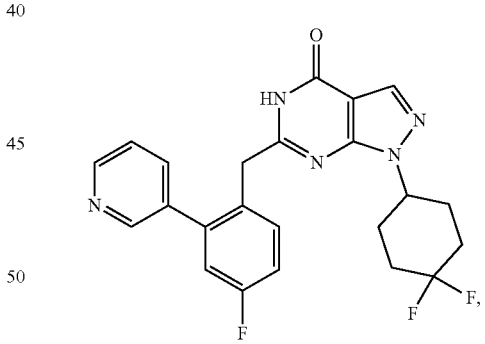
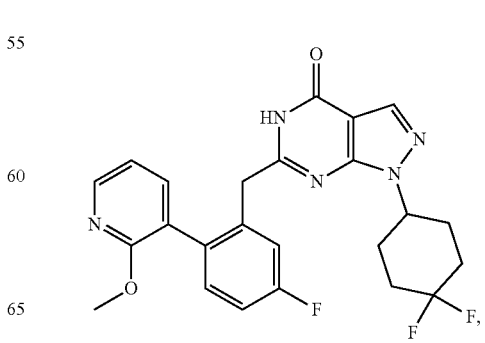

181
-continued
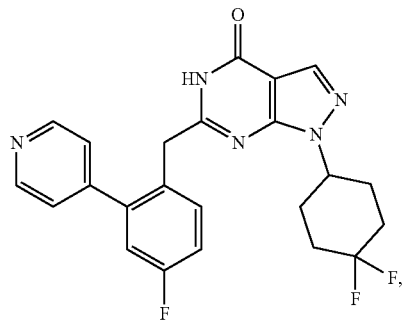
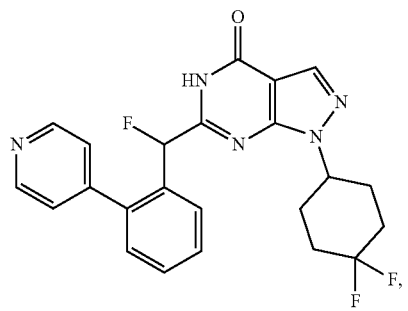
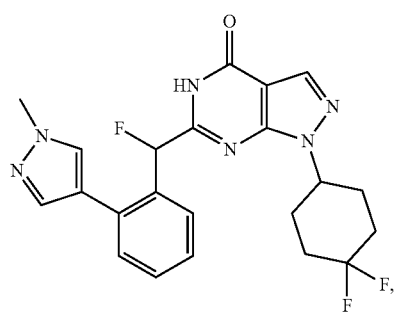
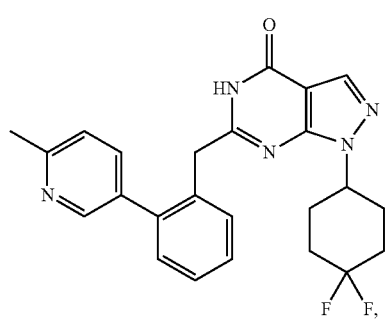
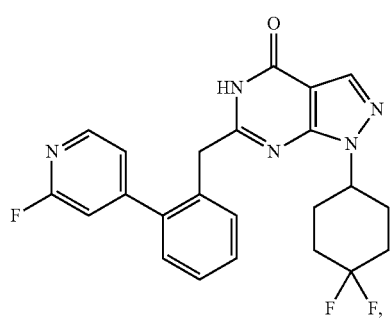
182
-continued
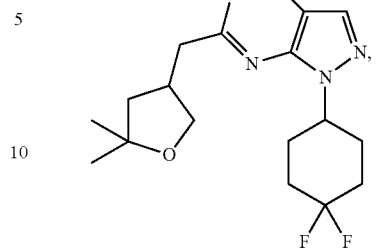
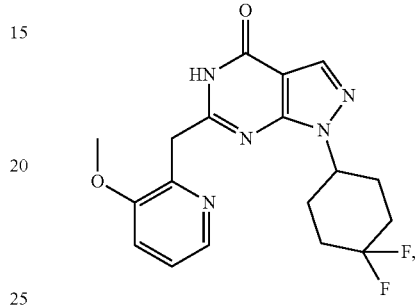
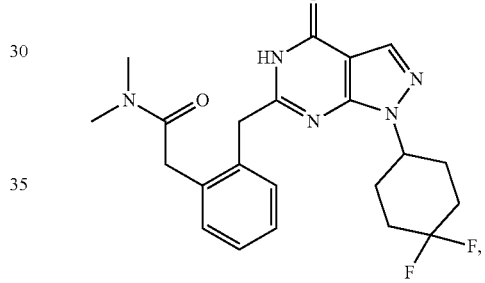
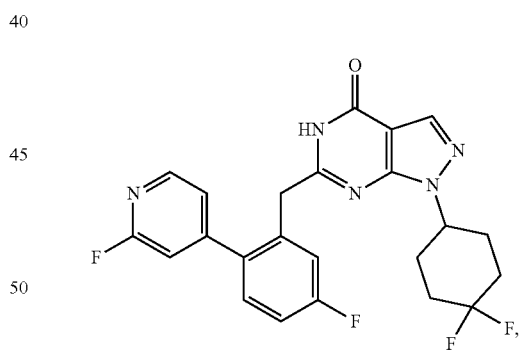
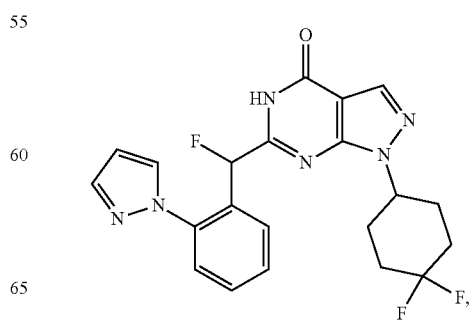

183
-continued
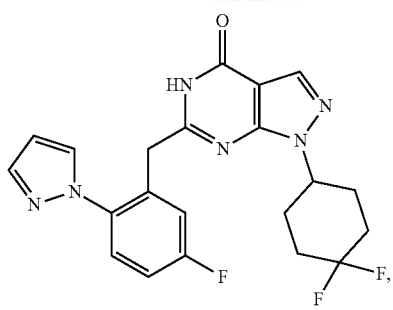
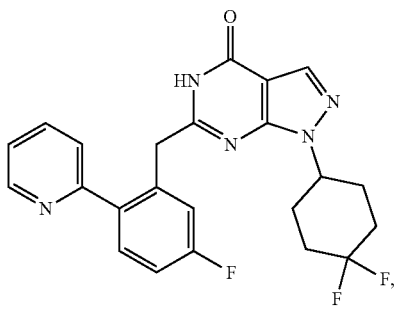
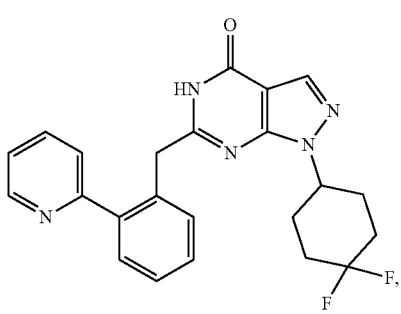
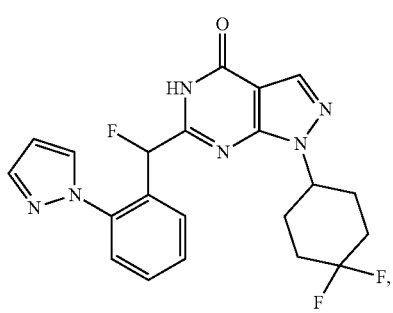
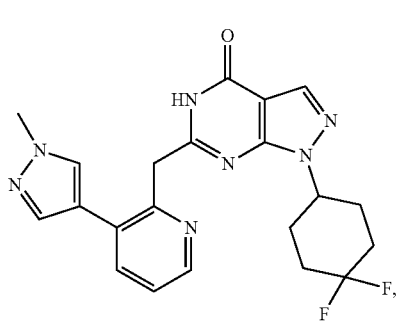
184
-continued
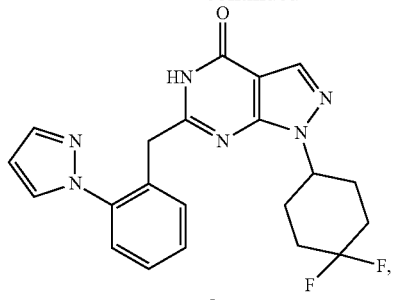
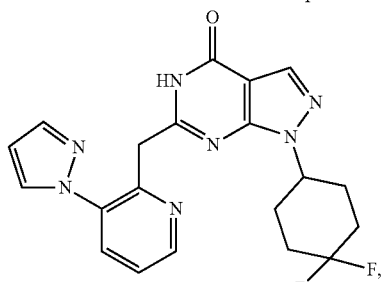
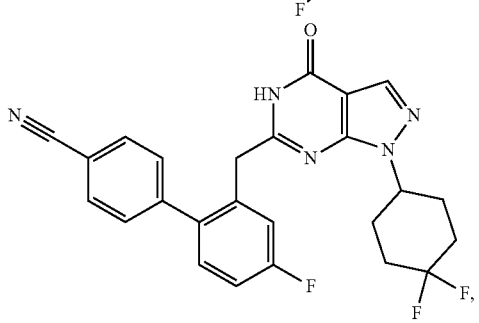
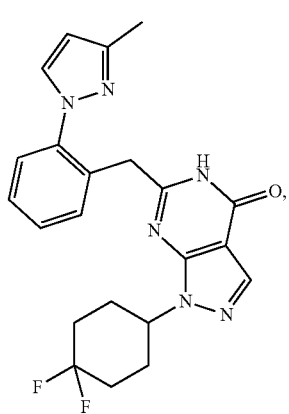
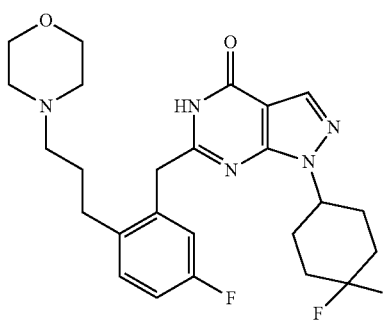 and -continued

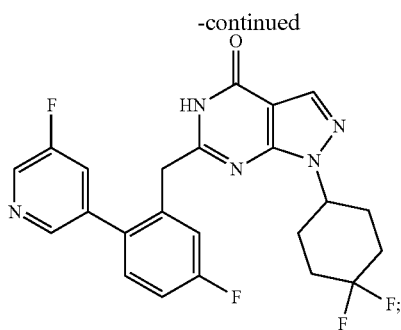

and the pharmaceutically acceptable salts thereof.

3. A pharmaceutical composition comprising a compound according to claim 1 and a pharmaceutical carrier.

4. A combination of a compound according to claim 1 with another active agent wherein the active agent is selected from beta-secretase inhibitors, gamma-secretase inhibitors, gamma-secretase modulators, amyloid aggregation inhibitors, anti-oxidants, anti-inflammatory substances, HMG-CoA reductase inhibitors, acetylcholine esterase inhibitors, NMDA receptor antagonists, AMPA receptor agonists, AMPA receptor positive modulators, AMPkines, glycine transporter 1 inhibitors, monoamine receptor reuptake inhibitors, substances inducing the secretion of growth hormone, CB-1 receptor antagonists or inverse agonists, antibiotics, PDE1, PDE2, PDE4, PDE5 and/or PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists, histamine receptor H3 antagonists, 5-HT4 receptor agonists or partial agonists, 5-HT6 receptor antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate receptor 5 positive modulators and metabotropic glutamate receptor 2 antagonists.

* * * * *